US008975286B2

(12) United States Patent
Dudkin et al.

(10) Patent No.: US 8,975,286 B2
(45) Date of Patent: Mar. 10, 2015

(54) ETHER BENZOTRIAZOLE DERIVATIVES

(75) Inventors: Vadim Y. Dudkin, West Point, PA (US); Mark E. Fraley, West Point, PA (US); Cheng Wang, West Point, PA (US); Robert M. Garbaccio, West Point, PA (US); Douglas C. Beshore, West Point, PA (US); Scott K. Kuduk, West Point, PA (US); Jason W. Skudlarek, West Point, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 357 days.

(21) Appl. No.: 13/391,315

(22) PCT Filed: Aug. 16, 2010

(86) PCT No.: PCT/US2010/045566
§ 371 (c)(1),
(2), (4) Date: Feb. 20, 2012

(87) PCT Pub. No.: WO2011/022312
PCT Pub. Date: Feb. 24, 2011

(65) Prior Publication Data
US 2012/0149677 A1 Jun. 14, 2012

Related U.S. Application Data

(60) Provisional application No. 61/235,522, filed on Aug. 20, 2009.

(51) Int. Cl.
| | |
|---|---|
| C07D 409/14 | (2006.01) |
| C07D 405/14 | (2006.01) |
| C07D 401/14 | (2006.01) |
| C07D 401/12 | (2006.01) |
| C07D 403/12 | (2006.01) |
| C07D 249/18 | (2006.01) |
| A61K 31/506 | (2006.01) |
| A61K 31/497 | (2006.01) |
| A61K 31/496 | (2006.01) |
| A61K 31/454 | (2006.01) |
| A61K 31/4545 | (2006.01) |
| A61K 31/444 | (2006.01) |
| A61K 31/4439 | (2006.01) |
| A61K 31/4192 | (2006.01) |
| C07D 417/14 | (2006.01) |
| C07D 403/14 | (2006.01) |
| C07D 413/14 | (2006.01) |
| C07D 417/12 | (2006.01) |
| C07D 471/04 | (2006.01) |
| C07D 471/08 | (2006.01) |
| C07D 471/10 | (2006.01) |
| C07D 487/04 | (2006.01) |

(Continued)

(52) U.S. Cl.
CPC .......... *C07D 417/14* (2013.01); *A61K 31/4439* (2013.01); *A61K 31/4192* (2013.01); *A61K 31/454* (2013.01); *A61K 31/444* (2013.01); *A61K 31/497* (2013.01); *A61K 31/4545* (2013.01); *A61K 31/506* (2013.01); *A61K 31/496* (2013.01); *C07D 249/18* (2013.01); *C07D 401/12* (2013.01); *C07D 401/14* (2013.01); *C07D 403/12* (2013.01); *C07D 403/14* (2013.01); *C07D 405/14* (2013.01); *C07D 409/14* (2013.01); *C07D 413/14* (2013.01); *C07D 417/12* (2013.01); *C07D 471/04* (2013.01); *C07D 471/08* (2013.01); *C07D 471/10* (2013.01); *C07D 487/04* (2013.01); *C07D 487/08* (2013.01); *C07D 487/10* (2013.01); *C07D 495/04* (2013.01)
USPC ................. 514/359; 514/253.09; 514/254.08; 514/255.05; 514/256; 514/333; 514/338; 544/333; 544/357; 544/405; 546/193; 546/194; 546/199; 546/268.4; 548/259

(58) Field of Classification Search
CPC .. C07D 409/14; C07D 405/14; C07D 401/14; C07D 401/12; C07D 403/12; C07D 249/18; A61K 31/506; A61K 31/497; A61K 31/496; A61K 31/454; A61K 31/4545; A61K 31/444; A61K 31/4439; A61K 31/4192
USPC .......... 514/253.09, 254.08, 255.05, 256, 333, 514/338, 359; 544/333, 357, 405; 546/193, 546/194, 199, 268.4; 548/259
See application file for complete search history.

(56) References Cited

U.S. PATENT DOCUMENTS

| 5,322,853 A | 6/1994 | Ackermann et al. |
| 5,587,392 A * | 12/1996 | Murakami et al. ............ 514/359 |
| 7,094,764 B2 | 8/2006 | Urbanski |
| 2003/0207875 A1 | 11/2003 | Gymer et al. |

OTHER PUBLICATIONS

Klosterkötter et al. World Psychiatry 2011, 10, 165-174.*

(Continued)

*Primary Examiner* — Joseph Kosack
*Assistant Examiner* — Matthew Coughlin
(74) *Attorney, Agent, or Firm* — Keith D. MacMillan; John C. Todaro

(57) ABSTRACT

The present invention is directed to ether benzotriazole derivatives which are potentiators of metabotropic glutamate receptors, particularly the mGluR2 receptor, and which are useful in the treatment or prevention of neurological and psychiatric disorders associated with glutamate dysfunction and diseases in which metabotropic glutamate receptors are involved. The invention is also directed to pharmaceutical compositions comprising these compounds and the use of these compounds and compositions in the prevention or treatment of such diseases in which metabotropic glutamate receptors are involved.

18 Claims, No Drawings

(51) Int. Cl.
*C07D 487/08* (2006.01)
*C07D 487/10* (2006.01)
*C07D 495/04* (2006.01)

(56) References Cited

OTHER PUBLICATIONS

Mayo Clinic, Schizophrenia—Prevention, obtained from http://www.mayoclinic.org/diseases-conditions/schizophrenia/basics/prevention/con-20021077 on Mar. 21, 2014.*

Pilc et al. Biochemical Pharmacology 2008, 75, 997-1006.*
Nickols et al. Neurobiology of Disease 2014, 61, 55-71.*
WebMD, Obsessive-Compulsive Disorder (OCD)—Prevention, obtained from http://www.webmd.com/anxiety-panic/tc/obsessive-compulsive-disorder-ocd-prevention on Mar. 22, 2014.*
El-Sabbagh, et al., "Synthesis and Pharmacological Studies for New Benzotriazole and Dibenzodiazepine Derivatives as Antipsychotic Agents," Bull Korean Chem. Soc., 2003, vol. 30, No. 7, pp. 1445-1451.
PCT/US2010/045566 PCT Search Report dated Feb. 24, 2011.

* cited by examiner

ETHER BENZOTRIAZOLE DERIVATIVES

BACKGROUND OF THE INVENTION

The excitatory amino acid L-glutamate (sometimes referred to herein simply as glutamate) through its many receptors mediates most of the excitatory neurotransmission within the mammalian central nervous system (CNS). The excitatory amino acids, including glutamate, are of great physiological importance, playing a role in a variety of physiological processes, such as long-term potentiation (learning and memory), the development of synaptic plasticity, motor control, respiration, cardiovascular regulation, and sensory perception.

Glutamate acts via at least two distinct classes of receptors. One class is composed of the ionotropic glutamate (iGlu) receptors that act as ligand-gated ionic channels. Via activation of the iGlu receptors, glutamate is thought to regulate fast neuronal transmission within the synapse of two connecting neurons in the CNS. The second general type of receptor is the G-protein or second messenger-linked "metabotropic" glutamate (mGluR) receptor. Both types of receptors appear not only to mediate normal synaptic transmission along excitatory pathways, but also participate in the modification of synaptic connections during development and throughout life. Schoepp, Boekaert, and Sladeczek, Trends in Pharmacol. Sci., 11, 508 (1990); McDonald and Johnson, Brain Research Reviews, 15, 41 (1990).

The present invention relates to potentiators of mGlu receptors, in particular mGluR2 receptors. The mGluR receptors belong to the Type III G-protein coupled receptor (GPCR) superfamily. This superfamily of GPCR's including the calcium-sensing receptors, GABAB receptors and pheromone receptors, which are unique in that they are activated by binding of effectors to the amino-terminus portion of the receptor protein. The mGlu receptors are thought to mediate glutamate's demonstrated ability to modulate intracellular signal transduction pathways. Ozawa, Kamiya and Tsuzuski, Prog. Neurobio., 54, 581 (1998). They have been demonstrated to be localized both pre- and post-synaptically where they can regulate neurotransmitter release, either glutamate or other neurotransmitters, or modify the post-synaptic response of neurotransmitters, respectively.

At present, there are eight distinct mGlu receptors that have been positively identified, cloned, and their sequences reported. These are further subdivided based on their amino acid sequence homology, their ability to affect certain signal transduction mechanisms, and their known pharmacological properties. Ozawa, Kamiya and Tsuzuski, Prog. Neurobio., 54, 581 (1998). For instance, the Group 1 mGluR receptors, which include the mGluR1 and mGluR5, are known to activate phospholipase C (PLC) via G$\alpha$q-proteins thereby resulting in the increased hydrolysis of phosphoinositides and intracellular calcium mobilization. There are several compounds that are reported to activate the Group I mGlu receptors including DHPG, (R/S)-3,5-dihydroxyphenylglycine. Schoepp, Goldworthy, Johnson, Salhoff and Baker, J. Neurochem., 63, 769 (1994); Ito, et al., keurorep., 3, 1013 (1992). The Group II mGlu receptors consist of the two distinct receptors, mGluR2 and mGluR3 receptors. Both have been found to be negatively coupled to adenylate cyclase via activation of G$\alpha$i-protein. These receptors can be activated by a selective compound such as 1S,2S,5R,6S-2 aminobicyclo [3.1.0]hexane-2,6-dicarboxylate. Monn, et al., J. Med. Chem., 40, 528 (1997); Schoepp, et al., Neuropharmacol., 36, 1 (1997). This activation leads to inhibition of glutamate release in the synapse (Cartmell et al, J Neurochem 75, 889 (2000)). Similarly, the Group III mGlu receptors, including mGluR4, mGluR6, mGluR7 and mGluR8, are negatively coupled to adenylate cyclase via G$\alpha$i and are potently activated by L-AP4 (L-(+)-2-amino-4-phosphonobutyric acid). Schoepp, Neurochem. Int., 24, 439 (1994).

Nonselective mGluR2/mGluR3 receptor agonists (Monn, et al., J. Med. Chem., 43, 4893, (2000)) have shown efficacy in numerous animal models of anxiety and psychosis as well as human clinical trials in schizophrenia patients; Patil et al, Nature Medicine, 13, 1102 (2007). Recent reports indicate that mGluR2 but not the mGluR3 receptor mediates the actions of the dual mGluR2/mGluR3 agonist LY379268 in mouse models predictive of antipsychotic activity. Woolley et al, Psycopharmacology, 196, 431 (2008). Additionally, recent animal studies demonstrate that selective potentiation of the mGluR2 receptor has similar effects to such non-selective agonists (Galici et al, Journal of Pharmacology and Experimental Therapeutics, 315, 1181 (2005)) suggesting an alternative strategy concerning the discovery of selective, positive allosteric modulators (PAMs or allosteric potentiators) of mGluR2 (Johnson et al, J. Med. Chem. 46, 3189, (2003); Pinkerton et al., J. Med. Chem., 47, 4595 (2004). These potentiators act by enabling the receptor to produce an enhanced response to endogenous glutamate. Such allosteric potentiators do not bind at the glutamate binding site also known as the "orthosteric site", and may benefit by binding to a site other than the highly conserved orthosteric site. A potential advantage to this approach includes the opportunity to have a distinct pharmacological profile by enhancing the activity of the endogenous ligand upon its binding to the orthosteric site. The pharmacological distinctions include the potential for pharmacological specificity between related receptor types that share the same endogenous ligand. In addition, positive allosteric modulators of mGluR2 have been shown to potentiate the response of mGluR2 agonists such as LY379268 (Johnson et. Al. Biochemical Soc. Trans. 32, 881 (2004) and this represents an alternative strategy for treatment using mGluR2 selective PAMs.

It has become increasingly clear that there is a link between modulation of excitatory amino acid receptors, including the glutamatergic system, through changes in glutamate release or alteration in postsynaptic receptor activation, and a variety of neurological and psychiatric disorders. e.g. Monaghan, Bridges and Cotman, Ann. Rev. Pharmacol. Toxicol., 29, 365-402 (1989); Schoepp and Sacann, Neurobio. Aging, 15, 261-263 (1994); Meldrum and Garthwaite, Tr. Pharmacol. Sci., 11, 379-387 (1990). The medical consequences of such glutamate dysfunction make the abatement of these neurological processes an important therapeutic goal.

SUMMARY OF THE INVENTION

The present invention is directed to ether benzotriazole derivatives which are potentiators of metabotropic glutamate receptors, particularly the mGluR2 receptor, and which are useful in the treatment or prevention of neurological and psychiatric disorders associated with glutamate dysfunction and diseases in which metabotropic glutamate receptors are involved. The invention is also directed to pharmaceutical compositions comprising these compounds and the use of these compounds and compositions in the prevention or treatment of such diseases in which metabotropic glutamate receptors are involved.

DETAILED DESCRIPTION OF THE INVENTION

The invention encompasses a compound according to Formula A

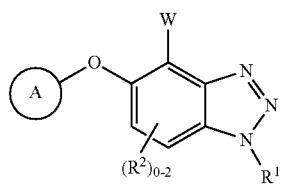

or a pharmaceutically acceptable salt thereof, wherein:

W is H, Cl, Br, CN or $CF_3$;

$R^1$ is selected from the group consisting of: $C_{1-8}$alkyl, $C_{2-8}$alkenyl, $C_{2-8}$alkynyl, $C_{3-6}$cycloalkyl and $C_{3-6}$cycloalkyl$C_{1-4}$alkyl, any of which may bear up to 5 halogen substituents;

each $R^2$ is independently selected from the group consisting of halogen, methyl, $CF_3$, methoxy and CN;

A is selected from phenyl, naphthyl or heteroaryl, any of which is optionally substituted with up to 4 substituents selected from $R^3$;

each $R^3$ is independently selected from the group consisting of halo, —CN, —$NO_2$, —$C(R^a)_2$—$N(X)_2$, —$C(R^a)_2$—N(X)C(O)—X, —$C(R^a)_2$—N(X)S(O)$_k$—X, —$C(R^a)_2$—N(X)C(O)—O—X, —C(O)—X, —C(O)—O—X, —C(O)—N(X)$_2$, —S(O)$_k$—X, —S(O)$_k$N(X)$_2$, —N(X)$_2$, —O—X, —N(X)C(O)—X, —N(X)S(O)$_k$—X, —N(X)C(O)—O—X, —N(X)C(O)N(X)$_2$, —N(R)$SO_2$N(X)$_2$ and X, excluding H;

each X is independently selected from the group consisting of: H, $C_{1-8}$alkyl, $C_{2-6}$alkenyl, $C_{2-6}$alkynyl, $C_{3-10}$cycloalkyl, $C_{3-10}$cycloalkenyl, aryl, heteroaryl, heterocycle, $C_{3-10}$cycloalkyl-$C(R^a)_2$—, $C_{3-10}$cycloalkenyl-$C(R^a)_2$—, aryl-$C(R^a)_2$—, heteroaryl-$C(R^a)_2$— and heterocycle-$C(R^a)_2$—, wherein each member of the group excluding hydrogen is optionally substituted from one up to the maximum number of substitutable positions with one or more substituents independently selected from the group consisting of: CN, halo, $R^b$, —O—$R^b$, —N(R)—$R^b$, —N(R)C(O)—$R^b$, —N(R)S(O)$_2$—$R^b$, —N(R)—C(O)—O—$R^b$, —C(O)—N(R)—$R^b$, —C(O)—O—$R^b$, —C(O)—$R^b$, —C(O)—$C(Ra)_2$-$R^b$, —C(O)—$C(R^a)_2$—S(O)$_2$—$R^b$, —$C(R^a)_2$—N(R)—$R^b$, —$SO_2$—N(R)—$R^b$, —$Si(CH_3)_2(R^b)$, —$C(R^a)_2$—$R^b$ and —$SO_2$—$R^b$;

each k is independently 0, 1 or 2;

each R is independently selected from the group consisting of H and $C_{1-4}$alkyl;

each $R^a$ is independently selected from the group consisting of: H, OH and $C_{1-4}$alkyl;

each $R^b$ is independently selected from the group consisting of: H, $C_{1-4}$alkyl, $C_{2-4}$alkenyl, $C_{2-4}$alkynyl, $C_{3-6}$cycloalkyl, phenyl, benzyl, heterocycle and heteroaryl, wherein each member of the group excluding hydrogen is optionally substituted with 1 to 3 substituents independently selected from: halogen, cyano, hydroxy and methyl;

heteroaryl at each occurrence independently means a 5- or 6-membered monocyclic aromatic or 9- or 10-membered bicyclic aromatic, wherein at least one atom in the aromatic is selected from N,N-oxide, O and S, the sulfur optionally oxidized to sulfone or sulfoxide, and the remaining atoms are selected from C, N,N-oxide, O and S, the sulfur optionally oxidized to sulfone or sulfoxide; and heterocycle at each occurrence independently means a 4- to 7-membered monocyclic non-aromatic ring, an 8- to 11-membered bi-cyclic, including spiro-cyclic, non- or partially-aromatic ring or a 12- to 20-membered tri-cyclic, including spiro-cyclic portions, non- or partially-aromatic ring, each optionally substituted with 1 to 2 oxo groups, wherein at least one atom is selected from N(R), O and S, the sulfur optionally oxidized to sulfone or sulfoxide, and the remaining atoms are selected from C, N(R), O and S, the sulfur optionally oxidized to sulfone or sulfoxide.

The invention also encompasses a genus of compounds of Formula I

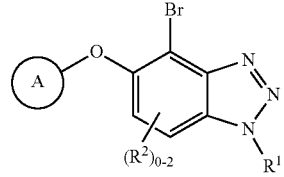

or a pharmaceutically acceptable salt thereof, wherein:

$R^1$ is selected from the group consisting of: $C_{1-8}$alkyl, $C_{2-8}$alkenyl, $C_{2-8}$alkynyl, $C_{3-6}$cycloalkyl and $C_{3-6}$cycloalkyl$C_{1-4}$alkyl, any of which may bear up to 5 halogen substituents;

each $R^2$ is independently selected from the group consisting of halogen, methyl, $CF_3$, methoxy and CN;

A is selected from phenyl, naphthyl or heteroaryl, any of which is optionally substituted with up to 4 substituents selected from $R^3$;

each $R^3$ is independently selected from the group consisting of: halogen, OH, CN, $CF_3$, $R^5$, $OR^4$, $SR^5$, $SO_2R^5$, $SO_2N(R^4)_2$, $COR^4$, $CO_2R^5$, $CON(R^4)_2$, $N(R^4)_2$, $NR^4COR^5$, $NR^4CO_2R^5$, —$C_{1-4}$alkyl-$N(R^4)_2$, —$C_{1-4}$alkyl-$NR^4COR^5$ and —$C_{1-4}$alkyl-$NR^4CO_2R^5$;

each $R^4$ independently represents: (1) H, $C_{1-6}$alkyl, $C_{2-6}$alkenyl, $C_{2-6}$alkynyl, $C_{3-10}$cycloalkyl, $C_{3-10}$cycloalkyl$C_{1-4}$alkyl, $C_{3-10}$cycloalkenyl or $C_{3-10}$cycloalkenyl$C_{1-4}$alkyl, any of which except H optionally bear up to 3 halogen atoms or OH, CN, $CF_3$ and $C_{1-4}$alkoxy; (2) phenyl, benzyl or heteroaryl, optionally bridged with a methylene, any of which optionally bear up to 3 substituents independently selected from halogen, OH, CN, $CF_3$, $C_{1-4}$alkyl, $C_{3-6}$cycloalkyl, phenyl, $C_{1-4}$alkoxy, amino, $C_{1-4}$alkylamino and di($C_{1-4}$alkyl)amino; and (3) Het, optionally bridged with a methylene and said Het optionally bearing up to 3 substituents independently selected from halogen, OH, oxo, CN, $CF_3$, $C_{1-4}$alkyl, $C_{3-6}$cycloalkyl, phenyl, heteroaryl, $C_{1-4}$alkoxy, acetyl, amino, $C_{1-4}$alkylamino and di($C_{1-4}$alkyl)amino;

or when two $R^4$ group are attached to the same nitrogen atom, they may be joined together with said nitrogen atom to form a non-aromatic monocyclic, a non-aromatic or partially aromatic bicyclic or a non-aromatic spiro-linked heterocyclic system of up to 12 ring atoms which optionally bears up to 4 substitutents independently selected from halogen, OH, oxo, CN, $CF_3$, $C_{1-4}$alkyl, $C_{3-6}$cycloalkyl, phenyl, heteroaryl, $C_{1-4}$alkoxy, acetyl, amino, $C_{1-4}$alkylamino and di($C_{1-4}$alkyl) amino;

$R^5$ has the same definition as $R^4$ except that $R^5$ is not H;

each "heteroaryl" independently refers to 5- or 6-membered aromatic monocyclic or 9- or 10-membered aromatic bicyclic ring systems, in which at least one ring atom is selected from N, O and S, excluding tetrazole; and "Het" refers to nonaromatic or partially aromatic mono- or bicyclic heterocyclic systems of up to 10 ring atoms, in which at least one ring atom is selected from N, O and S, where the sulfur atom may be in the form of the S-oxide or S,S-dioxide.

Within the genus, the invention encompasses a first subgenus of compounds of Formula I wherein $R^2$ is not present.

Also within the genus, the invention encompasses a second sub-genus of compounds of Formula I wherein $R^1$ is selected from 2,2-dimethylpropyl, 1,2,2-trimethylpropyl, 4,4,4-trifluorobutyl, cyclopropylmethyl and cyclobutylmethyl.

Also within the genus, the invention encompasses a third sub-genus of compounds of Formula I wherein A is selected from pyridine, pyrazine and pyrimidine.

Within the third sub-genus, the invention encompasses a first class of compounds of Formula I wherein A is pyridine.

Also within the genus, the invention encompasses a fourth sub-genus of compounds of Formula Ia

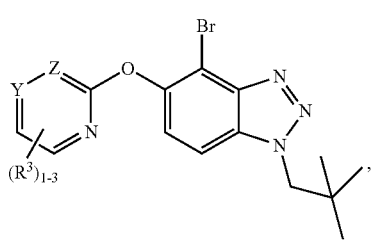

or a pharmaceutically acceptable salt thereof, wherein: one of Y or Z is nitrogen and the other is carbon, or both Y and Z are carbon.

Within the fourth sub-genus, the invention encompasses a second class of compounds of Formula Ia wherein Y and Z are carbon.

Also within the fourth sub-genus, the invention encompasses a third class of compounds of Formula Ia wherein Y is nitrogen and Z is carbon.

Also within the fourth sub-genus, the invention encompasses a fourth class of compounds of Formula Ia wherein Y is carbon and Z is nitrogen.

Also within the fourth sub-genus, the invention encompasses a fifth class of compounds of Formula Ia wherein each $R^3$ is independently selected from the group consisting of: cyano, trifluoromethyl, methoxy, methoxycarbonyl, acetyl, formyl, halogen, phenyl and $C_{1-4}$alkyl, wherein said phenyl is optionally substituted with 1 to 5 halogen atoms and said $C_{1-4}$alkyl is optionally substituted with hydroxy.

Also within the genus, the invention encompasses a fifth sub-genus of compounds of formula Ib:

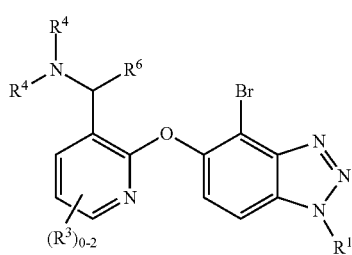

or a pharmaceutically acceptable salt thereof, wherein $R^6$ is H or $C_{1-3}$alkyl.

Within the fifth sub-genus, the invention encompasses a sixth class of compounds of Formula Ia wherein: $R^1$ is selected from 2,2-dimethylpropyl, 1,2,2-trimethylpropyl, 4,4,4-trifluorobutyl, cyclopropylmethyl and cyclobutylmethyl; and $R^3$ is halogen.

The invention also encompasses a compound according to Formula B

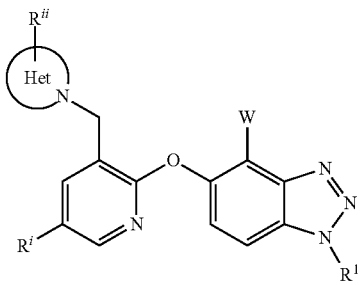

or a pharmaceutically acceptable salt thereof, wherein:
W is Cl, Br, CN or $CF_3$;
$R^1$ is selected from the group consisting of: $C_{1-8}$alkyl, $C_{2-8}$alkenyl, $C_{2-8}$alkynyl, $C_{3-6}$cycloalkyl and $C_{3-6}$cycloalkyl$C_{1-4}$alkyl, any of which may bear up to 5 halogen substituents;
$R^i$ is selected from H, F and Cl;
$R^{ii}$ is selected from the group consisting of: CN, halo, $R^b$, —N(R)—$R^b$, —N(R)C(O)—$R^b$, —N(R)S(O)$_2$—$R^b$, —N(R)—C(O)—O—$R^b$, —C(O)—N(R)—$R^b$, —C(O)—O—$R^b$, —C(O)—$R^b$, —C(O)—C(Ra)$_2$-$R^b$, —C(O)—C($R^a$)$_2$—S(O)$_2$—$R^b$, —C($R^a$)$_2$—N(R)—$R^b$, —SO$_2$—N(R)—$R^b$, —Si(CH$_3$)$_2$($R^b$), —C($R^a$)$_2$—$R^b$ and —SO$_2$—$R^b$;
each R is independently selected from the group consisting of: H and $C_{1-4}$alkyl;
each $R^a$ is independently selected from the group consisting of: H, OH and $C_{1-4}$alkyl;
each $R^b$ is independently selected from the group consisting of: H, $C_{1-4}$alkyl, $C_{2-4}$alkenyl, $C_{2-4}$alkynyl, $C_{3-6}$cycloalkyl, phenyl, benzyl, heterocycle and heteroaryl, wherein each member of the group excluding hydrogen is optionally substituted with 1 to 3 substituents independently selected from: halogen, cyano, hydroxy and methyl;
N-Het is a 6-membered monocyclic non-aromatic ring having a nitrogen atom bonded to the methylene bridge, optionally containing one additional heteroatom selected from N(R), O and S, the sulfur optionally oxidized to sulfone or sulfoxide, and the remaining atoms being carbon. In an embodiment, the invention encompasses compounds of Formula B wherein N-Het is piperazine; and Heterocycle and heteroaryl are as previously defined. In another embodiment, the invention encompasses compounds of Formula B wherein W is Cl, Br or $CF_3$.

The invention also encompasses a compound according to Formula C

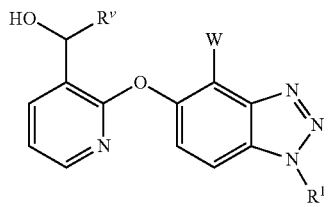

or a pharmaceutically acceptable salt thereof, wherein:
W is Cl, Br, CN or $CF_3$;
$R^1$ is selected from the group consisting of: $C_{1-8}$alkyl, $C_{2-8}$alkenyl, $C_{2-8}$alkynyl, $C_{3-6}$cycloalkyl and $C_{3-6}$cycloalkyl$C_{1-4}$alkyl, any of which may bear up to 5 halogen substituents;

$R^v$ is independently selected from the group consisting of $C_{1-6}$alkyl, $C_{3-10}$cycloalkyl, aryl, heteroaryl and heterocycle, wherein each member of the group excluding hydrogen is optionally substituted from one up to the maximum number of substitutable positions with one or more substituents independently selected from the group consisting of: CN, halo, $R^b$, —O—$R^b$, —N(R)—$R^b$, —N(R)C(O)—$R^b$, —N(R)S(O)$_2$—$R^b$, —N(R)—C(O)—O—$R^b$, —C(O)—N(R)—$R^b$, —C(O)—O—$R^b$, —C(O)—$R^b$, —C(O)—C(Ra)$_2$-$R^b$, —C(O)—C($R^a$)$_2$—S(O)$_2$—$R^b$, —C($R^a$)$_2$—N(R)—$R^b$, —SO$_2$—N(R)—$R^b$, —Si(CH$_3$)$_2$($R^b$), —C($R^a$)$_2$—$R^b$ and —SO$_2$—$R^b$;

each R is independently selected from the group consisting of: H and $C_{1-4}$alkyl;

each $R^a$ is independently selected from the group consisting of H, OH and $C_{1-4}$alkyl;

each $R^b$ is independently selected from the group consisting of: H, $C_{1-4}$alkyl, $C_{2-4}$alkenyl, $C_{2-4}$alkynyl, $C_{3-6}$cycloalkyl, phenyl, benzyl, heterocycle and heteroaryl, wherein each member of the group excluding hydrogen is optionally substituted with 1 to 3 substituents independently selected from: halogen, cyano, hydroxy and methyl;

heteroaryl at each occurrence independently means a 5- or 6-membered monocyclic aromatic or 9- or 10-membered bicyclic aromatic, wherein at least one atom in the aromatic is selected from N,N-oxide, O and S, the sulfur optionally oxidized to sulfone or sulfoxide, and the remaining atoms are selected from C, N,N-oxide, O and S, the sulfur optionally oxidized to sulfone or sulfoxide; and heterocycle at each occurrence independently means a 4- to 7-membered monocyclic non-aromatic ring, an 8- to 11-membered bi-cyclic, including spiro-cyclic, non- or partially-aromatic ring or a 12- to 20-membered tri-cyclic, including spiro-cyclic portions, non- or partially-aromatic ring, each optionally substituted with 1 to 2 oxo groups, wherein at least one atom is selected from N(R), O and S, the sulfur optionally oxidized to sulfone or sulfoxide, and the remaining atoms are selected from C, N(R), O and S, the sulfur optionally oxidized to sulfone or sulfoxide. In an embodiment, the invention encompasses compounds of Formula C wherein W is Cl, Br or CF$_3$.

Within Formula A described above, the invention encompasses compounds of Formula D

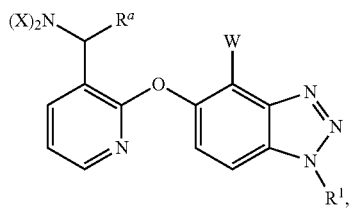

D or a pharmaceutically acceptable salt thereof, wherein all variables are as previously defined.

The invention also encompasses Examples 1 to 423 that follow.

The invention also encompasses a pharmaceutical composition comprising a compound of Formulas I, Ia, Ib, A, B, C or D in combination with a pharmaceutically acceptable carrier.

The invention also encompasses a method for treating a neurological or psychiatric disorder associated with glutamate dysfunction in a patient in need thereof comprising administering to the patient a therapeutically effective amount of a compound of Formulas I, Ia, Ib, A, B, C or D. The invention also encompasses this method wherein the neurological or psychiatric disorder associated with glutamate dysfunction is schizophrenia.

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

For the groups "—$C_{1-4}$alkyl-N(R$^4$)$_2$", "—$C_{1-4}$alkyl-NR$^4$COR$^5$" and "—$C_{1-4}$alkyl-NR$^4$CO$_2$R$^5$" the alkyl portion may be linear or branched or combinations thereof.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono-, bi- or tri-cyclic structures, optionally combined with linear or branched structures, having the indicated number of carbon atoms. Examples of cycloalkyl groups include cyclopropyl, cyclopentyl, cycloheptyl, adamantyl, cyclododecylmethyl, 2-ethyl-1-bicyclo[4.4.0]decyl, and the like.

"Cycloalkenyl" means cycloalkyl as defined above having at least one double bond, excluding aromatics.

"Alkoxy" means alkoxy groups of a straight or branched having the indicated number of carbon atoms. $C_{1-6}$alkoxy, for example, includes methoxy, ethoxy, propoxy, isopropoxy, and the like.

Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Halogen" and "halo" includes fluorine, chlorine, bromine and iodine.

When two R$^4$ group are attached to the same nitrogen atom, they may be joined together with said nitrogen atom to form a non-aromatic monocyclic, a non-aromatic or partially aromatic bicyclic or a non-aromatic spiro-linked heterocyclic system of up to 12 ring atoms, which optionally bears up to 4 substitutents as defined above. Examples include morpholine, 1,1-dioxothiomorpholine and the like.

The compounds of the present invention are potentiators of metabotropic glutamate (mGluR) receptor function, in particular they are potentiators of mGluR2 receptors. That is, the compounds of the present invention do not appear to bind at the glutamate recognition site on the mGluR receptor, but in the presence of glutamate or a glutamate agonist, the compounds of the present invention increase mGluR receptor response. The present potentiators are expected to have their effect at mGluR receptors by virtue of their ability to increase the response of such receptors to glutamate or glutamate agonists, enhancing the function of the receptors. It is recognized that the compounds of the present invention would be expected to increase the effectiveness of glutamate and glutamate agonists of the mGluR2 receptor. Thus, the potentiators of the present invention are expected to be useful in the treatment of various neurological and psychiatric disorders associated with glutamate dysfunction described to be treated herein and others that can be treated by such potentiators as are appreciated by those skilled in the art.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of generic Formulas I, Ia, Ib, A, B, C or D, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formulas I, Ia, Ib, A, B, C or D. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formulas I, Ia, Ib, A, B, C or D can be prepared without undue experimentation by conventional techniques well known to those skilled in the art or by processes analogous to those described in the Schemes and Examples herein using appropriate isotopically-enriched reagents and/or intermediates.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. A subgroup is the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. A subgroup is citric, hydrobromic, hydrochloric, maleic, phosphoric, sulfuric, fumaric, and tartaric acids. It will be understood that, as used herein, references to the compounds of Formulas I, Ia, Ib, A, B, C or D are meant to also include a pharmaceutically acceptable salts.

Exemplifying the invention are Examples 1 to 423, described herein. The subject compounds are useful in a method of potentiating metabotorpic glutamate receptor activity in a patient such as a mammal in need of such inhibition comprising the administration of an effective amount of the compound. The present invention is directed to the use of the subject compounds disclosed herein as potentiators of metabotropic glutamate receptor activity. In addition to primates, especially humans, a variety of other mammals can be treated according to the method of the present invention.

The present invention is further directed to a method for the manufacture of a medicament for potentiating metabotropic glutamate receptor activity in humans and animals comprising combining a compound of the present invention with a pharmaceutical carrier or diluent.

The subject treated in the present methods is generally a mammal, preferably a human being, male or female, in whom potentiation of metabotropic glutamate receptor activity is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as potentiators or agonists of metabotropic glutamate receptor activity, in particular mGluR2 activity, may be demonstrated by methodology known in the art. Potencies are determined as follows. The compounds of the present invention may be tested in a fluorescence laser imaging plate reader (FLIPR) based assay. This assay is a common functional assay to monitor $Ca^{2+}$ mobilization in whole cells expressing recombinant receptor coupled with a promiscuous G-protein. CHO dhfr– cells stably expressing recombinant human mGluR2 and Gα16 loaded with Fluo-4 AM (Invitrogen, Carlsbad Calif.) are treated with varying concentrations of compounds and the $Ca^{2+}$ response is monitored on a FLIPR384 (Molecular Devices, Sunnydale Calif.) for agonist activity. The potentiation response is monitored after a subsequent addition of an EC20 concentration of glutamate (900 nM). The maximum calcium response at each concentration of compound for agonism or potentiation are plotted as dose responses curves fitted with a four parameters logistic equation giving $EC_{50}$ and Hill coefficient using the iterative non linear curve fitting software program.

The compounds of the present invention may also be tested in a [$^{35}$S]-GTPγS assay. [$^{35}$S]-GTPγS binding is a common functional assay to monitor Gαi-coupled receptor in native and recombinant receptor membrane preparation. Membranes from CHO$_{dhfr}$ cells stably expressing recombinant hmGluR2 and Gα16 (25 µg) or HEK293 cells stably expressing recombinant rat mGluR2 (25 µg) are incubated in a 96 well plate for 1 hour in the presence of [$^{35}$S]-GTPγS (0.05 nM), GDP (5 µM), and varying concentrations of compounds, with (for potentiation) or without (for agonism) a sub-threshold ($EC_{10}$) concentration of glutamate (1500 nM for hmGluR2 or 750 nM for rat mGluR2). The reaction is stopped by rapid filtration over Unifilter GF/B plate (Packard, Bioscience, Meriden Conn.) using a 96-well cell harvester (Brandel Gaithersburg, Md.). After the addition of Microscint 20 (Packard, Bioscience, Meriden Conn.), the filter plates are counted using a Topcount counter (Packard, Bioscience, Meriden Conn., USA). The agonist or the potentiator curves are fitted with a four parameters logistic equation giving $EC_{50}$ and Hill coefficient using an iterative non linear curve fitting software program.

In particular, Examples 1 to 423 were tested and demonstrated activity in potentiating the mGluR2 receptor in the FLIPR assay, generally with an $EC_{50}$ of less than about 10 µM. Compounds within the present invention had activity in potentiating the mGluR2 receptor in the FLIPR and GTPγS assays with an $EC_{50}$ of less than about 1 µM. Examples 1 to 423 resulted in a minimum 1.8-fold potentiation of glutamate response in the presence of an EC20 concentration of glutamate (900 nM). Such results are indicative of the intrinsic activity of the compounds in use as potentiators of mGluR2 receptor activity.

| Representative FLIPR $EC_{50}$ Values | |
| --- | --- |
| Ex. | $EC_{50}$ |
| 52 | 814 nM |
| 55 | 95 nM |
| 72 | 5 nM |
| 91 | 6 nM |
| 93 | 11 nM |
| 111 | 64 nM |
| 122 | 80 nM |
| 148 | 23 nM |
| 151 | 122 nM |
| 169 | 425 nM |
| 184 | 21 nM |
| 194 | 32 nM |
| 198 | 3 nM |
| 204 | 39 nM |
| 213 | 40 nM |
| 215 | 129 nM |
| 227 | 705 nM |
| 253 | 52 nM |
| 280 | 8 nM |
| 284 | 64 nM |
| 290 | 2 nM |
| 297 | 19 nM |
| 320 | 5 nM |
| 357 | 13 nM |
| 365 | 8 nM |
| 384 | 8 nM |
| 396 | 556 nM |
| 398 | 556 nM |
| 411 | 257 nM |
| 418 | 49 nM |
| 421 | 20 nM |
| 423 | 141 nM |

Metabotropic glutamate receptors including the mGluR2 receptor have been implicated in a wide range of biological functions. This has suggested a potential role for these receptors in a variety of disease processes in humans or other species.

The compounds of the present invention have utility in treating, preventing, ameliorating, controlling or reducing the risk of a variety of neurological and psychiatric disorders associated with glutamate dysfunction, including one or more of the following conditions or diseases: acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), autism, autism spectrum disorders, attention deficit/hyperactivity disorder, and conduct disorder.

Of the disorders above, the treatment of migraine, anxiety, schizophrenia, and epilepsy are of particular importance. In an embodiment the present invention provides a method for treating migraine, comprising: administering to a patient in need thereof an effective amount of a compound of Formulas I, Ia, Ib, A, B, C or D. In another embodiment the present invention provides a method for preventing or treating anxiety, comprising: administering to a patient in need thereof an effective amount of a compound of Formulas I, Ia, Ib, A, B, C or D. Particularly anxiety disorders are generalized anxiety disorder, panic disorder, and obsessive compulsive disorder. In another embodiment the present invention provides a method for treating schizophrenia, comprising: administering to a patient in need thereof an effective amount of a compound of Formulas I, Ia, Ib, A, B, C or D. In yet another embodiment the present invention provides a method for treating epilepsy, comprising: administering to a patient in need thereof an effective amount of a compound of Formulas I, Ia, Ib, A, B, C or D.

Of the neurological and psychiatric disorders associated with glutamate dysfunction which are treated according to the present invention, the treatment of migraine, anxiety, schizophrenia, and epilepsy encompass a subgroup of the invention. Particular anxiety disorders are generalized anxiety disorder, panic disorder, and obsessive compulsive disorder.

In an embodiment, the present invention provides a method for the treatment of schizophrenia comprising: administering to a patient in need thereof an effective amount of a compound of Formulas I, Ia, Ib, A, B, C or D or a pharmaceutical composition thereof. In one of the available sources of diagnostic tools, The Merck Manual (2006-2007), schizophrenia is characterized by psychosis (loss of contact with reality), hallucinations (false perceptions), delusions (false beliefs), disorganized speech and behavior, flattened affect (restricted range of emotions), cognitive deficits (impaired reasoning and problem solving), and occupational and social dysfunction. The skilled artisan will recognize that there are alternative nomenclatures, nosologies, and classification systems for neurological and psychiatric disorders, including schizophrenia, and that these systems evolve with medical scientific progress.

Thus, in an embodiment the present invention provides a method for treating migraine, comprising: administering to a patient in need thereof an effective amount of a compound of Formulas I, Ia, Ib, A, B, C or D or a pharmaceutical composition thereof. In one of the available sources of diagnostic tools, Dorland's Medical Dictionary (23'd Ed., 1982, W. B. Saunders Company, Philadelphia, Pa.), migraine is defined as a symptom complex of periodic headaches, usually temporal and unilateral, often with irritability, nausea, vomiting, constipation or diarrhea, and photophobia. As used herein the term "migraine" includes these periodic headaches, both temporal and unilateral, the associated irritability, nausea, vomiting, constipation or diarrhea, photophobia, and other associated symptoms. The skilled artisan will recognize that there are alternative nomenclatures, nosologies, and classification systems for neurological and psychiatric disorders, including migraine, and that these systems evolve with medical scientific progress.

In another embodiment the present invention provides a method for treating anxiety, comprising: administering to a patient in need thereof an effective amount of a compound of Formulas I, Ia, Ib, A, B, C or D or a pharmaceutical composition thereof. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-W. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

In another embodiment the present invention provides a method for treating depression, comprising: administering to a patient in need thereof an effective amount of a compound of Formulas I, Ia, Ib, A, B, C or D or a pharmaceutical composition thereof. At present, the fourth edition of the Diagnostic and Statistical Manual of Mental Disorders (DSM-IV) (1994, American Psychiatric Association, Washington, D.C.), provides a diagnostic tool including depression and related disorders. Depressive disorders include, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder. As used herein the term "depression" includes treatment of those depression disorders and related disorder as described in the DSM-IV.

In another embodiment the present invention provides a method for treating epilepsy, comprising: administering to a patient in need thereof an effective amount of a compound of Formulas I, Ia, Ib, A, B, C or D or a pharmaceutical composition thereof. At present, there are several types and subtypes of seizures associated with epilepsy, including idiopathic, symptomatic, and cryptogenic. These epileptic seizures can be focal (partial) or generalized. They can also be simple or complex. Epilepsy is described in the art, such as Epilepsy: A comprehensive textbook. Ed. by Jerome Engel, Jr. and Timothy A. Pedley. (Lippincott-Raven, Philadelphia, 1997). At present, the International Classification of Diseases, Ninth Revision, (ICD-9) provides a diagnostic tool including epilepsy and related disorders. These include: generalized non-convulsive epilepsy, generalized convulsive epilepsy, petit mal status epilepticus, grand mal status epilepticus, partial epilepsy with impairment of consciousness, partial epilepsy without impairment of consciousness, infantile spasms, epilepsy partialis continua, other forms of epilepsy, epilepsy, unspecified, NOS. As used herein the term "epilepsy" includes these all types and subtypes. The skilled artisan will recognize that there are alternative nomenclatures, nosologies, and classification systems for neurological and psychiatric disorders, including epilepsy, and that these systems evolve with medical scientific progress.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents, including an mGluR agonist.

The term "potentiated amount" refers to an amount of an mGluR agonist, that is, the dosage of agonist which is effective in treating the neurological and psychiatric disorders described herein when administered in combination with an effective amount of a compound of the present invention. A potentiated amount is expected to be less than the amount that is required to provided the same effect when the mGluR agonist is administered without an effective amount of a compound of the present invention.

A potentiated amount can be readily determined by the attending diagnostician, as one skilled in the art, by the use of conventional techniques and by observing results obtained under analogous circumstances. In determining a potentiated amount, the dose of an mGluR agonist to be administered in combination with a compound of Formulas I, Ia, Ib, A, B, C or D, a number of factors are considered by the attending diagnostician, including, but not limited to: the mGluR agonist selected to be administered, including its potency and selectivity; the compound of Formulas I, Ia, Ib, A, B, C or D to be coadministered; the species of mammal; its size, age, and general health; the specific disorder involved; the degree of involvement or the severity of the disorder; the response of the individual patient; the modes of administration; the bioavailability characteristics of the preparations administered; the dose regimens selected; the use of other concomitant medication; and other relevant circumstances.

A potentiated amount of an mGluR agonist to be administered in combination with an effective amount of a compound of Formulas I, Ia, Ib, A, B, C or D is expected to vary from about 0.1 milligram per kilogram of body weight per day (mg/kg/day) to about 100 mg/kg/day and is expected to be less than the amount that is required to provided the same effect when administered without an effective amount of a compound of Formulas I, Ia, Ib, A, B, C or D. Preferred amounts of a co-administered mGlu agonist are able to be determined by one skilled in the art.

The compounds of the present invention may be used in combination with one or more other drugs in the treatment, prevention, control, amelioration, or reduction of risk of diseases or conditions for which compounds of Formulas I, Ia, Ib, A, B, C or D or the other drugs may have utility, where the combination of the drugs together are safer or more effective than either drug alone. Such other drug(s) may be administered, by a route and in an amount commonly used therefor, contemporaneously or sequentially with a compound of Formulas I, Ia, Ib, A, B, C or D. When a compound of Formulas I, Ia, Ib, A, B, C or D is used contemporaneously with one or more other drugs, a pharmaceutical composition in unit dosage form containing such other drugs and the compound of Formulas I, Ia, Ib, A, B, C or D is encompassed as an embodiment of the invention. However, the combination therapy may also includes therapies in which the compound of Formulas I, Ia, Ib, A, B, C or D and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formulas I, Ia, Ib, A, B, C or D.

The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is encompassed as part of the invention. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives.

Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require potentiation of metabotorpic glutamate receptor activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

When treating, preventing, controlling, ameliorating, or reducing the risk of neurological and psychiatric disorders associated with glutamate dysfunction or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Abbreviations used in the description of the chemistry and in the Examples that follow are: $Ac_2O$ (acetic anhydride); AcOH (acetic acid); AEBSF (p-aminoethylbenzenesulfonyl fluoride); Boc (di-tert-butyl carbamate); $(Boc)_2O$ (di-tert-butyl dicarbonate); BSA (bovine serum albumin); BuLi (n-Butyl lithium); $CDCl_3$ (chloroform-d); CuI (copper iodide); $CuSO_4$ (copper sulfate); DBU (1,8-DIAZABICYCLO[5.4.0] UNDEC-7-ENE); DCE (dichloroethane); DCM (dichloromethane); DEAD (diethyl azodicarboxylate); DIPEA (diisopropylethylamine); DMBA (1,3-dimethylbarbituric acid); DMF (N,N-dimethylformamide); DMP (Dess-Martin periodinane); DMSO (dimethyl sulfoxide); DPPA (diphenylphosphoryl azide); DTT (dithiothreitol); EDTA (ethylene-diamine-tetra-acetic acid); EGTA (ethylene-glycol-tetra-acetic acid); $Et_2O$ (diethylether); EtOAc (ethyl acetate); EtOH (ethanol); HOAc (acetic acid); HPLC (high-performance liquid chromatography); HRMS (high resolution mass spectrum); LAH (lithium aluminum hydride); LCMS (liquid chromatograph-mass spectrometer); LHMDS (lithium bis(trimethylsilyl)amide); LRMS (low resolution mass spectrum); mCPBA (3-chloroperoxybenzoic acid); MeOH (methanol); $MP-B(CN)H_3$ (Macroporous cyanoborohydride); $NaHCO_3$ (sodium bicarbonate); $Na_2SO_4$ (sodium sulfate); $Na(OAc)_3BH$ (sodium triacetoxyborohydride); $NH_4OAc$ (ammonium acetate); NBS (N-bromosuccinamide); NFSi (N-fluorobenzenesulfonimide); NMP (1-methyl-2-pyrrolidinone); NMR (nuclear magnetic resonance); PBS (phosphate buffered saline); PCR (polymerase chain reaction); Pd(dppf) ([1,1'-bis(diphenylphosphino)ferrocene] palladium); $Pd(Ph_3)_4$ (palladium(0) tetrakis-triphenylphosphine); $POCl_3$ (phosphorous oxychloride); PS-DIEA (polystyrene diisopropylethylamine); $PS-PPh_3$ (polystyrenetriphenyl phosphine); PTSA (para-toluene sulfonic acid); Pyr (pyridine); Selectfluor (1-chloromethyl-4-fluoro-1,4-diazoniabicyclo[2.2.2]octane bis(tetrafluoroborate); TBAF (tetrabutylammonium fluoride); T-BuOH (tert-butanol); THF (tetrahydrofuran); Tf (trifluoromethanesulfonyl); TFA (trifluoroacteic acid); and TMSCH$_2$N$_2$ (trimethylsilyldiazomethane).

The compounds of this invention may be prepared by employing reactions as shown in the following Reaction Schemes, in addition to other standard manipulations that are known in the literature or exemplified in the experimental procedures. The illustrative Reaction Schemes below, therefore, are not limited by the compounds listed or by any particular substituents employed for illustrative purposes. Substituent numbering as shown in the Reaction Schemes do not necessarily correlate to that used in the claims and often, for clarity, a single substituent is shown attached to the compound where multiple substituents are optionally allowed under the definitions of Formula A hereinabove.

Reactions used to generate the compounds of this invention are prepared by employing reactions as shown in Reaction Schemes I-VII.

SYNOPSIS OF REACTION SCHEMES

The key intermediate phenol (7a) can be synthesized via following two routes as illustrated in Scheme I and Scheme II. Reaction Scheme I starts from 4-methoxy-2-nitroaniline (1a), which undergoes reductive amination with corresponding aldehyde (2a) to provide a nitroaniline intermediate (3a). The nitroaniline (3a) can be reduced through either palladium catalyzed hydrogenation or Zinc/HOAc or SnCl$_2$/HCl reduction conditions to yield the dianiline (4a) which cyclizes to form 5-methoxybenzotriazole (5a) under diazotization conditions with NaNO$_2$ in HOAc. Subsequent bromination of compound (5a), employing pyridinium tribromide can be carried out in the same pot or separately using HOAc/H$_2$O as solvents to yield bromobenzotriazole (6a), which upon treatment with BBr$_3$ provides phenol (7a).

Alternatively, Reaction Scheme II starts from 2-fluoro-5-nitroaniline (8a) which undergoes aromatic nucleophilic substitution with amine (9a) to provide nitrodianiline intermediate which cyclizes to form 5-nitrobenzotriazole (10a) under diazotization conditions using NaNO$_2$ with HOAc. Nitrobenzotriazole (10a) can be reduced either through Pd/C catalyzed hydrogenation or via Zinc/HOAc reduction conditions to provide 5-aminobenzotriazole (11a), which upon treatment of NaNO$_2$ in 20% H$_2$SO$_4$ gives the corresponding diazonium salt (12a) that hydrolyzes to form the phenol (13a). Subsequent bromination of phenol (13) with pyridinium tribromide yields phenol (7a).

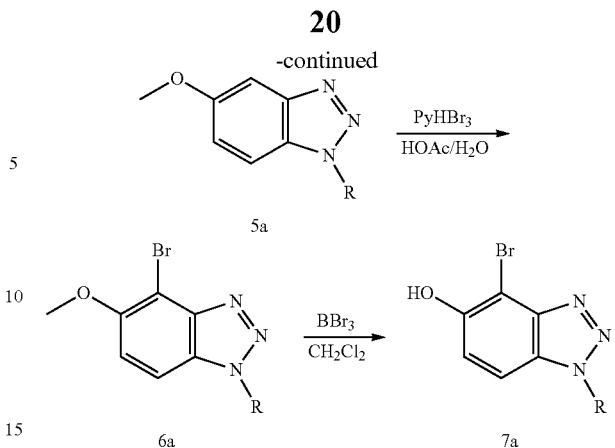

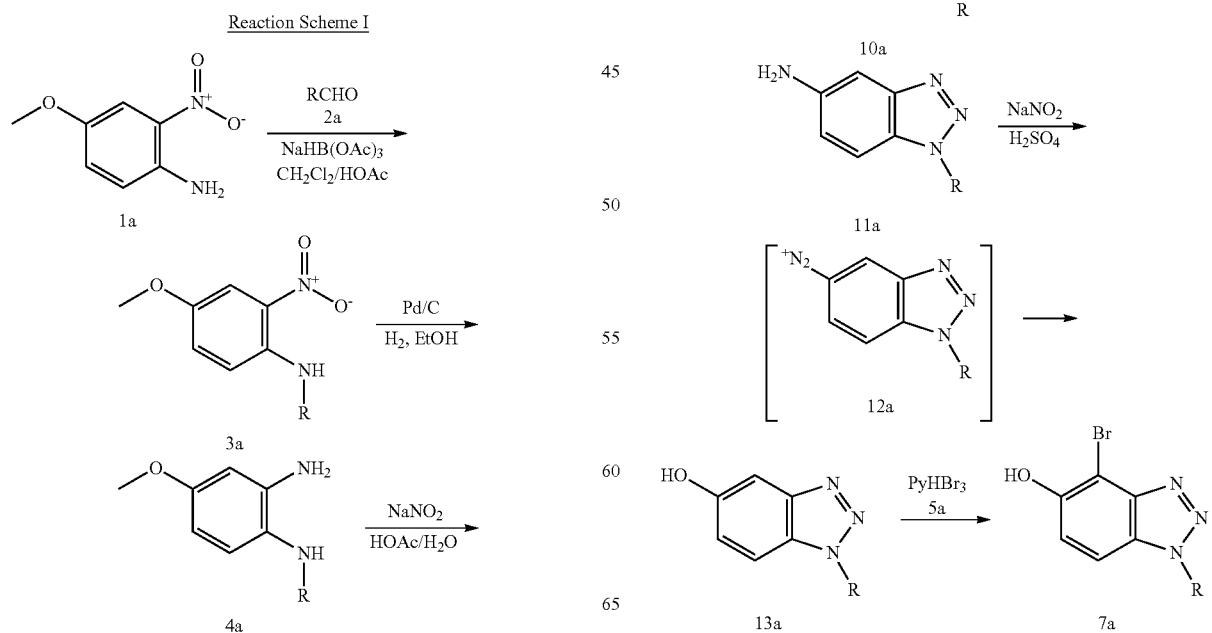

Arylation of the phenol (7a) can be carried out via (Scheme III) or aromatic nucleophilic substitution in polar solvents (Scheme IV), or other cross-coupling reactions, such as Chan coupling (Scheme V).

Reaction Scheme III

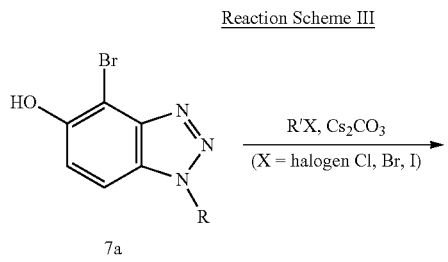

Reaction Scheme IV

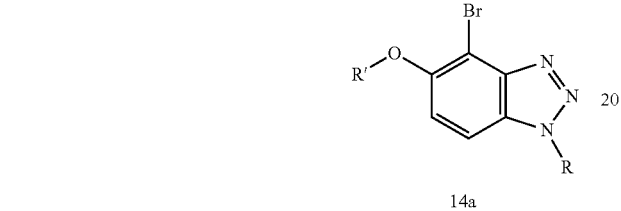

Reaction Scheme V

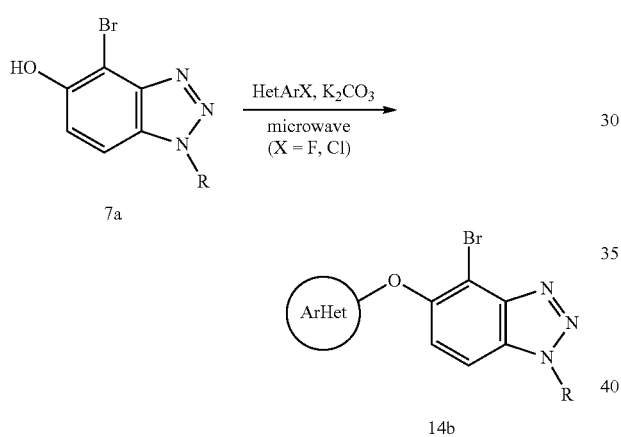

Reaction Scheme VI

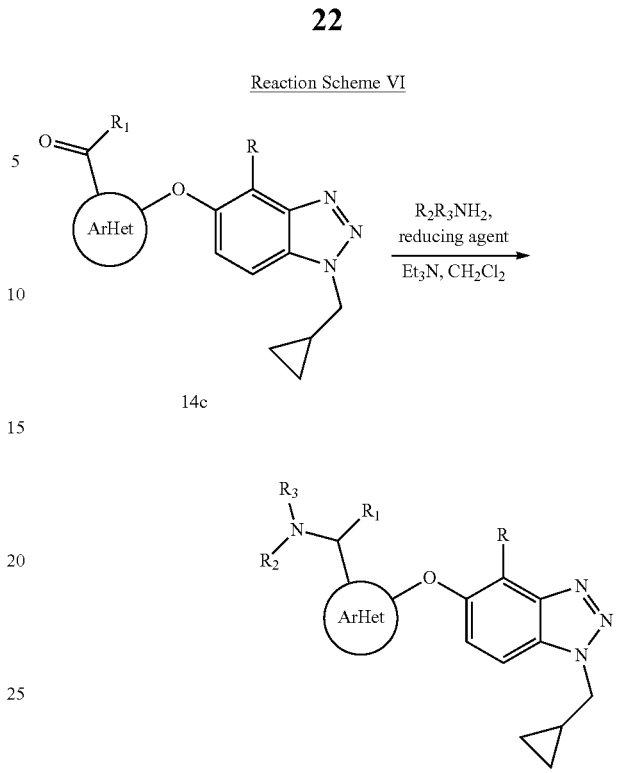

Reaction Scheme VII

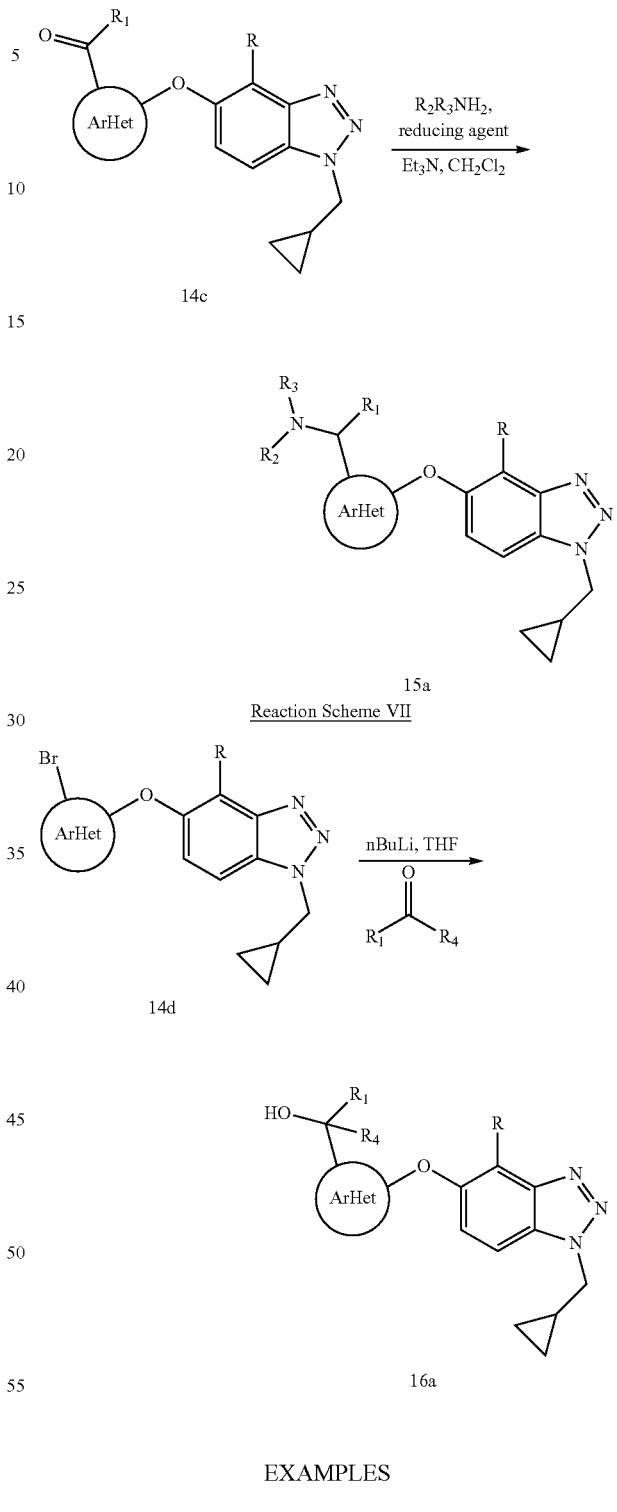

Functionalization of the aryl ethers like 14c or 14d can be carried out via reductive amination (Scheme VI) and gringnard or hydride additions (Scheme VII) to provide benzylamines 15a or benzylalcohols 16a. Alternatively, benzylalcohols like 16a can be synthesized via lithium halogen exchange (Scheme VIII).

EXAMPLES

Examples provided are intended to assist in a further understanding of the invention. Particular materials employed, species and conditions are intended to be further illustrative of the invention and not limitative of the reasonable scope thereof. The reagents utilized in synthesizing the compounds depicted in the following Tables are either commercially available or are readily prepared by one of ordinary skill in the art.

Intermediate Example A

4-Bromo-1-(2,2-dimethylpropyl)-5-methoxy-1H-1,2,3-benzotriazole (1-4) and 4-bromo-1-(2,2-dimethylpropyl)-1H-benzotriazol-5-ol (1-5)

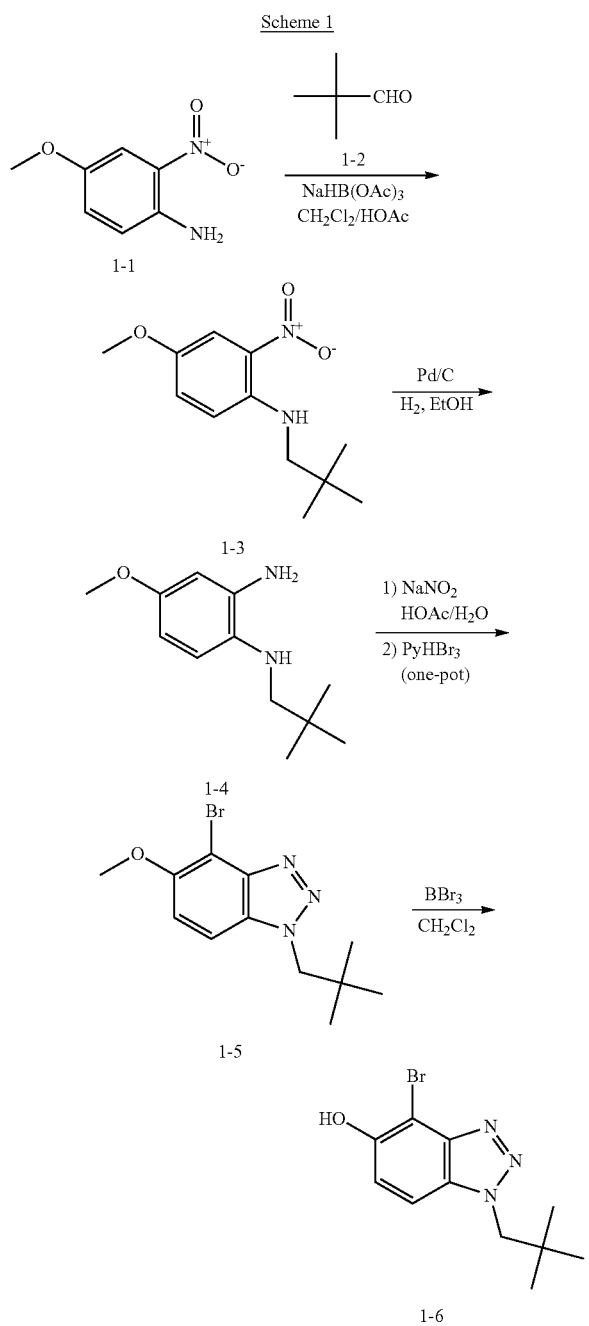

Scheme 1

Step 1: N-(2,2-dimethylpropyl)-4-methoxy-2-nitroaniline (1-3)

4-Methoxy-2-nitroaniline (10 g, 59.5 mmol, 1.0 equiv.) and trimethyl-acetaldehyde (9.73 g, 113 mmol, 1.9 equiv.) were dissolved in anhydrous dichloromethane (100 ml). The resulting solution was then treated with acetic acid (18.72 ml, 327 mmol, 5.5 equiv.), followed by sodium triacetoxyborohydride (30.3 g, 143 mmol, 2.4 equiv.). The mixture was stirred at room temperature. When LCMS showed completion of the reaction, the mixture was treated with saturated aqueous $NaHCO_3$, then extracted with EtOAc. The combined organic layers were dried over $Na_2SO_4$ and concentrated to give the crude N-(2,2-dimethylpropyl)-4-methoxy-2-nitroaniline (1-3), which was used without purification. LRMS m/z (M+H) 239.0 found, 238.1 required.

Step 2: $N^1$-(2,2-dimethylpropyl)-4-methoxybenzene-1,2-diamine (1-4)

N-(2,2-dimethylpropyl)-4-methoxy-2-nitroaniline (1-4) (15.3 g, 64.2 mmol, 1.0 equiv.) was taken up into ethanol (200 ml). After purging the reaction mixture with nitrogen, 10% palladium on carbon (13.67 g, 12.84 mmol, 0.2 equiv.) was added. The mixture was sparged under hydrogen and stirred at ambient temperature. When LCMS showed completion of the hydrogenation, the reaction mixture was filtered through Celite, which was washed thoroughly with MeOH. The filtrate was then concentrated in vacuo to give crude $N^1$-(2,2-dimethylpropyl)-4-methoxybenzene-1,2-diamine (1-4) as a dark red oil. LRMS m/z (M+H) 209.0 found, 209.2 required.

Step 3: 4-bromo-1-(2,2-dimethylpropyl)-5-methoxy-1H-1,2,3-benzotriazole (1-5)

$N^1$-(2,2-Dimethylpropyl)-4-methoxybenzene-1,2-diamine (1-4) (13 g, 62.4 mmol, 1.0 equiv.) was dissolved in AcOH (284 ml). After cooling to 0° C., the reaction mixture was treated with a solution of $NaNO_2$ (12.06 g, 175 mmol, 2.8 equiv.) in water (28.4 ml) dropwise. The reaction mixture was allowed to gradually warm up to room temperature. After stirring for 3 hrs, LCMS showed only the cyclized product. To the reaction mixture, was added pyridinium bromide perbromide (23.95 g, 74.9 mmol, 1.2 equiv.) in several small portions. The resulting mixture was stirred at room temperature until LCMS showed completion of bromination. The reaction mixture was concentrated to dryness. The residue was then partitioned between EtOAc and NaOH (pH~10). The organic layer was washed with brine, then dried over $Na_2SO_4$, filtered and concentrated to give crude 4-bromo-1-(2,2-dimethylpropyl)-5-methoxy-1H-1,2,3-benzotriazole (1-5). $^1$H NMR (500 MHz, $CDCl_3$) δ 7.41 (d, 1H, J=9.0 Hz), 7.23 (d, 1H, J=9.0 Hz), 4.38 (s, 2H), 4.00 (s, 3H), 1.04 (s, 9H) ppm. LRMS m/z (M+H) 298.0 and 300.0 (intensity ratio ~1:1) found, 298.0 and 300.0 required.

Step 4: 4-bromo-1-(2,2-dimethylpropyl)-1H-1,2,3-benzotriazol-5-ol (1-6)

To a solution of 4-bromo-1-(2,2-dimethylpropyl)-5-methoxy-1H-1,2,3-benzotriazole (1-5) (8.97 g, 30.1 mmol, 1.0 equiv.) in dichloromethane (150 ml) at 0° C., was added slowly a 1M solution of $BBr_3$ (60.2 ml, 60.2 mmol, 2.0 equiv.) in dichloromethane. The reaction mixture was allowed to warm up to room temperature and was stirred for an additional 14 hours. LCMS showed completion. The reaction mixture was treated with water, neutralized to pH=7, then extracted with EtOAc. The combined organic layers were dried over $Na_2SO_4$, filtered and concentrated to give provide 4-bromo-1-(2,2-dimethylpropyl)-1H-1,2,3-benzotriazol-5-ol (1-6). $^1$H NMR (500 MHz, $CDCl_3$) δ 7.36 (d, 1H, J=9.0 Hz), 7.24 (d, 1H, J=9.0 Hz), 4.37 (s, 2H), 1.04 (s, 9H) ppm. LRMS m/z (M+H) 283.9 and 285.9 (intensity ratio ~1:1) found, 284.0 and 286.0 required.

Intermediate Example B

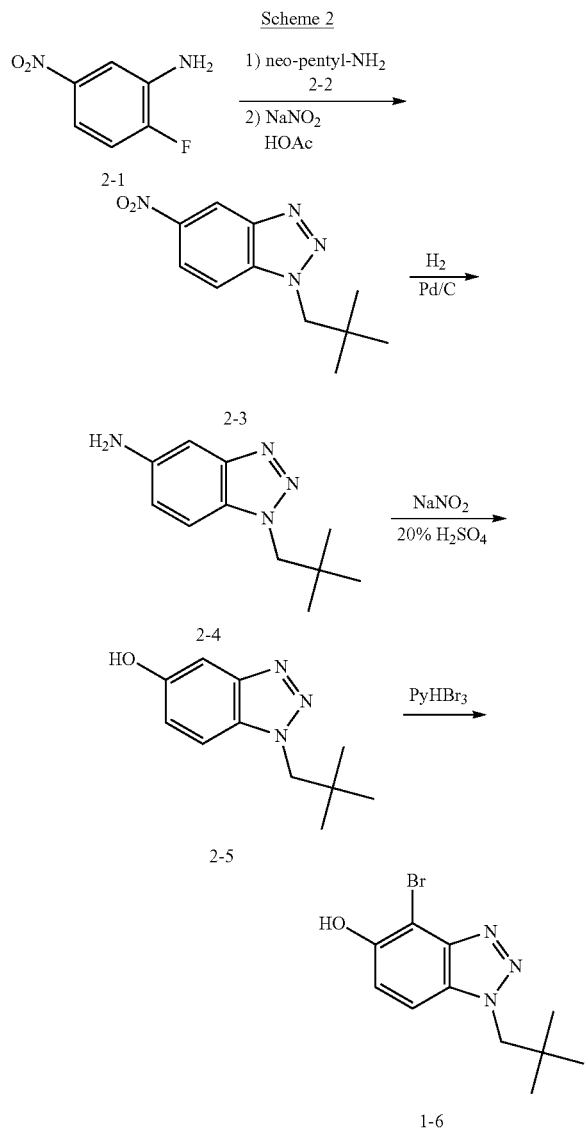

Step 1: 1-(2,2-dimethylpropyl)-5-nitro-1H-1,2,3-benzotriazole (2-3)

2-Fluoro-5-nitroaniline (2-1) (10.22 g, 65.5 mmol, 1.0 equiv.) was dissolved in anhydrous DMSO (100 ml), and treated with neopentylamine (2-2) (7.71 ml, 65.5 mmol, 1.0 equiv.). The reaction mixture was heated at 120° C. for 2 days when LCMS showed mostly product with trace of starting material. The reaction mixture was cooled to room temperature and treated with acetic acid (25 ml), followed by addition of 2.0 M aqueous solution of sodium nitrite (121 ml, 79 mmol, 1.2 equiv.). LCMS showed product after the reaction mixture was stirred at ambient temperature for 20 minutes. The mixture was then neutralized to pH=7 with NaOH (1N) and diluted with water which caused a precipitation. The solid was collected on top of filter and washed twice with water. The crude solid was purified with silica gel chromatography (EtOAc/hexanes gradient from 0 to 100%) to yield 1-(2,2-dimethylpropyl)-5-nitro-1H-1,2,3-benzotriazole (2-3). $^1$H NMR (CDCl$_3$) δ 9.02 (d, 1H, J=2.0 Hz), 8.40 (dd, 1H, J=9.1, 2.0 Hz), 7.62 (d, 1H, J=9.1 Hz), 4.47 (s, 2H), 1.07 (s, 9H) ppm. LRMS m/z (M+H) 235.1 found, 235.3 required.

Step 2: 1-(2,2-dimethylpropyl)-1H-1,2,3-benzotriazol-5-amine (2-4)

1-(2,2-Dimethylpropyl)-5-nitro-1H-1,2,3-benzotriazole (2-3) (4.46 g, 19.04 mmol, 1.0 equiv) was dissolved in ethanol (50 ml) and flushed with nitrogen, then charged with 10% Pd/C (2.026 g, 1.904 mmol, 0.1 equiv). The mixture was sparged under hydrogen (1 atm) and stirred at room temperature for 5 hrs. The mixture was filtered through a pad of Celite and the residue was washed with MeOH. The filtrate was concentrated to give the crude 1-(2,2-dimethylpropyl)-1H-1,2,3-benzotriazol-5-amine (2-4 LRMS m/z (M+H) 205.0 found, 205.3 required.

Step 3: 1-(2,2-dimethylpropyl)-1H-1,2,3-benzotriazol-5-ol (2-5)

To a solution of 1-(2,2-dimethylpropyl)-1H-1,2,3-benzotriazol-5-amine (2-4, 150 mg, 0.734 mmol, 1.0 eqv.) in 20% H$_2$SO$_4$ (5 mL), was slowly added sodium nitrite (70.8 mg, 1.026 mmol, 1.4 equiv.). The reaction mixture was stirred at room temperature until LCMS showed complete conversion to diazonium ion. The reaction solution was transferred to a microwave vial, and then irradiated at 120° C. for 50 minutes. LCMS showed complete hydrolysis of the diazonium salt. The reaction mixture was diluted with water, then extracted with EtOAc. The combined organic layers were dried over Na$_2$SO$_4$, filtered and concentrated to give the crude product, which was purified with normal phase silica gel chromatography (EtOAc/hexane gradient from 0 to 100%) to yield 1-(2,2-dimethylpropyl)-1H-1,2,3-benzotriazol-5-ol (2-5 LRMS m/z (M+H) 206.0 found, 206.1 required.

Step 4: 4-bromo-1-(2,2-dimethylpropyl)-1H-1,2,3-benzotriazol-5-ol (1-6)

To a solution of 1-(2,2-dimethylpropyl)-1H-1,2,3-benzotriazol-5-ol (2-5) (3 mg, 0.015 mmol, 1.0 equiv.) in chloroform (500 µL), was added slowly pyridinium tribromide (4.67 mg, 0.015 mmol, 1.0 equiv.). The reaction mixture was stirred at room temperature. LCMS showed mostly the desired product. The reaction mixture was quenched with water, neutralized to pH=7, then extracted with EtOAc. The organic layer was dried over Na$_2$SO$_4$, filtered and concentrated to give the crude 4-bromo-1-(2,2-dimethylpropyl)-1H-1,2,3-benzotriazol-5-ol (1-6). LRMS m/z (M+H) 283.9 and 285.9 (intensity ratio ~1:1) found, 284.0 and 286.0 required.

Example 1

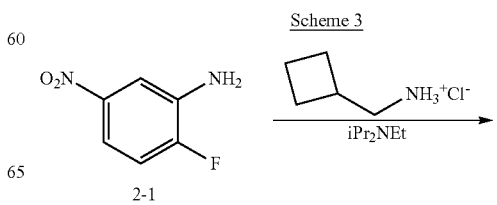

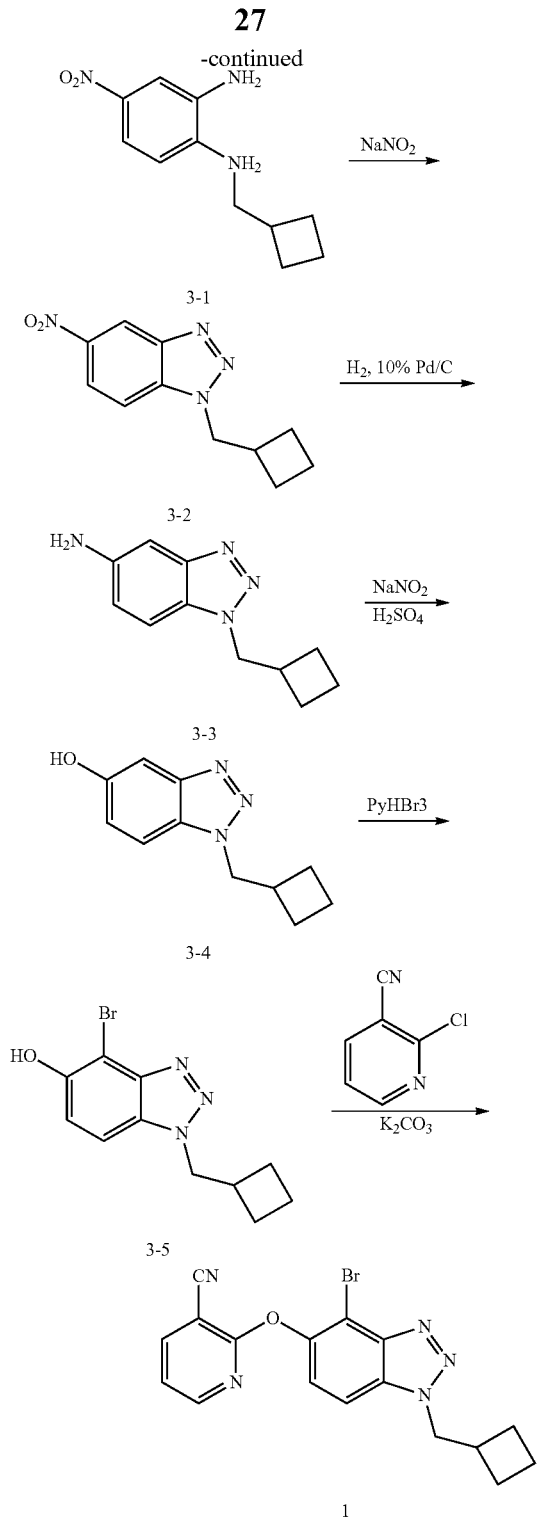

and the combined organic layers were dried over sodium sulfate and concentrated. The residue was purified silica gel chromatography (hexanes, grading to 100% ethyl acetate) to give N-1-(cyclobutylmethyl)-4-nitrobenzene-1,2-diamine (3-1) as a red solid. $^1$H NMR (300 MHz, CDCl$_3$) δ 7.84 (dd, 1H, J=8.9, 2.4 Hz), 7.63 (d, 1H, J=2.8 Hz), 6.55 (d, 1H, J=8.9 Hz), 4.20 (br s, 1H), 3.31 (br s, 2H), 3.24 (dd, 2H, J=7.0, 5.2 Hz), 2.66 (p, 1H, J=7.6 Hz), 2.20 (m, 2H), 1.96 (m, 2H), 1.78 (m, 2H) ppm. LRMS m/z (M+H) 222.0 found, 222.1 required.

Step 2: 1-(cyclobutylmethyl)-5-nitro-1H-benzotriazole (3-2)

A solution of sodium nitrite (405 mg, 5.88 mmol, 1.00 equiv) in water (10 mL) was added to a solution of N-1-(cyclobutylmethyl)-4-nitrobenzene-1,2-diamine (3-1, 1.3 g, 5.88 mmol, 1 equiv) in acetic acid (20 mL) at 23° C. and the resulting mixture was stirred for 2 hours. The mixture was concentrated and the residue was then partitioned between saturated aqueous sodium bicarbonate solution (150 mL) and ethyl acetate (2×150 mL). The combined organic layers were dried over sodium sulfate and concentrated. The residue was purified by silica gel chromatography (0 to 100% ethyl acetate in hexanes) to give 1-(cyclobutylmethyl)-5-nitro-1H-benzotriazole (3-2) as an orange oil. $^1$H NMR (300 MHz, CDCl$_3$) δ 9.01 (dd, 1H, J=1.8, 0.6 Hz), 8.40 (dd, 1H, J=9.2, 1.8 Hz), 7.64 (dd, 1H, J=9.2, 0.6 Hz), 4.70 (d, 2H, J=7.3 Hz), 3.00 (p, 1H, J=7.3 Hz), 2.10 (m, 2H), 1.93 (m, 4H) ppm. LRMS m/z (M+H) 233.0 found, 233.1 required.

Step 3: 1-(cyclobutylmethyl)-1H-benzotriazol-5-amine (3-3)

A mixture of 1-(cyclobutylmethyl)-5-nitro-1H-benzotriazole (3-2, 1.2 g, 5.17 mmol, 1 equiv) and 10% palladium on carbon (0.6 g) in ethanol (50 mL) was stirred at 23° C. under a hydrogen balloon for 20 h. The catalyst was filtered onto a pad of diatomaceous earth and washed with ethanol (100 mL). The filtrate was concentrated to give 1-(cyclobutylmethyl)-1H-benzotriazol-5-amine (3-3) as a grey solid. $^1$H NMR (300 MHz, CDCl$_3$) δ 7.32 (d, 1H, J=8.9 Hz), 7.20 (d, 1H, J=1.8 Hz), 6.92 (dd, 1H, J=8.5, 1.8 Hz), 4.56 (d, 2H, J=7.3 Hz), 3.80 (br s, 2H), 2.95 (p, 1H, J=7.3 Hz), 2.05 (m, 2H), 1.88 (m, 4H) ppm. LRMS m/z (M+H) 203.0 found, 203.1 required.

Step 4: 1-(cyclobutylmethyl)-1H-benzotriazol-5-ol (3-4)

Sodium nitrite (61 mg, 0.89 mmol, 1.2 equiv) was added to a solution of 1-(cyclobutylmethyl)-1H-benzotriazol-5-amine (3-3, 150 mg, 0.74 mmol, 1 equiv) in 20% aqueous sulfuric acid solution (5 mL) and the resulting mixture was irradiated at 120° C. in a microwave reactor for 40 min. The reaction mixture was cooled to ambient temperature and then partitioned between water (300 mL) and ethyl acetate (2×100 mL). The combined organic layers were dried over sodium sulfate and concentrated in vacuo. The residue was purified by silica gel chromatography (hexanes, grading to 100% ethyl acetate) to give 1-(cyclobutylmethyl)-1H-benzotriazol-5-ol (3-4) as a light yellow solid. $^1$H NMR (300 MHz, CDCl$_3$) δ 7.45 (d, 1H, J=2.1 Hz), 7.42 (d, 1H, J=8.9 Hz), 7.16 (dd, 1H, J=8.9, 2.1 Hz), 6.39 (br s, 1H), 4.61 (d, 2H, J=7.3 Hz), 2.99 (p, 1H, J=7.6 Hz), 2.08 (m, 2H), 1.91 (m, 4H) ppm. LRMS m/z (M+H) 204.0 found, 204.1 required.

Step 1: N-1-(cyclobutylmethyl)-4-nitrobenzene-1,2-diamine (3-1)

A solution of 2-fluoro-5-nitroaniline (2-1, 5.00 g, 32.0 mmol, 1 equiv), 1-cyclobutylmethanamine hydrochloride (4.67 g, 38.4 mmol, 1.20 equiv), and N,N-diisopropylethylamine (6.71 mL, 38.4 mmol, 1.20 equiv) in DMSO (20 mL) was heated at 80° C. for 24 h. The mixture was then partitioned between water (750 mL) and ethyl acetate (2×200 mL)

Step 5: 4-bromo-1-(cyclobutylmethyl)-1H-benzotriazol-5-ol (3-5)

A solution of 1-(cyclobutylmethyl)-1H-benzotriazol-5-ol (3-4, 280 mg, 1.38 mmol, 1 equiv) and pyridinium tribromide (551 mg, 1.72 mmol, 1.25 equiv) in chloroform (20 mL) was stirred at 23° C. for 4 h. The mixture was concentrated and the residue partitioned between saturated aqueous sodium bicarbonate solution (100 mL) and ethyl acetate (2×50 mL). The combined organic layers were dried over sodium sulfate and concentrated to give 4-bromo-1-(cyclobutylmethyl)-1H-benzotriazol-5-ol (3-5) as an orange solid. $^1$H NMR (300 MHz, CDCl$_3$) δ 7.38 (d, 1H, J=8.9 Hz), 7.25 (d, 1H, J=8.9 Hz), 5.92 (br s, 1H), 4.60 (d, 2H, J=7.0 Hz), 2.96 (p, 1H, J=7.6 Hz), 2.06 (m, 2H), 1.89 (m, 4H) ppm. LRMS m/z (M+H) 283.9 found, 284.0 required.

Step 6: 2-{[4-bromo-1-(cyclobutylmethyl)-1H-benzotriazol-5-yl]oxy}pyridine-3-carbonitrile (1)

A mixture of 4-bromo-1-(cyclobutylmethyl)-1H-benzotriazol-5-ol (3-5, 25 mg, 0.12 mmol, 1 equiv), 2-chloropyridine-3-carbonitrile (76 mg, 0.62 mmol, 5.0 equiv) and potassium carbonate (34 mg, 0.25 mmol, 5.0 equiv) in acetonitrile (3 mL) was irradiated at 170° C. in microwave reactor for 10 min. The mixture was purified by silica gel chromatography (0 to 100% ethyl acetate in hexanes) to give 2-{[4-bromo-1-(cyclobutylmethyl)-1H-benzotriazol-5-yl]oxy}pyridine-3-carbonitrile (1) as a white solid. $^1$H NMR (300 MHz, CDCl$_3$) δ 8.26 (dd, 1H, J=4.9, 1.8 Hz), 8.08 (dd, 1H, J=7.3, 1.8 Hz), 7.54 (d, 1H, J=8.8 Hz), 7.39 (d, 1H, J=8.8 Hz), 7.15 (dd, 1H, J=7.3, 4.9 Hz), 4.66 (d, 2H, J=7.3 Hz), 3.00 (p, 1H, J=7.3 Hz), 2.11 (m, 2H), 1.92 (m, 4H) ppm. LRMS m/z (M+H) 386.0 found, 386.0 required.

Intermediate Example C

Scheme 4

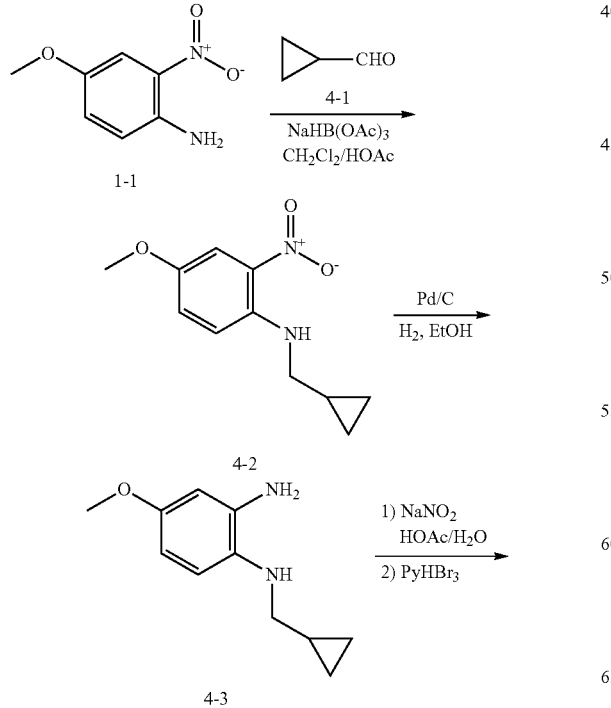

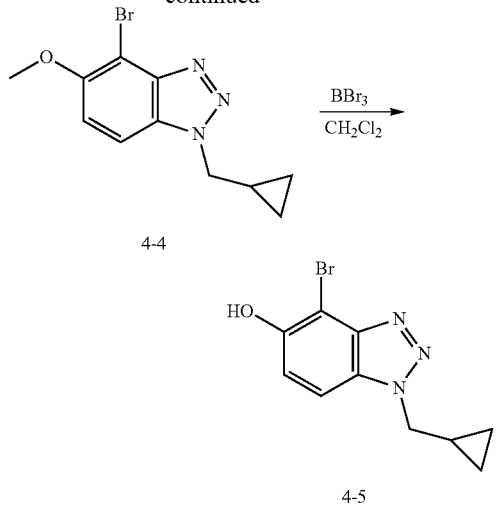

Examples 2 and 3

1-(2-{[4-bromo-1-(2,2-dimethylpropyl)-1H-1,2,3-benzotriazol-5-yl]oxy}pyridin-3-yl)ethanone (2) and 1-(2-{[4-bromo-1-(2,2-dimethylpropyl)-1H-1,2,3-benzotriazol-5-yl]oxy}pyridin-3-yl)ethanol (3)

Scheme 5

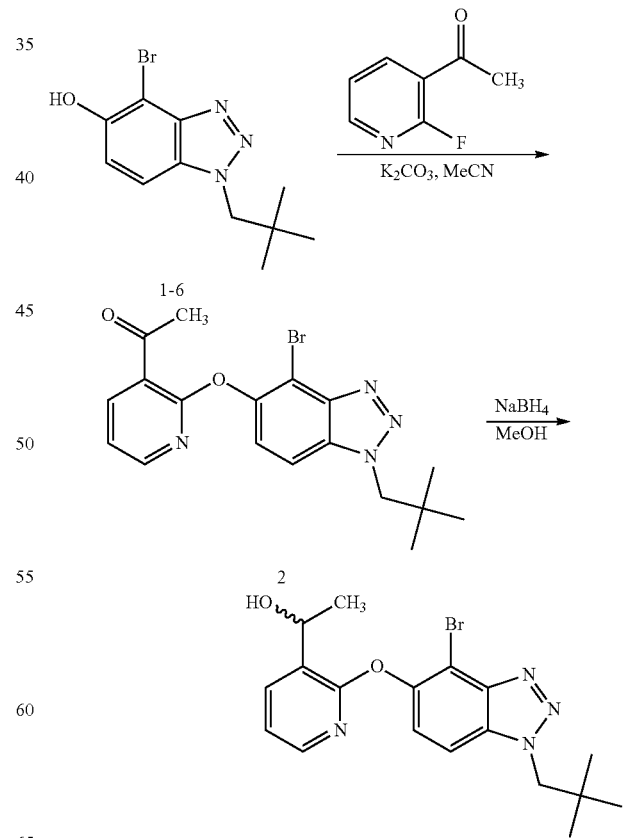

Step 1: 1-(2-{[4-bromo-1-(2,2-dimethylpropyl)-1H-1,2,3-benzotriazol-5-yl]oxy}pyridin-3-yl)ethanone (2)

4-Bromo-1-(2,2-dimethylpropyl)-1H-1,2,3-benzotriazol-5-ol (1-6) (1 g, 3.52 mmol, 1.0 equiv.), 3-acetyl-2-fluoropyridine (0.979 g, 7.04 mmol, 2.0 equiv.) and potassium carbonate (0.973 g, 7.04 mmol, 2.0 equiv.) were dissolved in acetonitrile (10 ml). The mixture was irradiated at 200° C. in microwave reactor until LCMS showed mostly desired product. The solvent was evaporated in vacuo, the mixture was neutralized with saturated aqueous $NH_4Cl$, and then extracted with EtOAc. The organic layers were dried over $Na_2SO_4$, filtered and concentrated in vacuo. The residue was purified by silica gel chromatography (EtOAc/Hexane gradient from 0 to 100%) to obtain 2. $^1H$ NMR ($CDCl_3$) δ 8.30-8.24 (1H, m), 8.24 (1H, s), 7.83 (1H, d, J=2.06 Hz), 7.56 (1H, d, J=8.91 Hz), 7.29 (1H, dd, J=2.1, 8.9 Hz), 7.16-7.10 (1H, m), 4.42 (2H, s), 2.80 (3H, s), 1.09 (9H, s) ppm. LRMS m/z (M+H) 403.0 and 405.0 (intensity ratio ~1:1) found, 403.1 and 405.1 required.

Step 2: 1-(2-{[4-bromo-1-(2,2-dimethylpropyl)-1H-1,2,3-benzotriazol-5-yl]oxy}pyridin-3-yl)ethanol (3)

To a suspension of 1-(2-{[4-bromo-1-(2,2-dimethylpropyl)-1H-1,2,3-benzotriazol-5-yl]oxy}pyridin-3-yl)ethanone (2) (790 mg, 1.959 mmol, 1.0 equiv.) in MeOH (19.6 mL) was slowly added $NaBH_4$ (148 mg, 3.92 mmol, 2.0 equiv.). The mixture was stirred at room temperature until LCMS showed only the desired product. The solvent was evaporated in vacuo and the mixture was partitioned between EtOAc and saturated aqueous $NaHCO_3$. The combined organic extracts were dried with $Na_2SO_4$, filtered and concentrated in vacuo. The residue was purified silica gel chromatography (EtOAc/Hexane gradient from 0 to 100%) to obtain product 3 $^1H$ NMR ($CDCl_3$) δ 7.96 (1H, d, J=4.9 Hz), 7.89 (1H, d, J=7.4 Hz), 7.48 (1H, d, J=8.8 Hz), 7.38-7.33 (1H, m), 7.05 (1H, dd, J=7.3, 5.0 Hz), 5.40-5.33 (1H, m), 4.41 (2H, s), 1.70 (3H, d, J=6.48 Hz), 1.08 (9H, s) ppm. LRMS m/z (M+H) 405.0 and 407.0 (intensity ratio ~1:1) found, 405.1 and 407.1 required. The racemic mixture was further separated via chiral HPLC (ChiralPak IC, EtOH/Heptane with 0.1% DEA=1:9, v/v) to obtain enantiomers 3a and 3b.

The following compounds were prepared according to the general procedure described in the schemes above. The starting materials are either commercially available, known in the literature or may be prepared from commercially available reagents using conventional reactions well known in the art.

TABLE 1

| Ex. | Structure | Name | LRMS or HRMS |
|---|---|---|---|
| 4 | 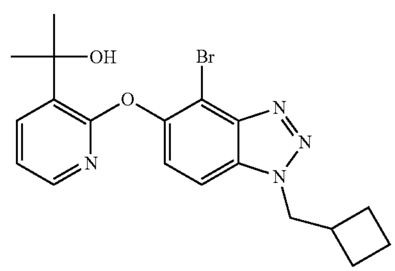 [SMILES: CC(C)(O)c1cccnc1Oc1ccc2c(nnn2CC2CCC2)c1Br] | 2-(2-{[4-bromo-1-(cyclobutylmethyl)-1H-benzotriazol-5-yl]oxy}pyridin-3-yl)propan-2-ol | [M + H] calc. 417.0 obs. 417.1 |
| 5 | 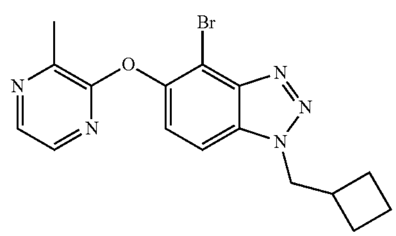 [SMILES: Cc1nccnc1Oc1ccc2c(nnn2CC2CCC2)c1Br] | 4-bromo-1-(cyclobutylmethyl)-5-[(3-methylpyrazin-2-yl)oxy]-1H-benzotriazole | [M + H] calc. 374.1 obs. 374.0 |
| 6 | 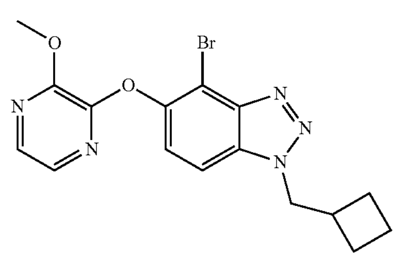 [SMILES: COc1nccnc1Oc1ccc2c(nnn2CC2CCC2)c1Br] | 4-bromo-1-(cyclobutylmethyl)-5-[(3-methoxypyrazin-2-yl)oxy]-1H-benzotriazole | [M + H] calc. 390.0 obs. 390.0 |

TABLE 1-continued

| Ex. | Structure | Name | LRMS or HRMS |
|---|---|---|---|
| 7 | 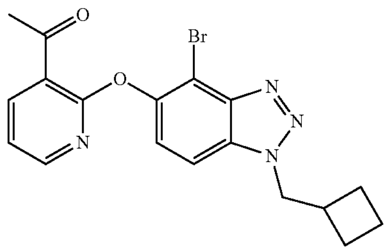 [SMILES: CC(=O)c1cccnc1Oc1ccc2c(nnn2CC2CCC2)c1Br] | 4-bromo-1-(cyclobutylmethyl)-5-[(3-methylpyrazin-2-yl)oxy]-1H-benzotriazole | [M + H] calc. 401.1 obs. 401.0 |
| 8 | 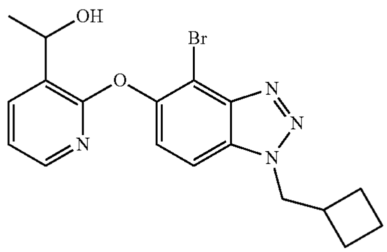 [SMILES: CC(O)c1cccnc1Oc1ccc2c(nnn2CC2CCC2)c1Br] | 1-(2-{[4-bromo-1-(cyclobutylmethyl)-1H-benzotriazol-5-yl]oxy}pyridin-3-yl)ethanol | [M + H] calc. 403.1 obs. 403.0 |
| 9 | 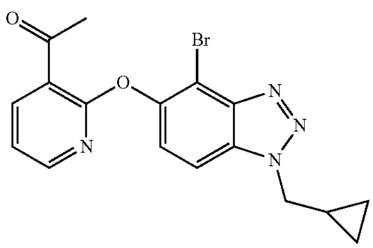 | 1-(2-{[4-bromo-1-(cyclopropylmethyl)-1H-benzotriazol-5-yl]oxy}pyridin-3-yl)ethanone | [M + H] calc. 378.0 obs. 378.0 |
| 10 | 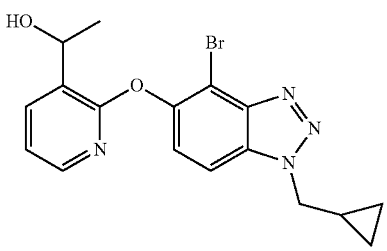 [SMILES: CC(O)c1cccnc1Oc1ccc2c(nnn2CC2CC2)c1Br] | 1-(2-{[4-bromo-1-(cyclopropylmethyl)-1H-benzotriazol-5-yl]oxy}pyridin-3-yl)ethanol | [M + H] calc. 389.1 obs. 389.0 |
| 11 | 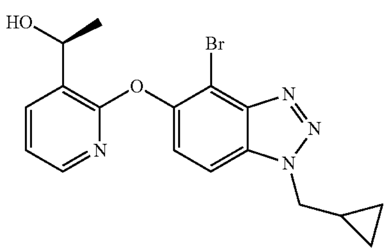 [SMILES: C[C@H](O)c1cccnc1Oc1ccc2c(nnn2CC2CC2)c1Br] | (1S)-(2-{[4-bromo-1-(cyclopropylmethyl)-1H-benzotriazol-5-yl]oxy}pyridin-3-yl)ethanol | [M + H] calc. 389.1 obs. 389.0 |
| 12 | 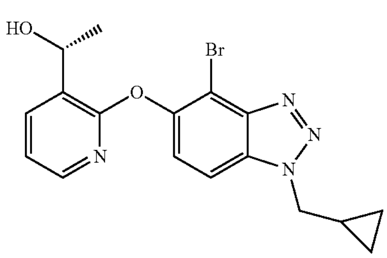 [SMILES: C[C@@H](O)c1cccnc1Oc1ccc2c(nnn2CC2CC2)c1Br] | (1R)-(2-{[4-bromo-1-(cyclopropylmethyl)-1H-benzotriazol-5-yl]oxy}pyridin-3-yl)ethanol | [M + H] calc. 389.1 obs. 389.0 |

TABLE 1-continued

| Ex. | Structure | Name | LRMS or HRMS |
|---|---|---|---|
| 13 | 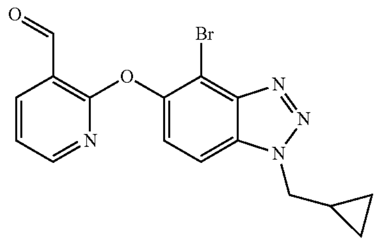 [SMILES: O=Cc1cccnc1Oc1ccc2c(nnn2CC2CC2)c1Br] | 2-{[4-bromo-1-(cyclopropylmethyl)-1H-benzotriazol-5-yl]oxy}pyridine-3-carbaldehyde | [M + H] calc. 373.0 obs. 372.9 |
| 14 | 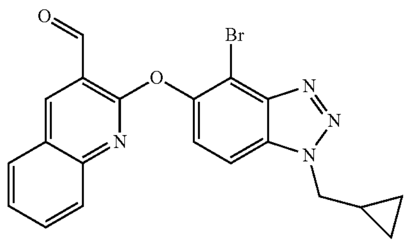 [SMILES: O=Cc1cc2ccccc2nc1Oc1ccc2c(nnn2CC2CC2)c1Br] | 2-{[4-bromo-1-(cyclopropylmethyl)-1H-benzotriazol-5-yl]oxy}quinoline-3-carbaldehyde | [M + H] calc. 423.0 obs. 423.0 |
| 15 | 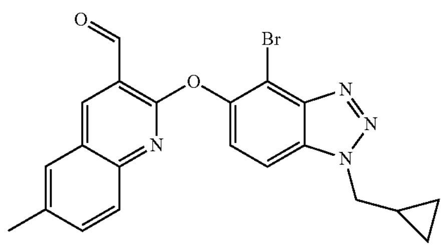 [SMILES: Cc1ccc2nc(Oc3ccc4c(nnn4CC4CC4)c3Br)c(C=O)cc2c1] | 2-{[4-bromo-1-(cyclopropylmethyl)-1H-benzotriazol-5-yl]oxy}-6-methylquinoline-3-carbaldehyde | [M + H] calc. 437.1 obs. 437.0 |
| 16 | 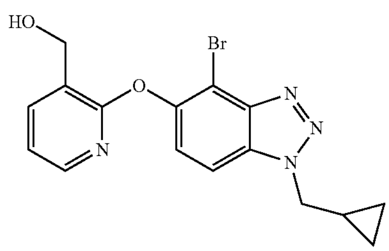 [SMILES: OCc1cccnc1Oc1ccc2c(nnn2CC2CC2)c1Br] | (2-{[4-bromo-1-(cyclopropylmethyl)-1H-benzotriazol-5-yl]oxy}pyridin-3-yl)methanol | [M + H] calc. 375.0 obs. 374.9 |
| 17 | 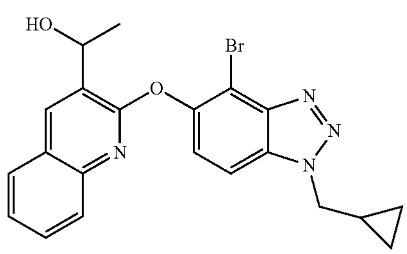 [SMILES: CC(O)c1cc2ccccc2nc1Oc1ccc2c(nnn2CC2CC2)c1Br] | 1-(2-{[4-bromo-1-(cyclopropylmethyl)-1H-benzotriazol-5-yl]oxy}quinolin-3-yl)ethanol | [M + H] calc. 439.1 obs. 439.0 |
| 18 | 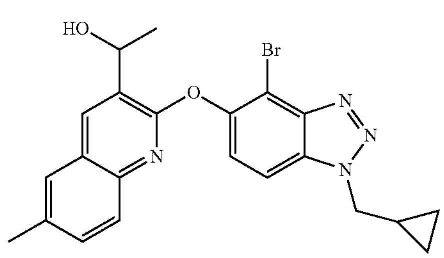 [SMILES: Cc1ccc2nc(Oc3ccc4c(nnn4CC4CC4)c3Br)c(C(C)O)cc2c1] | 1-(2-{[4-bromo-1-(cyclopropylmethyl)-1H-benzotriazol-5-yl]oxy}-6-methylquinolin-3-yl)ethanol | [M + H] calc. 453.1 obs. 453.0 |

TABLE 1-continued

| Ex. | Structure | Name | LRMS or HRMS |
|---|---|---|---|
| 19 | 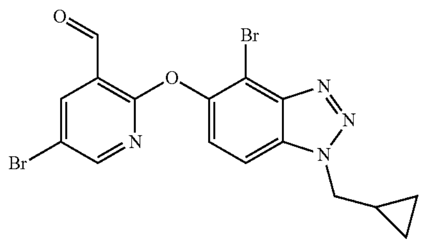 | 5-bromo-2-{[4-bromo-1-(cyclopropylmethyl)-1H-benzotriazol-5-yl]oxy}pyridine-3-carbaldehyde | [M + H] calc. 453.0 obs. 452.9 |
| 20 | 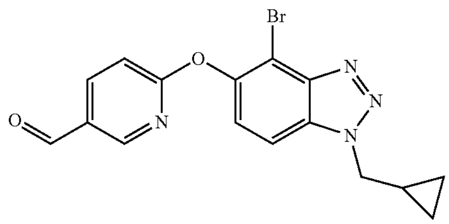 [SMILES: O=Cc1ccc(Oc2ccc3c(nnn3CC3CC3)c2Br)nc1] | 6-{[4-bromo-1-(cyclopropylmethyl)-1H-benzotriazol-5-yl]oxy}pyridine-3-carbaldehyde | [M + H] calc. 373.0 obs. 373.0 |
| 21 | 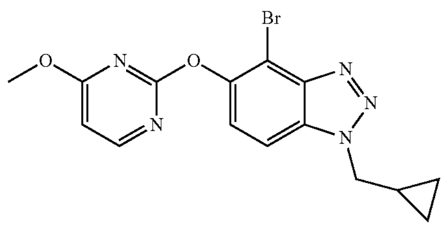 [SMILES: COc1ccnc(Oc2ccc3c(nnn3CC3CC3)c2Br)n1] | 4-bromo-1-(cyclopropylmethyl)-5-[(4-methoxypyrimidin-2-yl)oxy]-1H-benzotriazole | [M + H] calc. 376.0 obs. 376.0 |
| 22 | 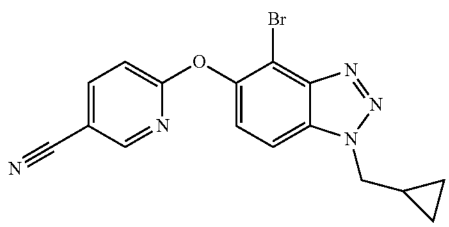 [SMILES: N#Cc1ccc(Oc2ccc3c(nnn3CC3CC3)c2Br)nc1] | 6-{[4-bromo-1-(cyclopropylmethyl)-1H-benzotriazol-5-yl]oxy}pyridine-3-carbonitrile | [M + H] calc. 370.0 obs. 369.9 |
| 23 | 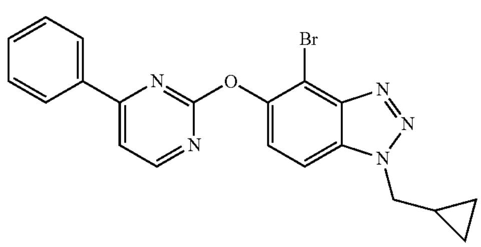 [SMILES: Brc1c(Oc2nccc(-c3ccccc3)n2)ccc2c1nnn2CC1CC1] | 4-bromo-1-(cyclopropylmethyl)-5-[(4-phenylpyrimidin-2-yl)oxy]-1H-benzotriazole | [M + H] calc. 422.1 obs. 422.0 |
| 24 | 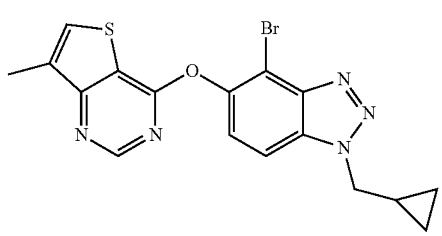 [SMILES: Cc1csc2c(Oc3ccc4c(nnn4CC4CC4)c3Br)ncnc12] | 4-{[4-bromo-1-(cyclopropylmethyl)-1H-benzotriazol-5-yl]oxy}-7-methylthieno[3,2-d]pyrimidine | [M + H] calc. 416.0 obs. 416.0 |

TABLE 1-continued

| Ex. | Structure | Name | LRMS or HRMS |
|---|---|---|---|
| 25 | 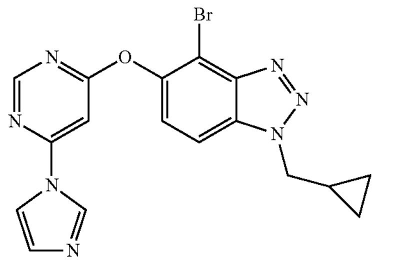 [SMILES: Brc1c(Oc2cc(-n3ccnc3)ncn2)ccc2c1nnn2CC1CC1] | 4-bromo-1-(cyclopropylmethyl)-5-{[6-(1H-imidazol-1-yl)pyrimidin-4-yl]oxy}-1H-benzotriazole | [M + H] calc. 412.0 obs. 412.0 |
| 26 | 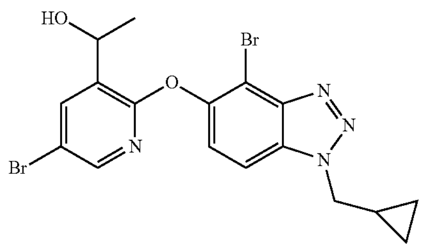 | 1-(5-bromo-2-{[4-bromo-1-(cyclopropylmethyl)-1H-benzotriazol-5-yl]oxy}pyridin-3-yl)ethanol | [M + H] calc. 469.0 obs. 468.9 |
| 27 | 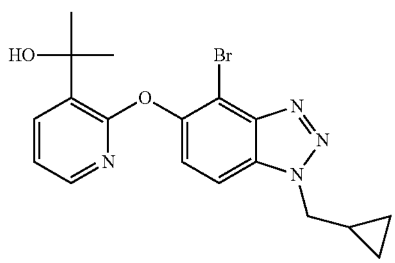 [SMILES: CC(C)(O)c1cccnc1Oc1ccc2c(nnn2CC2CC2)c1Br] | 2-(2-{[4-bromo-1-(cyclopropylmethyl)-1H-benzotriazol-5-yl]oxy}pyridin-3-yl)propan-2-ol | [M + H] calc. 403.1 obs. 403.0 |
| 28 | 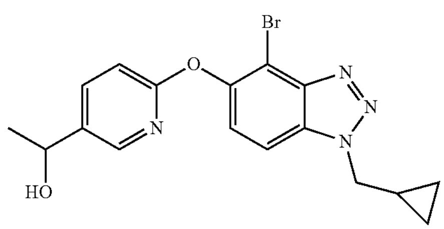 [SMILES: CC(O)c1ccc(Oc2ccc3c(nnn3CC3CC3)c2Br)nc1] | 1-(6-{[4-bromo-1-(cyclopropylmethyl)-1H-benzotriazol-5-yl]oxy}pyridin-3-yl)ethanol | [M + H] calc. 389.1 obs. 389.0 |
| 29 | 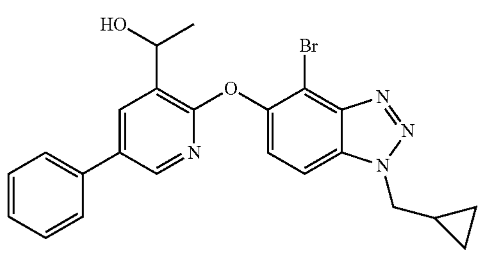 [SMILES: CC(O)c1cc(-c2ccccc2)cnc1Oc1ccc2c(nnn2CC2CC2)c1Br] | 1-(2-{[4-bromo-1-(cyclopropylmethyl)-1H-benzotriazol-5-yl]oxy}-5-phenylpyridin-3-yl)ethanol | [M + H] calc. 465.1 obs. 465.0 |
| 30 | 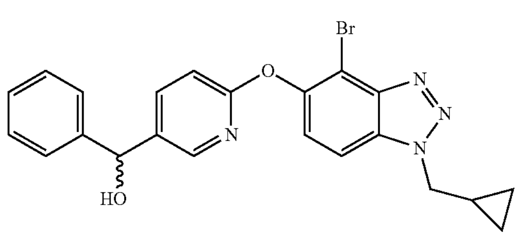 [SMILES: OC(c1ccccc1)c1ccc(Oc2ccc3c(nnn3CC3CC3)c2Br)nc1] | (6-{[4-bromo-1-(cyclopropylmethyl)-1H-benzotriazol-5-yl]oxy}pyridin-3-yl)(phenyl)methanol | [M + H] calc. 451.1 obs. 451.1 |

TABLE 1-continued

| Ex. | Structure | Name | LRMS or HRMS |
|---|---|---|---|
| 31 | 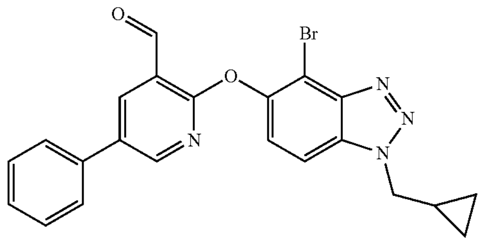 [SMILES: O=Cc1cc(-c2ccccc2)cnc1Oc1ccc2c(nnn2CC2CC2)c1Br] | 2-{[4-bromo-1-(cyclopropylmethyl)-1H-benzotriazol-5-yl]oxy}-5-phenylpyridine-3-carbaldehyde | [M + H] calc. 449.1 obs. 449.0 |
| 32 | 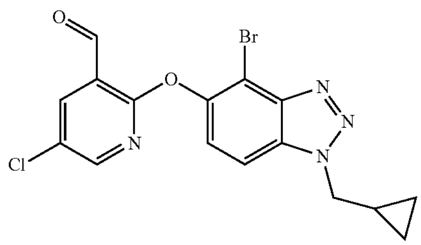 [SMILES: O=Cc1cc(Cl)cnc1Oc1ccc2c(nnn2CC2CC2)c1Br] | 2-{[4-bromo-1-(cyclopropylmethyl)-1H-benzotriazol-5-yl]oxy}-5-chloropyridine-3-carbaldehyde | [M + H] calc. 407.0 obs. 407.0 |
| 33 | 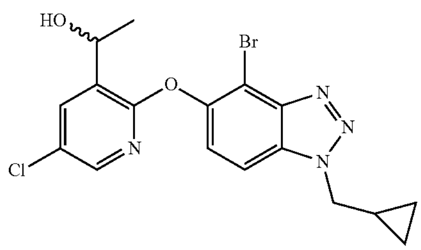 [SMILES: CC(O)c1cc(Cl)cnc1Oc1ccc2c(nnn2CC2CC2)c1Br] | 1-(2-{[4-bromo-1-(cyclopropylmethyl)-1H-benzotriazol-5-yl]oxy}-5-chloropyridin-3-yl)ethanol | [M + H] calc. 423.0 obs. 423.0 |
| 34 | 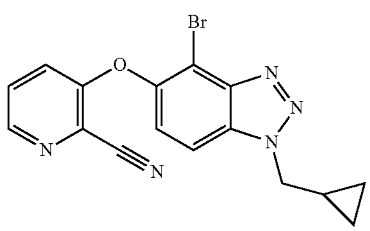 [SMILES: N#Cc1ncccc1Oc1ccc2c(nnn2CC2CC2)c1Br] | 3-{[4-bromo-1-(cyclopropylmethyl)-1H-benzotriazol-5-yl]oxy}pyridine-2-carbonitrile | [M + H] calc. 372.0 obs. 372.0 |
| 35 | 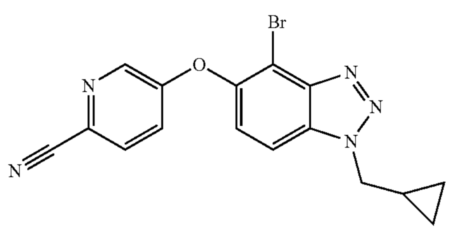 [SMILES: N#Cc1ccc(Oc2ccc3c(nnn3CC3CC3)c2Br)cn1] | 5-{[4-bromo-1-(cyclopropylmethyl)-1H-benzotriazol-5-yl]oxy}pyridine-2-carbonitrile | [M + H] calc. 372.0 obs. 372.0 |
| 36 | 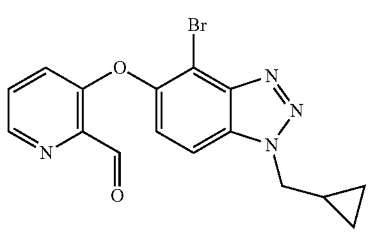 [SMILES: O=Cc1ncccc1Oc1ccc2c(nnn2CC2CC2)c1Br] | 3-{[4-bromo-1-(cyclopropylmethyl)-1H-benzotriazol-5-yl]oxy}pyridine-2-carbaldehyde | [M + H] calc. 373.0 obs. 373.0 |

TABLE 1-continued

| Ex. | Structure | Name | LRMS or HRMS |
|---|---|---|---|
| 37 | 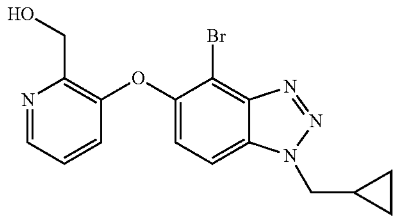 [SMILES: OCc1ncccc1Oc1ccc2c(nnn2CC2CC2)c1Br] | (3-{[4-bromo-1-(cyclopropylmethyl)-1H-benzotriazol-5-yl]oxy}pyridin-2-yl)methanol | [M + H] calc. 377.0 obs. 377.0 |
| 38 | 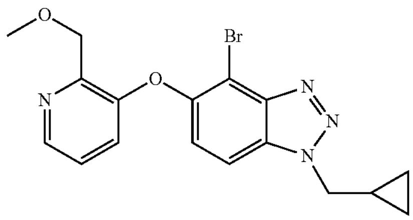 [SMILES: COCc1ncccc1Oc1ccc2c(nnn2CC2CC2)c1Br] | 4-bromo-1-(cyclopropylmethyl)-5-{[2-(methoxymethyl)pyridin-3-yl]oxy}-1H-benzotriazole | [M + H] calc. 389.0 obs. 389.0 |
| 39 | 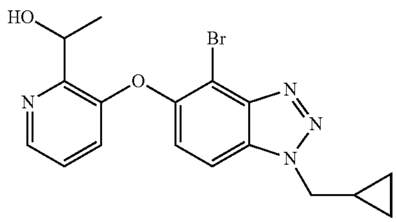 [SMILES: CC(O)c1ncccc1Oc1ccc2c(nnn2CC2CC2)c1Br] | 1-(3-{[4-bromo-1-(cyclopropylmethyl)-1H-benzotriazol-5-yl]oxy}pyridin-2-yl)ethanol | [M + H] calc. 389.0 obs. 389.0 |
| 40 | 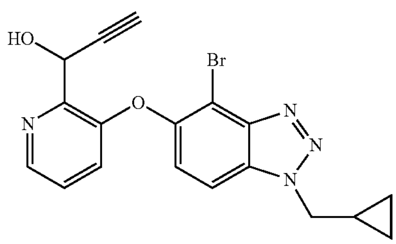 [SMILES: C#CC(O)c1ncccc1Oc1ccc2c(nnn2CC2CC2)c1Br] | 1-(3-{[4-bromo-1-(cyclopropylmethyl)-1H-benzotriazol-5-yl]oxy}pyridin-2-yl)prop-2-yn-1-ol | [M + H] calc. 399.1 obs. 399.1 |
| 41 | 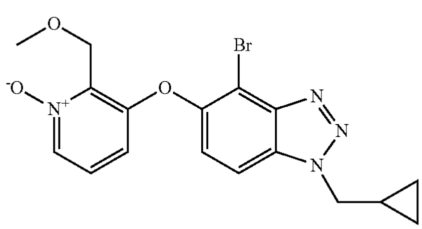 | 4-bromo-1-(cyclopropylmethyl)-5-{[2-(methoxymethyl)-1-oxidopyridin-3-yl]oxy}-1H-benzotriazole | [M + H] calc. 405.1 obs. 405.1 |
| 42 | 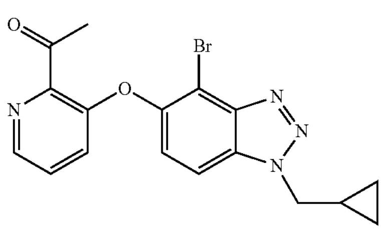 [SMILES: CC(=O)c1ncccc1Oc1ccc2c(nnn2CC2CC2)c1Br] | 1-(3-{[4-bromo-1-(cyclopropylmethyl)-1H-benzotriazol-5-yl]oxy}pyridin-2-yl)ethanone | [M + H] calc. 387.1 obs. 387.1 |
| 43 | 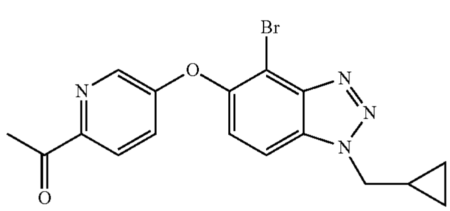 [SMILES: CC(=O)c1ccc(Oc2ccc3c(nnn3CC3CC3)c2Br)cn1] | 1-(5-{[4-bromo-1-(cyclopropylmethyl)-1H-benzotriazol-5-yl]oxy}pyridin-2-yl)ethanone | [M + H] calc. 387.1 obs. 387.1 |

TABLE 1-continued

| Ex. | Structure | Name | LRMS or HRMS |
|---|---|---|---|
| 44 | 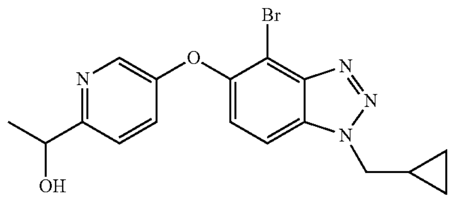 [SMILES: CC(O)c1ccc(Oc2ccc3c(nnn3CC3CC3)c2Br)cn1] | 1-(5-{[4-bromo-1-(cyclopropylmethyl)-1H-benzotriazol-5-yl]oxy}pyridin-2-yl)ethanol | [M + H] calc. 389.1 obs. 389.1 |
| 45 | 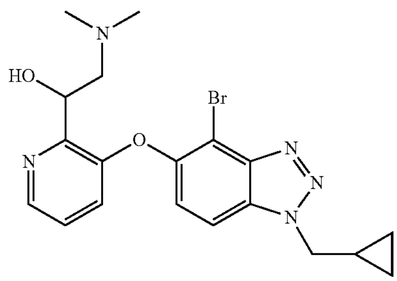 [SMILES: CN(C)CC(O)c1ncccc1Oc1ccc2c(nnn2CC2CC2)c1Br] | 1-(3-{[4-bromo-1-(cyclopropylmethyl)-1H-benzotriazol-5-yl]oxy}pyridin-2-yl)-2-(dimethylamino)ethanol | [M + H] calc. 432.1 obs. 432.1 |
| 46 | 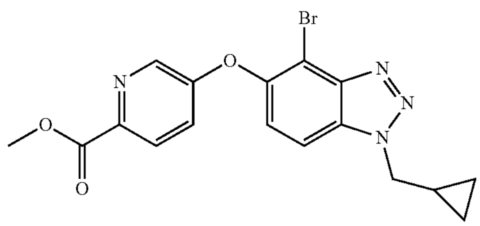 [SMILES: COC(=O)c1ccc(Oc2ccc3c(nnn3CC3CC3)c2Br)cn1] | methyl 5-{[4-bromo-1-(cyclopropylmethyl)-1H-benzotriazol-5-yl]oxy}pyridine-2-carboxylate | [M + H] calc. 405.1 obs. 405.1 |
| 47 | 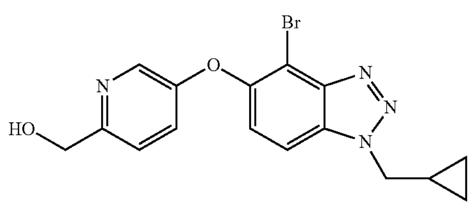 [SMILES: OCc1ccc(Oc2ccc3c(nnn3CC3CC3)c2Br)cn1] | (5-{[4-bromo-1-(cyclopropylmethyl)-1H-benzotriazol-5-yl]oxy}pyridin-2-yl)methanol | [M + H] calc. 375.1 obs. 375.1 |
| 48 | 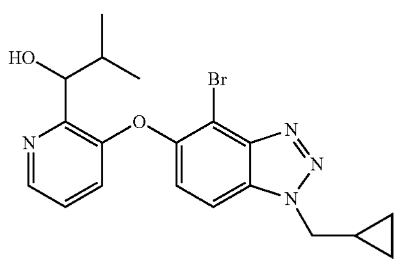 [SMILES: CC(C)C(O)c1ncccc1Oc1ccc2c(nnn2CC2CC2)c1Br] | 1-(3-{[4-bromo-1-(cyclopropylmethyl)-1H-benzotriazol-5-yl]oxy}pyridin-2-yl)-2-methylpropan-1-ol | [M + H] calc. 419.1 obs. 419.1 |
| 49 | 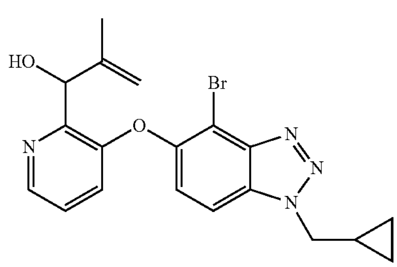 [SMILES: C=C(C)C(O)c1ncccc1Oc1ccc2c(nnn2CC2CC2)c1Br] | 1-(3-{[4-bromo-1-(cyclopropylmethyl)-1H-benzotriazol-5-yl]oxy}pyridin-2-yl)-2-methylprop-2-en-1-ol | [M + H] calc. 417.1 obs. 417.1 |

TABLE 1-continued

| Ex. | Structure | Name | LRMS or HRMS |
|---|---|---|---|
| 50 | 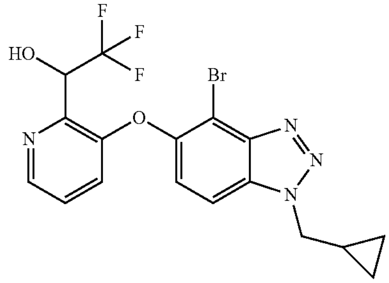 [SMILES: OC(c1ncccc1Oc1ccc2c(nnn2CC2CC2)c1Br)C(F)(F)F] | 1-(3-{[4-bromo-1-(cyclopropylmethyl)-1H-benzotriazol-5-yl]oxy}pyridin-2-yl)-2,2,2-trifluoroethanol | [M + H] calc. 443.0 obs. 443.0 |
| 51 | 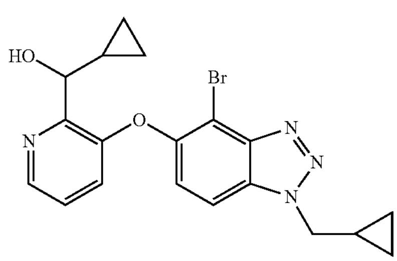 [SMILES: OC(c1ncccc1Oc1ccc2c(nnn2CC2CC2)c1Br)C1CC1] | (3-{[4-bromo-1-(cyclopropylmethyl)-1H-benzotriazol-5-yl]oxy}pyridin-2-yl)(cyclopropyl)methanol | [M + H] calc. 415.1 obs. 415.1 |
| 52 | 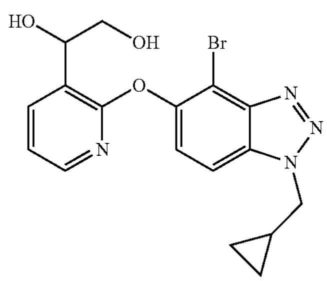 [SMILES: OCC(O)c1cccnc1Oc1ccc2c(nnn2CC2CC2)c1Br] | 1-(2-{[4-bromo-1-(cyclopropylmethyl)-1H-benzotriazol-5-yl]oxy}pyridin-3-yl)ethane-1,2-diol | [M + H] calc. 405.0557 obs. 405.0563 |
| 53 | 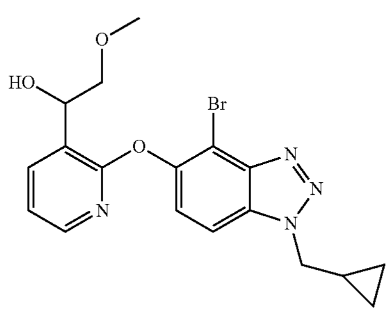 [SMILES: COCC(O)c1cccnc1Oc1ccc2c(nnn2CC2CC2)c1Br] | 1-(2-{[4-bromo-1-(cyclopropylmethyl)-1H-benzotriazol-5-yl]oxy}pyridin-3-yl)-2-methoxyethanol | [M + H] calc. 419.0713 obs. 419.0707 |
| 54 | 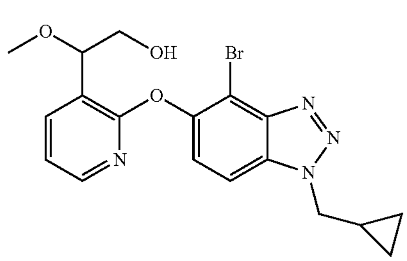 [SMILES: COC(CO)c1cccnc1Oc1ccc2c(nnn2CC2CC2)c1Br] | 2-(2-{[4-bromo-1-(cyclopropylmethyl)-1H-benzotriazol-5-yl]oxy}pyridin-3-yl)-2-methoxyethanol | [M + H] calc. 419.0713 obs. 419.0711 |

TABLE 1-continued

| Ex. | Structure | Name | LRMS or HRMS |
|---|---|---|---|
| 55 | 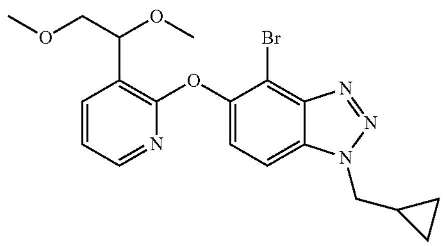 [SMILES: COCC(OC)c1cccnc1Oc1ccc2c(nnn2CC2CC2)c1Br] | 4-bromo-1-(cyclopropylmethyl)-5-{[3-(1,2-dimethoxyethyl)pyridin-2-yl]oxy}-1H-benzotriazole | [M + H] calc. 433.0870 obs. 433.0866 |
| 56 | 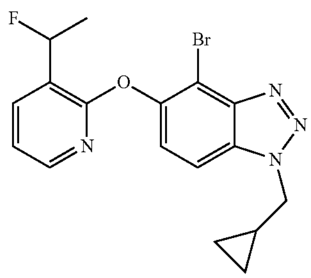 [SMILES: CC(F)c1cccnc1Oc1ccc2c(nnn2CC2CC2)c1Br] | 4-bromo-1-(cyclopropylmethyl)-5-{[3-(1-fluoroethyl)pyridin-2-yl]oxy}-1H-benzotriazole | [M + H] calc. 391.0564 obs. 391.0559 |
| 57 | 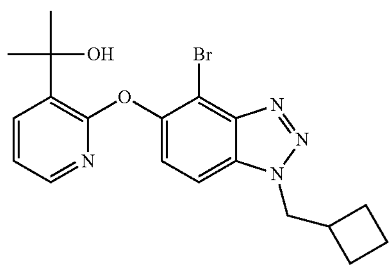 [SMILES: CC(C)(O)c1cccnc1Oc1ccc2c(nnn2CC2CCC2)c1Br] | 2-(2-{[4-bromo-1-(cyclobutylmethyl)-1H-benzotriazol-5-yl]oxy}pyridin-3-yl)propan-2-ol | [M + H] calc. 417.1 obs. 417.0 |
| 58 | 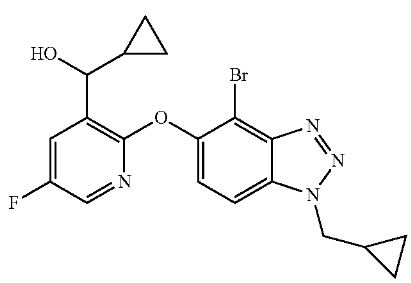 [SMILES: OC(c1cc(F)cnc1Oc1ccc2c(nnn2CC2CC2)c1Br)C1CC1] | (2-{[4-bromo-1-(cyclopropylmethyl)-1H-benzotriazol-5-yl]oxy}-5-fluoropyridin-3-yl)(cyclopropyl)methanol | [M + H] calc. 433.1 obs. 432.9 |
| 59 | 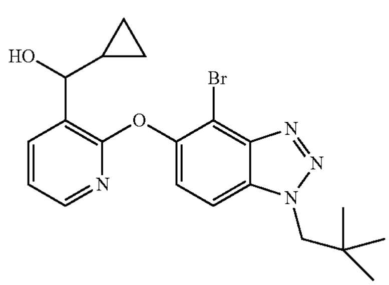 [SMILES: CC(C)(C)Cn1nnc2c(Br)c(Oc3ncccc3C(O)C3CC3)ccc21] | (2-{[4-bromo-1-(2,2-dimethylpropyl)-1H-benzotriazol-5-yl]oxy}pyridin-3-yl)(cyclopropyl)methanol | [M + H] calc. 431.1 obs. 431.1 |

TABLE 1-continued

| Ex. | Structure | Name | LRMS or HRMS |
|---|---|---|---|
| 60 | 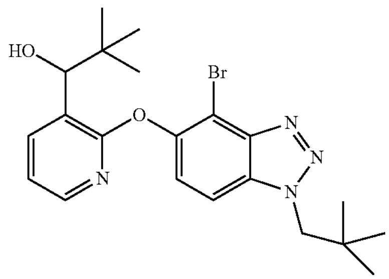 [SMILES: CC(C)(C)Cn1nnc2c(Br)c(Oc3ncccc3C(O)C(C)(C)C)ccc21] | 1-(2-{[4-bromo-1-(2,2-dimethylpropyl)-1H-benzotriazol-5-yl]oxy}pyridin-3-yl)-2,2-dimethylpropan-1-ol | [M + H] calc. 447.1 obs. 447.1 |
| 61 | 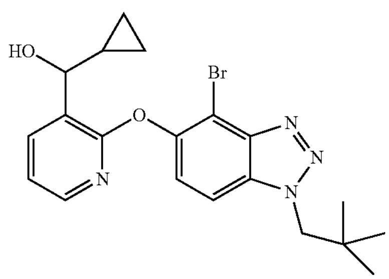 [SMILES: CC(C)(C)Cn1nnc2c(Br)c(Oc3ncccc3C(O)C3CC3)ccc21] | (2-{[4-bromo-1-(2,2-dimethylpropyl)-1H-benzotriazol-5-yl]oxy}pyridin-3-yl)(cyclopropyl)methanol | [M + H] calc. 431.1 obs. 431.0 |
| 62 | 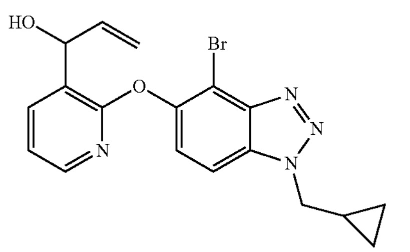 [SMILES: C=CC(O)c1cccnc1Oc1ccc2c(nnn2CC2CC2)c1Br] | 1-(2-{[4-bromo-1-(cyclopropylmethyl)-1H-benzotriazol-5-yl]oxy}pyridin-3-yl)prop-2-en-1-ol | [M + H] calc. 401.1 obs. 400.7 |
| 63 | 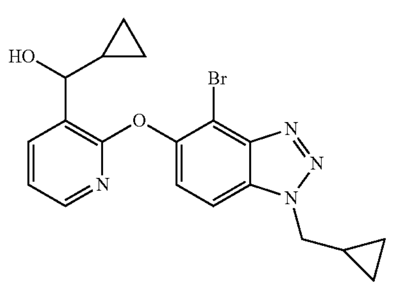 [SMILES: OC(c1cccnc1Oc1ccc2c(nnn2CC2CC2)c1Br)C1CC1] | (2-{[4-bromo-1-(cyclopropylmethyl)-1H-benzotriazol-5-yl]oxy}pyridin-3-yl)(cyclopropyl)methanol | [M + H] calc. 415.1 obs. 414.7 |
| 64 | 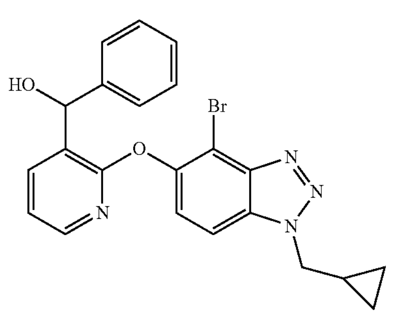 [SMILES: OC(c1ccccc1)c1cccnc1Oc1ccc2c(nnn2CC2CC2)c1Br] | (2-{[4-bromo-1-(cyclopropylmethyl)-1H-benzotriazol-5-yl]oxy}pyridin-3-yl)(phenyl)methanol | [M + H] calc. 451.1 obs. 450.7 |

TABLE 1-continued

| Ex. | Structure | Name | LRMS or HRMS |
|---|---|---|---|
| 65 | 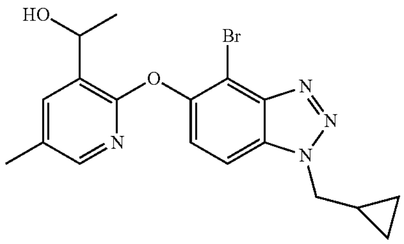 [SMILES: Cc1cnc(Oc2ccc3c(nnn3CC3CC3)c2Br)c(C(C)O)c1] | 1-(2-{[4-bromo-1-(cyclopropylmethyl)-1H-benzotriazol-5-yl]oxy}-5-methylpyridin-3-yl)ethanol | [M + H] calc. 403.1 obs. 402.8 |
| 66 | 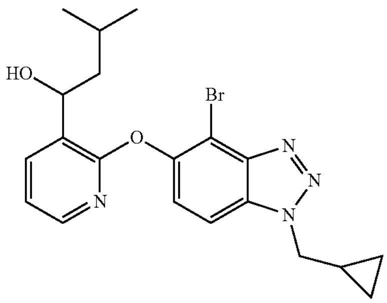 [SMILES: CC(C)CC(O)c1cccnc1Oc1ccc2c(nnn2CC2CC2)c1Br] | 1-(2-{[4-bromo-1-(cyclopropylmethyl)-1H-benzotriazol-5-yl]oxy}pyridin-3-yl)-3-methylbutan-1-ol | [M + H] calc. 431.1 obs. 430.7 |
| 67 | 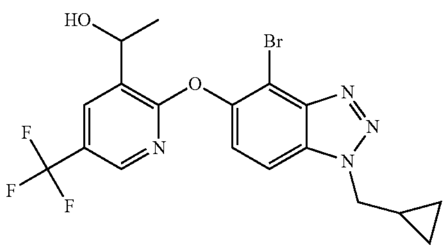 [SMILES: CC(O)c1cc(C(F)(F)F)cnc1Oc1ccc2c(nnn2CC2CC2)c1Br] | 1-[2-{[4-bromo-1-(cyclopropylmethyl)-1H-benzotriazol-5-yl]oxy}-5-(trifluoromethyl)pyridin-3-yl]ethanol | [M + H] calc. 457.0 obs. 456.7 |
| 68 | 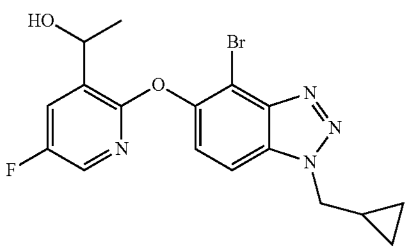 [SMILES: CC(O)c1cc(F)cnc1Oc1ccc2c(nnn2CC2CC2)c1Br] | 1-(2-{[4-bromo-1-(cyclopropylmethyl)-1H-benzotriazol-5-yl]oxy}-5-fluoropyridin-3-yl)ethanol | [M + H] calc. 407.1 obs. 406.7 |
| 69 | 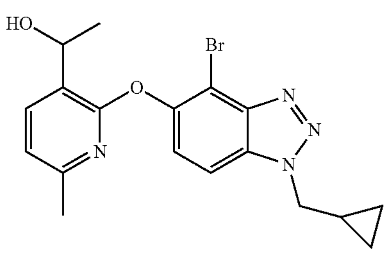 [SMILES: Cc1ccc(C(C)O)c(Oc2ccc3c(nnn3CC3CC3)c2Br)n1] | 1-(2-{[4-bromo-1-(cyclopropylmethyl)-1H-benzotriazol-5-yl]oxy}-6-methylpyridin-3-yl)ethanol | [M + H] calc. 403.1 obs. 402.8 |
| 70 | 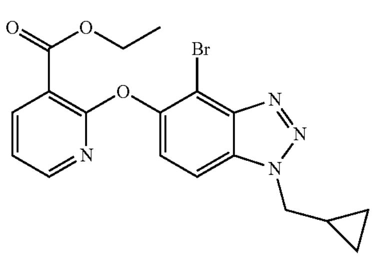 [SMILES: CCOC(=O)c1cccnc1Oc1ccc2c(nnn2CC2CC2)c1Br] | ethyl 2-{[4-bromo-1-(cyclopropylmethyl)-1H-benzotriazol-5-yl]oxy}pyridine-3-carboxylate | [M + H] calc. 417.1 obs. 416.7 |

TABLE 1-continued

| Ex. | Structure | Name | LRMS or HRMS |
|---|---|---|---|
| 71 | 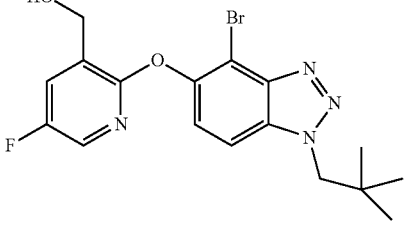 | (2-{[4-bromo-1-(2,2-dimethylpropyl)-1H-benzotriazol-5-yl]oxy}-5-fluoropyridin-3-yl)methanol | [M + H] calc. 409.1 obs. 408.7 |
| 72 | 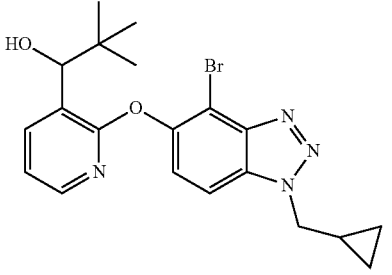 [SMILES: CC(C)(C)C(O)c1cccnc1Oc1ccc2c(nnn2CC2CC2)c1Br] | 1-(2-{[4-bromo-1-(cyclopropylmethyl)-1H-benzotriazol-5-yl]oxy}pyridin-3-yl)-2,2-dimethylpropan-1-ol | [M + H] calc. 431.1 obs. 430.7 |
| 73 | 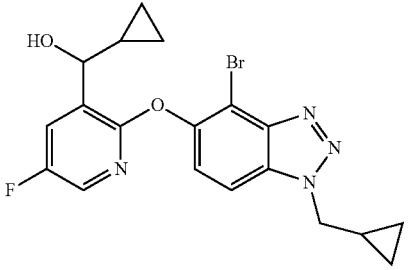 [SMILES: OC(c1cc(F)cnc1Oc1ccc2c(nnn2CC2CC2)c1Br)C1CC1] | (2-{[4-bromo-1-(cyclopropylmethyl)-1H-benzotriazol-5-yl]oxy}-5-fluoropyridin-3-yl)(cyclopropyl)methanol | [M + H] calc. 433.1 obs. 432.9 |
| 74 | 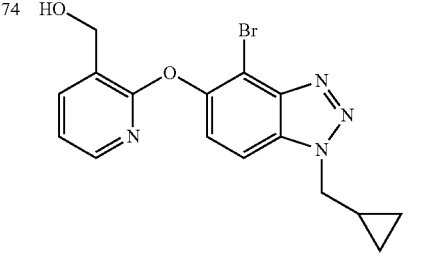 | (2-{[4-bromo-1-(cyclopropylmethyl)-1H-benzotriazol-5-yl]oxy}pyridin-3-yl)methanol | [M + H] calc. 375.0 obs. 374.9 |
| 75 | 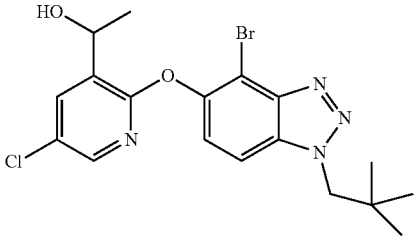 [SMILES: CC(O)c1cc(Cl)cnc1Oc1ccc2c(nnn2CC(C)(C)C)c1Br] | 1-(2-{[4-bromo-1-(2,2-dimethylpropyl)-1H-benzotriazol-5-yl]oxy}-5-chloropyridin-3-yl)ethanol | [M + H] calc. 439.1 obs. 438.7 |
| 76 | 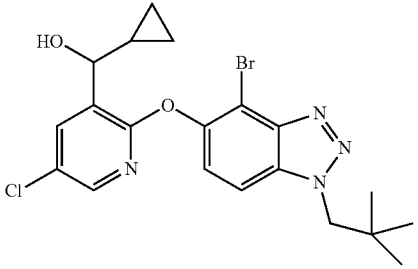 [SMILES: CC(C)(C)Cn1nnc2c(Br)c(Oc3ncc(Cl)cc3C(O)C3CC3)ccc21] | (2-{[4-bromo-1-(2,2-dimethylpropyl)-1H-benzotriazol-5-yl]oxy}-5-chloropyridin-3-yl)(cyclopropyl)methanol | [M + H] calc. 465.1 obs. 464.9 |

TABLE 1-continued

| Ex. | Structure | Name | LRMS or HRMS |
|---|---|---|---|
| 77 | 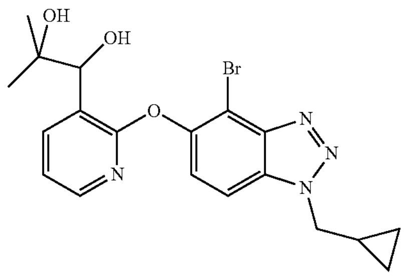 [SMILES: CC(C)(O)C(O)c1cccnc1Oc1ccc2c(nnn2CC2CC2)c1Br] | 1-(2-{[4-bromo-1-(cyclopropylmethyl)-1H-benzotriazol-5-yl]oxy}pyridin-3-yl)-2-methylpropane-1,2-diol | [M + H] calc. 433.1 obs. 432.9 |
| 78 | 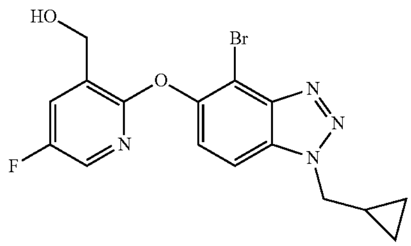 [SMILES: OCc1cc(F)cnc1Oc1ccc2c(nnn2CC2CC2)c1Br] | (2-{[4-bromo-1-(cyclopropylmethyl)-1H-benzotriazol-5-yl]oxy}-5-fluoropyridin-3-yl)methanol | [M + H] calc. 393.0 obs. 392.9 |
| 79 | 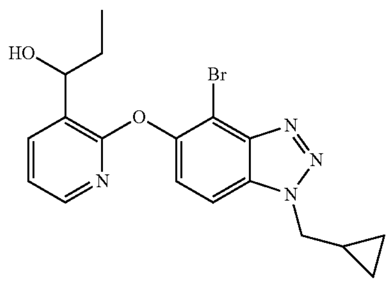 [SMILES: CCC(O)c1cccnc1Oc1ccc2c(nnn2CC2CC2)c1Br] | 1-(2-{[4-bromo-1-(cyclopropylmethyl)-1H-benzotriazol-5-yl]oxy}pyridin-3-yl)propan-1-ol | [M + H] calc. 403.1 obs. 403.1 |
| 80 | 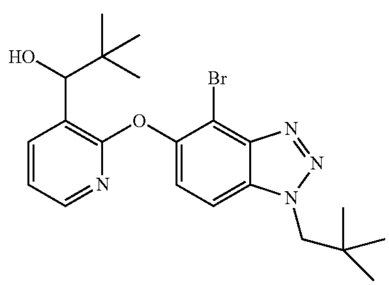 [SMILES: CC(C)(C)Cn1nnc2c(Br)c(Oc3ncccc3C(O)C(C)(C)C)ccc21] | 1-(2-{[4-bromo-1-(2,2-dimethylpropyl)-1H-benzotriazol-5-yl]oxy}pyridin-3-yl)-2,2-dimethylpropan-1-ol | [M + H] calc. 447.1 obs. 447.0 |
| 81 | 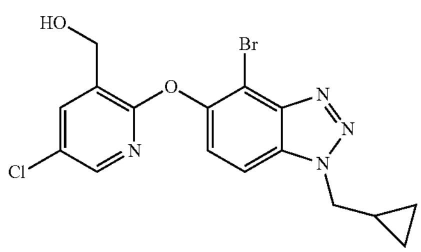 [SMILES: OCc1cc(Cl)cnc1Oc1ccc2c(nnn2CC2CC2)c1Br] | (2-{[4-bromo-1-(cyclopropylmethyl)-1H-benzotriazol-5-yl]oxy}-5-chloropyridin-3-yl)methanol | [M + H] calc. 409.0 obs. 408.9 |
| 82 | 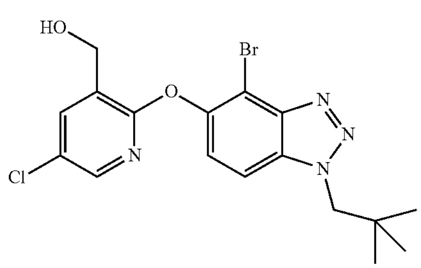 [SMILES: CC(C)(C)Cn1nnc2c(Br)c(Oc3ncc(Cl)cc3CO)ccc21] | (2-{[4-bromo-1-(2,2-dimethylpropyl)-1H-benzotriazol-5-yl]oxy}-5-chloropyridin-3-yl)methanol | [M + H] calc. 425.0 obs. 424.9 |

TABLE 1-continued

| Ex. | Structure | Name | LRMS or HRMS |
|---|---|---|---|
| 83 | 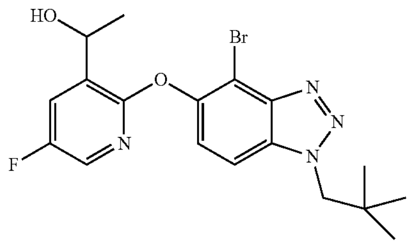 | 1-(2-{[4-bromo-1-(2,2-dimethylpropyl)-1H-benzotriazol-5-yl]oxy}-5-fluoropyridin-3-yl)ethanol | [M + H] calc. 423.1 obs. 422.8 |
| 84 | 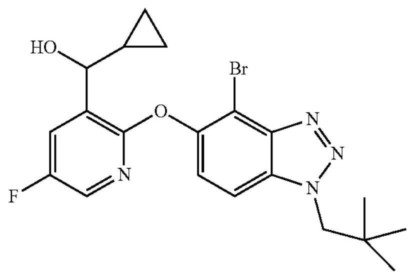 [SMILES: CC(C)(C)Cn1nnc2c(Br)c(Oc3ncc(F)cc3C(O)C3CC3)ccc21] | (2-{[4-bromo-1-(2,2-dimethylpropyl)-1H-benzotriazol-5-yl]oxy}-5-fluoropyridin-3-yl)(cyclopropyl)methanol | [M + H] calc. 449.1 obs. 448.8 |
| 85 | 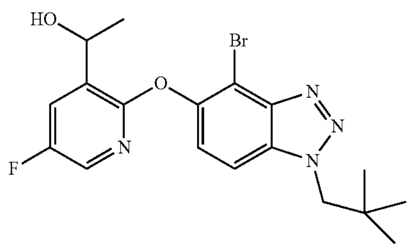 [SMILES: CC(O)c1cc(F)cnc1Oc1ccc2c(nnn2CC(C)(C)C)c1Br] | 1-(2-{[4-bromo-1-(2,2-dimethylpropyl)-1H-benzotriazol-5-yl]oxy}-5-fluoropyridin-3-yl)ethanol | [M + H] calc. 423.1 obs. 424.8 |
| 86 | 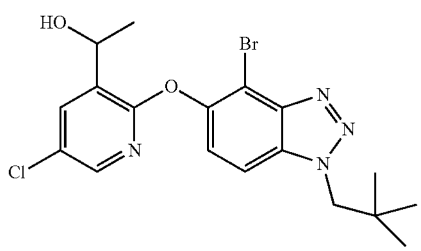 [SMILES: CC(O)c1cc(Cl)cnc1Oc1ccc2c(nnn2CC(C)(C)C)c1Br] | 1-(2-{[4-bromo-1-(2,2-dimethylpropyl)-1H-benzotriazol-5-yl]oxy}-5-chloropyridin-3-yl)ethanol | [M + H] calc. 439.1 obs. 438.7 |
| 87 | 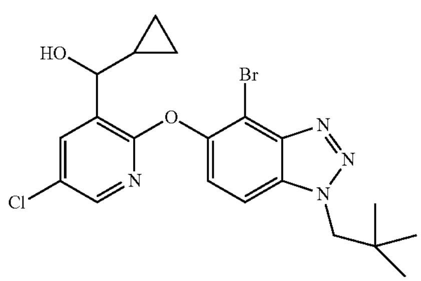 [SMILES: CC(C)(C)Cn1nnc2c(Br)c(Oc3ncc(Cl)cc3C(O)C3CC3)ccc21] | (2-{[4-bromo-1-(2,2-dimethylpropyl)-1H-benzotriazol-5-yl]oxy}-5-chloropyridin-3-yl)(cyclopropyl)methanol | [M + H] calc. 465.1 obs. 464.8 |
| 88 | 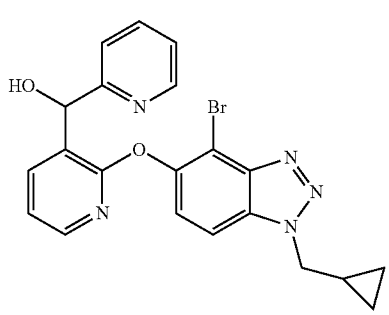 [SMILES: OC(c1ccccn1)c1cccnc1Oc1ccc2c(nnn2CC2CC2)c1Br] | (2-{[4-bromo-1-(cyclopropylmethyl)-1H-benzotriazol-5-yl]oxy}pyridin-3-yl)(pyridin-2-yl)methanol | [M + H] calc. 452.1 obs. 451.7 |

TABLE 1-continued

| Ex. | Structure | Name | LRMS or HRMS |
|---|---|---|---|
| 89 | 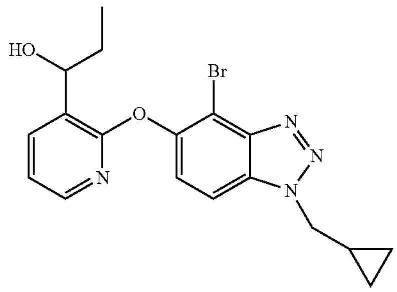 [SMILES: CCC(O)c1cccnc1Oc1ccc2c(nnn2CC2CC2)c1Br] | 1-(2-{[4-bromo-1-(cyclopropylmethyl)-1H-benzotriazol-5-yl]oxy}pyridin-3-yl)propan-1-ol | [M + H] calc. 403.1 obs. 402.8 |
| 90 | 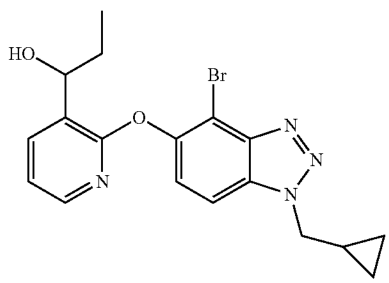 [SMILES: CCC(O)c1cccnc1Oc1ccc2c(nnn2CC2CC2)c1Br] | 1-(2-{[4-bromo-1-(cyclopropylmethyl)-1H-benzotriazol-5-yl]oxy}pyridin-3-yl)propan-1-ol | [M + H] calc. 403.1 obs. 402.8 |
| 91 | 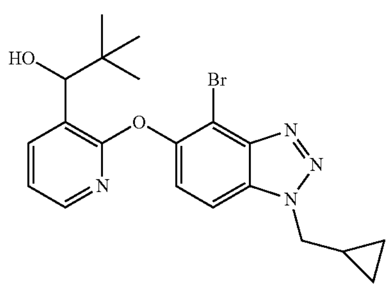 [SMILES: CC(C)(C)C(O)c1cccnc1Oc1ccc2c(nnn2CC2CC2)c1Br] | 1-(2-{[4-bromo-1-(cyclopropylmethyl)-1H-benzotriazol-5-yl]oxy}pyridin-3-yl)-2,2-dimethylpropan-1-ol | [M + H] calc. 431.1 obs. 430.8 |
| 92 | 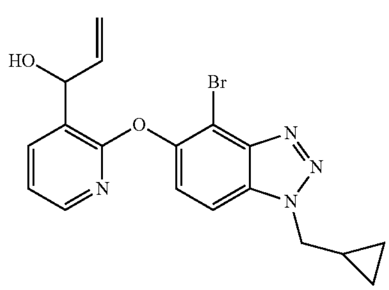 [SMILES: C=CC(O)c1cccnc1Oc1ccc2c(nnn2CC2CC2)c1Br] | 1-(2-{[4-bromo-1-(cyclopropylmethyl)-1H-benzotriazol-5-yl]oxy}pyridin-3-yl)prop-2-en-1-ol | [M + H] calc. 401.1 obs. 400.7 |
| 93 | 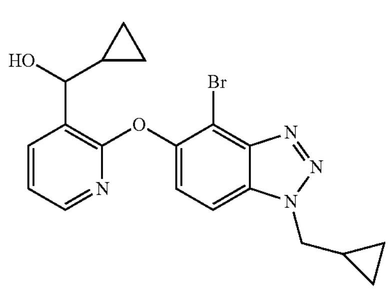 [SMILES: OC(c1cccnc1Oc1ccc2c(nnn2CC2CC2)c1Br)C1CC1] | (2-{[4-bromo-1-(cyclopropylmethyl)-1H-benzotriazol-5-yl]oxy}pyridin-3-yl)(cyclopropyl)methanol | [M + H] calc. 415.1 obs. 414.9 |

TABLE 1-continued

| Ex. | Structure | Name | LRMS or HRMS |
|---|---|---|---|
| 94 | 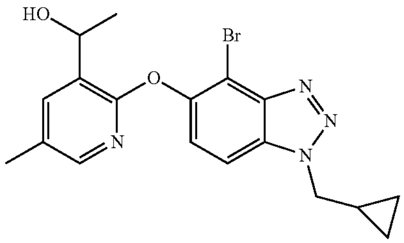 [SMILES: Cc1cnc(Oc2ccc3c(nnn3CC3CC3)c2Br)c(C(C)O)c1] | 1-(2-{[4-bromo-1-(cyclopropylmethyl)-1H-benzotriazol-5-yl]oxy}-5-methylpyridin-3-yl)ethanol | [M + H] calc. 403.1 obs. 402.8 |
| 95 | 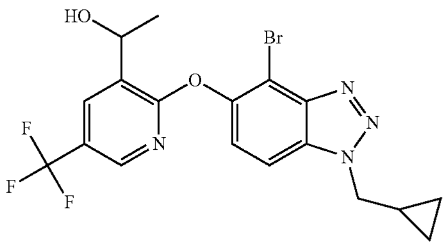 [SMILES: CC(O)c1cc(C(F)(F)F)cnc1Oc1ccc2c(nnn2CC2CC2)c1Br] | 1-[2-{[4-bromo-1-(cyclopropylmethyl)-1H-benzotriazol-5-yl]oxy}-5-(trifluoromethyl)pyridin-3-yl]ethanol | [M + H] calc. 457.0 obs. 456.7 |
| 96 | 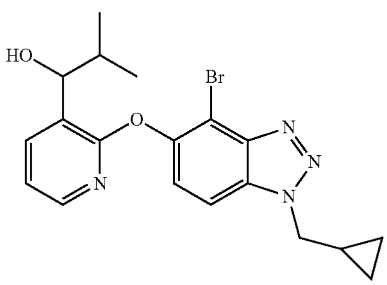 [SMILES: CC(C)C(O)c1cccnc1Oc1ccc2c(nnn2CC2CC2)c1Br] | 1-(2-{[4-bromo-1-(cyclopropylmethyl)-1H-benzotriazol-5-yl]oxy}pyridin-3-yl)-2-methylpropan-1-ol | [M + H] calc. 417.1 obs. 416.8 |
| 97 | 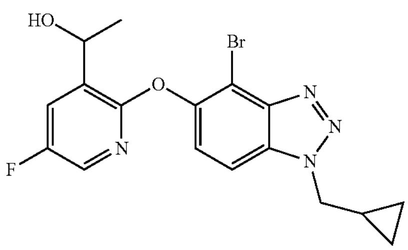 [SMILES: CC(O)c1cc(F)cnc1Oc1ccc2c(nnn2CC2CC2)c1Br] | 1-(2-{[4-bromo-1-(cyclopropylmethyl)-1H-benzotriazol-5-yl]oxy}-5-fluoropyridin-3-yl)ethanol | [M + H] calc. 407.1 obs. 406.9 |
| 98 | 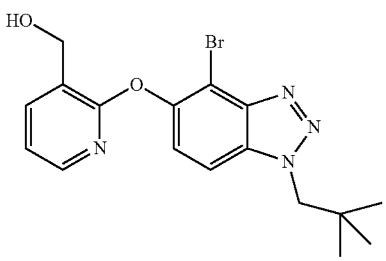 [SMILES: CC(C)(C)Cn1nnc2c(Br)c(Oc3ncccc3CO)ccc21] | (2-{[4-bromo-1-(2,2-dimethylpropyl)-1H-benzotriazol-5-yl]oxy}pyridin-3-yl)methanol | [M + H] calc. 391.1 obs. 390.9 |
| 99 | 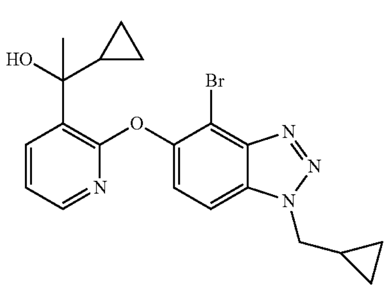 [SMILES: CC(O)(c1cccnc1Oc1ccc2c(nnn2CC2CC2)c1Br)C1CC1] | 1-(2-{[4-bromo-1-(cyclopropylmethyl)-1H-benzotriazol-5-yl]oxy}pyridin-3-yl)-1-cyclopropylethanol | [M + H] calc. 429.1 obs. 428.9 |

TABLE 1-continued

| Ex. | Structure | Name | LRMS or HRMS |
|---|---|---|---|
| 100 | 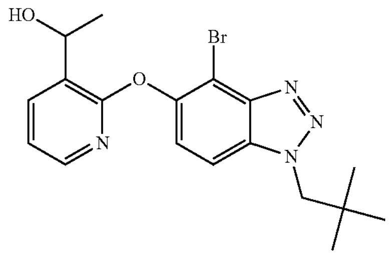 [SMILES: CC(O)c1cccnc1Oc1ccc2c(nnn2CC(C)(C)C)c1Br] | 1-(2-{[4-bromo-1-(2,2-dimethylpropyl)-1H-benzotriazol-5-yl]oxy}pyridin-3-yl)ethanol | [M + H] calc. 405.1 obs. 404.9 |
| 101 | 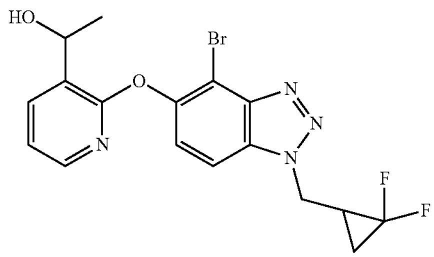 [SMILES: CC(O)c1cccnc1Oc1ccc2c(nnn2CC2CC2(F)F)c1Br] | 1-[2-({4-bromo-1-[(2,2-difluorocyclopropyl)methyl]-1H-benzotriazol-5-yl}oxy)pyridin-3-yl]ethanol | [M + H] calc. 425.0 obs. 424.8 |
| 102 | 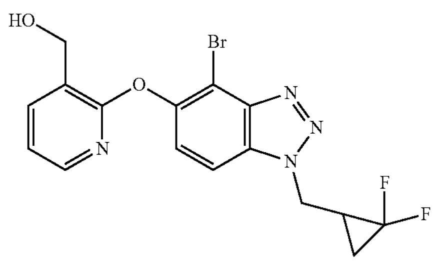 [SMILES: OCc1cccnc1Oc1ccc2c(nnn2CC2CC2(F)F)c1Br] | [2-({4-bromo-1-[(2,2-difluorocyclopropyl)methyl]-1H-benzotriazol-5-yl}oxy)pyridin-3-yl]methanol | [M + H] calc. 411.1 obs. 410.8 |
| 103 | 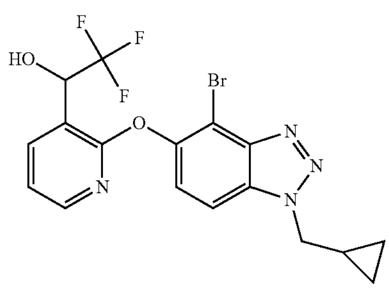 [SMILES: OC(c1cccnc1Oc1ccc2c(nnn2CC2CC2)c1Br)C(F)(F)F] | 1-(2-{[4-bromo-1-(cyclopropylmethyl)-1H-benzotriazol-5-yl]oxy}pyridin-3-yl)-2,2,2-trifluoroethanol | [M + H] calc. 443.0 obs. 442.8 |
| 104 | 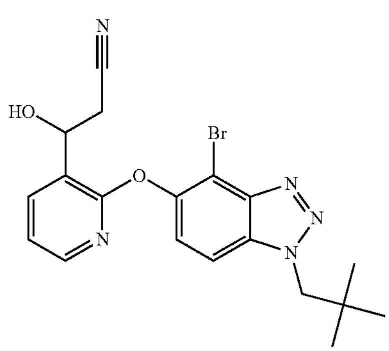 [SMILES: CC(C)(C)Cn1nnc2c(Br)c(Oc3ncccc3C(O)CC#N)ccc21] | 3-(2-{[4-bromo-1-(2,2-dimethylpropyl)-1H-benzotriazol-5-yl]oxy}pyridin-3-yl)-3-hydroxypropanenitrile | [M + H] calc. 430.1 obs. 429.9 |

TABLE 1-continued

| Ex. | Structure | Name | LRMS or HRMS |
|---|---|---|---|
| 105 | 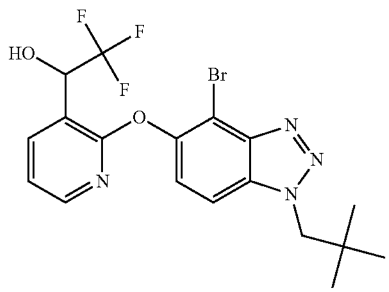 [SMILES: CC(C)(C)Cn1nnc2c(Br)c(Oc3ncccc3C(O)C(F)(F)F)ccc21] | 1-(2-{[4-bromo-1-(2,2-dimethylpropyl)-1H-benzotriazol-5-yl]oxy}pyridin-3-yl)-2,2,2-trifluoroethanol | [M + H] calc. 459.1 obs. 458.9 |
| 106 | 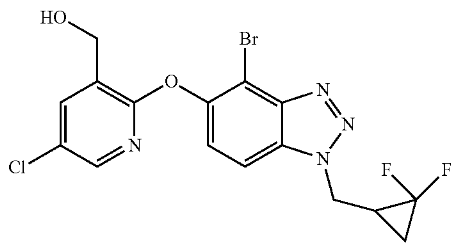 [SMILES: OCc1cc(Cl)cnc1Oc1ccc2c(nnn2CC2CC2(F)F)c1Br] | [2-({4-bromo-1-[(2,2-difluorocyclopropyl)methyl]-1H-benzotriazol-5-yl}oxy)-5-chloropyridin-3-yl]methanol | [M + H] calc. 445.0 obs. 444.8 |
| 107 | 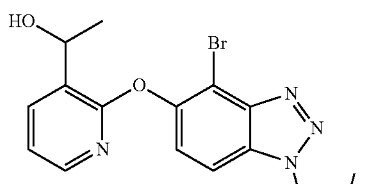 | (1S)-(2-{[4-bromo-1-(2,2-dimethylpropyl)-1H-benzotriazol-5-yl]oxy}pyridin-3-yl)ethanol | [M + H] calc. 405.1 obs. 405.0 |
| 108 | 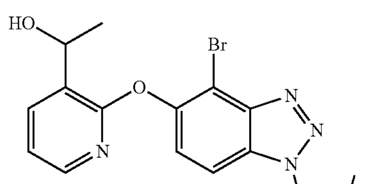 | (1R)-(2-{[4-bromo-1-(2,2-dimethylpropyl)-1H-benzotriazol-5-yl]oxy}pyridin-3-yl)ethanol | [M + H] calc. 405.1 obs. 405.0 |
| 109 | 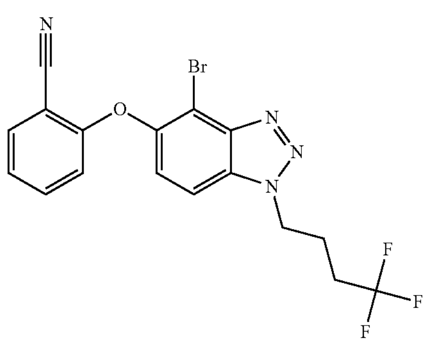 [SMILES: N#Cc1ccccc1Oc1ccc2c(nnn2CCCC(F)(F)F)c1Br] | 2-{[4-bromo-1-(4,4,4-trifluorobutyl)-1H-benzotriazol-5-yl]oxy}benzonitrile | [M + H] calc. 425.0 obs. 425.0 |

TABLE 1-continued

| Ex. | Structure | Name | LRMS or HRMS |
|---|---|---|---|
| 110 | 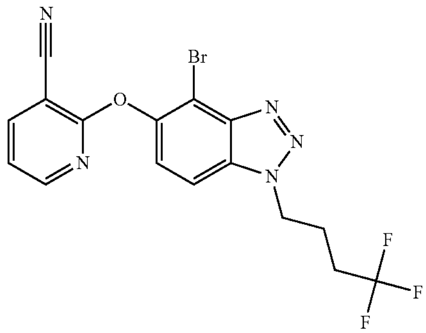 [SMILES: N#Cc1cccnc1Oc1ccc2c(nnn2CCCC(F)(F)F)c1Br] | 2-{[4-bromo-1-(4,4,4-trifluorobutyl)-1H-benzotriazol-5-yl]oxy}pyridine-3-carbonitrile | [M + H] calc. 426.0 obs. 426.1 |
| 111 | 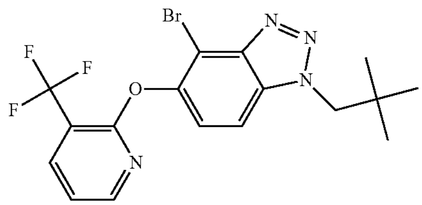 [SMILES: CC(C)(C)Cn1nnc2c(Br)c(Oc3ncccc3C(F)(F)F)ccc21] | 4-bromo-1-(2,2-dimethylpropyl)-5-{[3-(trifluoromethyl)pyridin-2-yl]oxy}-1H-benzotriazole | [M + H] calc. 429.0 obs. 429.1 |
| 112 | 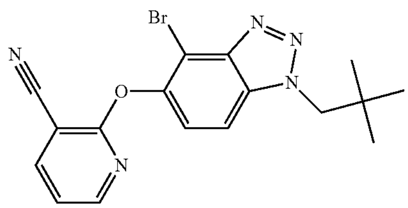 | 2-{[4-bromo-1-(2,2-dimethylpropyl)-1H-benzotriazol-5-yl]oxy}pyridine-3-carbonitrile | [M + H] calc. 386.1 obs. 386.0 |
| 113 | 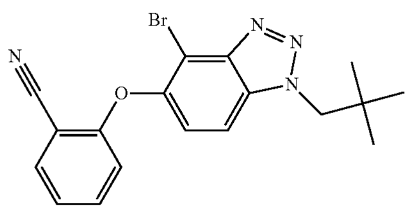 [SMILES: CC(C)(C)Cn1nnc2c(Br)c(Oc3ccccc3C#N)ccc21] | 2-{[4-bromo-1-(2,2-dimethylpropyl)-1H-benzotriazol-5-yl]oxy}benzonitrile | [M + H] calc. 385.1 obs. 385.1 |
| 114 | 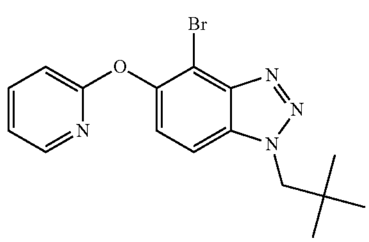 [SMILES: CC(C)(C)Cn1nnc2c(Br)c(Oc3ccccn3)ccc21] | 4-bromo-1-(2,2-dimethylpropyl)-5-(pyridin-2-yloxy)-1H-benzotriazole | [M + H] calc. 361.1 obs. 361.1 |
| 115 | 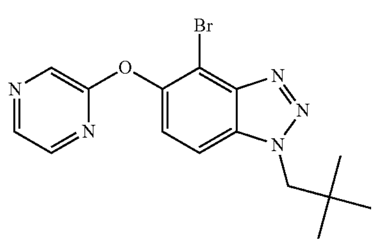 [SMILES: CC(C)(C)Cn1nnc2c(Br)c(Oc3cnccn3)ccc21] | 4-bromo-1-(2,2-dimethylpropyl)-5-(pyrazin-2-yloxy)-1H-benzotriazole | [M + H] calc. 362.1 obs. 362.1 |

TABLE 1-continued

| Ex. | Structure | Name | LRMS or HRMS |
|---|---|---|---|
| 116 | 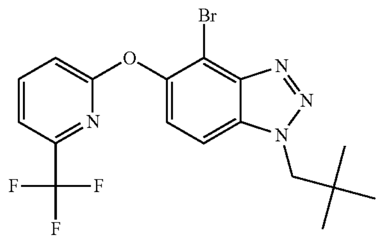 [SMILES: CC(C)(C)Cn1nnc2c(Br)c(Oc3cccc(C(F)(F)F)n3)ccc21] | 4-bromo-1-(2,2-dimethylpropyl)-5-{[6-(trifluoromethyl)pyridin-2-yl]oxy}-1H-benzotriazole | [M + H] calc. 429.0 obs. 429.1 |
| 117 | 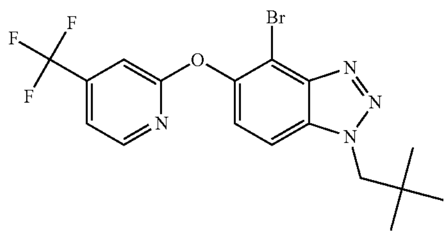 [SMILES: CC(C)(C)Cn1nnc2c(Br)c(Oc3cc(C(F)(F)F)ccn3)ccc21] | 4-bromo-1-(2,2-dimethylpropyl)-5-{[4-(trifluoromethyl)pyridin-2-yl]oxy}-1H-benzotriazole | [M + H] calc. 429.0 obs. 429.1 |
| 118 | 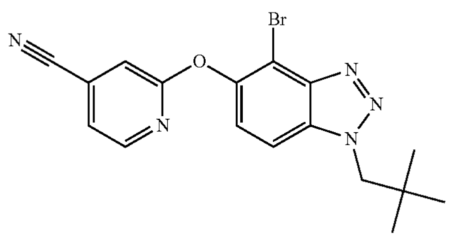 [SMILES: CC(C)(C)Cn1nnc2c(Br)c(Oc3cc(C#N)ccn3)ccc21] | 2-{[4-bromo-1-(2,2-dimethylpropyl)-1H-benzotriazol-5-yl]oxy}pyridine-4-carbonitrile | [M + H] calc. 386.1 obs. 386.1 |
| 119 | 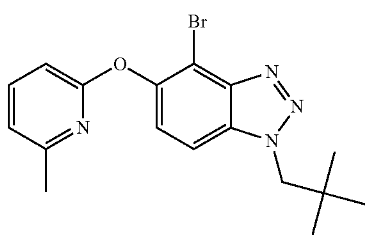 [SMILES: Cc1cccc(Oc2ccc3c(nnn3CC(C)(C)C)c2Br)n1] | 4-bromo-1-(2,2-dimethylpropyl)-5-[(6-methylpyridin-2-yl)oxy]-1H-benzotriazole | [M + H] calc. 375.1 obs. 375.1 |
| 120 | 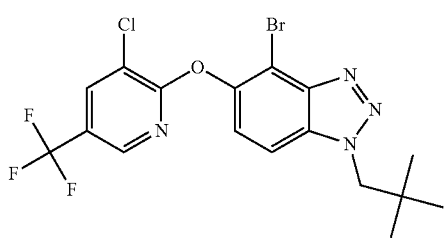 [SMILES: CC(C)(C)Cn1nnc2c(Br)c(Oc3ncc(C(F)(F)F)cc3Cl)ccc21] | 4-bromo-5-{[3-chloro-5-(trifluoromethyl)pyridin-2-yl]oxy}-1-(2,2-dimethylpropyl)-1H-benzotriazole | [M + H] calc. 463.0 obs. 463.0 |
| 121 | 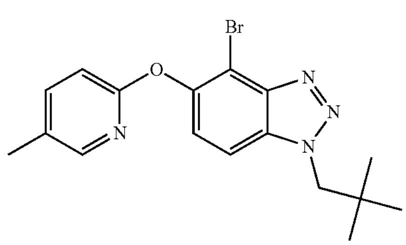 [SMILES: Cc1ccc(Oc2ccc3c(nnn3CC(C)(C)C)c2Br)nc1] | 4-bromo-1-(2,2-dimethylpropyl)-5-[(5-methylpyridin-2-yl)oxy]-1H-benzotriazole | [M + H] calc. 375.1 obs. 375.1 |

TABLE 1-continued

| Ex. | Structure | Name | LRMS or HRMS |
|---|---|---|---|
| 122 | 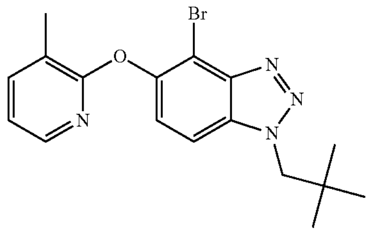 [SMILES: Cc1cccnc1Oc1ccc2c(nnn2CC(C)(C)C)c1Br] | 4-bromo-1-(2,2-dimethylpropyl)-5-[(3-methylpyridin-2-yl)oxy]-1H-benzotriazole | [M + H] calc. 375.1 obs. 375.1 |
| 123 | 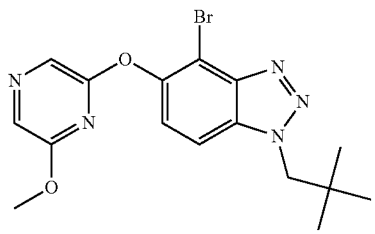 [SMILES: COc1cncc(Oc2ccc3c(nnn3CC(C)(C)C)c2Br)n1] | 4-bromo-1-(2,2-dimethylpropyl)-5-[(6-methoxypyrazin-2-yl)oxy]-1H-benzotriazole | [M + H] calc. 392.1 obs. 392.1 |
| 124 | 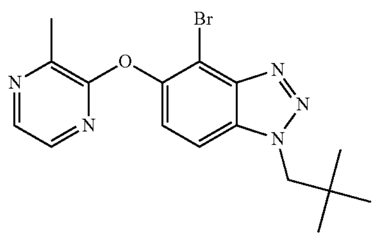 [SMILES: Cc1nccnc1Oc1ccc2c(nnn2CC(C)(C)C)c1Br] | 4-bromo-1-(2,2-dimethylpropyl)-5-[(3-methylpyrazin-2-yl)oxy]-1H-benzotriazole | [M + H] calc. 376.1 obs. 376.1 |
| 125 | 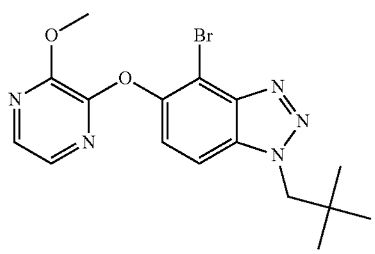 [SMILES: COc1nccnc1Oc1ccc2c(nnn2CC(C)(C)C)c1Br] | 4-bromo-1-(2,2-dimethylpropyl)-5-[(3-methoxypyrazin-2-yl)oxy]-1H-benzotriazole | [M + H] calc. 392.1 obs. 392.1 |
| 126 | 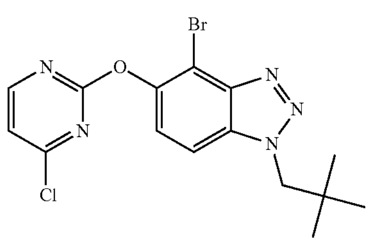 [SMILES: CC(C)(C)Cn1nnc2c(Br)c(Oc3nccc(Cl)n3)ccc21] | 4-bromo-5-[(4-chloropyrimidin-2-yl)oxy]-1-(2,2-dimethylpropyl)-1H-benzotriazole | [M + H] calc. 396.0 obs. 396.0 |
| 127 | 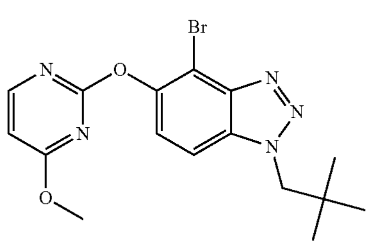 [SMILES: COc1ccnc(Oc2ccc3c(nnn3CC(C)(C)C)c2Br)n1] | 4-bromo-1-(2,2-dimethylpropyl)-5-[(4-methoxypyrimidin-2-yl)oxy]-1H-benzotriazole | [M + H] calc. 392.1 obs. 392.1 |

TABLE 1-continued

| Ex. | Structure | Name | LRMS or HRMS |
|---|---|---|---|
| 128 | 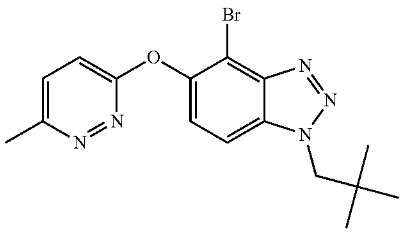 [SMILES: Cc1ccc(Oc2ccc3c(nnn3CC(C)(C)C)c2Br)nn1] | 4-bromo-1-(2,2-dimethylpropyl)-5-[(6-methylpyridazin-3-yl)oxy]-1H-benzotriazole | [M + H] calc. 376.1 obs. 376.1 |
| 129 | 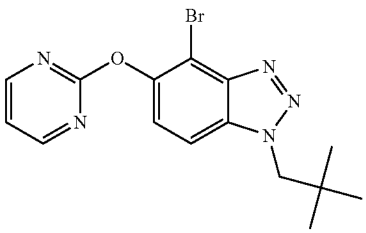 [SMILES: CC(C)(C)Cn1nnc2c(Br)c(Oc3ncccn3)ccc21] | 4-bromo-1-(2,2-dimethylpropyl)-5-(pyrimidin-2-yloxy)-1H-benzotriazole | [M + H] calc. 362.1 obs. 362.1 |
| 130 | 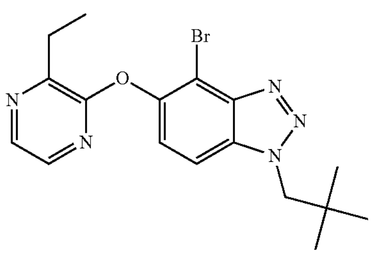 [SMILES: CCc1nccnc1Oc1ccc2c(nnn2CC(C)(C)C)c1Br] | 4-bromo-1-(2,2-dimethylpropyl)-5-(pyrimidin-2-yloxy)-1H-benzotriazole | [M + H] calc. 390.1 obs. 390.1 |
| 131 | 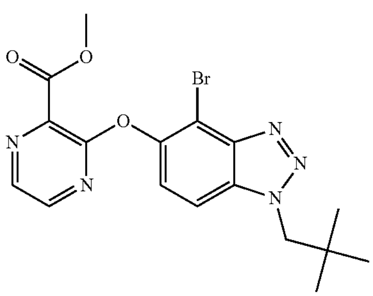 [SMILES: COC(=O)c1nccnc1Oc1ccc2c(nnn2CC(C)(C)C)c1Br] | methyl 3-{[4-bromo-1-(2,2-dimethylpropyl)-1H-benzotriazol-5-yl]oxy}pyrazine-2-carboxylate | [M + H] calc. 420.1 obs. 420.1 |
| 132 | 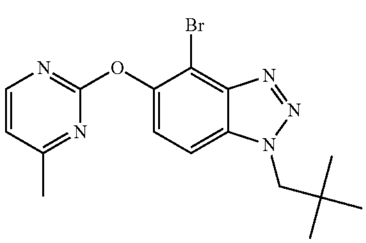 [SMILES: Cc1ccnc(Oc2ccc3c(nnn3CC(C)(C)C)c2Br)n1] | 4-bromo-1-(2,2-dimethylpropyl)-5-[(4-methylpyrimidin-2-yl)oxy]-1H-benzotriazole | [M + H] calc. 376.1 obs. 376.1 |
| 133 | 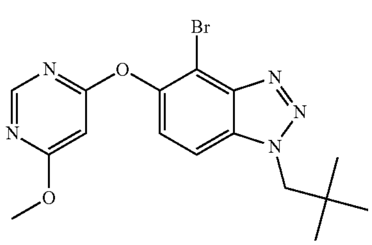 [SMILES: COc1cc(Oc2ccc3c(nnn3CC(C)(C)C)c2Br)ncn1] | 4-bromo-1-(2,2-dimethylpropyl)-5-[(6-methoxypyrimidin-4-yl)oxy]-1H-benzotriazole | [M + H] calc. 392.1 obs. 392.1 |

TABLE 1-continued

| Ex. | Structure | Name | LRMS or HRMS |
|---|---|---|---|
| 134 | 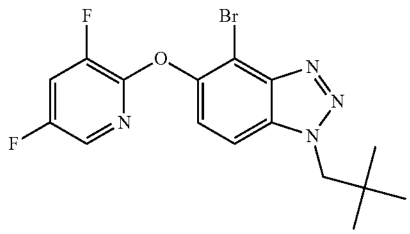 [SMILES: CC(C)(C)Cn1nnc2c(Br)c(Oc3ncc(F)cc3F)ccc21] | 4-bromo-5-[(3,5-difluoropyridin-2-yl)oxy]-1-(2,2-dimethylpropyl)-1H-benzotriazole | [M + H] calc. 397.0 obs. 397.1 |
| 135 | 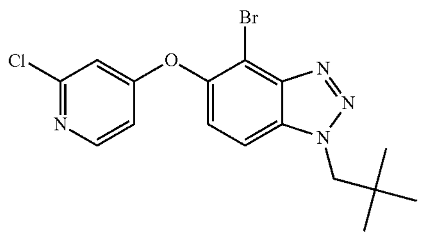 [SMILES: CC(C)(C)Cn1nnc2c(Br)c(Oc3ccnc(Cl)c3)ccc21] | 4-bromo-5-[(2-chloropyridin-4-yl)oxy]-1-(2,2-dimethylpropyl)-1H-benzotriazole | [M + H] calc. 395.0 obs. 395.0 |
| 136 | 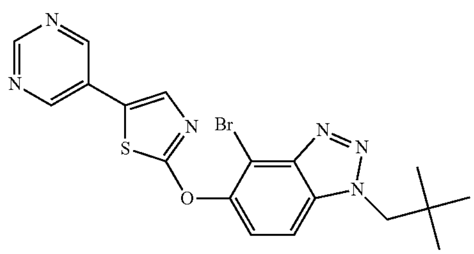 [SMILES: CC(C)(C)Cn1nnc2c(Br)c(Oc3ncc(-c4cncnc4)s3)ccc21] | 4-bromo-1-(2,2-dimethylpropyl)-5-[(5-pyrimidin-5-yl-1,3-thiazol-2-yl)oxy]-1H-benzotriazole | [M + H] calc. 445.0 obs. 445.1 |
| 137 | 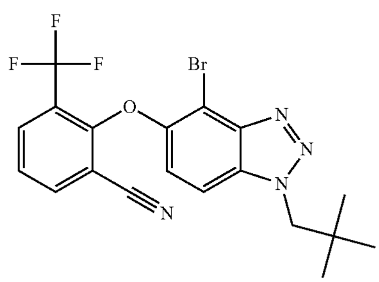 [SMILES: CC(C)(C)Cn1nnc2c(Br)c(Oc3c(C#N)cccc3C(F)(F)F)ccc21] | 2-{[4-bromo-1-(2,2-dimethylpropyl)-1H-benzotriazol-5-yl]oxy}-3-(trifluoromethyl)benzonitrile | [M + H] calc. 453.0 obs. 453.1 |
| 138 | 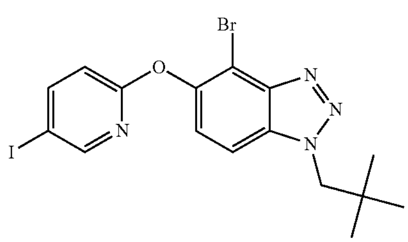 [SMILES: CC(C)(C)Cn1nnc2c(Br)c(Oc3ccc(I)cn3)ccc21] | 4-bromo-1-(2,2-dimethylpropyl)-5-[(5-iodopyridin-2-yl)oxy]-1H-benzotriazole | [M + H] calc. 487.0 obs. 487.0 |
| 139 | 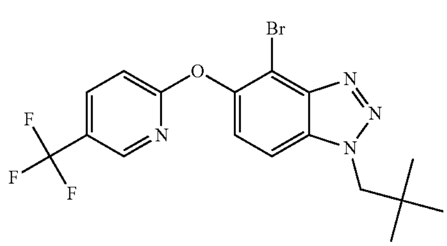 [SMILES: CC(C)(C)Cn1nnc2c(Br)c(Oc3ccc(C(F)(F)F)cn3)ccc21] | 4-bromo-1-(2,2-dimethylpropyl)-5-{[5-(trifluoromethyl)pyridin-2-yl]oxy}-1H-benzotriazole | [M + H] calc. 429.0 obs. 429.1 |

TABLE 1-continued

| Ex. | Structure | Name | LRMS or HRMS |
|---|---|---|---|
| 140 | 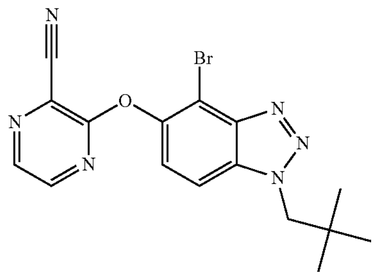 [SMILES: CC(C)(C)Cn1nnc2c(Br)c(Oc3nccnc3C#N)ccc21] | 3-{[4-bromo-1-(2,2-dimethylpropyl)-1H-benzotriazol-5-yl]oxy}pyrazine-2-carbonitrile | [M + H] calc. 387.0 obs. 387.1 |
| 141 | 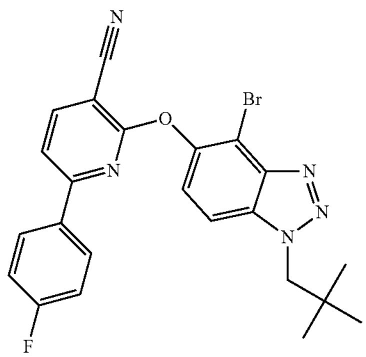 [SMILES: CC(C)(C)Cn1nnc2c(Br)c(Oc3nc(-c4ccc(F)cc4)ccc3C#N)ccc21] | 2-{[4-bromo-1-(2,2-dimethylpropyl)-1H-benzotriazol-5-yl]oxy}-6-(4-fluorophenyl)pyridine-3-carbonitrile | [M + H] calc. 480.1 obs. 480.1 |
| 142 | 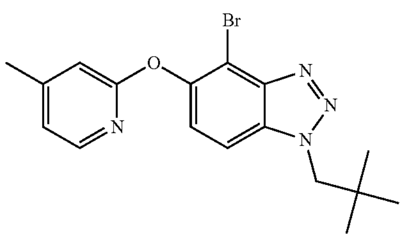 [SMILES: Cc1ccnc(Oc2ccc3c(nnn3CC(C)(C)C)c2Br)c1] | 4-bromo-1-(2,2-dimethylpropyl)-5-[(4-methylpyridin-2-yl)oxy]-1H-benzotriazole | [M + H] calc. 375.1 obs. 375.0 |
| 143 | 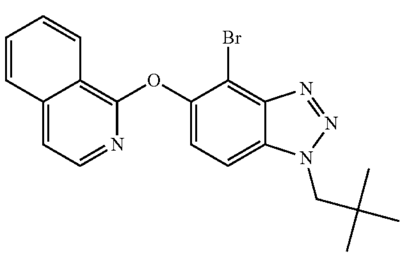 [SMILES: CC(C)(C)Cn1nnc2c(Br)c(Oc3nccc4ccccc34)ccc21] | 1-{[4-bromo-1-(2,2-dimethylpropyl)-1H-benzotriazol-5-yl]oxy}isoquinoline | [M + H] calc. 411.1 obs. 411.1 |
| 144 | 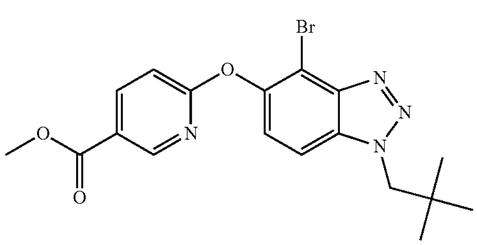 [SMILES: COC(=O)c1ccc(Oc2ccc3c(nnn3CC(C)(C)C)c2Br)nc1] | methyl 6-{[4-bromo-1-(2,2-dimethylpropyl)-1H-benzotriazol-5-yl]oxy}pyridine-3-carboxylate | [M + H] calc. 419.1 obs. 419.1 |

TABLE 1-continued

| Ex. | Structure | Name | LRMS or HRMS |
|---|---|---|---|
| 145 | 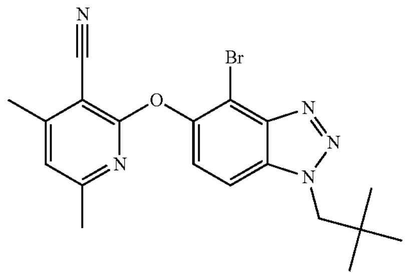 [SMILES: Cc1cc(C)c(C#N)c(Oc2ccc3c(nnn3CC(C)(C)C)c2Br)n1] | 2-{[4-bromo-1-(2,2-dimethylpropyl)-1H-benzotriazol-5-yl]oxy}-4,6-dimethylpyridine-3-carbonitrile | [M + H] calc. 414.1 obs. 414.1 |
| 146 | 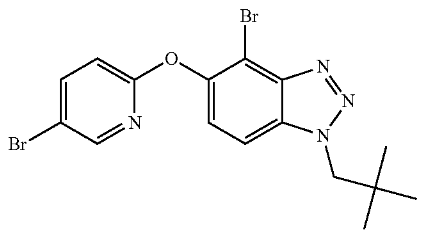 [SMILES: CC(C)(C)Cn1nnc2c(Br)c(Oc3ccc(Br)cn3)ccc21] | 4-bromo-5-[(5-bromopyridin-2-yl)oxy]-1-(2,2-dimethylpropyl)-1H-benzotriazole | [M + H] calc. 441.0 obs. 441.0 |
| 147 | 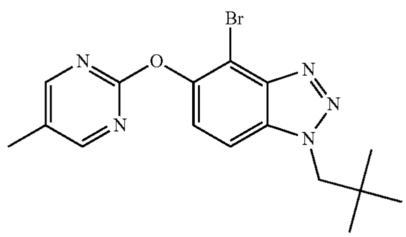 [SMILES: Cc1cnc(Oc2ccc3c(nnn3CC(C)(C)C)c2Br)nc1] | 4-bromo-1-(2,2-dimethylpropyl)-5-[(5-methylpyrimidin-2-yl)oxy]-1H-benzotriazole | [M + H] calc. 376.1 obs. 376.0 |
| 148 | 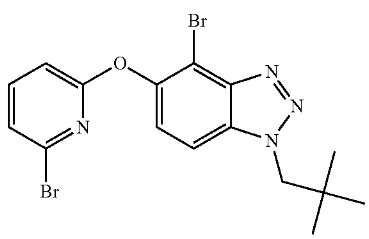 [SMILES: CC(C)(C)Cn1nnc2c(Br)c(Oc3cccc(Br)n3)ccc21] | 4-bromo-5-[(6-bromopyridin-2-yl)oxy]-1-(2,2-dimethylpropyl)-1H-benzotriazole | [M + H] calc. 441.0 obs. 441.0 |
| 149 | 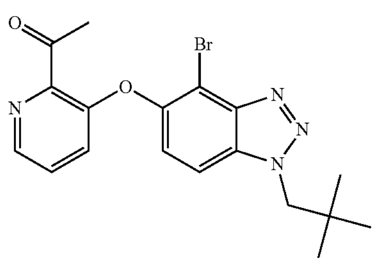 [SMILES: CC(=O)c1ncccc1Oc1ccc2c(nnn2CC(C)(C)C)c1Br] | 1-(3-{[4-bromo-1-(2,2-dimethylpropyl)-1H-benzotriazol-5-yl]oxy}pyridin-2-yl)ethanone | [M + H] calc. 403.1 obs. 403.1 |
| 150 | 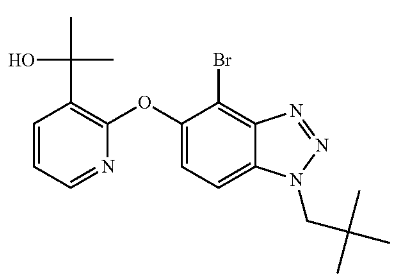 [SMILES: CC(C)(C)Cn1nnc2c(Br)c(Oc3ncccc3C(C)(C)O)ccc21] | 2-(2-{[4-bromo-1-(2,2-dimethylpropyl)-1H-benzotriazol-5-yl]oxy}pyridin-3-yl)propan-2-ol | [M + H] calc. 419.1 obs. 419.1 |

TABLE 1-continued

| Ex. | Structure | Name | LRMS or HRMS |
|---|---|---|---|
| 151 | 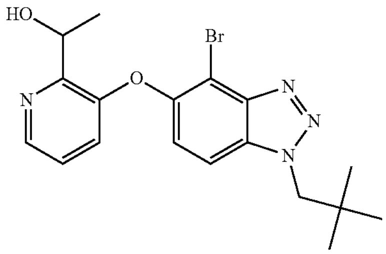 [SMILES: CC(O)c1ncccc1Oc1ccc2c(nnn2CC(C)(C)C)c1Br] | 1-(3-{[4-bromo-1-(2,2-dimethylpropyl)-1H-benzotriazol-5-yl]oxy}pyridin-2-yl)ethanol | [M + H] calc. 405.1 obs. 405.1 |
| 152 | 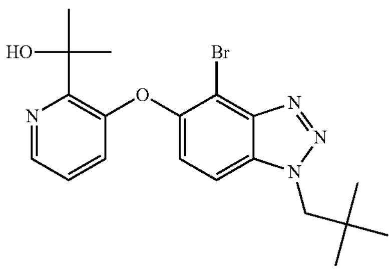 [SMILES: CC(C)(C)Cn1nnc2c(Br)c(Oc3cccnc3C(C)(C)O)ccc21] | 2-(3-{[4-bromo-1-(2,2-dimethylpropyl)-1H-benzotriazol-5-yl]oxy}pyridin-2-yl)propan-2-ol | [M + H] calc. 419.1 obs. 419.1 |
| 153 | 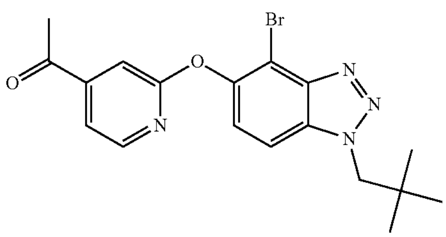 [SMILES: CC(=O)c1ccnc(Oc2ccc3c(nnn3CC(C)(C)C)c2Br)c1] | 1-(2-{[4-bromo-1-(2,2-dimethylpropyl)-1H-benzotriazol-5-yl]oxy}pyridin-4-yl)ethanone | [M + H] calc. 403.1 obs. 403.1 |
| 154 | 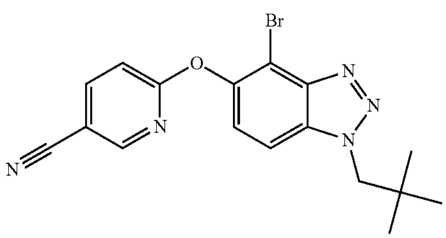 [SMILES: CC(C)(C)Cn1nnc2c(Br)c(Oc3ccc(C#N)cn3)ccc21] | 6-{[4-bromo-1-(2,2-dimethylpropyl)-1H-benzotriazol-5-yl]oxy}pyridine-3-carbonitrile | [M + H] calc. 386.1 obs. 386.0 |
| 155 | 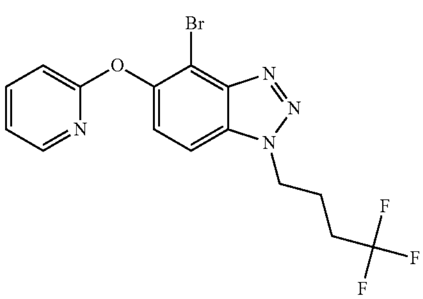 [SMILES: FC(F)(F)CCCn1nnc2c(Br)c(Oc3ccccn3)ccc21] | 4-bromo-5-(pyridin-2-yloxy)-1-(4,4,4-trifluorobutyl)-1H-benzotriazole | [M + H] calc. 401.1 obs. 401.0 |
| 156 | 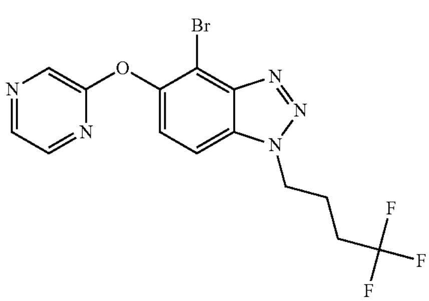 [SMILES: FC(F)(F)CCCn1nnc2c(Br)c(Oc3cnccn3)ccc21] | 4-bromo-5-(pyrazin-2-yloxy)-1-(4,4,4-trifluorobutyl)-1H-benzotriazole | [M + H] calc. 402.1 obs. 402.0 |

TABLE 1-continued

| Ex. | Structure | Name | LRMS or HRMS |
|---|---|---|---|
| 157 | 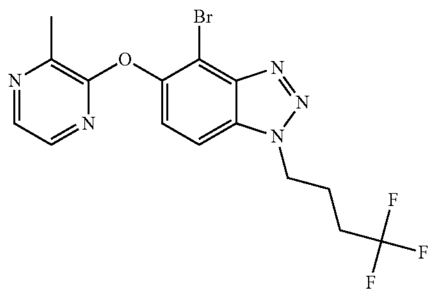 [SMILES: Cc1nccnc1Oc1ccc2c(nnn2CCCC(F)(F)F)c1Br] | 4-bromo-5-[(3-methylpyrazin-2-yl)oxy]-1-(4,4,4-trifluorobutyl)-1H-benzotriazole | [M + H] calc. 416.1 obs. 416.0 |
| 158 | 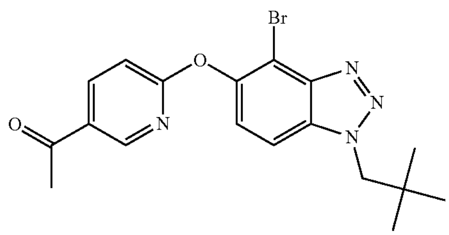 [SMILES: CC(=O)c1ccc(Oc2ccc3c(nnn3CC(C)(C)C)c2Br)nc1] | 1-(6-{[4-bromo-1-(2,2-dimethylpropyl)-1H-benzotriazol-5-yl]oxy}pyridin-3-yl)ethanone | [M + H] calc. 403.1 obs. 403.1 |
| 159 | 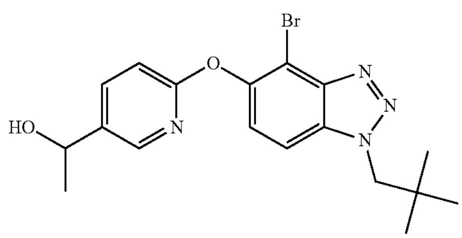 [SMILES: CC(O)c1ccc(Oc2ccc3c(nnn3CC(C)(C)C)c2Br)nc1] | 1-(6-{[4-bromo-1-(2,2-dimethylpropyl)-1H-benzotriazol-5-yl]oxy}pyridin-3-yl)ethanol | [M + H] calc. 405.1 obs. 405.1 |
| 160 | 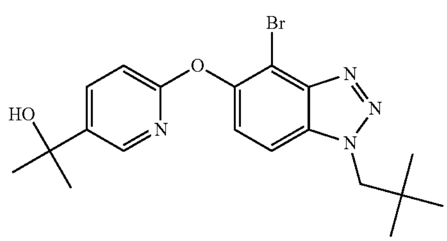 [SMILES: CC(C)(C)Cn1nnc2c(Br)c(Oc3ccc(C(C)(C)O)cn3)ccc21] | 2-(6-{[4-bromo-1-(2,2-dimethylpropyl)-1H-benzotriazol-5-yl]oxy}pyridin-3-yl)propan-2-ol | [M + H] calc. 419.1 obs. 419.1 |
| 161 | 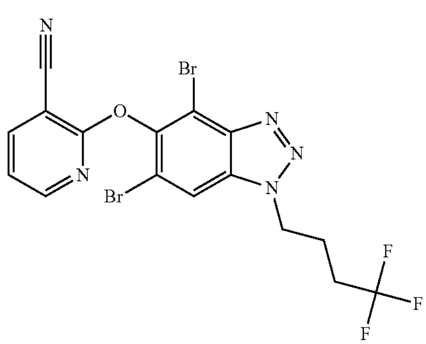 [SMILES: N#Cc1cccnc1Oc1c(Br)cc2c(nnn2CCCC(F)(F)F)c1Br] | 2-{[4,6-dibromo-1-(4,4,4-trifluorobutyl)-1H-benzotriazol-5-yl]oxy}pyridine-3-carbonitrile | [M + H] calc. 506.0 obs. 506.0 |

TABLE 1-continued

| Ex. | Structure | Name | LRMS or HRMS |
|---|---|---|---|
| 162 | 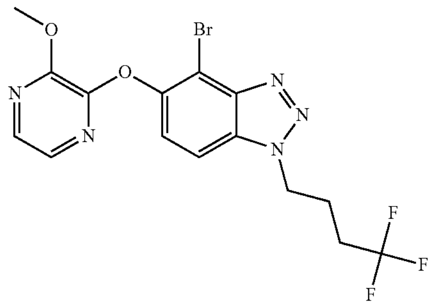 [SMILES: COc1nccnc1Oc1ccc2c(nnn2CCCC(F)(F)F)c1Br] | 4-bromo-5-[(3-methoxypyrazin-2-yl)oxy]-1-(4,4,4-trifluorobutyl)-1H-benzotriazole | [M + H] calc. 432.0 obs. 432.0 |
| 163 | 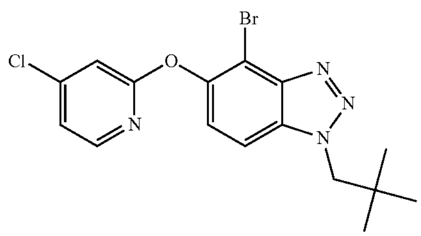 [SMILES: CC(C)(C)Cn1nnc2c(Br)c(Oc3cc(Cl)ccn3)ccc21] | 4-bromo-5-[(4-chloropyridin-2-yl)oxy]-1-(2,2-dimethylpropyl)-1H-benzotriazole | [M + H] calc. 395.0 obs. 395.0 |
| 164 | 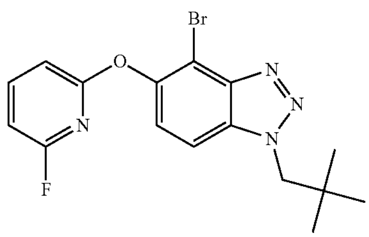 | 4-bromo-1-(2,2-dimethylpropyl)-5-[(6-fluoropyridin-2-yl)oxy]-1H-benzotriazole | [M + H] calc. 379.0 obs. 379.0 |
| 165 | 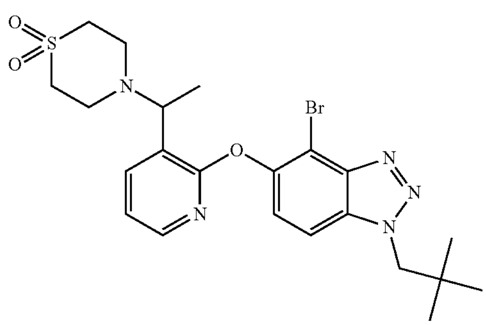 [SMILES: CC(c1cccnc1Oc1ccc2c(nnn2CC(C)(C)C)c1Br)N1CCS(=O)(=O)CC1] | 4-bromo-1-(2,2-dimethylpropyl)-5-({3-[1-(1,1-dioxidothio-morpholin-4-yl)ethyl]pyridin-2-yl}oxy)-1H-benzotriazole | [M + H] calc. 522.1 obs. 522.0 |
| 166 | 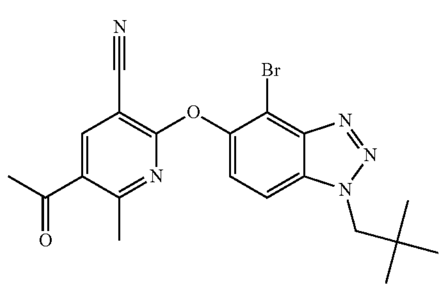 [SMILES: CC(=O)c1cc(C#N)c(Oc2ccc3c(nnn3CC(C)(C)C)c2Br)nc1C] | 5-acetyl-2-{[4-bromo-1-(2,2-dimethylpropyl)-1H-benzotriazol-5-yl]oxy}-6-methylpyridine-3-carbonitrile | [M + H] calc. 442.1 obs. 442.1 |

TABLE 1-continued

| Ex. | Structure | Name | LRMS or HRMS |
|---|---|---|---|
| 167 | 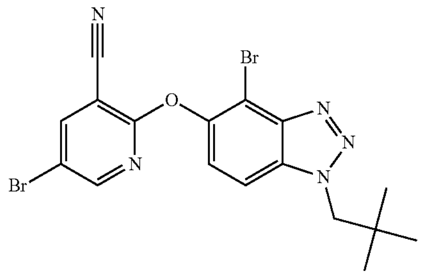 [SMILES: CC(C)(C)Cn1nnc2c(Br)c(Oc3ncc(Br)cc3C#N)ccc21] | 5-acetyl-2-{[4-bromo-1-(2,2-dimethylpropyl)-1H-benzotriazol-5-yl]oxy}-6-methylpyridine-3-carbonitrile | [M + H] calc. 464.0 obs. 464.0 |
| 168 | 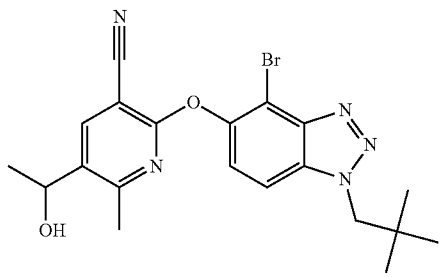 [SMILES: Cc1nc(Oc2ccc3c(nnn3CC(C)(C)C)c2Br)c(C#N)cc1C(C)O] | 2-{[4-bromo-1-(2,2-dimethylpropyl)-1H-benzotriazol-5-yl]oxy}-5-(1-hydroxyethyl)-6-methylpyridine-3-carbonitrile | [M + H] calc. 444.1 obs. 444.0 |
| 169 | 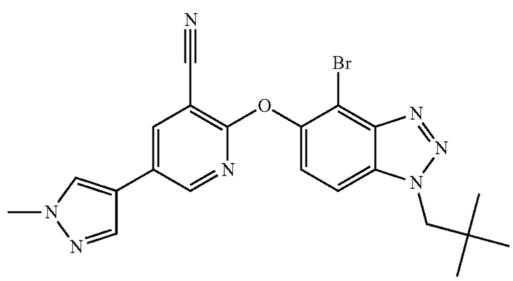 [SMILES: Cn1cc(-c2cnc(Oc3ccc4c(nnn4CC(C)(C)C)c3Br)c(C#N)c2)cn1] | 2-{[4-bromo-1-(2,2-dimethylpropyl)-1H-benzotriazol-5-yl]oxy}-5-(1-methyl-1H-pyrazol-4-yl)pyridine-3-carbonitrile | [M + H] calc. 466.1 obs. 466.1 |
| 170 | 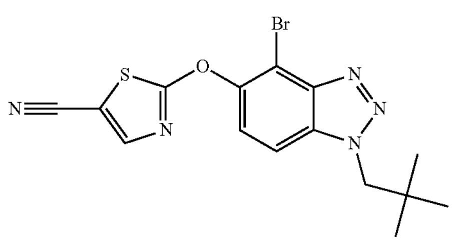 [SMILES: CC(C)(C)Cn1nnc2c(Br)c(Oc3ncc(C#N)s3)ccc21] | 2-{[4-bromo-1-(2,2-dimethylpropyl)-1H-benzotriazol-5-yl]oxy}-1,3-thiazole-5-carbonitrile | [M + H] calc. 392.0 obs. 392.0 |
| 171 | 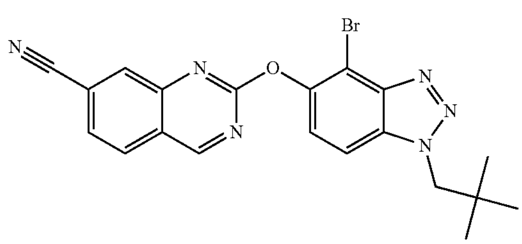 [SMILES: CC(C)(C)Cn1nnc2c(Br)c(Oc3ncc4ccc(C#N)cc4n3)ccc21] | 2-{[4-bromo-1-(2,2-dimethylpropyl)-1H-benzotriazol-5-yl]oxy}quinazoline-7-carbonitrile | [M + H] calc. 437.1 obs. 437.0 |
| 172 | 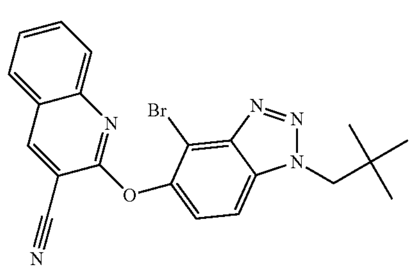 [SMILES: CC(C)(C)Cn1nnc2c(Br)c(Oc3nc4ccccc4cc3C#N)ccc21] | 2-{[4-bromo-1-(2,2-dimethylpropyl)-1H-benzotriazol-5-yl]oxy}quinoline-3-carbonitrile | [M + H] calc. 436.1 obs. 436.0 |

TABLE 1-continued

| Ex. | Structure | Name | LRMS or HRMS |
|---|---|---|---|
| 173 | 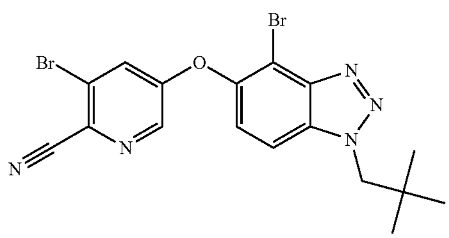 [SMILES: CC(C)(C)Cn1nnc2c(Br)c(Oc3cnc(C#N)c(Br)c3)ccc21] | 3-bromo-5-{[4-bromo-1-(2,2-dimethylpropyl)-1H-benzotriazol-5-yl]oxy}pyridine-2-carbonitrile | [M + H] calc. 466.0 obs. 465.9 |
| 174 | 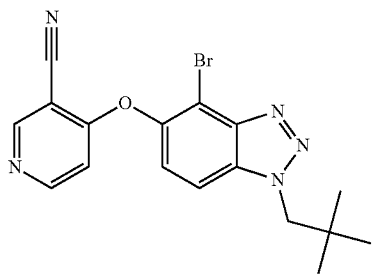 [SMILES: CC(C)(C)Cn1nnc2c(Br)c(Oc3ccncc3C#N)ccc21] | 4-{[4-bromo-1-(2,2-dimethylpropyl)-1H-benzotriazol-5-yl]oxy}pyridine-3-carbonitrile | [M + H] calc. 386.1 obs. 386.0 |
| 175 | 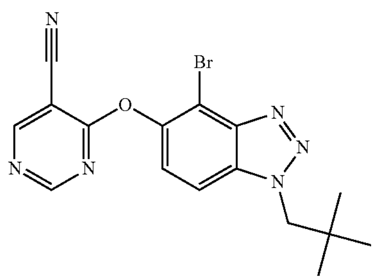 [SMILES: CC(C)(C)Cn1nnc2c(Br)c(Oc3ncncc3C#N)ccc21] | 4-{[4-bromo-1-(2,2-dimethylpropyl)-1H-benzotriazol-5-yl]oxy}pyrimidine-5-carbonitrile | [M + H] calc. 387.0 obs. 387.0 |
| 176 | 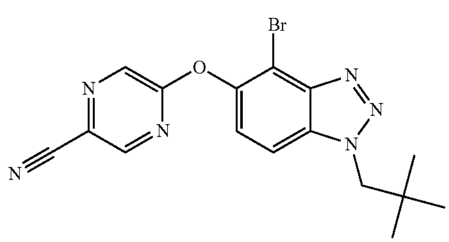 [SMILES: CC(C)(C)Cn1nnc2c(Br)c(Oc3cnc(C#N)cn3)ccc21] | 5-{[4-bromo-1-(2,2-dimethylpropyl)-1H-benzotriazol-5-yl]oxy}pyrazine-2-carbonitrile | [M + H] calc. 387.0 obs. 387.0 |
| 177 | 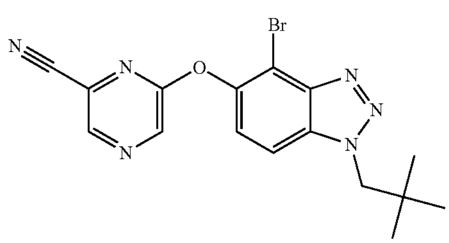 [SMILES: CC(C)(C)Cn1nnc2c(Br)c(Oc3cncc(C#N)n3)ccc21] | 6-{[4-bromo-1-(2,2-dimethylpropyl)-1H-benzotriazol-5-yl]oxy}pyrazine-2-carbonitrile | [M + H] calc. 387.0 obs. 387.0 |
| 178 | 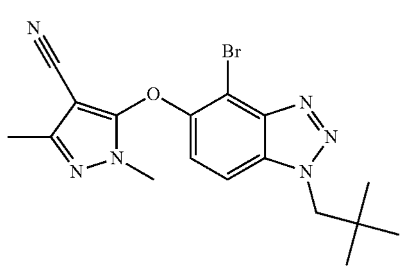 [SMILES: Cc1nn(C)c(Oc2ccc3c(nnn3CC(C)(C)C)c2Br)c1C#N] | 5-{[4-bromo-1-(2,2-dimethylpropyl)-1H-benzotriazol-5-yl]oxy}-1,3-dimethyl-1H-pyrazole-4-carbonitrile | [M + H] calc. 403.1 obs. 405.0 |

TABLE 1-continued

| Ex. | Structure | Name | LRMS or HRMS |
|---|---|---|---|
| 179 | 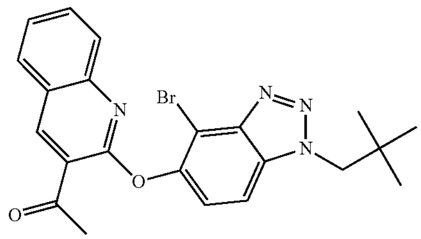 [SMILES: CC(=O)c1cc2ccccc2nc1Oc1ccc2c(nnn2CC(C)(C)C)c1Br] | 1-(2-{[4-bromo-1-(2,2-dimethylpropyl)-1H-benzotriazol-5-yl]oxy}quinolin-3-yl)ethanone | [M + H] calc. 453.1 obs. 453.0 |
| 180 | 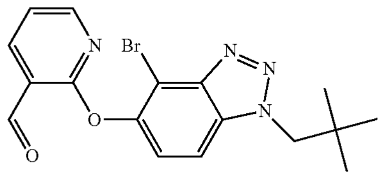 [SMILES: CC(C)(C)Cn1nnc2c(Br)c(Oc3ncccc3C=O)ccc21] | 2-{[4-bromo-1-(2,2-dimethylpropyl)-1H-benzotriazol-5-yl]oxy}pyridine-3-carbaldehyde | [M + H] calc. 389.1 obs. 389.0 |
| 181 | 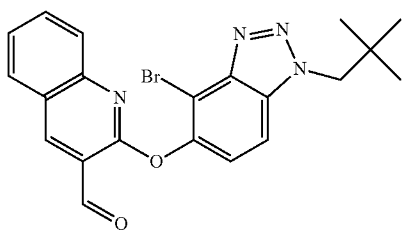 [SMILES: CC(C)(C)Cn1nnc2c(Br)c(Oc3nc4ccccc4cc3C=O)ccc21] | 2-{[4-bromo-1-(2,2-dimethylpropyl)-1H-benzotriazol-5-yl]oxy}quinoline-3-carbaldehyde | [M + H] calc. 439.1 obs. 439.0 |
| 182 | 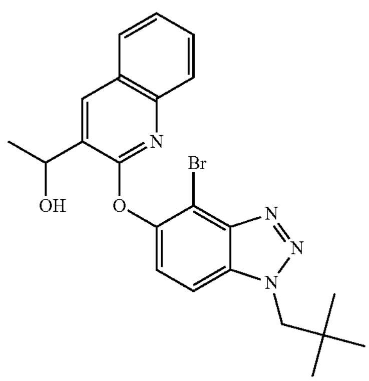 | 1-(2-{[4-bromo-1-(2,2-dimethylpropyl)-1H-benzotriazol-5-yl]oxy}quinolin-3-yl)ethanol | [M + H] calc. 455.1 obs. 455.0 |
| 183 | 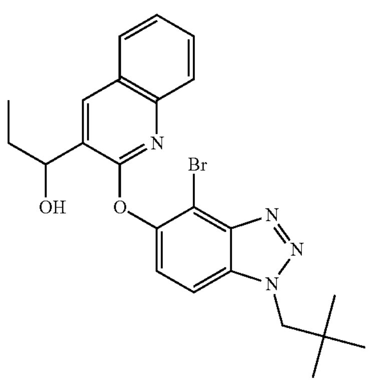 [SMILES: CCC(O)c1cc2ccccc2nc1Oc1ccc2c(nnn2CC(C)(C)C)c1Br] | 1-(2-{[4-bromo-1-(2,2-dimethylpropyl)-1H-benzotriazol-5-yl]oxy}quinolin-3-yl)propan-1-ol | [M + H] calc. 469.1 obs. 469.0 |

TABLE 1-continued

| Ex. | Structure | Name | LRMS or HRMS |
|---|---|---|---|
| 184 | 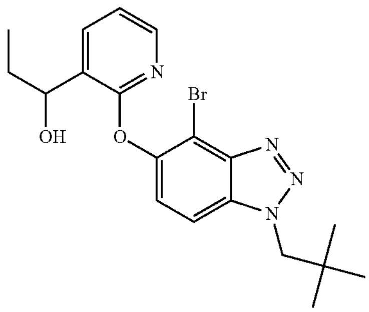 [SMILES: CCC(O)c1cccnc1Oc1ccc2c(nnn2CC(C)(C)C)c1Br] | 1-(2-{[4-bromo-1-(2,2-dimethylpropyl)-1H-benzotriazol-5-yl]oxy}pyridin-3-yl)propan-1-ol | [M + H] calc. 419.1 obs. 419.0 |
| 185 | 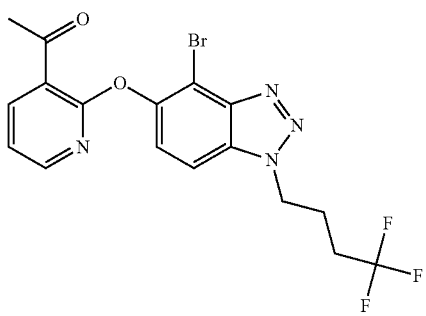 [SMILES: CC(=O)c1cccnc1Oc1ccc2c(nnn2CCCC(F)(F)F)c1Br] | 1-(2-{[4-bromo-1-(4,4,4-trifluorobutyl)-1H-benzotriazol-5-yl]oxy}pyridin-3-yl)ethanone | [M + H] calc. 443.0 obs. 443.0 |
| 186 | 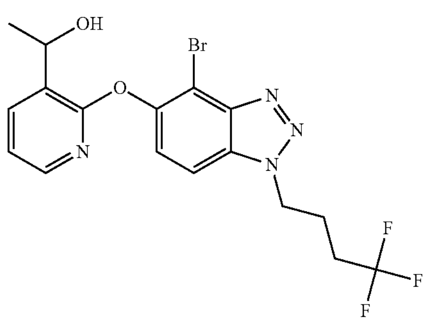 [SMILES: CC(O)c1cccnc1Oc1ccc2c(nnn2CCCC(F)(F)F)c1Br] | 1-(2-{[4-bromo-1-(4,4,4-trifluorobutyl)-1H-benzotriazol-5-yl]oxy}pyridin-3-yl)ethanol | [M + H] calc. 445.0 obs. 445.0 |
| 187 | 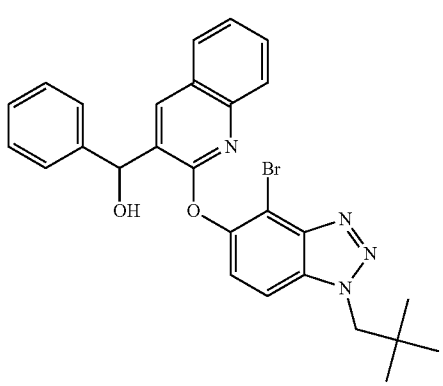 [SMILES: CC(C)(C)Cn1nnc2c(Br)c(Oc3nc4ccccc4cc3C(O)c3ccccc3)ccc21] | (2-{[4-bromo-1-(2,2-dimethylpropyl)-1H-benzotriazol-5-yl]oxy}quinolin-3-yl)(phenyl)methanol | [M + H] calc. 517.1 obs. 517.1 |

TABLE 1-continued

| Ex. | Structure | Name | LRMS or HRMS |
|---|---|---|---|
| 188 | 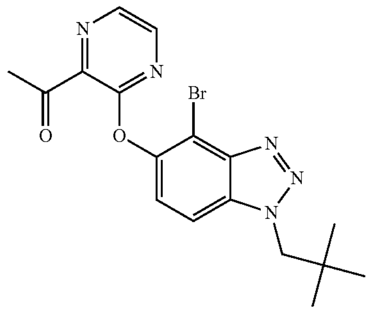 [SMILES: CC(=O)c1nccnc1Oc1ccc2c(nnn2CC(C)(C)C)c1Br] | 1-(3-{[4-bromo-1-(2,2-dimethylpropyl)-1H-benzotriazol-5-yl]oxy}pyrazin-2-yl)ethanone | [M + H] calc. 404.1 obs. 404.1 |
| 189 | 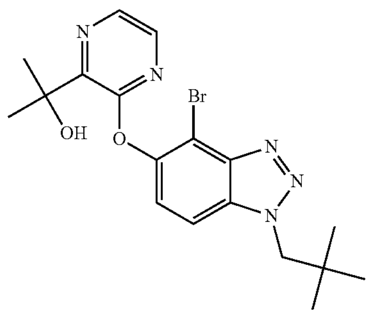 [SMILES: CC(C)(C)Cn1nnc2c(Br)c(Oc3nccnc3C(C)(C)O)ccc21] | 2-(3-{[4-bromo-1-(2,2-dimethylpropyl)-1H-benzotriazol-5-yl]oxy}pyrazin-2-yl)propan-2-ol | [M + H] calc. 420.1 obs. 420.1 |
| 190 | 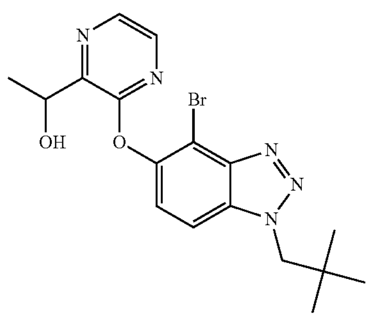 [SMILES: CC(O)c1nccnc1Oc1ccc2c(nnn2CC(C)(C)C)c1Br] | 1-(3-{[4-bromo-1-(2,2-dimethylpropyl)-1H-benzotriazol-5-yl]oxy}pyrazin-2-yl)ethanol | [M + H] calc. 406.1 obs. 406.1 |
| 191 | 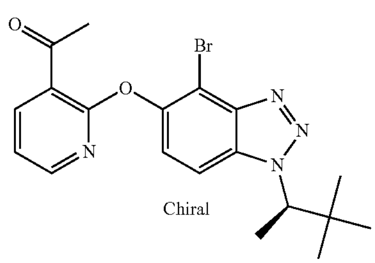 [SMILES: CC(=O)c1cccnc1Oc1ccc2c(nnn2[C@H](C)C(C)(C)C)c1Br] | 1-[2-({4-bromo-1-[(1R)-1,2,2-trimethylpropyl]-1H-benzotriazol-5-yl}oxy)pyridin-3-yl]ethanone | [M + H] calc. 417.1 obs. 417.0 |
| 192 | 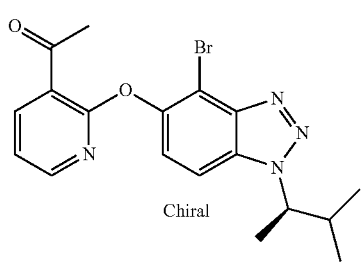 [SMILES: CC(=O)c1cccnc1Oc1ccc2c(nnn2[C@H](C)C(C)C)c1Br] | 1-[2-({4-bromo-1-[(1R)-1,2-dimethylpropyl]-1H-benzotriazol-5-yl}oxy)pyridin-3-yl]ethanone | [M + H] calc. 403.1 obs. 403.0 |

| Ex. | Structure | Name | LRMS or HRMS |
|---|---|---|---|
| 193 | (structure with HO, Br, benzotriazole, pyridine, Chiral label) | 1-[2-({4-bromo-1-[(1R)-1,2,2-trimethylpropyl]-1H-benzotriazol-5-yl}oxy)pyridin-3-yl]ethanol | [M + H] calc. 419.1 obs. 419.1 |

Example 194

4-Bromo-1-(cyclopropylmethyl)-5-({3-[(4,4-difluoropiperidin-1-yl)methyl]pyridin-2-yl}oxy)-1H-benzotriazole (194)

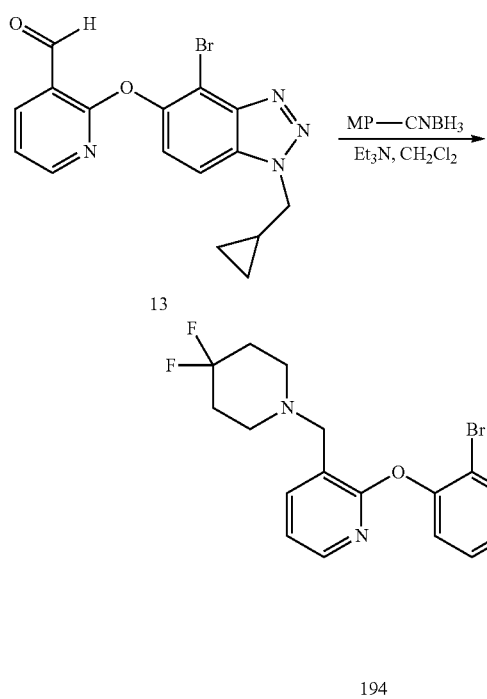

A mixture of 2-{[4-bromo-1-(cyclopropylmethyl)-1H-benzotriazol-5-yl]oxy}pyridine-3-carbaldehyde (13, 20 mg, 0.05 mmol, 1 equiv.) and 4,4-difluoropiperidine hydrochloride (13 mg, 0.08 mmol, 1.5 equiv) in dichloroethane (1 mL) was treated with triethylamine (14 uL, 0.10 mmol, 2 equiv) and stirred for 5 min. The mixture was treated with acetic acid (14 uL, 0.25 mmol, 5 equiv) and resin-bound MP-cyanoborohydride (50 mg, 2.08 mmol/g, 2 equiv.) and was irradiated at 110° C. in a microwave reactor for 20 min. The mixture was cooled to ambient temperature and partitioned between sodium bicarbonate (saturated aqueous, 50 mL) and ethyl acetate (3×30 mL). The combined organic layers were dried with sodium sulfate, filtered and concentrated in vacuo. The residue was purified via silica gel chromatography (100:0 to 30:70; hexanes:ethyl acetate) to afford 4-bromo-1-(cyclopropylmethyl)-5-({3-[(4,4-difluoropiperidin-1-yl)methyl]pyridin-2-yl}oxy)-1H-benzotriazole (194) as a white powder, $^1$H NMR (400 MHz, CDCl$_3$) δ 7.98 (dd, 1H, J=4.9, 2.0 Hz), 7.85 (br d, 1H, J=7.4 Hz), 7.56 (d, 1H, J=8.8 Hz), 7.36 (d, 1H, J=8.8 Hz), 7.04 (dd, 1H, J=7.5, 4.9 Hz), 4.52 (d, 2H, J=7.1 Hz), 3.85 (s, 2H), 2.73 (ap t, 4H, J=5.3 Hz), 2.11-2.01 (m, 4H), 1.47-1.37 (m, 1H), 0.71-0.67 (m, 2H), 0.54-0.50 (m, 2H) ppm. High resolution mass spectrometry (ES+) m/z=478.1062, [(M+H)$^+$ calculated for C$_{21}$H$_{23}$BrF$_2$N$_5$O: 478.1049].

Examples 195, 196 and 197

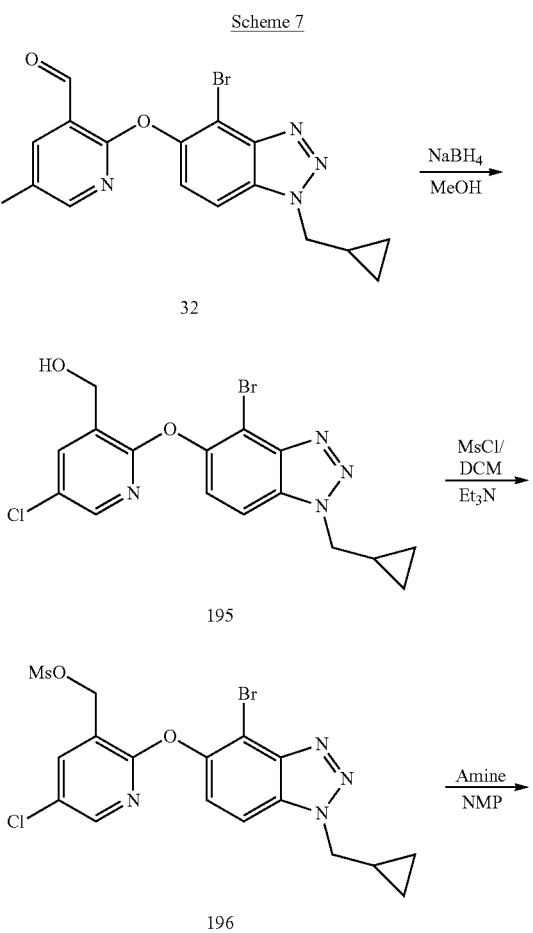

-continued

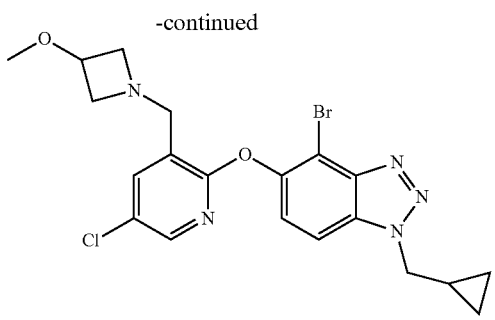

197

Step 1

(2-{[4-bromo-1-(cyclopropylmethyl)-1H-1,2,3-benzotriazol-5-yl]oxy}-5-chloropyridin-3-yl)methanol (195)

To a suspension of 2-{[4-bromo-1-(cyclopropylmethyl)-1H-benzotriazol-5-yl]oxy}-5-chloropyridine-3-carbaldehyde (32, 722 mg, 1.77 mmol, 1.0 equiv.) in EtOH (17.7 mL), was added slowly NaBH$_4$ (101 mg, 2.66 mmol, 2.0 equiv.). The reaction mixture was stirred at room temperature until LCMS showed only the desired product. The solvent was evaporated in vacuo. The mixture was partitioned between EtOAc and saturated aqueous NaHCO$_3$. The extracted organic layers were dried over Na$_2$SO$_4$, filtered and concentrated to give the crude product which was purified with normal phase silica gel chromatography (EtOAc/Hexane gradient from 0 to 100%) to obtain product 195 $^1$H NMR (400 MHz, CDCl$_3$): δ 7.89 (s, 2H); 7.57 (d, J=8.8 Hz, 1H); 7.38 (d, J=8.8 Hz, 1H); 4.96 (d, J=5.3 Hz, 2H); 4.52 (d, J=7.1 Hz, 2H); 1.43 (m, 1H); 0.69 (m, 2H); 0.52 (m, 2H). LRMS m/z (M+H) 408.9 and 410.9 found, 408.0 and 410.0 required.

Step 2

(2-{[4-bromo-1-(cyclopropylmethyl)-1H-1,2,3-benzotriazol-5-yl]oxy}pyridin-3-yl)methyl methanesulfonate (196)

(2-{[4-bromo-1-(cyclopropylmethyl)-1H-1,2,3-benzotriazol-5-yl]oxy}pyridin-3-yl)methanol (195) (1 g, 2.62 mmol, 1.0 equiv.) and Et$_3$N (1.1 ml, 7.85 mmol, 3.0 equiv.) in DCM (13 ml) were cooled to 0° C., followed by MsCl (265 ul, 3.40 mmol, 1.3 equiv.), then stirred @ 0° C. for 1 hour. The reaction mixture then quenched with NaHCO$_3$(sat) and extracted with DCM (2×40 ml). The combined DCM layer was washed with brine and dried over Na$_2$SO$_4$, filtered and concentrated down solvent. LRMS m/z (M+H) 486.8 and 488.8 found, 487.0 and 489.0 required.

Step 3

4-bromo-5-({5-chloro-3-[(3-methoxyazetidin-1-yl)methyl]pyridin-2-yl}oxy)-1-(cyclopropylmethyl)-1H-1,2,3-benzotriazole (197)

(2-{[4-bromo-1-(cyclopropylmethyl)-1H-1,2,3-benzotriazol-5-yl]oxy}pyridin-3-yl)methyl methanesulfonate (196) (20 mg, 0.04 mmol, 1.0 equiv.), 3-methoxyazetidine (7.14 mg, 0.082 mmol, 2.0 equiv.) and Hunig's base (71.6 ul, 0.41 mmol, 10.0 equiv.) in NMP (1 ml) was stirred at 25° C. overnight. The reaction mixture was filtered and was purified by reverse phase HPLC (H$_2$O/CH$_3$CN gradient w/0.1% TFA present) to afford product 197. $^1$H NMR (400 MHz, CDCl$_3$): δ 7.86 (d, J=2.6 Hz, 1H); 7.78 (d, J=2.6 Hz, 1H); 7.56 (d, J=8.8 Hz, 1H); 7.35 (d, J=8.8 Hz, 1H); 4.52 (d, J=7.1 Hz, 2H); 4.18-4.10 (m, 1H); 3.90 (s, 2H); 3.78 (t, J=6.8 Hz, 2H); 3.30 (s, 3H); 3.17 (t, J=6.6 Hz, 2H); 1.47-1.39 (m, 1H); 0.72-0.67 (m, 3 H); 0.53 (m, 2H). LRMS m/z (M+H) 477.8 and 479.8 found, 478.1 and 480.1 required.

Example 198

Scheme 8

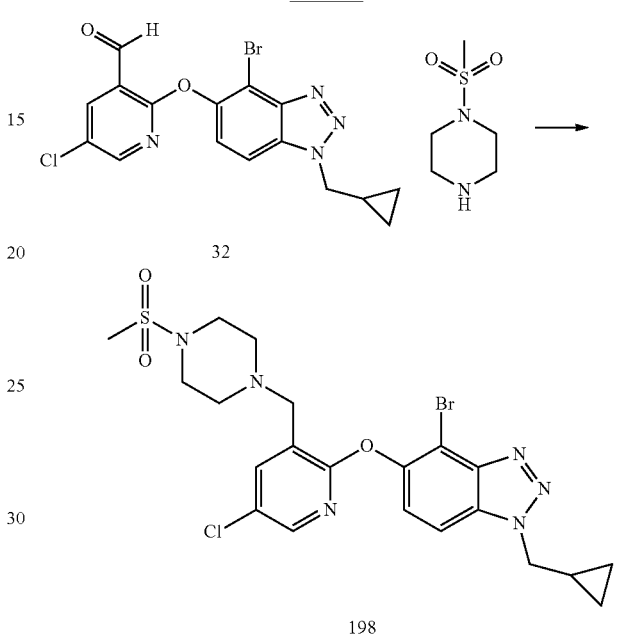

4-bromo-5-[(5-chloro-3-{[4-(methylsulfonyl)piperazin-1-yl]methyl}pyridin-2-yl)oxy]-1-(cyclopropylmethyl)-1H-benzotriazole (198)

2-{[4-bromo-1-(cyclopropylmethyl)-1H-benzotriazol-5-yl]oxy}-5-chloropyridine-3-carbaldehyde (32, 2.60 g, 6.38 mmol) was dissolved in anhydrous dichloroethane (63.8 mL, 0.1M) and treated with 1-(methylsulfonyl)piperazine (2.10 g, 12.8 mmol, 2 equiv.) and acetic acid (3.65 mL, 63.8 mmol, 10 equiv.). After 30 minutes the solution formed a thick suspension and was treated with sodium triacetoxyborohydride (1.76 g, 8.29 mmol, 1.3 equiv) in small portions over 1 hour. After completion of this addition, the reaction was allowed to stir an additional 2 h at ambient temperature. Upon completion as judged by TLC and LCMS, the reaction was quenched by the slow addition of water (20 mL) and NaHCO$_3$. The mixture was extracted 3× with dichloromethane (3×30 mL), and the combined organic layers were dried over MgSO4. The crude mixture was purified using flash column chromatography (Redisep SiO$_2$, 80 g, 0-100% EtOAc/hexanes) to provide pure 198: $^1$H NMR (300 MHz, CDCl$_3$) δ 7.89 (d, 1H, J=2.5 Hz), 7.84 (d, 1H, J=2.5 Hz), 7.56 (d, 1H, J=8.8 Hz), 7.33 (d, 1H, 8.8 Hz), 4.53 (d, 2H, J=7.1 Hz), 3.82 (s, 2H), 3.33 (m, 4H), 2.83 (s, 3H), 2.74 (m, 4H), 1.41 (m, 1H), 0.69 (m, 2H), 0.52 (dd, 2H, J=10.8, 5.1 Hz, 2H). LRMS m/z (M+H) 556.9 found, 556.9 required.

The following compounds were prepared according to the general procedures described above. The starting materials are either commercially available, known in the literature or may be prepared from commercially available reagents using conventional reactions well known in the art.

TABLE 2

| Ex. | STRUCTURE | NAME | HRMS/LRMS |
|---|---|---|---|
| 199 | 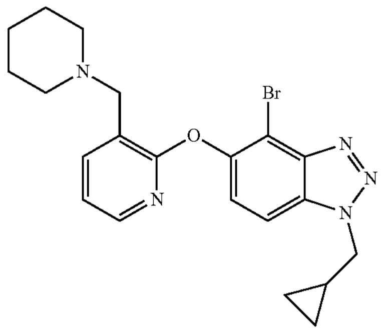 [SMILES: Brc1c(Oc2ncccc2CN2CCCCC2)ccc2c1nnn2CC1CC1] | 4-bromo-1-(cyclopropylmethyl)-5-{[3-(piperidin-1-ylmethyl)pyridin-2-yl]oxy}-1H-benzotriazole | [M + H] calc. 442.1237 obs. 442.1246 |
| 200 | 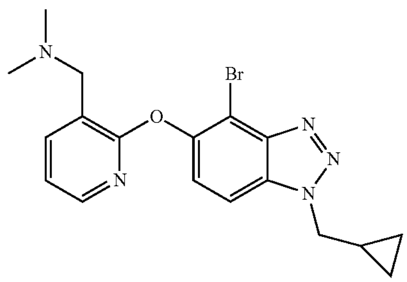 [SMILES: CN(C)Cc1cccnc1Oc1ccc2c(nnn2CC2CC2)c1Br] | 1-(2-{[4-bromo-1-(cyclopropylmethyl)-1H-benzotriazol-5-yl]oxy}pyridin-3-yl)-N,N-dimethylmethanamine | [M + H] calc. 402.1 obs. 402.0 |
| 201 | 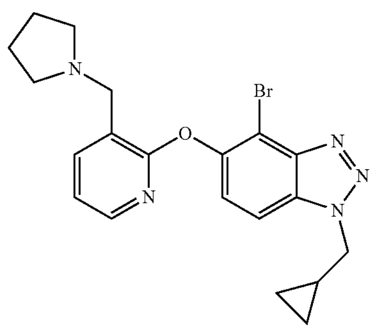 [SMILES: Brc1c(Oc2ncccc2CN2CCCC2)ccc2c1nnn2CC1CC1] | 4-bromo-1-(cyclopropylmethyl)-5-{[3-(pyrrolidin-1-ylmethyl)pyridin-2-yl]oxy}-1H-benzotriazole | [M + H] calc. 428.1080 obs. 428.1087 |
| 202 | 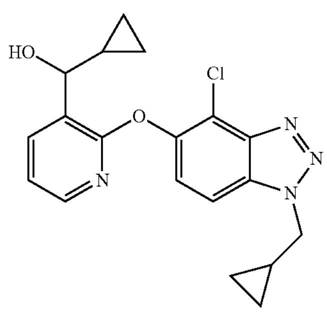 [SMILES: OC(c1cccnc1Oc1ccc2c(nnn2CC2CC2)c1Cl)C1CC1] | (2-{[4-chloro-1-(cyclopropylmethyl)-1H-benzotriazol-5-yl]oxy}pyridin-3-yl)(cyclopropyl)methanol | [M + H] calc. 371.1269 obs. 371.1273 |
| 203 | 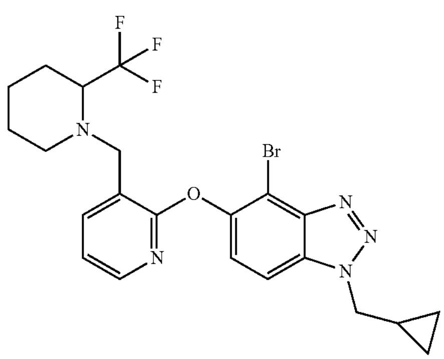 [SMILES: FC(F)(F)C1CCCCN1Cc1cccnc1Oc1ccc2c(nnn2CC2CC2)c1Br] | 4-bromo-1-(cyclopropylmethyl)-5-[(3-{[2-(trifluoromethyl)piperidin-1-yl]methyl}pyridin-2-yl)oxy]-1H-benzotriazole | [M + H] calc. 510.1111 obs. 510.1128 |

TABLE 2-continued

| Ex. | STRUCTURE | NAME | HRMS/LRMS |
|---|---|---|---|
| 204 | 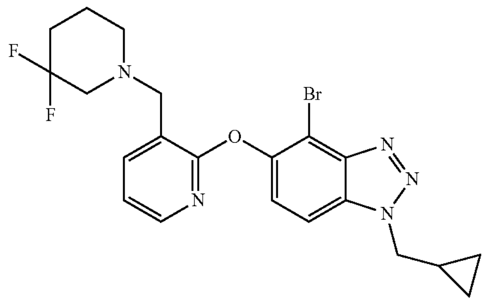 [SMILES: FC1(F)CCCN(Cc2cccnc2Oc2ccc3c(nnn3CC3CC3)c2Br)C1] | 4-bromo-1-(cyclopropylmethyl)-5-({3-[(3,3-difluoropiperidin-1-yl)methyl]pyridin-2-yl}oxy)-1H-benzotriazole | [M + H] calc. 478.1049 obs. 478.1059 |
| 205 | 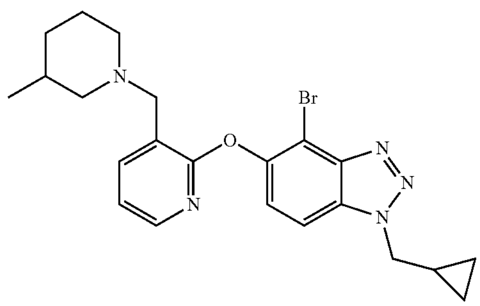 [SMILES: CC1CCCN(Cc2cccnc2Oc2ccc3c(nnn3CC3CC3)c2Br)C1] | 4-bromo-1-(cyclopropylmethyl)-5-({3-[(3-methylpiperidin-1-yl)methyl]pyridin-2-yl}oxy)-1H-benzotriazole | [M + H] calc. 456.1394 obs. 456.1397 |
| 205a | 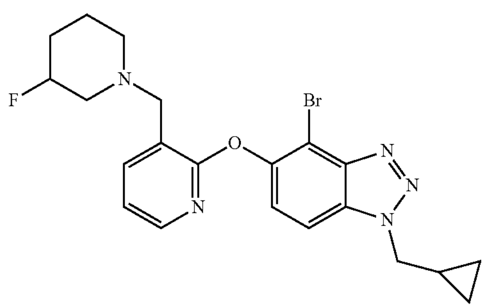 [SMILES: FC1CCCN(Cc2cccnc2Oc2ccc3c(nnn3CC3CC3)c2Br)C1] | 4-bromo-1-(cyclopropylmethyl)-5-({3-[(3-fluoropiperidin-1-yl)methyl]pyridin-2-yl}oxy)-1H-benzotriazole | [M + H] calc. 460.1143 obs. 460.1151 |
| 206 | 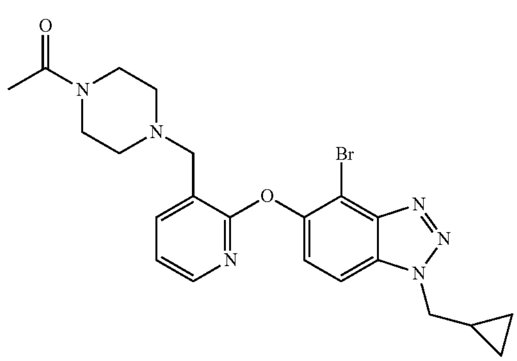 [SMILES: CC(=O)N1CCN(Cc2cccnc2Oc2ccc3c(nnn3CC3CC3)c2Br)CC1] | 5-({3-[(4-acetylpiperazin-1-yl)methyl]pyridin-2-yl}oxy)-4-bromo-1-(cyclopropylmethyl)-1H-benzotriazole | [M + H] calc. 485.1295 obs. 485.1304 |

TABLE 2-continued

| Ex. | STRUCTURE | NAME | HRMS/LRMS |
|---|---|---|---|
| 207 | 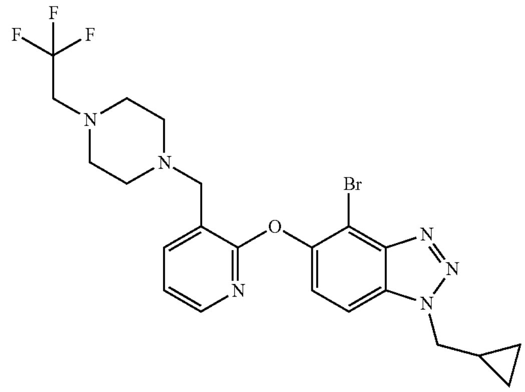 [SMILES: FC(F)(F)CN1CCN(Cc2cccnc2Oc2ccc3c(nnn3CC3CC3)c2Br)CC1] | 4-bromo-1-(cyclopropylmethyl)-5-[(3-{[4-(2,2,2-trifluoroethyl)piperazin-1-yl]methyl}pyridin-2-yl)oxy]-1H-benzotriazole | [M + H] calc. 525.1220 obs. 525.1237 |
| 208 | 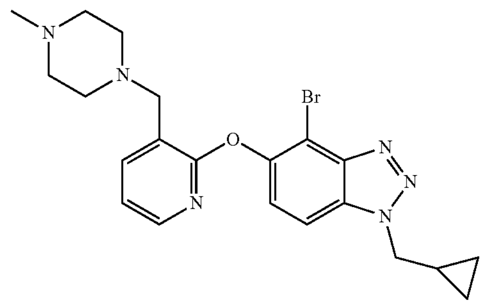 [SMILES: CN1CCN(Cc2cccnc2Oc2ccc3c(nnn3CC3CC3)c2Br)CC1] | 4-bromo-1-(cyclopropylmethyl)-5-({3-[(4-methylpiperazin-1-yl)methyl]pyridin-2-yl}oxy)-1H-benzotriazole | [M + H] calc. 457.1346 obs. 457.1351 |
| 209 | 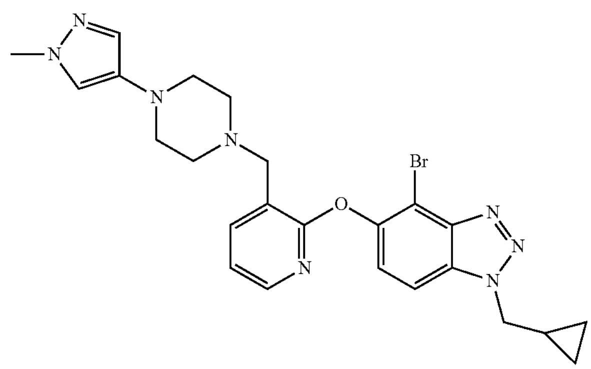 [SMILES: Cn1cc(N2CCN(Cc3cccnc3Oc3ccc4c(nnn4CC4CC4)c3Br)CC2)cn1] | 4-bromo-1-(cyclopropylmethyl)-5-[(3-{[4-(1-methyl-1H-pyrazol-4-yl)piperazin-1-yl]methyl}pyridin-2-yl)oxy]-1H-benzotriazole | [M + H] calc. 523.1564 obs. 523.1570 |
| 210 | 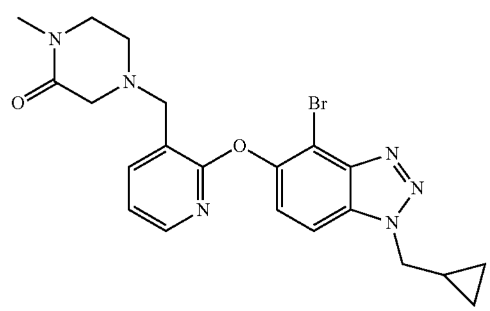 [SMILES: CN1CCN(Cc2cccnc2Oc2ccc3c(nnn3CC3CC3)c2Br)CC1=O] | 4-[(2-{[4-bromo-1-(cyclopropylmethyl)-1H-benzotriazol-5-yl]oxy}pyridin-3-yl)methyl]-1-methylpiperazin-2-one | [M + H] calc. 471.1139 obs. 471.1155 |

TABLE 2-continued

| Ex. | STRUCTURE | NAME | HRMS/LRMS |
|---|---|---|---|
| 211 | 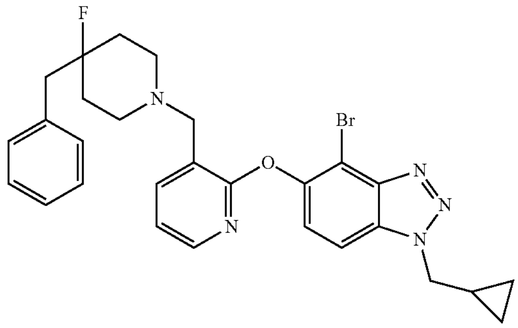 [SMILES: FC1(Cc2ccccc2)CCN(Cc2cccnc2Oc2ccc3c(nnn3CC3CC3)c2Br)CC1] | 5-({3-[(4-benzyl-4-fluoropiperidin-1-yl)methyl]pyridin-2-yl}oxy)-4-bromo-1-(cyclopropylmethyl)-1H-benzotriazole | $C_{28}H_{30}BrFN_5O$<br>[M + H]<br>calc. 550.1612<br>obs. 550.1625 |
| 212 | 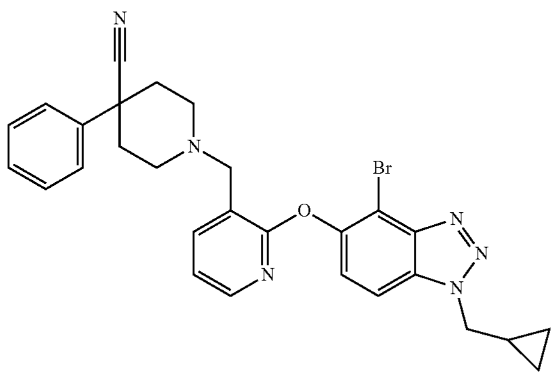 [SMILES: N#CC1(c2ccccc2)CCN(Cc2cccnc2Oc2ccc3c(nnn3CC3CC3)c2Br)CC1] | 1-[(2-{[4-bromo-1-(cyclopropylmethyl)-1H-benzotriazol-5-yl]oxy}pyridin-3-yl)methyl]-4-phenylpiperidine-4-carbonitrile | [M + H]<br>calc. 543.1502<br>obs. 543.1516 |
| 213 | 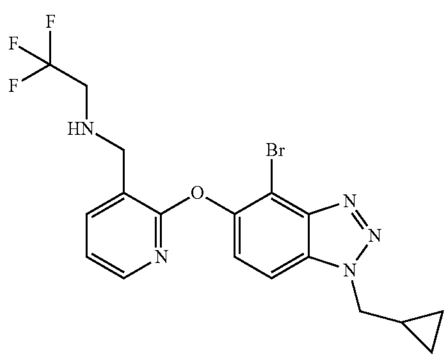 [SMILES: FC(F)(F)CNCc1cccnc1Oc1ccc2c(nnn2CC2CC2)c1Br] | N-[(2-{[4-bromo-1-(cyclopropylmethyl)-1H-benzotriazol-5-yl]oxy}pyridin-3-yl)methyl]-2,2,2-trifluoroethanamine | [M + H]<br>calc. 456.0641<br>obs. 456.0654 |
| 214 | 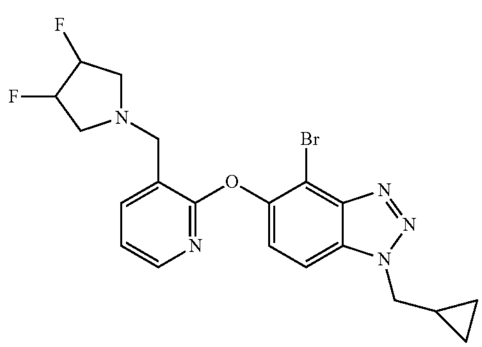 [SMILES: FC1CN(Cc2cccnc2Oc2ccc3c(nnn3CC3CC3)c2Br)CC1F] | 4-bromo-1-(cyclopropylmethyl)-5-({3-[(3,4-difluoropyrrolidin-1-yl)methyl]pyridin-2-yl}oxy)-1H-benzotriazole | [M + H]<br>calc. 464.0892<br>obs. 464.0898 |

TABLE 2-continued

| Ex. | STRUCTURE | NAME | HRMS/LRMS |
|---|---|---|---|
| 215 | 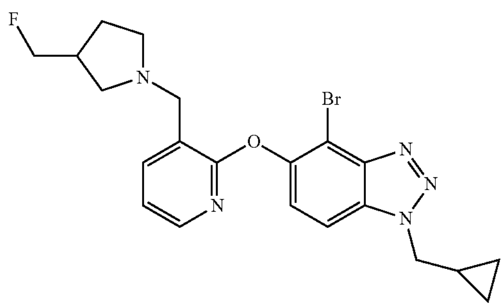 [SMILES: FCC1CCN(Cc2cccnc2Oc2ccc3c(nnn3CC3CC3)c2Br)C1] | 4-bromo-1-(cyclopropylmethyl)-5-[(3-{[3-(fluoromethyl)pyrrolidin-1-yl]methyl}pyridin-2-yl)oxy]-1H-benzotriazole | [M + H] calc. 460.1143 obs. 460.1151 |
| 216 | 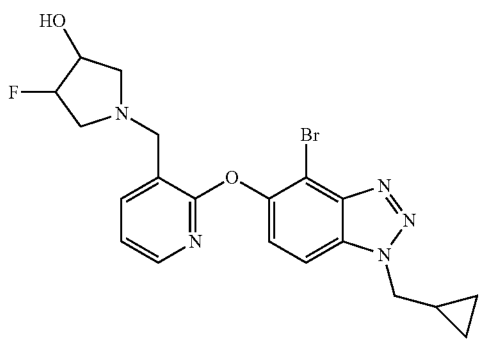 [SMILES: OC1CN(Cc2cccnc2Oc2ccc3c(nnn3CC3CC3)c2Br)CC1F] | 1-[(2-{[4-bromo-1-(cyclopropylmethyl)-1H-benzotriazol-5-yl]oxy}pyridin-3-yl)methyl]-4-fluoropyrrolidin-3-ol | [M + H] calc. 462.0935 obs. 462.0945 |
| 217 | 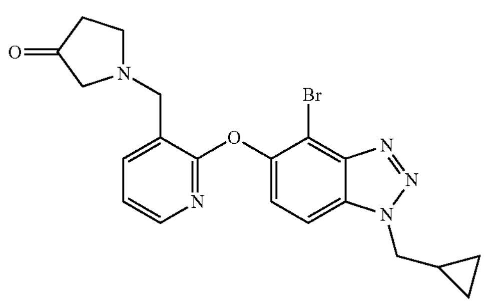 [SMILES: O=C1CCN(Cc2cccnc2Oc2ccc3c(nnn3CC3CC3)c2Br)C1] | 1-[(2-{[4-bromo-1-(cyclopropylmethyl)-1H-benzotriazol-5-yl]oxy}pyridin-3-yl)methyl]pyrrolidin-3-one | $C_{20}H_{21}BrN_5O_2$ [M + H] calc. 442.0873 obs. 442.0877 |
| 218 | 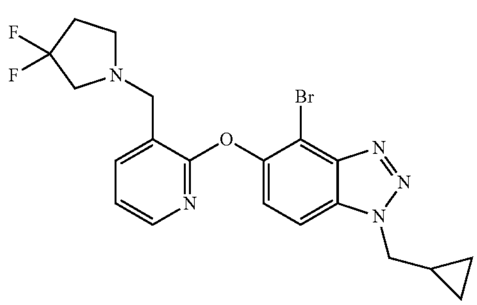 [SMILES: FC1(F)CCN(Cc2cccnc2Oc2ccc3c(nnn3CC3CC3)c2Br)C1] | 4-bromo-1-(cyclopropylmethyl)-5-({3-[(3,3-difluoropyrrolidin-1-yl)methyl]pyridin-2-yl}oxy)-1H-benzotriazole | [M + H] calc. 464.0892 obs. 464.0898 |
| 219 | 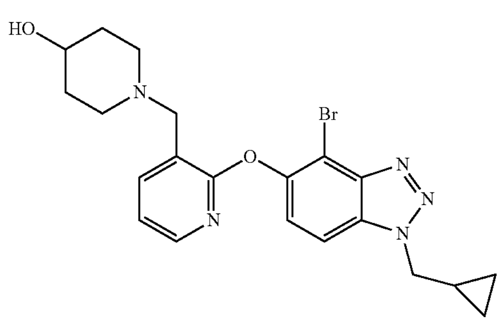 [SMILES: OC1CCN(Cc2cccnc2Oc2ccc3c(nnn3CC3CC3)c2Br)CC1] | 1-[(2-{[4-bromo-1-(cyclopropylmethyl)-1H-benzotriazol-5-yl]oxy}pyridin-3-yl)methyl]piperidin-4-ol | [M + H] calc. 458.1186 obs. 458.1189 |

TABLE 2-continued

| Ex. | STRUCTURE | NAME | HRMS/LRMS |
|---|---|---|---|
| 220 | 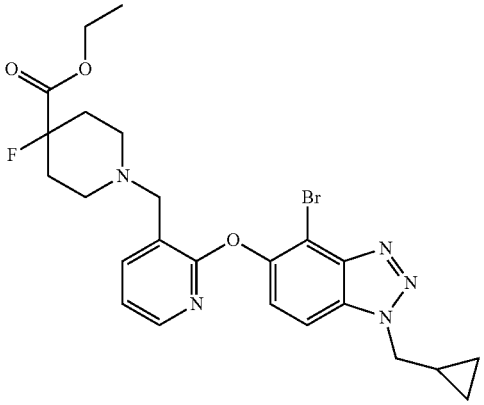 [SMILES: CCOC(=O)C1(F)CCN(Cc2cccnc2Oc2ccc3c(nnn3CC3CC3)c2Br)CC1] | ethyl 1-[(2-{[4-bromo-1-(cyclopropylmethyl)-1H-benzotriazol-5-yl]oxy}pyridin-3-yl)methyl]-4-fluoropiperidine-4-carboxylate | [M + H] calc. 532.1354 obs. 532.1365 |
| 221 | 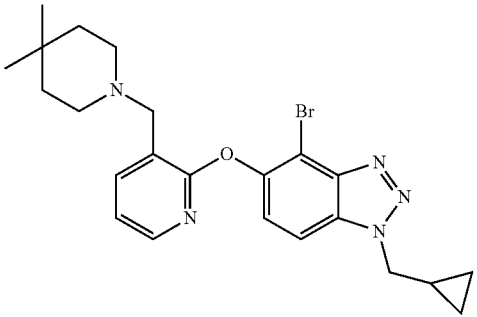 [SMILES: CC1(C)CCN(Cc2cccnc2Oc2ccc3c(nnn3CC3CC3)c2Br)CC1] | 4-bromo-1-(cyclopropylmethyl)-5-({3-[(4,4-dimethylpiperidin-1-yl)methyl]pyridin-2-yl}oxy)-1H-benzotriazole | [M + H] calc. 470.1550 obs. 470.1555 |
| 222 | 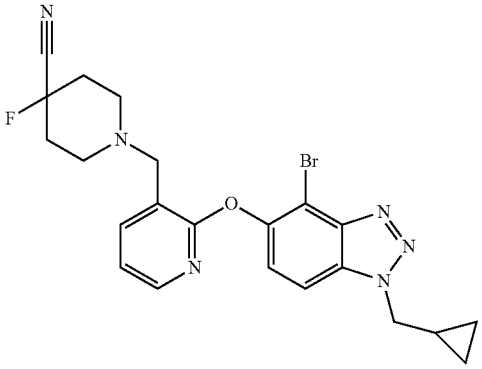 [SMILES: N#CC1(F)CCN(Cc2cccnc2Oc2ccc3c(nnn3CC3CC3)c2Br)CC1] | 1-[(2-{[4-bromo-1-(cyclopropylmethyl)-1H-benzotriazol-5-yl]oxy}pyridin-3-yl)methyl]-4-fluoropiperidine-4-carbonitrile | [M + H] calc. 485.1095 obs. 485.1104 |
| 223 | 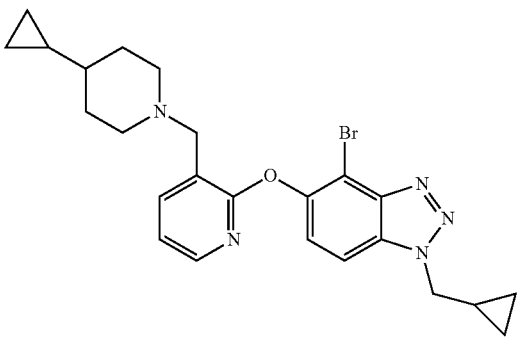 [SMILES: Brc1c(Oc2ncccc2CN2CCC(C3CC3)CC2)ccc2c1nnn2CC1CC1] | 4-bromo-1-(cyclopropylmethyl)-5-({3-[(4-cyclopropylpiperidin-1-yl)methyl]pyridin-2-yl}oxy)-1H-benzotriazole | $C_{24}H_{29}BrN_5O$ [M + H] calc. 482.1550 obs. 482.1559 |

TABLE 2-continued

| Ex. | STRUCTURE | NAME | HRMS/LRMS |
|---|---|---|---|
| 224 | 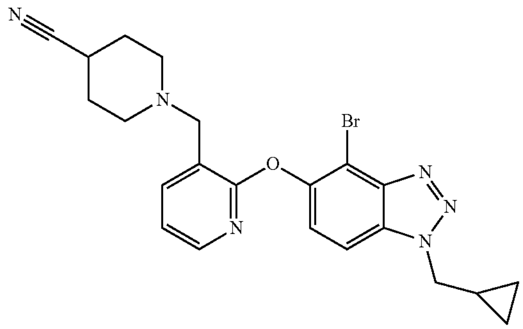 [SMILES: N#CC1CCN(Cc2cccnc2Oc2ccc3c(nnn3CC3CC3)c2Br)CC1] | 1-[(2-{[4-bromo-1-(cyclopropylmethyl)-1H-benzotriazol-5-yl]oxy}pyridin-3-yl)methyl]piperidine-4-carbonitrile | [M + H] calc. 467.1189 obs. 467.1207 |
| 225 | 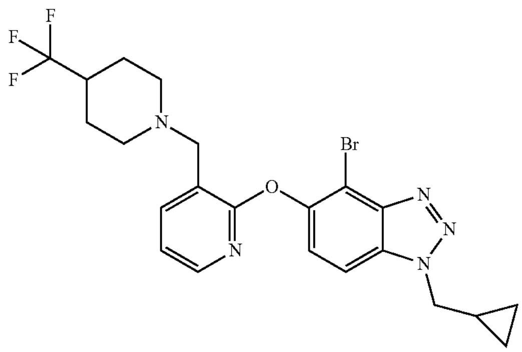 [SMILES: FC(F)(F)C1CCN(Cc2cccnc2Oc2ccc3c(nnn3CC3CC3)c2Br)CC1] | 4-bromo-1-(cyclopropylmethyl)-5-[(3-{[4-(trifluoromethyl)piperidin-1-yl]methyl}pyridin-2-yl)oxy]-1H-benzotriazole | [M + H] calc. 510.1111 obs. 510.1126 |
| 226 | 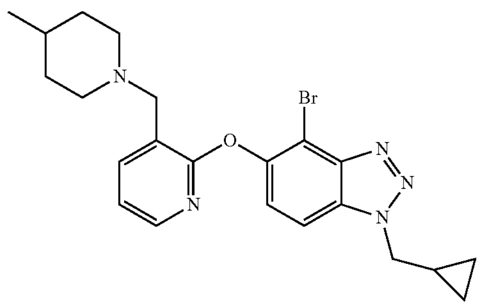 [SMILES: CC1CCN(Cc2cccnc2Oc2ccc3c(nnn3CC3CC3)c2Br)CC1] | 4-bromo-1-(cyclopropylmethyl)-5-({3-[(4-methylpiperidin-1-yl)methyl]pyridin-2-yl}oxy)-1H-benzotriazole | [M + H] calc. 456.1394 obs. 456.1402 |
| 227 | 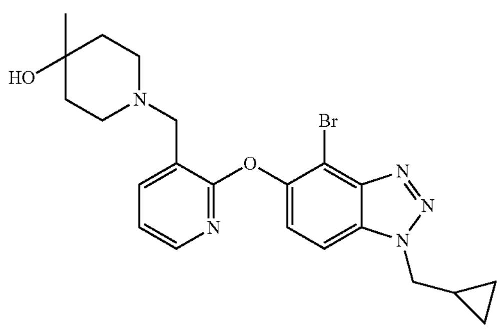 [SMILES: CC1(O)CCN(Cc2cccnc2Oc2ccc3c(nnn3CC3CC3)c2Br)CC1] | 1-[(2-{[4-bromo-1-(cyclopropylmethyl)-1H-benzotriazol-5-yl]oxy}pyridin-3-yl)methyl]-4-methylpiperidin-4-ol | [M + H] calc. 472.1343 obs. 472.1350 |
| 228 | 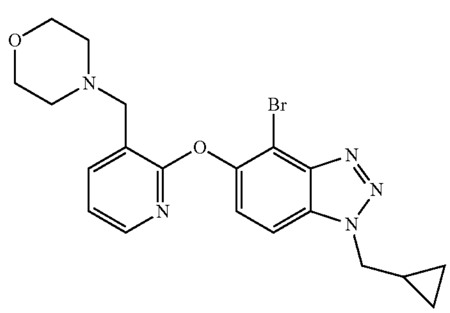 [SMILES: Brc1c(Oc2ncccc2CN2CCOCC2)ccc2c1nnn2CC1CC1] | 4-bromo-1-(cyclopropylmethyl)-5-{[3-(morpholin-4-ylmethyl)pyridin-2-yl]oxy}-1H-benzotriazole | [M + H] calc. 444.1030 obs. 444.1035 |

TABLE 2-continued

| Ex. | STRUCTURE | NAME | HRMS/LRMS |
|---|---|---|---|
| 229 | 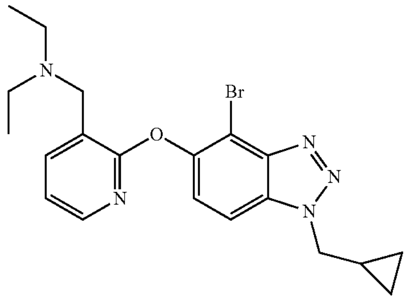 [SMILES: CCN(CC)Cc1cccnc1Oc1ccc2c(nnn2CC2CC2)c1Br] | N-[(2-{[4-bromo-1-(cyclopropylmethyl)-1H-benzotriazol-5-yl]oxy}pyridin-3-yl)methyl]-N-ethylethanamine | [M + H]<br>calc. 430.1237<br>obs. 430.1240 |
| 230 | 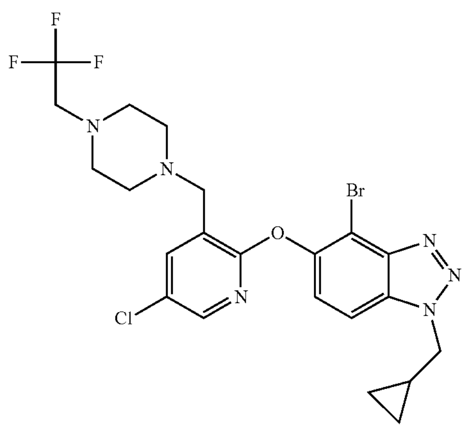 [SMILES: FC(F)(F)CN1CCN(Cc2cc(Cl)cnc2Oc2ccc3c(nnn3CC3CC3)c2Br)CC1] | 4-bromo-5-[(5-chloro-3-{[4-(2,2,2-trifluoroethyl)piperazin-1-yl]methyl}pyridin-2-yl)oxy]-1-(cyclopropylmethyl)-1H-benzotriazole | [M + H]<br>calc. 559.0830<br>obs. 559.0826 |
| 231 | 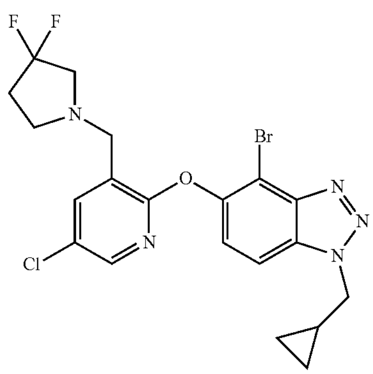 [SMILES: FC1(F)CCN(Cc2cc(Cl)cnc2Oc2ccc3c(nnn3CC3CC3)c2Br)C1] | 4-bromo-5-({5-chloro-3-[(3,3-difluoropyrrolidin-1-yl)methyl]pyridin-2-yl}oxy)-1-(cyclopropylmethyl)-1H-benzotriazole | [M + H]<br>calc. 498.0502<br>obs. 498.0506 |
| 232 | 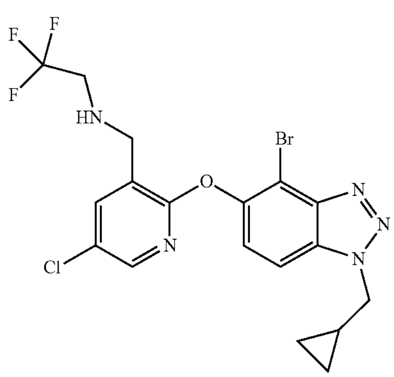 [SMILES: FC(F)(F)CNCc1cc(Cl)cnc1Oc1ccc2c(nnn2CC2CC2)c1Br] | N-[(2-{[4-bromo-1-(cyclopropylmethyl)-1H-benzotriazol-5-yl]oxy}-5-chloropyridin-3-yl)methyl]-2,2,2-trifluoroethanamine | [M + H]<br>calc. 490.0252<br>obs. 490.0247 |

TABLE 2-continued

| Ex. | STRUCTURE | NAME | HRMS/LRMS |
|---|---|---|---|
| 233 | 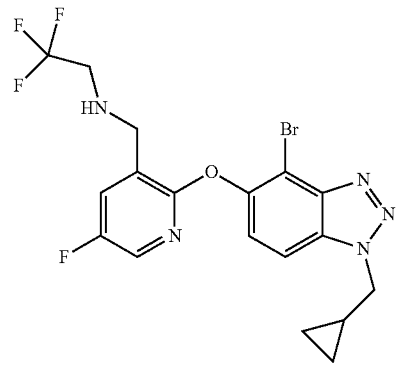 [SMILES: Fc1cnc(Oc2ccc3c(nnn3CC3CC3)c2Br)c(CNCC(F)(F)F)c1] | N-[(2-{[4-bromo-1-(cyclopropylmethyl)-1H-benzotriazol-5-yl]oxy}-5-fluoropyridin-3-yl)methyl]-2,2,2-trifluoroethanamine | [M + H] calc. 474.0547 obs. 474.0538 |
| 234 | 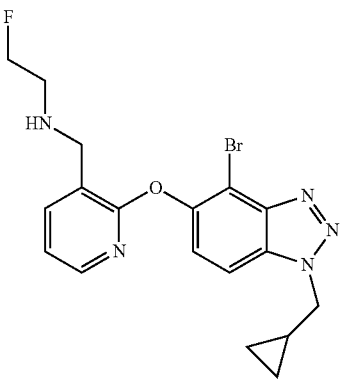 [SMILES: FCCNCc1cccnc1Oc1ccc2c(nnn2CC2CC2)c1Br] | N-[(2-{[4-bromo-1-(cyclopropylmethyl)-1H-benzotriazol-5-yl]oxy}pyridin-3-yl)methyl]-2-fluoroethanamine | [M + H] calc. 420.0830 obs. 420.0832 |
| 235 | 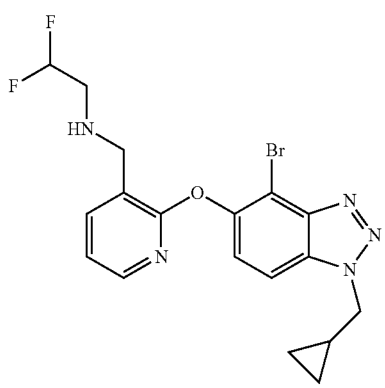 [SMILES: FC(F)CNCc1cccnc1Oc1ccc2c(nnn2CC2CC2)c1Br] | N-[(2-{[4-bromo-1-(cyclopropylmethyl)-1H-benzotriazol-5-yl]oxy}pyridin-3-yl)methyl]-2,2-difluoroethanamine | [M + H] calc. 438.0736 obs. 438.0738 |
| 236 | 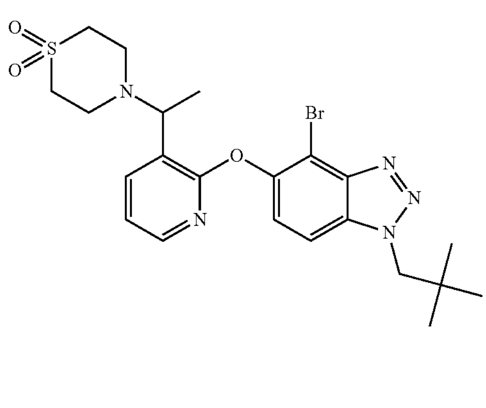 [SMILES: CC(c1cccnc1Oc1ccc2c(nnn2CC(C)(C)C)c1Br)N1CCS(=O)(=O)CC1] | 4-bromo-1-(2,2-dimethylpropyl)-5-({3-dioxidothiomorpholin-4-yl)ethyl]pyridin-2-yl}oxy)-1H-benzotriazole | [M + H] calc. 522.1 obs. 521.9 |

TABLE 2-continued

| Ex. | STRUCTURE | NAME | HRMS/LRMS |
|---|---|---|---|
| 237 | 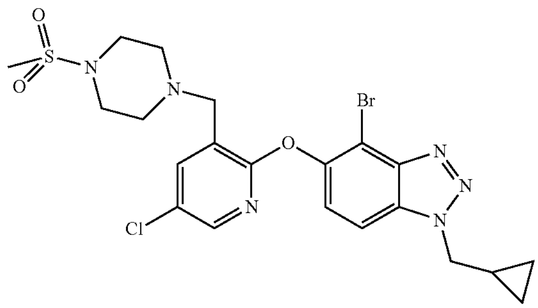 [SMILES: CS(=O)(=O)N1CCN(Cc2cc(Cl)cnc2Oc2ccc3c(nnn3CC3CC3)c2Br)CC1] | 4-bromo-5-[(5-chloro-3-{[4-(methylsulfonyl)piperazin-1-yl]methyl}pyridin-2-yl)oxy]-1-(cyclopropylmethyl)-1H-benzotriazole | [M + H] calc. 555.1 obs. 554.9 |
| 238 | 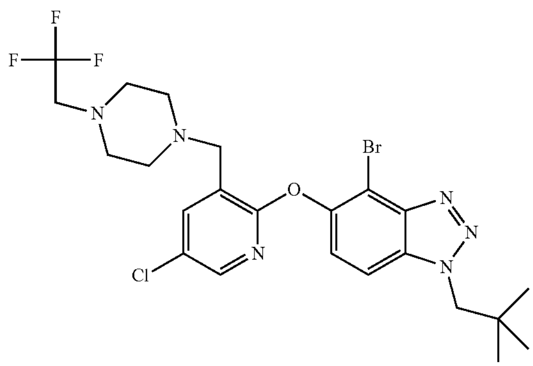 [SMILES: CC(C)(C)Cn1nnc2c(Br)c(Oc3ncc(Cl)cc3CN3CCN(CC(F)(F)F)CC3)ccc21] | 4-bromo-5-[(5-chloro-3-{[4-(2,2,2-trifluoroethyl)piperazin-1-yl]methyl}pyridin-2-yl)oxy]-1-(2,2-dimethylpropyl)-1H-benzotriazole | [M + H] calc. 575.1 obs. 574.9 |
| 239 | 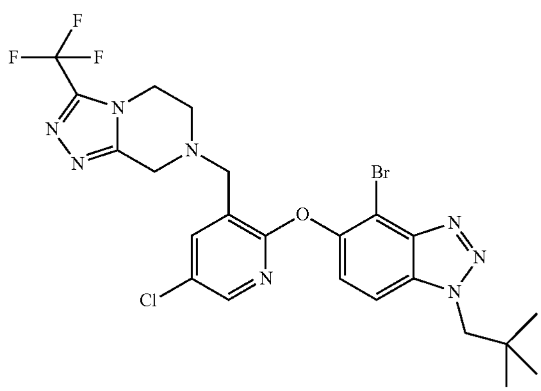 [SMILES: CC(C)(C)Cn1nnc2c(Br)c(Oc3ncc(Cl)cc3CN3CCn4c(nnc4C(F)(F)F)C3)ccc21] | 7-[(2-{[4-bromo-1-(2,2-dimethylpropyl)-1H-benzotriazol-5-yl]oxy}-5-chloropyridin-3-yl)methyl]-3-(trifluoromethyl)-5,6,7,8-tetrahydro[1,2,4]triazolo[4,3-a]pyrazine | [M + H] calc. 599.1 obs. 598.9 |
| 240 | 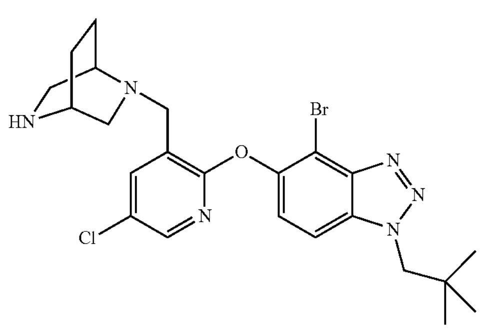 [SMILES: CC(C)(C)Cn1nnc2c(Br)c(Oc3ncc(Cl)cc3CN3CC4CCC3CN4)ccc21] | 4-bromo-5-{[5-chloro-3-(2,5-diazabicyclo[2.2.2]oct-2-ylmethyl)pyridin-2-yl]oxy}-1-(2,2-dimethylpropyl)-1H-benzotriazole | [M + H] calc. 519.1 obs. 519.0 |

TABLE 2-continued

| Ex. | STRUCTURE | NAME | HRMS/LRMS |
|---|---|---|---|
| 241 | 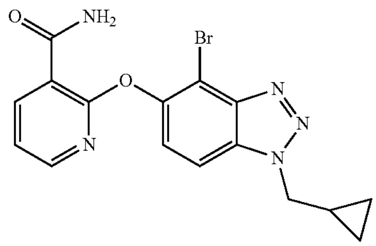 [SMILES: NC(=O)c1cccnc1Oc1ccc2c(nnn2CC2CC2)c1Br] | 2-{[4-bromo-1-(cyclopropylmethyl)-1H-benzotriazol-5-yl]oxy}pyridine-3-carboxamide | [M + H] calc. 388.0 obs. 387.8 |
| 242 | 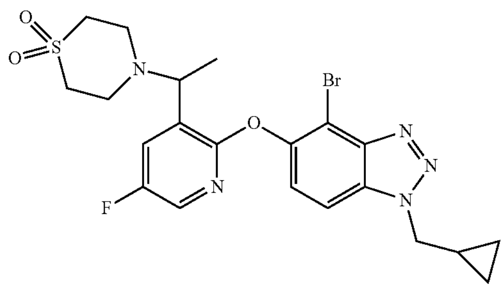 [SMILES: CC(c1cc(F)cnc1Oc1ccc2c(nnn2CC2CC2)c1Br)N1CCS(=O)(=O)CC1] | 4-bromo-1-(cyclopropylmethyl)-5-({3-[1-(1,1-dioxidothiomorpholin-4-yl)ethyl]-5-fluoropyridin-2-yl}oxy)-1H-benzotriazole | [M + H] calc. 524.1 obs. 523.9 |
| 243 | 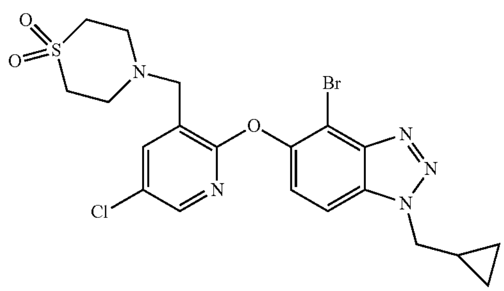 [SMILES: O=S1(=O)CCN(Cc2cc(Cl)cnc2Oc2ccc3c(nnn3CC3CC3)c2Br)CC1] | 4-bromo-5-({5-chloro-3-[(1,1-dioxidothiomorpholin-4-yl)methyl]pyridin-2-yl}oxy)-1-(cyclopropylmethyl)-1H-benzotriazole | [M + H] calc. 526.0 obs. 525.9 |
| 244 | 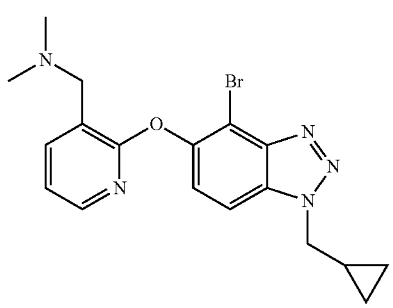 [SMILES: CN(C)Cc1cccnc1Oc1ccc2c(nnn2CC2CC2)c1Br] | 1-(2-{[4-bromo-1-(cyclopropylmethyl)-1H-benzotriazol-5-yl]oxy}pyridin-3-yl)-N,N-dimethylmethanamine | [M + H] calc. 402.1 obs. 401.9 |
| 245 | 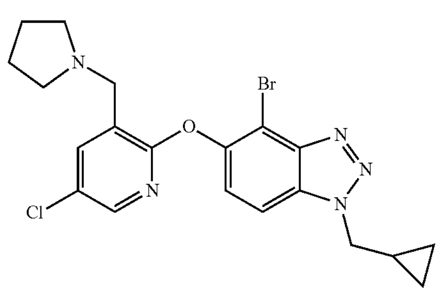 [SMILES: Clc1cnc(Oc2ccc3c(nnn3CC3CC3)c2Br)c(CN2CCCC2)c1] | 4-bromo-5-{[5-chloro-3-(pyrrolidin-1-ylmethyl)pyridin-2-yl]oxy}-1-(cyclopropylmethyl)-1H-benzotriazole | [M + H] calc. 462.1 obs. 461.9 |

TABLE 2-continued

| Ex. | STRUCTURE | NAME | HRMS/LRMS |
|---|---|---|---|
| 246 | 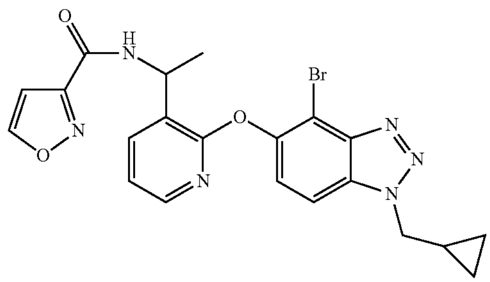 [SMILES: CC(NC(=O)c1ccon1)c1cccnc1Oc1ccc2c(nnn2CC2CC2)c1Br] | N-[1-(2-{[4-bromo-1-(cyclopropylmethyl)-1H-benzotriazol-5-yl]oxy}pyridin-3-yl)ethyl]isoxazole-3-carboxamide | [M + H] calc. 483.1 obs. 483.0 |
| 247 | 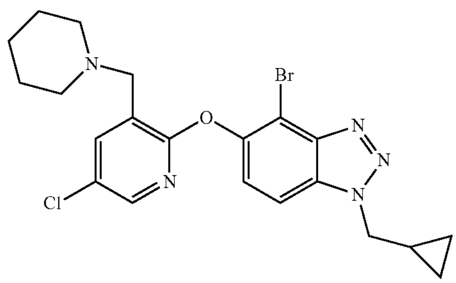 [SMILES: Clc1cnc(Oc2ccc3c(nnn3CC3CC3)c2Br)c(CN2CCCCC2)c1] | 4-bromo-5-{[5-chloro-3-(piperidin-1-ylmethyl)pyridin-2-yl]oxy}-1-(cyclopropylmethyl)-1H-benzotriazole | [M + H] calc. 476.1 obs. 475.9 |
| 248 | 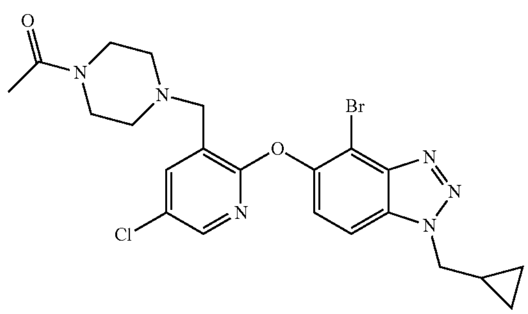 [SMILES: CC(=O)N1CCN(Cc2cc(Cl)cnc2Oc2ccc3c(nnn3CC3CC3)c2Br)CC1] | 5-({3-[(4-acetylpiperazin-1-yl)methyl]-5-chloropyridin-2-yl}oxy)-4-bromo-1-(cyclopropylmethyl)-1H-benzotriazole | [M + H] calc. 519.1 obs. 518.9 |
| 249 | 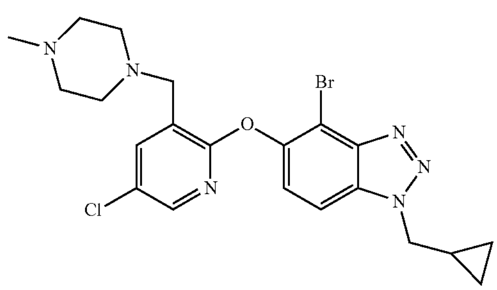 [SMILES: CN1CCN(Cc2cc(Cl)cnc2Oc2ccc3c(nnn3CC3CC3)c2Br)CC1] | 4-bromo-5-({5-chloro-3-[(4-methylpiperazin-1-yl)methyl]pyridin-2-yl}oxy)-1-(cyclopropylmethyl)-1H-benzotriazole | [M + H] calc. 491.1 obs. 490.9 |
| 250 | 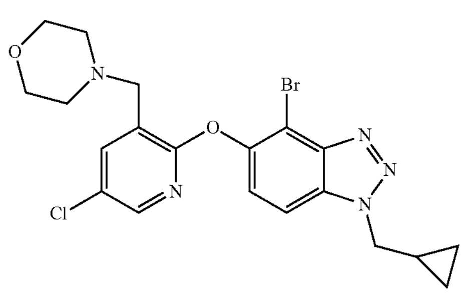 [SMILES: Clc1cnc(Oc2ccc3c(nnn3CC3CC3)c2Br)c(CN2CCOCC2)c1] | 4-bromo-5-{[5-chloro-3-(morpholin-4-ylmethyl)pyridin-2-yl]oxy}-1-(cyclopropylmethyl)-1H-benzotriazole | [M + H] calc. 478.1 obs. 477.9 |

TABLE 2-continued

| Ex. | STRUCTURE | NAME | HRMS/LRMS |
|---|---|---|---|
| 251 | 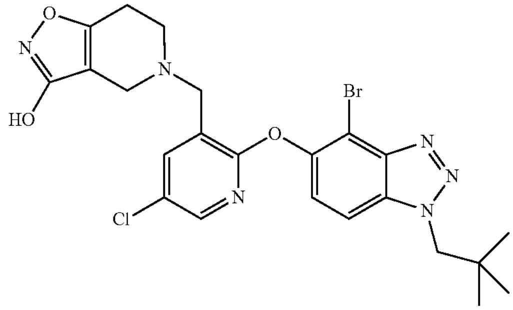 [SMILES: CC(C)(C)Cn1nnc2c(Br)c(Oc3ncc(Cl)cc3CN3CCc4onc(O)c4C3)ccc21] | 5-[(2-{[4-bromo-1-(2,2-dimethylpropyl)-1H-benzotriazol-5-yl]oxy}-5-chloropyridin-3-yl)methyl]-4,5,6,7-tetrahydroisoxazolo[4,5-c]pyridin-3-ol | [M + H] calc. 547.1 obs. 546.9 |
| 252 | 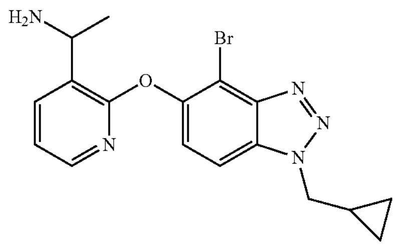 [SMILES: CC(N)c1cccnc1Oc1ccc2c(nnn2CC2CC2)c1Br] | 1-(2-{[4-bromo-1-(cyclopropylmethyl)-1H-benzotriazol-5-yl]oxy}pyridin-3-yl)ethanamine | [M + H] calc. 388.1 obs. 386.8 |
| 253 | 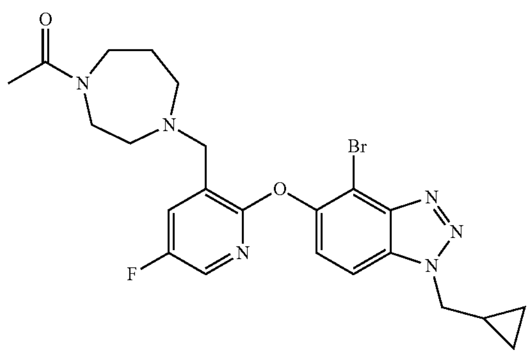 | 5-({3-[(4-acetyl-1,4-diazepan-1-yl)methyl]-5-fluoropyridin-2-yl}oxy)-4-bromo-1-(cyclopropylmethyl)-1H-benzotriazole | [M + H] calc. 517.1 obs. 517.0 |
| 254 | 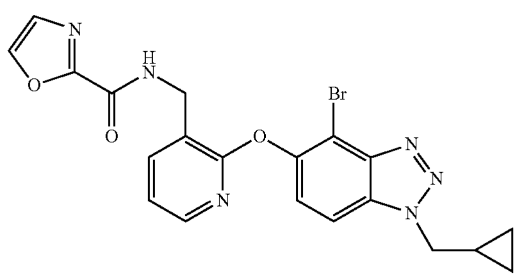 [SMILES: O=C(NCc1cccnc1Oc1ccc2c(nnn2CC2CC2)c1Br)c1ncco1] | N-[(2-{[4-bromo-1-(cyclopropylmethyl)-1H-benzotriazol-5-yl]oxy}pyridin-3-yl)methyl]-1,3-oxazole-2-carboxamide | [M + H] calc. 469.1 obs. 469.2 |
| 255 | 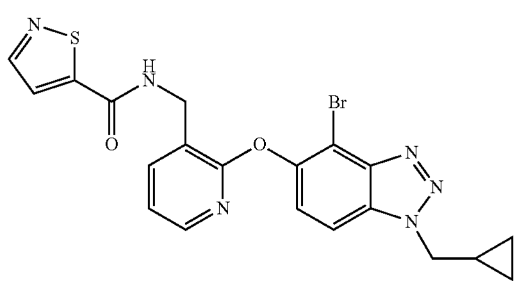 [SMILES: O=C(NCc1cccnc1Oc1ccc2c(nnn2CC2CC2)c1Br)c1ccns1] | N-[(2-{[4-bromo-1-(cyclopropylmethyl)-1H-benzotriazol-5-yl]oxy}pyridin-3-yl)methyl]isothiazole-5-carboxamide | [M + H] calc. 478.0 obs. 487.2 |

TABLE 2-continued

| Ex. | STRUCTURE | NAME | HRMS/LRMS |
|---|---|---|---|
| 256 | 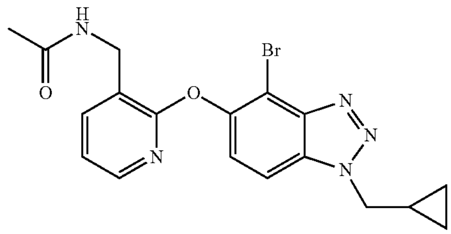 [SMILES: CC(=O)NCc1cccnc1Oc1ccc2c(nnn2CC2CC2)c1Br] | N-[(2-{[4-bromo-1-(cyclopropylmethyl)-3H-benzotriazol-5-yl]oxy}pyridin-3-yl)methyl]acetamide | [M + H] calc. 418.1 obs. 418.2 |
| 257 | 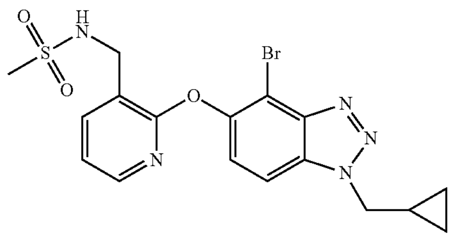 [SMILES: CS(=O)(=O)NCc1cccnc1Oc1ccc2c(nnn2CC2CC2)c1Br] | N-[(2-{[4-bromo-1-(cyclopropylmethyl)-1H-benzotriazol-5-yl]oxy}pyridin-3-yl)methyl]methanesulfonamide | [M + H] calc. 454.0 obs. 454.2 |
| 258 | 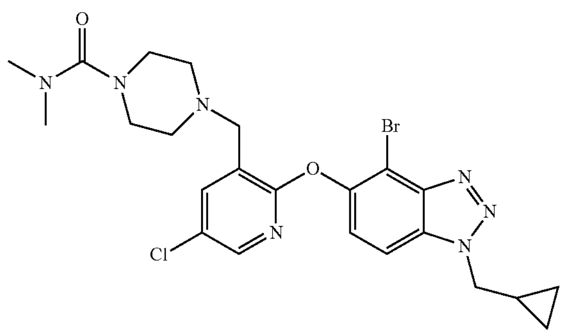 [SMILES: CN(C)C(=O)N1CCN(Cc2cc(Cl)cnc2Oc2ccc3c(nnn3CC3CC3)c2Br)CC1] | 4-[(2-{[4-bromo-1-(cyclopropylmethyl)-1H-benzotriazol-5-yl]oxy}-5-chloropyridin-3-yl)methyl]-N,N-dimethylpiperazine-1-carboxamide | [M + H] calc. 548.1 obs. 547.9 |
| 259 | 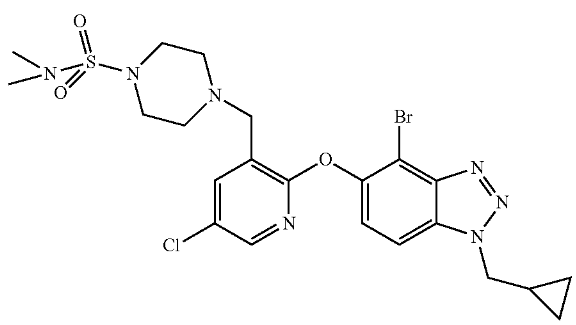 [SMILES: CN(C)S(=O)(=O)N1CCN(Cc2cc(Cl)cnc2Oc2ccc3c(nnn3CC3CC3)c2Br)CC1] | 4-[(2-{[4-bromo-1-(cyclopropylmethyl)-1H-benzotriazol-5-yl]oxy}-5-chloropyridin-3-yl)methyl]-N,N-dimethylpiperazine-1-sulfonamide | [M + H] calc. 584.1 obs. 583.8 |
| 260 | 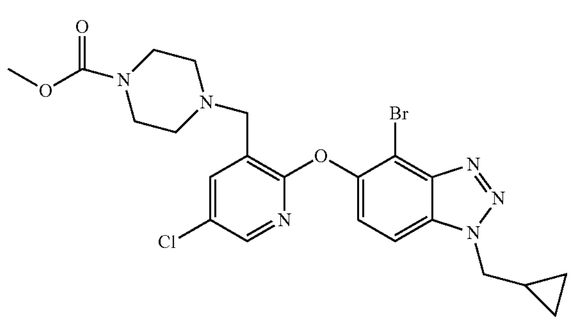 [SMILES: COC(=O)N1CCN(Cc2cc(Cl)cnc2Oc2ccc3c(nnn3CC3CC3)c2Br)CC1] | methyl 4-[(2-{[4-bromo-1-(cyclopropylmethyl)-1H-benzotriazol-5-yl]oxy}-5-chloropyridin-3-yl)methyl]piperazine-1-carboxylate | [M + H] calc. 535.1 obs. 534.9 |

TABLE 2-continued

| Ex. | STRUCTURE | NAME | HRMS/LRMS |
|---|---|---|---|
| 261 | 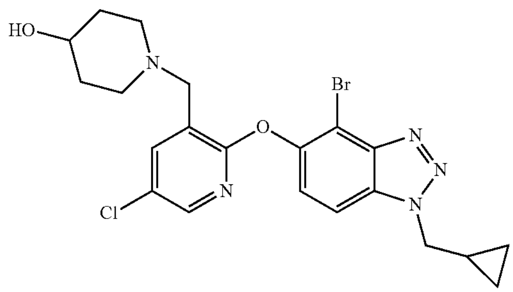 [SMILES: OC1CCN(Cc2cc(Cl)cnc2Oc2ccc3c(nnn3CC3CC3)c2Br)CC1] | 1-[(2-{[4-bromo-1-(cyclopropylmethyl)-1H-benzotriazol-5-yl]oxy}-5-chloropyridin-3-yl)methyl]piperidin-4-ol | [M + H] calc. 492.1 obs. 491.9 |
| 262 | 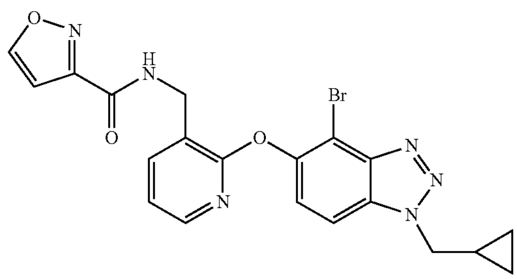 [SMILES: O=C(NCc1cccnc1Oc1ccc2c(nnn2CC2CC2)c1Br)c1ccon1] | N-[(2-{[4-bromo-1-(cyclopropylmethyl)-1H-benzotriazol-5-yl]oxy}pyridin-3-yl)methyl]isoxazole-3-carboxamide | [M + H] calc. 471.1 obs. 471.2 |
| 263 | 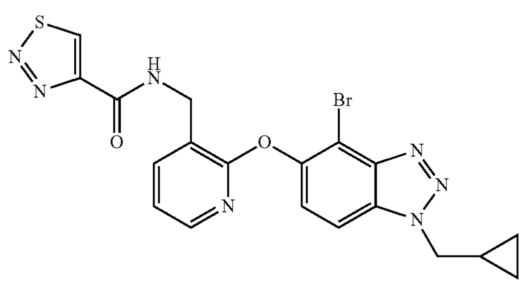 [SMILES: O=C(NCc1cccnc1Oc1ccc2c(nnn2CC2CC2)c1Br)c1csnn1] | N-[(2-{[4-bromo-1-(cyclopropylmethyl)-1H-benzotriazol-5-yl]oxy}pyridin-3-yl)methyl]-1,2,3-thiadiazole-4-carboxamide | [M + H] calc. 488.0 obs. 488.2 |
| 264 | 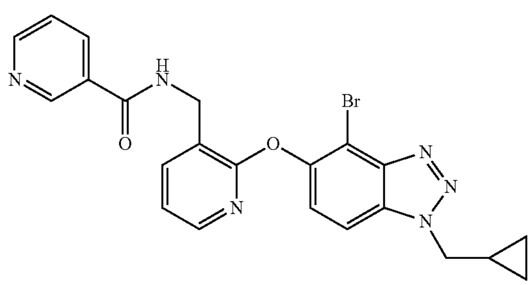 [SMILES: O=C(NCc1cccnc1Oc1ccc2c(nnn2CC2CC2)c1Br)c1cccnc1] | N-[(2-{[4-bromo-1-(cyclopropylmethyl)-1H-benzotriazol-5-yl]oxy}pyridin-3-yl)methyl]pyridine-3-carboxamide | [M + H] calc. 481.1 obs. 481.2 |
| 265 | 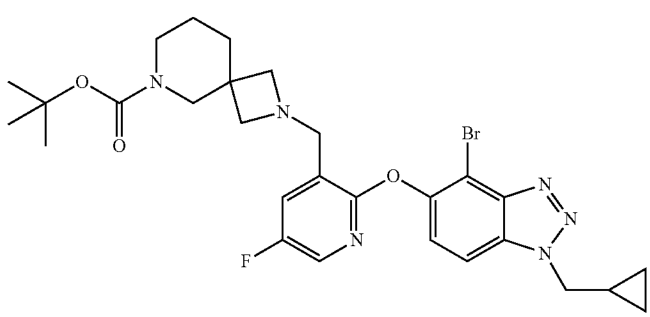 [SMILES: CC(C)(C)OC(=O)N1CCCC2(CN(Cc3cc(F)cnc3Oc3ccc4c(nnn4CC4CC4)c3Br)C2)C1] | tert-butyl 2-[(2-{[4-bromo-1-(cyclopropylmethyl)-1H-benzotriazol-5-yl]oxy}-5-fluoropyridin-3-yl)methyl]-2,6-diazaspiro[3.5]nonane-6-carboxylate | [M + H] calc. 603.2 obs. 603.4 |

TABLE 2-continued

| Ex. | STRUCTURE | NAME | HRMS/LRMS |
|---|---|---|---|
| 266 | 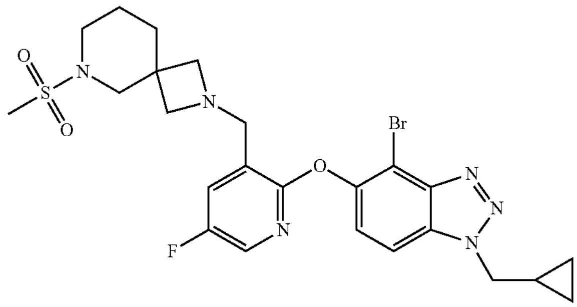 [SMILES: CS(=O)(=O)N1CCCC2(CN(Cc3cc(F)cnc3Oc3ccc4c(nnn4CC4CC4)c3Br)C2)C1] | 4-bromo-1-(cyclopropylmethyl)-5-[(5-fluoro-3-{[6-(methylsulfonyl)-2,6-diazaspiro[3.5]non-2-yl]methyl}pyridin-2-yl)oxy]-1H-benzotriazole | [M + H] calc. 581.1 obs. 583.3 |
| 267 | 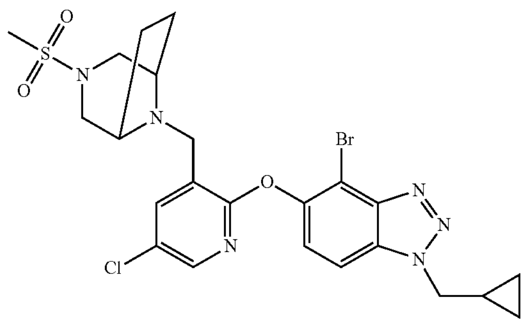 [SMILES: CS(=O)(=O)N1CC2CCC(C1)N2Cc1cc(Cl)cnc1Oc1ccc2c(nnn2CC2CC2)c1Br] | 4-bromo-5-[(5-chloro-3-{[3-(methylsulfonyl)-3,8-diazabicyclo[3.2.1]oct-8-yl]methyl}pyridin-2-yl)oxy]-1-(cyclopropylmethyl)-1H-benzotriazole | [M + H] calc. 583.1 obs. 583.3 |
| 268 | 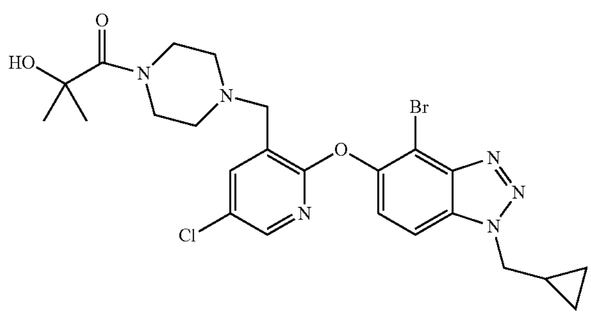 [SMILES: CC(C)(O)C(=O)N1CCN(Cc2cc(Cl)cnc2Oc2ccc3c(nnn3CC3CC3)c2Br)CC1] | 1-{4-[(2-{[4-bromo-1-(cyclopropylmethyl)-1H-benzotriazol-5-yl]oxy}-5-chloropyridin-3-yl)methyl]piperazin-1-yl}-2-methyl-1-oxopropan-2-ol | [M + H] calc. 563.1 obs. 563.3 |
| 269 | 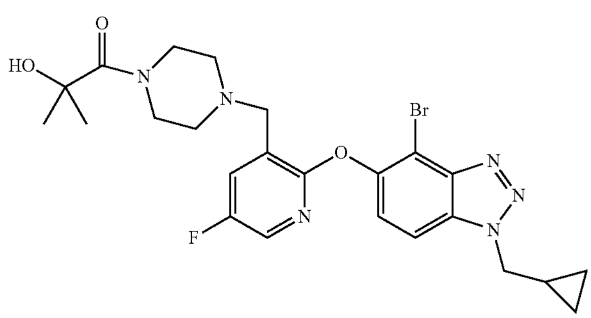 [SMILES: CC(C)(O)C(=O)N1CCN(Cc2cc(F)cnc2Oc2ccc3c(nnn3CC3CC3)c2Br)CC1] | 1-{4-[(2-{[4-bromo-1-(cyclopropylmethyl)-1H-benzotriazol-5-yl]oxy}-5-fluoropyridin-3-yl)methyl]piperazin-1-yl}-2-methyl-1-oxopropan-2-ol | [M + H] calc. 547.1 obs. 547.3 |
| 270 | 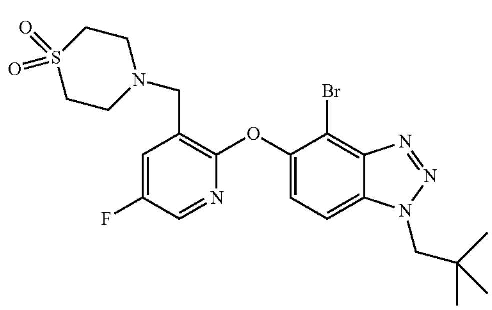 [SMILES: CC(C)(C)Cn1nnc2c(Br)c(Oc3ncc(F)cc3CN3CCS(=O)(=O)CC3)ccc21] | 4-bromo-1-(2,2-dimethylpropyl)-5-({3-[(1,1-dioxidothiomorpholin-4-yl)methyl]-5-fluoropyridin-2-yl}oxy)-2711H-benzotriazole | [M + H] calc. 526.1 obs. 525.9 |

TABLE 2-continued

| Ex. | STRUCTURE | NAME | HRMS/LRMS |
|---|---|---|---|
| 271 | 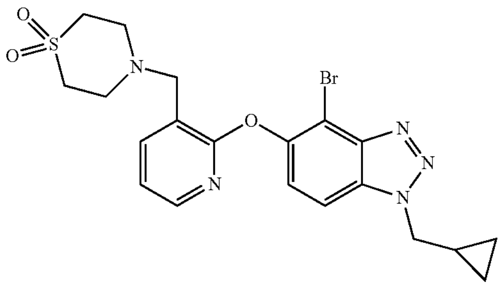 [SMILES: O=S1(=O)CCN(Cc2cccnc2Oc2ccc3c(nnn3CC3CC3)c2Br)CC1] | 2724-bromo-1-(cyclopropylmethyl)-5-({3-[(1,1-dioxidothiomorpholin-4-yl)methyl]pyridin-2-yl}oxy)-1H-benzotriazole | [M + H] calc. 492.1 obs. 491.8 |
| 272 | 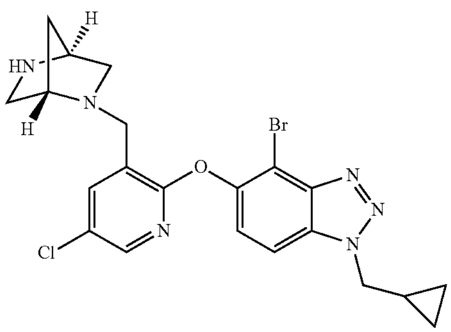 [SMILES: Clc1cnc(Oc2ccc3c(nnn3CC3CC3)c2Br)c(CN2C[C@@H]3C[C@H]2CN3)c1] | 4-bromo-5-({5-chloro-3-[(1S,4S)-2,5-diazabicyclo[2.2.1]hept-2-ylmethyl]pyridin-2-yl}oxy)-1-(cyclopropylmethyl)-1H-benzotriazole | [M + H] calc. 489.1 obs. 488.9 |
| 273 | 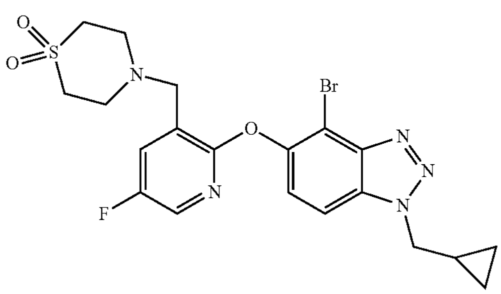 [SMILES: O=S1(=O)CCN(Cc2cc(F)cnc2Oc2ccc3c(nnn3CC3CC3)c2Br)CC1] | 4-bromo-1-(cyclopropylmethyl)-5-({3-[(1,1-dioxidothiomorpholin-4-yl)methyl]-5-fluoropyridin-2-yl}oxy)-1H-benzotriazole | [M + H] calc. 510.1 obs. 509.8 |
| 274 | 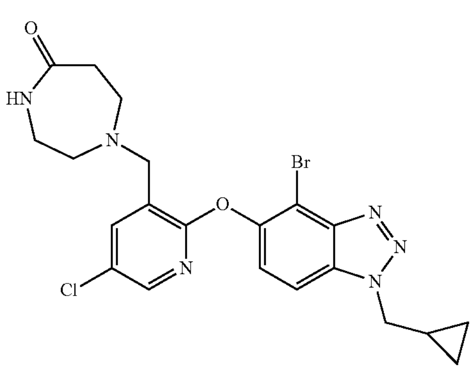 [SMILES: O=C1CCN(Cc2cc(Cl)cnc2Oc2ccc3c(nnn3CC3CC3)c2Br)CCN1] | 1-[(2-{[4-bromo-1-(cyclopropylmethyl)-1H-benzotriazol-5-yl]oxy}-5-chloropyridin-3-yl)methyl]-1,4-diazepan-5-one | [M + H] calc. 505.1 obs. 504.9 |

TABLE 2-continued

| Ex. | STRUCTURE | NAME | HRMS/LRMS |
|---|---|---|---|
| 275 | 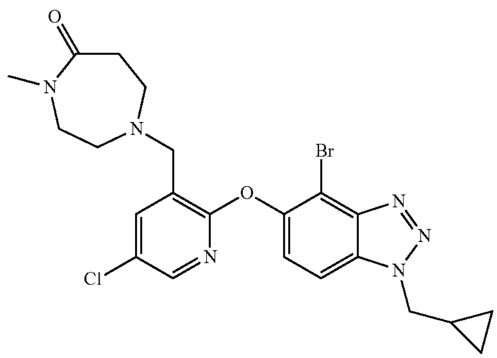 [SMILES: CN1CCN(Cc2cc(Cl)cnc2Oc2ccc3c(nnn3CC3CC3)c2Br)CCC1=O] | 1-[(2-{[4-bromo-1-(cyclopropylmethyl)-1H-benzotriazol-5-yl]oxy}-5-chloropyridin-3-yl)methyl]-4-methyl-1,4-diazepan-5-one | [M + H] calc. 519.1 obs. 518.9 |
| 276 | 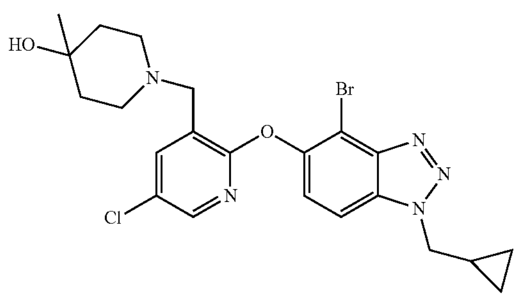 [SMILES: CC1(O)CCN(Cc2cc(Cl)cnc2Oc2ccc3c(nnn3CC3CC3)c2Br)CC1] | 1-[(2-{[4-bromo-1-(cyclopropylmethyl)-1H-benzotriazol-5-yl]oxy}-5-chloropyridin-3-yl)methyl]-4-methylpiperidin-4-ol | [M + H] calc. 506.1 obs. 505.9 |
| 277 | 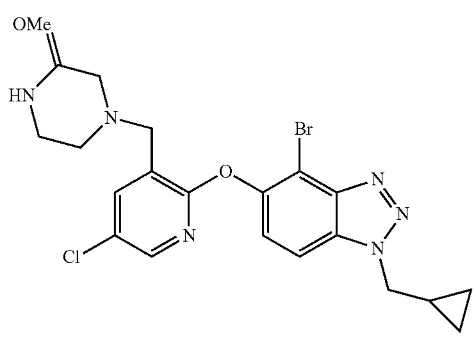 | 4-[(2-{[4-bromo-1-(cyclopropylmethyl)-1H-benzotriazol-5-yl]oxy}-5-chloropyridin-3-yl)methyl]piperazin-2-one | [M + H] calc. 491.1 obs. 490.9 |
| 278 | 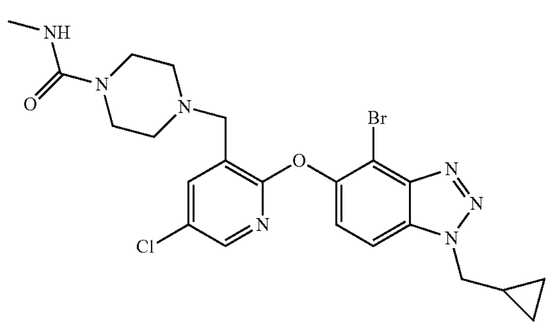 [SMILES: CNC(=O)N1CCN(Cc2cc(Cl)cnc2Oc2ccc3c(nnn3CC3CC3)c2Br)CC1] | 4-[(2-{[4-bromo-1-(cyclopropylmethyl)-1H-benzotriazol-5-yl]oxy}-5-chloropyridm-3-yl)methyl]-N-methylpiperazine-1-carboxamide | [M + H] calc. 534.1 obs. 533.9 |

TABLE 2-continued

| Ex. | STRUCTURE | NAME | HRMS/LRMS |
|---|---|---|---|
| 279 | 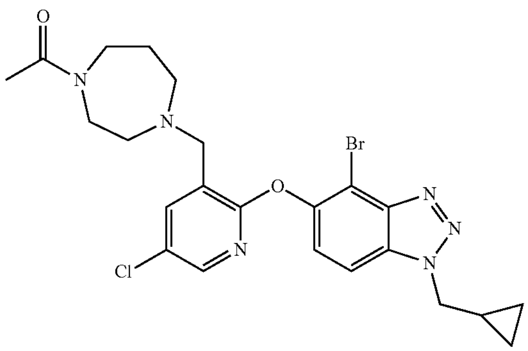 [SMILES: CC(=O)N1CCCN(Cc2cc(Cl)cnc2Oc2ccc3c(nnn3CC3CC3)c2Br)CC1] | 5-({3-[(4-acetyl-1,4-diazepan-1-yl)methyl]-5-chloropyridin-2-yl}oxy)-4-bromo-1-(cyclopropylmethyl)-1H-benzotriazole | [M + H] calc. 533.1 obs. 533.0 |
| 280 | 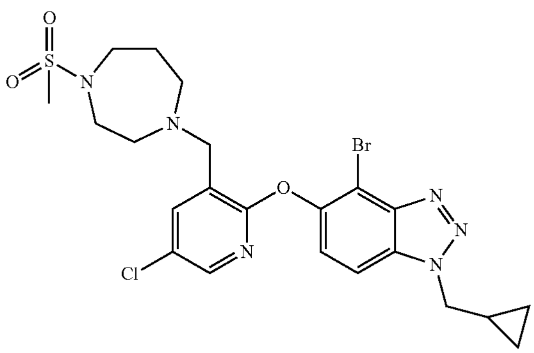 [SMILES: CS(=O)(=O)N1CCCN(Cc2cc(Cl)cnc2Oc2ccc3c(nnn3CC3CC3)c2Br)CC1] | 4-bromo-5-[(5-chloro-3-{[4-(methylsulfonyl)-1,4-diazepan-1-yl]methyl}pyridin-2-yl)oxy]-1-(cyclopropylmethyl)-1H-benzotriazole | [M + H] calc. 569.1 obs. 568.9 |
| 281 | 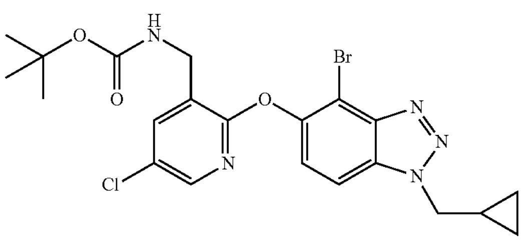 [SMILES: CC(C)(C)OC(=O)NCc1cc(Cl)cnc1Oc1ccc2c(nnn2CC2CC2)c1Br] | tert-butyl [(2-{[4-bromo-1-(cyclopropylmethyl)-1H-benzotriazol-5-yl)oxy}-5-chloropyridin-3-yl)methyl]carbamate | [M + H] calc. 510.1 obs. 510.3 |
| 282 | 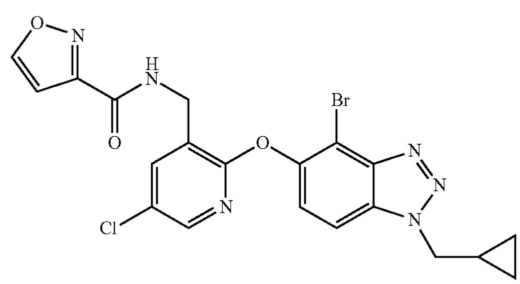 [SMILES: O=C(NCc1cc(Cl)cnc1Oc1ccc2c(nnn2CC2CC2)c1Br)c1ccon1] | N-[(2-{[4-bromo-1-(cyclopropylmethyl)-1H-benzotriazol-5-yl]oxy}-5-chloropyridin-3-yl)methyl]isoxazole-3-carboxamide | [M + H] calc. 505.1 obs. 505.2 |
| 283 | 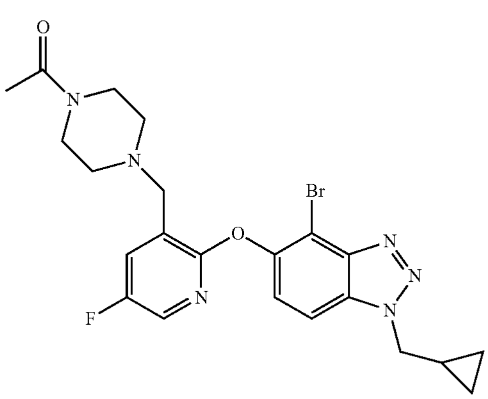 [SMILES: CC(=O)N1CCN(Cc2cc(F)cnc2Oc2ccc3c(nnn3CC3CC3)c2Br)CC1] | 5-({3-[(4-acetylpiperazin-1-yl)methyl]-5-fluoropyridin-2-yl}oxy)-4-bromo-1-(cyclopropylmethyl)-1H-benzotriazole | [M + H] calc. 505.1 obs. 505.2 |

TABLE 2-continued

| Ex. | STRUCTURE | NAME | HRMS/LRMS |
|---|---|---|---|
| 284 | 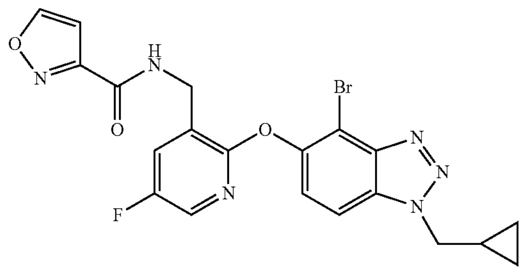 [SMILES: O=C(NCc1cc(F)cnc1Oc1ccc2c(nnn2CC2CC2)c1Br)c1ccon1] | N-[(2-{[4-bromo-1-(cyclopropylmethyl)-1H-benzotriazol-5-yl]oxy}-5-fluoropyridin-3-yl)methyl]isoxazole-3-carboxamide | [M + H] calc. 489.1 obs. 489.2 |
| 285 | 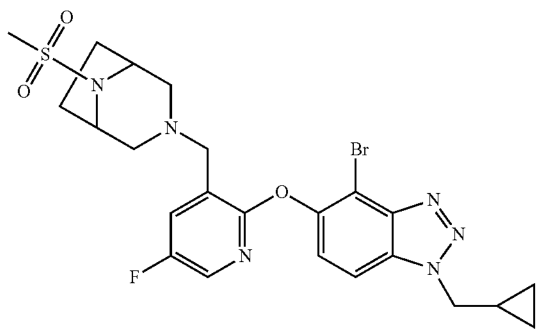 [SMILES: CS(=O)(=O)N1C2CCC1CN(Cc1cc(F)cnc1Oc1ccc3c(nnn3CC3CC3)c1Br)C2] | 4-bromo-1-(cyclopropylmethyl)-5-[(5-fluoro-3-{[8-(methylsulfonyl)-3,8-diazabicyclo[3.2.1]oct-3-yl]methyl}pyridin-2-yl)oxy]-1H-benzotriazole | [M + H] calc. 567.1 obs. 567.3 |
| 286 | 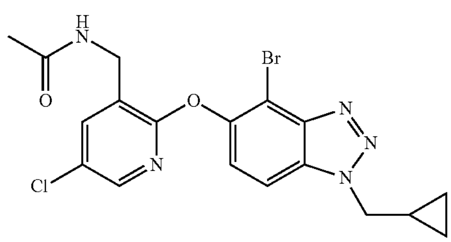 [SMILES: CC(=O)NCc1cc(Cl)cnc1Oc1ccc2c(nnn2CC2CC2)c1Br] | N-[(2-{[4-bromo-1-(cyclopropylmethyl)-1H-benzotriazol-5-yl]oxy}-5-chloropyridin-3-yl)methyl]acetamide | [M + H] calc. 452.0 obs. 452.2 |
| 287 | 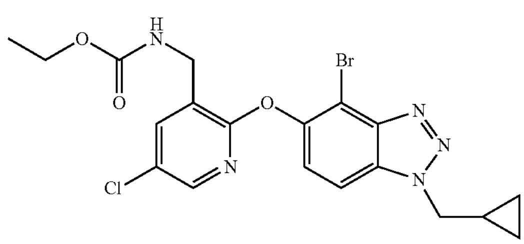 [SMILES: CCOC(=O)NCc1cc(Cl)cnc1Oc1ccc2c(nnn2CC2CC2)c1Br] | ethyl [(2-{[4-bromo-1-(cyclopropylmethyl)-1H-benzotriazol-5-yl]oxy}-5-chloropyridin-3-yl)methyl]carbamate | [M + H] calc. 482.0 obs. 482.2 |
| 288 | 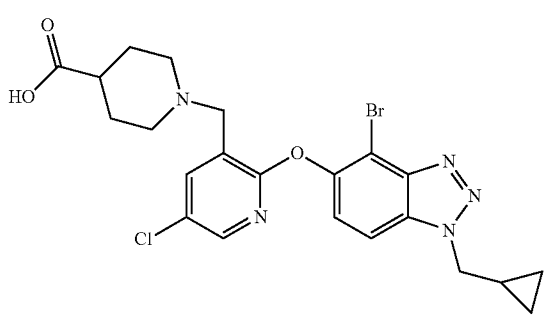 [SMILES: O=C(O)C1CCN(Cc2cc(Cl)cnc2Oc2ccc3c(nnn3CC3CC3)c2Br)CC1] | 1-[(2-{[4-bromo-1-(cyclopropylmethyl)-1H-benzotriazol-5-yl]oxy}-5-chloropyridin-3-yl)methyl]piperidine-4-carboxylic acid | [M + H] calc. 520.1 obs. 519.9 |

TABLE 2-continued

| Ex. | STRUCTURE | NAME | HRMS/LRMS |
|---|---|---|---|
| 289 | 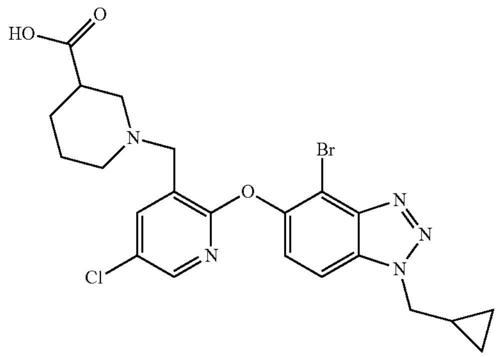 [SMILES: O=C(O)C1CCCN(Cc2cc(Cl)cnc2Oc2ccc3c(nnn3CC3CC3)c2Br)C1] | 1-[(2-{[4-bromo-1-(cyclopropylmethyl)-1H-benzotriazol-5-yl]oxy}-5-chloropyridin-3-yl)methyl]piperidine-3-carboxylic acid | [M + H] calc. 520.1 obs. 511.9 |
| 290 | (Abs) | 4-bromo-1-(cyclopropylmethyl)-5-[(5-fluoro-3-{[(3R)-3-methyl-4-(methylsulfonyl)piperazin-1-yl]methyl}pyridin-2-yl)oxy]-1H-benzotriazole | [M + H] calc. 553.1 obs. 552.9 |
| 291 | 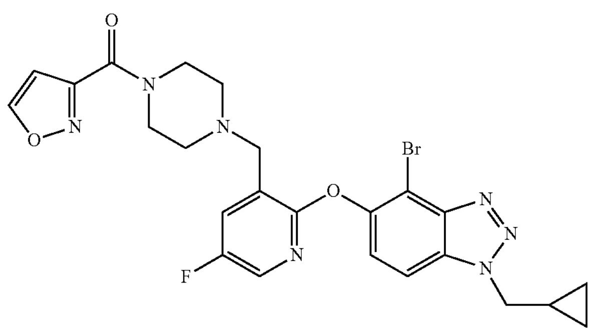 [SMILES: O=C(c1ccon1)N1CCN(Cc2cc(F)cnc2Oc2ccc3c(nnn3CC3CC3)c2Br)CC1] | 4-bromo-1-(cyclopropylmethyl)-5-[(5-fluoro-3-{[4-(isoxazol-3-ylcarbonyl)piperazin-1-yl]methyl}pyridin-2-yl)oxy]-1H-benzotriazole | [M + H] calc. 556.1 obs. 556.3 |
| 292 | 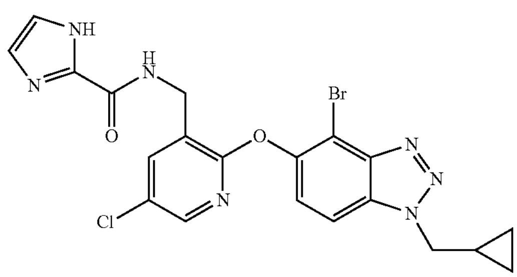 [SMILES: O=C(NCc1cc(Cl)cnc1Oc1ccc2c(nnn2CC2CC2)c1Br)c1ncc[nH]1] | N-[(2-{[4-bromo-1-(cyclopropylmethyl)-1H-benzotriazol-5-yl]oxy}-5-chloropyridin-3-yl)methyl]-1H-imidazole-2-carboxamide | [M + H] calc. 504.0 obs. 504.2 |

| Ex. | STRUCTURE | NAME | HRMS/LRMS |
|---|---|---|---|
| 293 | 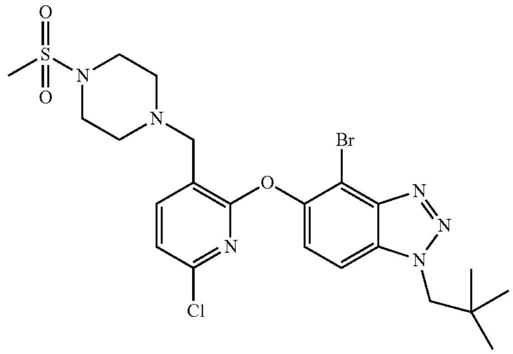 [SMILES: CC(C)(C)Cn1nnc2c(Br)c(Oc3nc(Cl)ccc3CN3CCN(S(C)(=O)=O)CC3)ccc21] | 4-bromo-5-[(6-chloro-3-{[4-(methylsulfonyl)piperazin-1-yl]methyl}pyridin-2-yl)oxy]-1-(2,2-dimethylpropyl)-1H-benzotriazole | [M + H] calc. 571.1 obs. 570.9 |
| 294 | 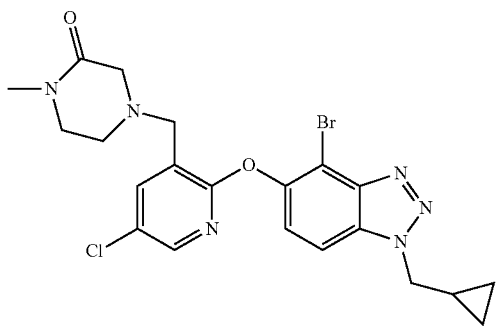 [SMILES: CN1CCN(Cc2cc(Cl)cnc2Oc2ccc3c(nnn3CC3CC3)c2Br)CC1=O] | 4-[(2-{[4-bromo-1-(cyclopropylmethyl)-1H-benzotriazol-5-yl]oxy}-5-chloropyridin-3-yl)methyl]-1-methylpiperazin-2-one | [M + H] calc. 505.1 obs. 504.9 |
| 295 | 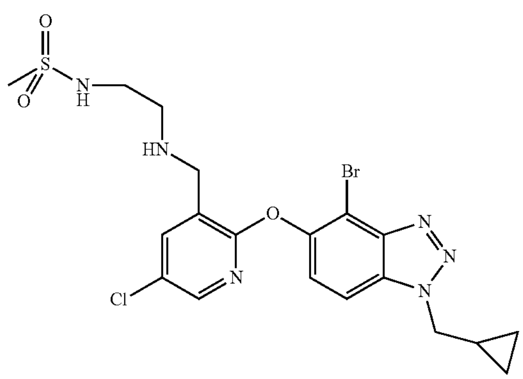 [SMILES: CS(=O)(=O)NCCNCc1cc(Cl)cnc1Oc1ccc2c(nnn2CC2CC2)c1Br] | N-(2-{[(2-{[4-bromo-1-(cyclopropylmethyl)-1H-benzotriazol-5-yl]oxy}-5-chloropyridin-3-yl)methyl]amino}ethyl)methanesulfonamide | [M + H] calc. 529.0 obs. 528.8 |
| 296 | 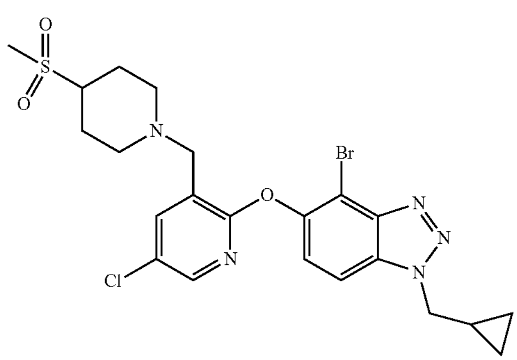 [SMILES: CS(=O)(=O)C1CCN(Cc2cc(Cl)cnc2Oc2ccc3c(nnn3CC3CC3)c2Br)CC1] | 4-bromo-5-[(5-chloro-3-{[4-(methylsulfonyl)piperidin-1-yl]methyl}pyridin-2-yl)oxy]-1-(cyclopropylmethyl)-1H-benzotriazole | [M + H] calc. 554.1 obs. 553.9 |

TABLE 2-continued

| Ex. | STRUCTURE | NAME | HRMS/LRMS |
|---|---|---|---|
| 297 | 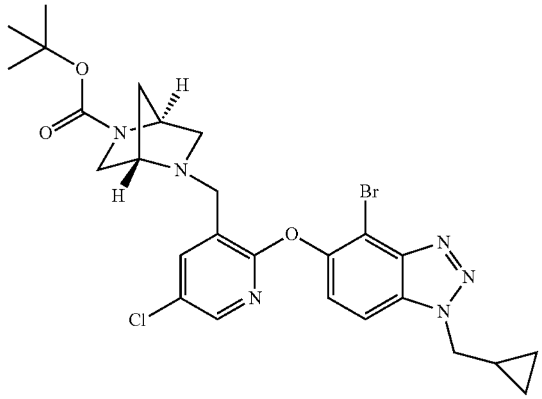 [SMILES: CC(C)(C)OC(=O)N1C[C@@H]2C[C@H]1CN2Cc1cc(Cl)cnc1Oc1ccc2c(nnn2CC2CC2)c1Br] | tert-butyl(1S,4S)-5-[(2-{[4-bromo-1-(cyclopropylmethyl)-1H-benzotriazol-5-yl]oxy}-5-chloropyridin-3-yl)methyl]-2,5-diazabicyclo[2.2.1]heptane-2-carboxylate | [M + H] calc. 589.1 obs. 588.9 |
| 298 | 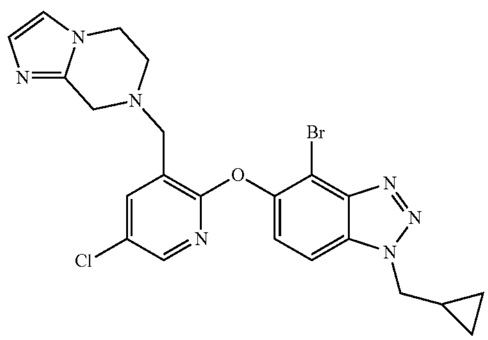 [SMILES: Clc1cnc(Oc2ccc3c(nnn3CC3CC3)c2Br)c(CN2CCn3ccnc3C2)c1] | 4-bromo-5-{[5-chloro-3-(5,6-dihydroimidazo[1,2-a]pyrazin-7(8H)-ylmethyl)pyridin-2-yl]oxy}-1-(cyclopropylmethyl)-1H-benzotriazole | [M + H] calc. 514.1 obs. 513.9 |
| 299 | 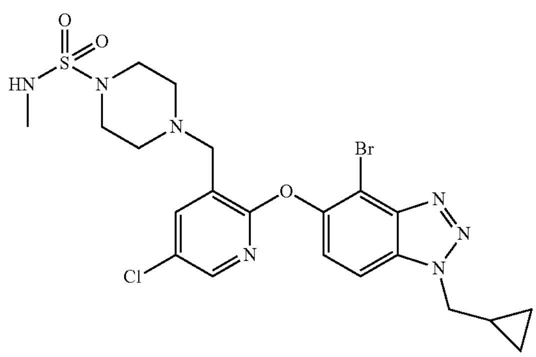 [SMILES: CNS(=O)(=O)N1CCN(Cc2cc(Cl)cnc2Oc2ccc3c(nnn3CC3CC3)c2Br)CC1] | 4-[(2-{[4-bromo-1-(cyclopropylmethyl)-1H-benzotriazol-5-yl]oxy}-5-chloropyridin-3-yl)methyl]-N-methylpiperazine-1-sulfonamide | [M + H] calc. 570.1 obs. 569.9 |
| 300 | 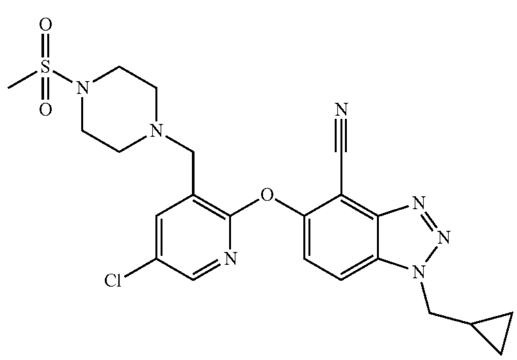 [SMILES: CS(=O)(=O)N1CCN(Cc2cc(Cl)cnc2Oc2ccc3c(nnn3CC3CC3)c2C#N)CC1] | 5-[(5-chloro-3-{[4-(methylsulfonyl)piperazin-1-yl]methyl}pyridin-2-yl)oxy]-1-(cyclopropylmethyl)-1H-benzotriazole-4-carbonitrile | [M + H] calc. 502.1 obs. 501.9 |

TABLE 2-continued

| Ex. | STRUCTURE | NAME | HRMS/LRMS |
|---|---|---|---|
| 301 | 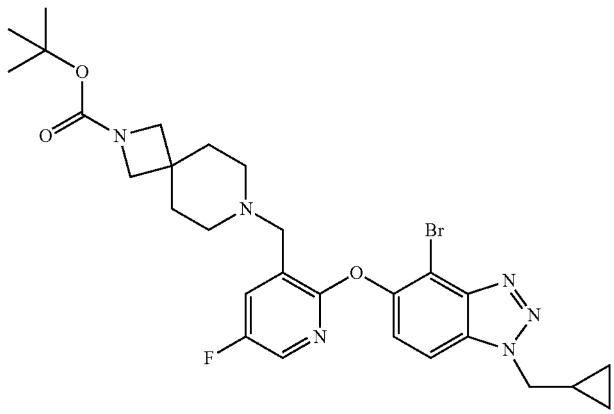 [SMILES: CC(C)(C)OC(=O)N1CC2(CCN(Cc3cc(F)cnc3Oc3ccc4c(nnn4CC4CC4)c3Br)CC2)C1] | tert-butyl 7-[(2-{[4-bromo-1-(cyclopropylmethyl)-1H-benzotriazol-5-yl]oxy}-5-fluoropyridin-3-yl)methyl]-2,7-diazaspiro[3.5]nonane-2-carboxylate | [M + H] calc. 603.2 obs. 602.9 |
| 302 | 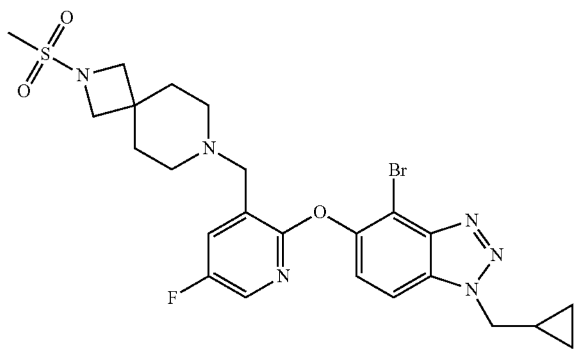 [SMILES: CS(=O)(=O)N1CC2(CCN(Cc3cc(F)cnc3Oc3ccc4c(nnn4CC4CC4)c3Br)CC2)C1] | 4-bromo-1-(cyclopropylmethyl)-5-[(5-fluoro-3-{[2-(methylsulfonyl)-2,7-diazaspiro[3.5]non-7-yl]methyl}pyridin-2-yl)oxy]-1H-benzotriazole | [M + H] calc. 581.1 obs. 580.8 |
| 303 | 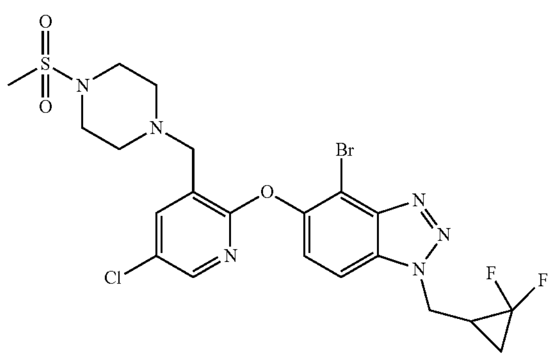 [SMILES: CS(=O)(=O)N1CCN(Cc2cc(Cl)cnc2Oc2ccc3c(nnn3CC3CC3(F)F)c2Br)CC1] | 4-bromo-5-[(5-chloro-3-{[4-(methylsulfonyl)piperazin-1-yl]methyl}pyridin-2-yl)oxy]-1-[(2,2-difluorocyclopropyl)methyl]-1H-benzotriazole | [M + H] calc. 591.0 obs. 590.9 |
| 304 | 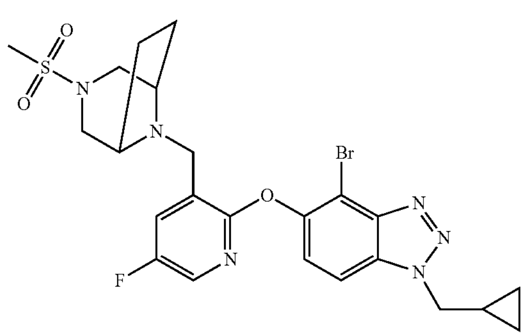 [SMILES: CS(=O)(=O)N1CC2CCC(C1)N2Cc1cc(F)cnc1Oc1ccc2c(nnn2CC2CC2)c1Br] | 4-bromo-1-(cyclopropylmethyl)-5-[(5-fluoro-3-{[3-(methylsulfonyl)-3,8-diazabicyclo[3.2.1]oct-8-yl]methyl}pyridin-2-yl)oxy]-1H-benzotriazole | [M + H] calc. 567.1 obs. 567.3 |

TABLE 2-continued

| Ex. | STRUCTURE | NAME | HRMS/LRMS |
|---|---|---|---|
| 305 | 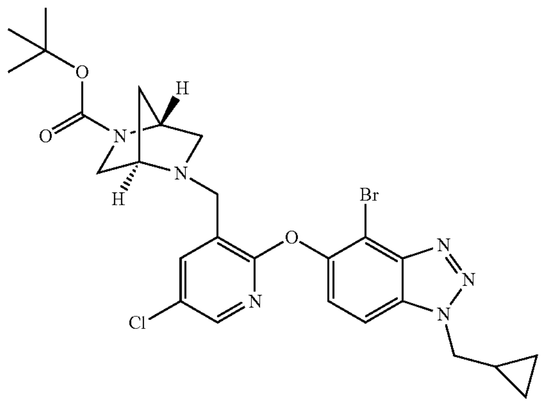 [SMILES: CC(C)(C)OC(=O)N1C[C@H]2C[C@@H]1CN2Cc1cc(Cl)cnc1Oc1ccc2c(nnn2CC2CC2)c1Br] | tert-butyl(1R,4R)-5-[(2-{[4-bromo-1-(cyclopropylmethyl)-1H-benzotriazol-5-yl]oxy}-5-chloropyridin-3-yl)methyl]-2,5-diazabicyclo[2.2.1]heptane-2-carboxylate | [M + H] calc. 589.1 obs. 588.9 |
| 306 | 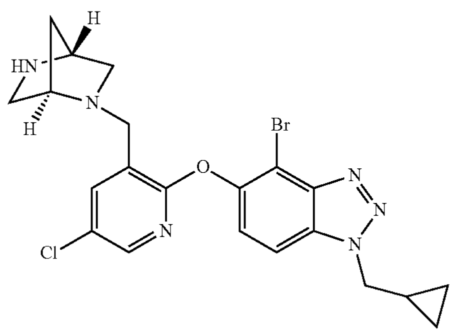 [SMILES: Clc1cnc(Oc2ccc3c(nnn3CC3CC3)c2Br)c(CN2C[C@H]3C[C@@H]2CN3)c1] | 4-bromo-5-({5-chloro 3-[(1R,4R)-2,5-diazabicyclo[2.2.1]hept-2-ylmethyl]pyridin-2-yl}oxy)-1-(cyclopropylmethyl)-1H-benzotriazole | [M + H] calc. 489.1 obs. 488.9 |
| 307 | 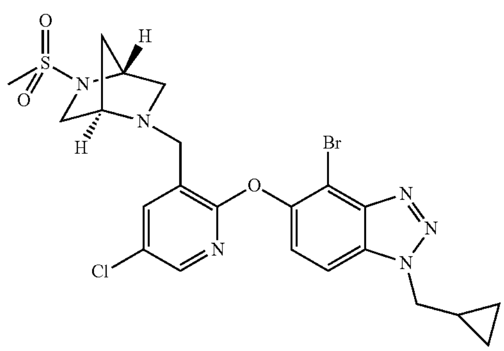 [SMILES: CS(=O)(=O)N1C[C@H]2C[C@@H]1CN2Cc1cc(Cl)cnc1Oc1ccc2c(nnn2CC2CC2)c1Br] | 4-bromo-5-[(5-chloro-3-{[(1R,4R)-5-(methylsulfonyl)-2,5-diazabicyclo[2.2.1]hept-2-yl]methyl}pyridin-2-yl)oxy]-1-(cyclopropylmethyl)-1H-benzotriazole | [M + H] calc. 567.1 obs. 566.8 |
| 308 | 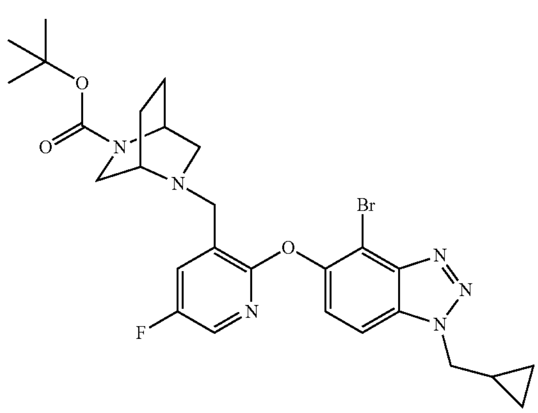 [SMILES: CC(C)(C)OC(=O)N1CC2CCC1CN2Cc1cc(F)cnc1Oc1ccc2c(nnn2CC2CC2)c1Br] | tert-butyl 5-[(2-{[4-bromo-1-(cyclopropylmethyl)-1H-benzotriazol-5-yl]oxy}-5-fluoropyridin-3-yl)methyl]-2,5-diazabicyclo[2.2.2]octane-2-carboxylate | [M + H] calc. 587.2 obs. 586.9 |

TABLE 2-continued

| Ex. | STRUCTURE | NAME | HRMS/LRMS |
|---|---|---|---|
| 309 | 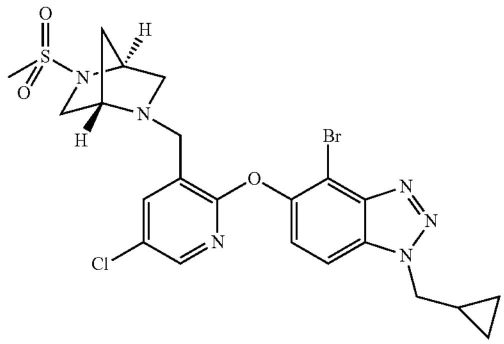 [SMILES: CS(=O)(=O)N1C[C@@H]2C[C@H]1CN2Cc1cc(Cl)cnc1Oc1ccc2c(nnn2CC2CC2)c1Br] | 4-bromo-5-[(5-chloro-3-{[(1S,4S)-5-(methylsulfonyl)-2,5-diazabicyclo[2.2.1]hept-2-yl]methyl}pyridin-2-yl)oxy]-1-(cyclopropylmethyl)-1H-benzotriazole | [M + H] calc. 567.1 obs. 566.8 |
| 310 | 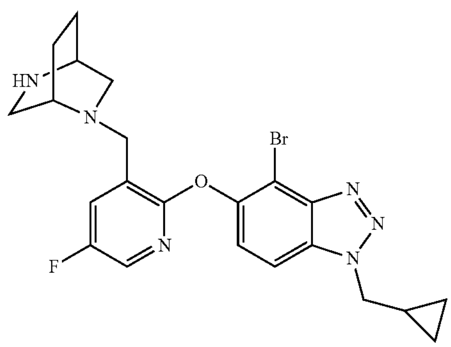 [SMILES: Fc1cnc(Oc2ccc3c(nnn3CC3CC3)c2Br)c(CN2CC3CCC2CN3)c1] | 4-bromo-1-(cyclopropylmethyl)-5-{[3-(2,5-diazabicyclo[2.2.2]oct-2-ylmethyl)-5-fluoropyridin-2-yl]oxy}-1H-benzotriazole | [M + H] calc. 487.1 obs. 486.9 |
| 311 | 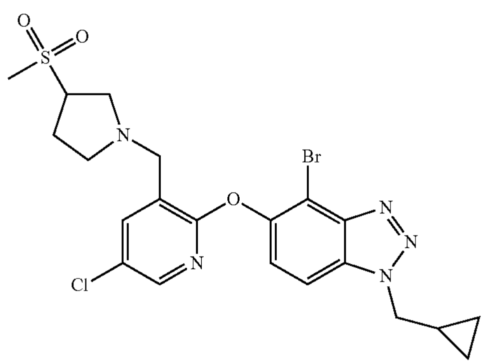 [SMILES: CS(=O)(=O)C1CCN(Cc2cc(Cl)cnc2Oc2ccc3c(nnn3CC3CC3)c2Br)C1] | 4-bromo-5-[(5-chloro-3-{[3-(methylsulfonyl)pyrrolidin-1-yl]methyl}pyridin-2-yl)oxy]-1-(cyclopropylmethyl)-1H-benzotriazole | [M + H] calc. 540.0 obs. 539.9 |
| 312 | 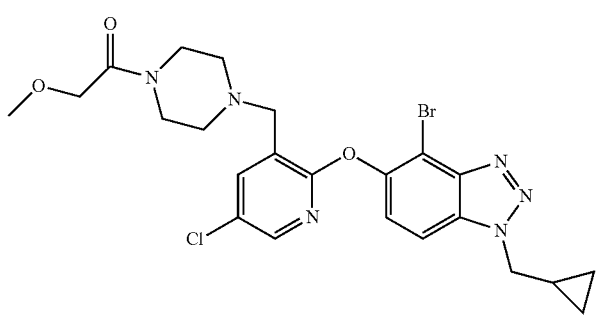 [SMILES: COCC(=O)N1CCN(Cc2cc(Cl)cnc2Oc2ccc3c(nnn3CC3CC3)c2Br)CC1] | 4-bromo-5-[(5-chloro-3-{[4-(methoxyacetyl)piperazin-1-yl]methyl}pyridin-2-yl)oxy]-1-(cyclopropylmethyl)-1H-benzotriazole | [M + H] calc. 549.1 obs. 548.8 |

TABLE 2-continued

| Ex. | STRUCTURE | NAME | HRMS/LRMS |
|---|---|---|---|
| 313 | 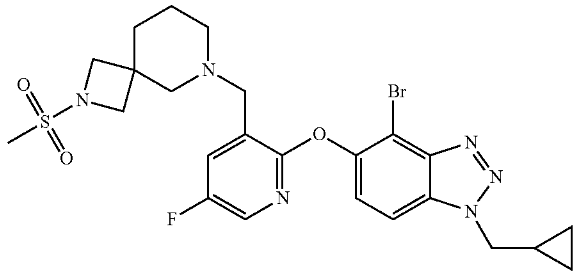 [SMILES: CS(=O)(=O)N1CC2(CCCN(Cc3cc(F)cnc3Oc3ccc4c(nnn4CC4CC4)c3Br)C2)C1] | 4-bromo-1-(cyclopropylmethyl)-5-[(5-fluoro-3-{[2-(methylsulfonyl)-2,6-diazaspiro[3.5]non-6-yl]methyl}pyridin-2-yl)oxy]-1H-benzotriazole | [M + H] calc. 578.1 obs. 580.9 |
| 314 | 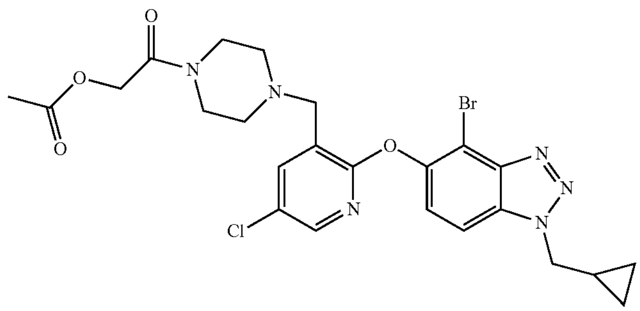 [SMILES: CC(=O)OCC(=O)N1CCN(Cc2cc(Cl)cnc2Oc2ccc3c(nnn3CC3CC3)c2Br)CC1] | 2-{4-[(2-{[4-bromo-1-(cyclopropylmethyl)-1H-benzotriazol-5-yl]oxy}-5-chloropyridin-3-yl)methyl]piperazin-1-yl}-2-oxoethyl acetate | [M + H] calc. 577.1 obs. 576.8 |
| 315 | 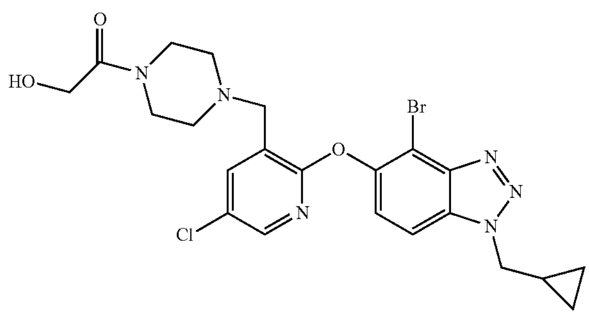 [SMILES: O=C(CO)N1CCN(Cc2cc(Cl)cnc2Oc2ccc3c(nnn3CC3CC3)c2Br)CC1] | 2-{4-[(2-{[4-bromo-1-(cyclopropylmethyl)-1H-benzotriazol-5-yl]oxy}-5-chloropyridin-3-yl)methyl]piperazin-1-yl}-2-oxoethanol | [M + H] calc. 535.1 obs. 534.9 |
| 316 | 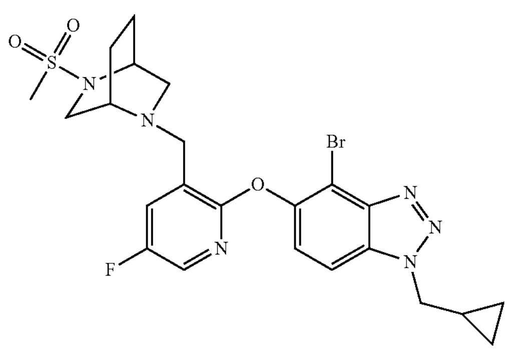 [SMILES: CS(=O)(=O)N1CC2CCC1CN2Cc1cc(F)cnc1Oc1ccc2c(nnn2CC2CC2)c1Br] | 4-bromo-1-(cyclopropylmethyl)-5-[(5-fluoro-3-{[5-(methylsulfonyl)-2,5-diazabicyclo[2.2.2]oct-2-yl]methyl}pyridin-2-yl)oxy]-1H-benzotriazole | [M + H] calc. 565.1 obs. 564.8 |
| 317 | 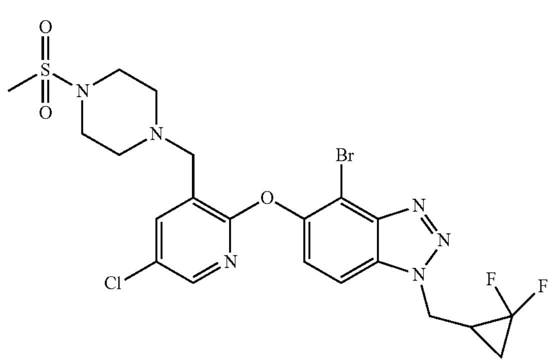 [SMILES: CS(=O)(=O)N1CCN(Cc2cc(Cl)cnc2Oc2ccc3c(nnn3CC3CC3(F)F)c2Br)CC1] | 4-bromo-5-[(5-chloro-3-{[4-(methylsulfonyl)piperazin-1-yl]methyl}pyridin-2-yl)oxy]-1-[(2,2-difluorocyclopropyl)methyl]-1H-benzotriazole | [M + H] calc. 591.0 obs. 590.9 |

TABLE 2-continued

| Ex. | STRUCTURE | NAME | HRMS/LRMS |
|---|---|---|---|
| 318 | 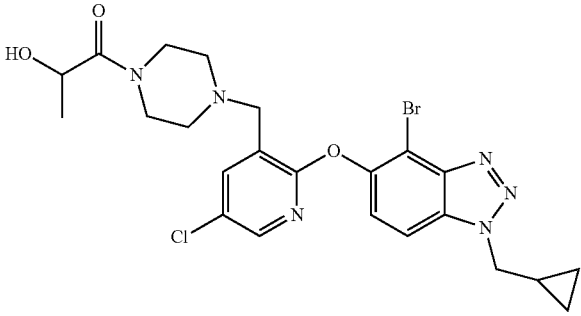 [SMILES: CC(O)C(=O)N1CCN(Cc2cc(Cl)cnc2Oc2ccc3c(nnn3CC3CC3)c2Br)CC1] | 1-{4-[(2-{[4-bromo-1-(cyclopropylmethyl)-1H-benzotriazol-5-yl]oxy}-5-chloropyridin-3-yl)methyl]piperazin-1-yl}-1-oxopropan-2-ol | [M + H] calc. 549.1 obs. 548.9 |
| 319 | 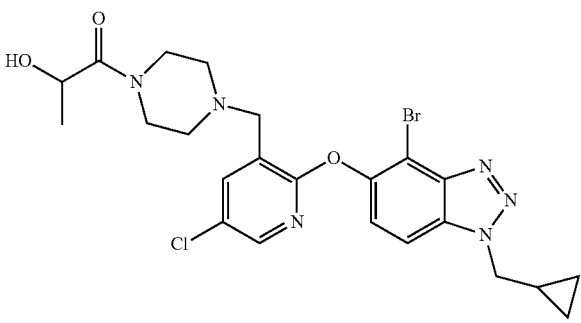 [SMILES: CC(O)C(=O)N1CCN(Cc2cc(Cl)cnc2Oc2ccc3c(nnn3CC3CC3)c2Br)CC1] | 1-{4-[(2-{[4-bromo-1-(cyclopropylmethyl)-1H-benzotriazol-5-yl]oxy}-5-chloropyridin-3-yl)methyl]piperazin-1-yl}-1-oxopropan-2-ol | [M + H] calc. 549.1 obs. 548.9 |
| 320 | 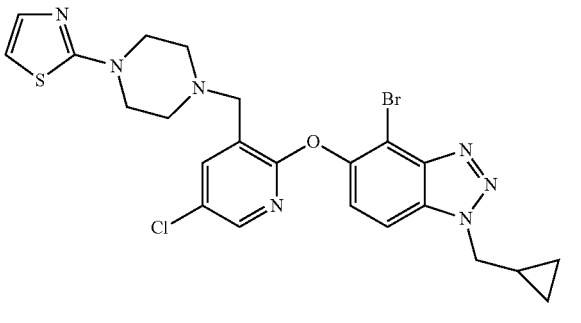 [SMILES: Clc1cnc(Oc2ccc3c(nnn3CC3CC3)c2Br)c(CN2CCN(c3nccs3)CC2)c1] | 4-bromo-5-[(5-chloro-3-{[4-(1,3-thiazol-2-yl)piperazin-1-yl]methyl}pyridin-2-yl)oxy]-1-(cyclopropylmethyl)-1H-benzotriazole | [M + H] calc. 560.1 obs. 560.3 |
| 321 | 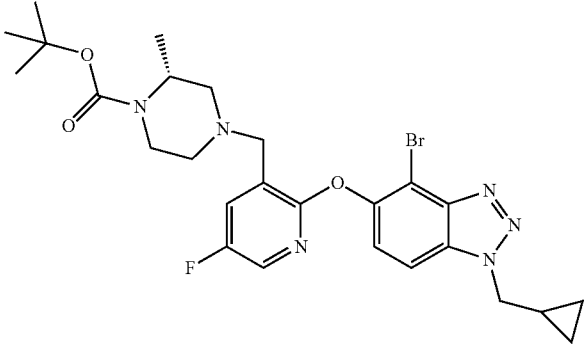 [SMILES: C[C@@H]1CN(Cc2cc(F)cnc2Oc2ccc3c(nnn3CC3CC3)c2Br)CCN1C(=O)OC(C)(C)C] | tert-butyl(2R)-4-[(2-{[4-bromo-1-(cyclopropylmethyl)-1H-benzotriazol-5-yl]oxy}-5-fluoropyridin-3-yl)methyl]-2-methylpiperazine-1-carboxylate | [M + H] calc. 575.2 obs. 575.4 |

TABLE 2-continued

| Ex. | STRUCTURE | NAME | HRMS/LRMS |
|---|---|---|---|
| 322 | 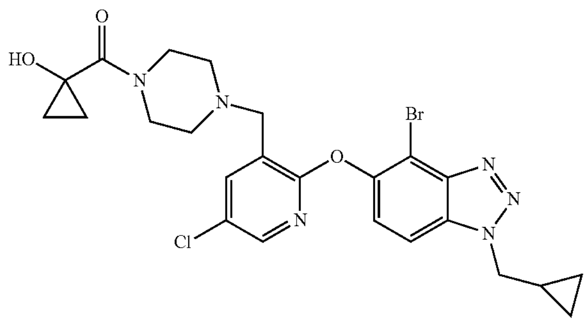 [SMILES: O=C(N1CCN(Cc2cc(Cl)cnc2Oc2ccc3c(nnn3CC3CC3)c2Br)CC1)C1(O)CC1] | 1-({4-[(2-{[4-bromo-1-(cyclopropylmethyl)-1H-benzotriazol-5-yl]oxy}-5-chloropyridin-3-yl)methyl]piperazin-1-yl}carbonyl)cyclopropanol | [M + H]<br>calc. 561.1<br>obs. 560.9 |
| 323 | 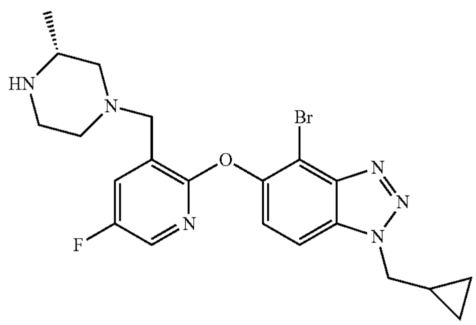 [SMILES: C[C@@H]1CN(Cc2cc(F)cnc2Oc2ccc3c(nnn3CC3CC3)c2Br)CCN1] | 4-bromo-1-(cyclopropylmethyl)-5-[(5-fluoro-3-{[(3R)-3-methylpiperazin-1-yl]methyl}pyridin-2-yl)oxy]-1H-benzotriazole | [M + H]<br>calc. 475.1<br>obs. 474.9 |
| 324 | 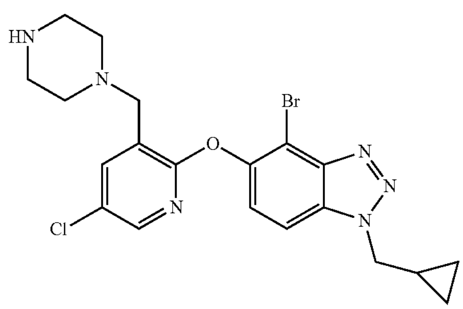 [SMILES: Clc1cnc(Oc2ccc3c(nnn3CC3CC3)c2Br)c(CN2CCNCC2)c1] | 4-bromo-5-{[5-chloro-3-(piperazin-1-ylmethyl)pyridin-2-yl]oxy}-1-(cyclopropylmethyl)-1H-benzotriazole | [M + H]<br>calc. 477.1<br>obs. 476.9 |
| 325 | 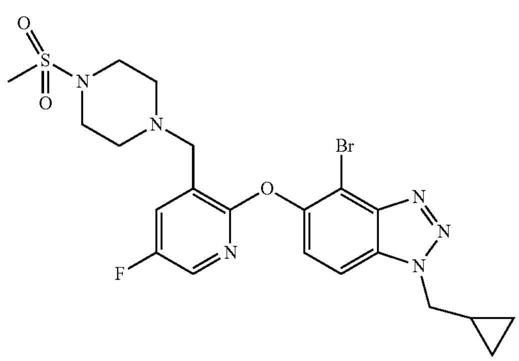 [SMILES: CS(=O)(=O)N1CCN(Cc2cc(F)cnc2Oc2ccc3c(nnn3CC3CC3)c2Br)CC1] | 4-bromo-1-(cyclopropylmethyl)-5-[(5-fluoro-3-{[4-(methylsulfonyl)piperazin-1-yl]methyl}pyridin-2-yl)oxy]-1H-benzotriazole | [M + H]<br>calc. 539.1<br>obs. 538.9 |

TABLE 2-continued

| Ex. | STRUCTURE | NAME | HRMS/LRMS |
|---|---|---|---|
| 326 | 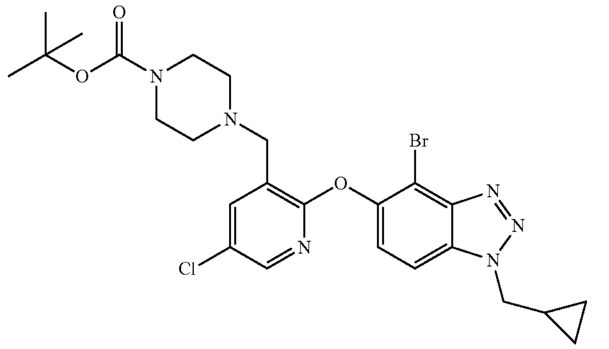 [SMILES: CC(C)(C)OC(=O)N1CCN(Cc2cc(Cl)cnc2Oc2ccc3c(nnn3CC3CC3)c2Br)CC1] | tert-butyl 4-[(2-{[4-bromo-1-(cyclopropylmethyl)-1H-benzotriazol-5-yl]oxy}-5-chloropyridin-3-yl)methyl]piperazine-1-carboxylate | [M + H] calc. 577.1 obs. 576.9 |
| 327 | 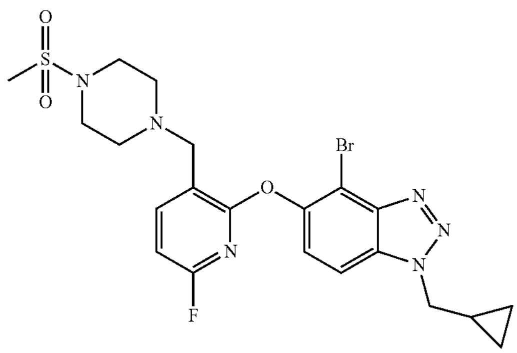 | 4-bromo-1-(cyclopropylmethyl)-5-[(6-fluoro-3-{[4-(methylsulfonyl)piperazin-1-yl]methyl}pyridin-2-yl)oxy]-1H-benzotriazole | [M + H] calc. 539.1 obs. 538.9 |
| 328 | 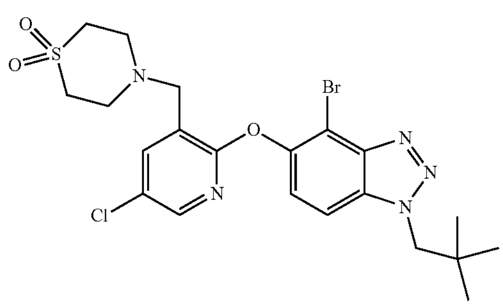 [SMILES: CC(C)(C)Cn1nnc2c(Br)c(Oc3ncc(Cl)cc3CN3CCS(=O)(=O)CC3)ccc21] | 4-bromo-5-({5-chloro-3-[(1,1-dioxidothiomorpholin-4-yl)methyl]pyridin-2-yl}oxy)-1-(2,2-dimethylpropyl)-1H-benzotriazole | [M + H] calc. 542.1 obs. 541.9 |
| 329 | 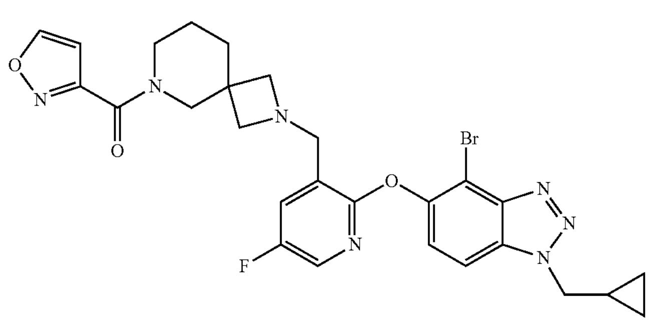 [SMILES: O=C(c1ccon1)N1CCCC2(CN(Cc3cc(F)cnc3Oc3ccc4c(nnn4CC4CC4)c3Br)C2)C1] | 4-bromo-1-(cyclopropylmethyl)-5-[(5-fluoro-3-{[6-(isoxazol-3-ylcarbonyl)-2,6-diazaspiro[3.5]non-2-yl]methyl}pyridin-2-yl)oxy]-1H-benzotriazole | [M + H] calc. 596.1 obs. 596.3 |

TABLE 2-continued

| Ex. | STRUCTURE | NAME | HRMS/LRMS |
|---|---|---|---|
| 330 | 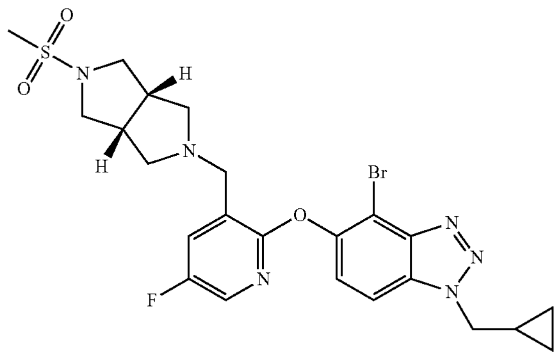 [SMILES: CS(=O)(=O)N1C[C@H]2CN(Cc3cc(F)cnc3Oc3ccc4c(nnn4CC4CC4)c3Br)C[C@H]2C1] | 4-bromo-1-(cyclopropylmethyl)-5-[(5-fluoro-3-{[(3aR,6aS)-5-(methylsulfonyl)hexahydropyrrolo[3,4-c]pyrrol-2(1H)-yl]methyl}pyridin-2-yl)oxy]-1H-benzotriazole | [M + H] calc. 567.1 obs. 567.3 |
| 331 | 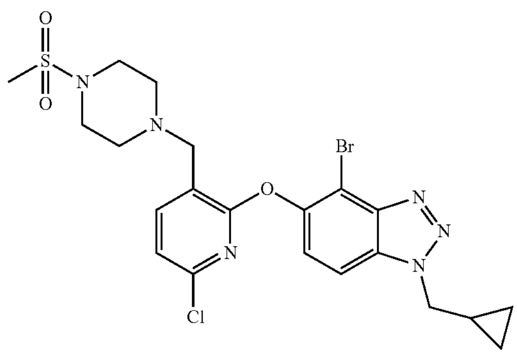 [SMILES: CS(=O)(=O)N1CCN(Cc2ccc(Cl)nc2Oc2ccc3c(nnn3CC3CC3)c2Br)CC1] | 4-bromo-5-[(6-chloro-3-{[4-(methylsulfonyl)piperazin-1-yl]methyl}pyridin-2-yl)oxy]-1-(cyclopropylmethyl)-1H-benzotriazole | [M + H] calc. 555.1 obs. 554.9 |
| 332 | 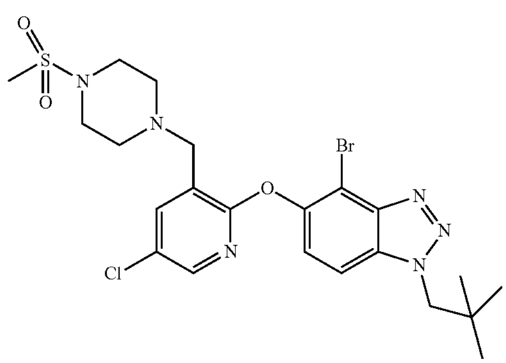 [SMILES: CC(C)(C)Cn1nnc2c(Br)c(Oc3ncc(Cl)cc3CN3CCN(S(C)(=O)=O)CC3)ccc21] | 4-bromo-5-[(5-chloro-3-{[4-(methylsulfonyl)piperazin-1-yl]methyl}pyridin-2-yl)oxy]-1-(2,2-dimethylpropyl)-1H-benzotriazole | [M + H] calc. 571.1 obs. 570.8 |
| 333 | 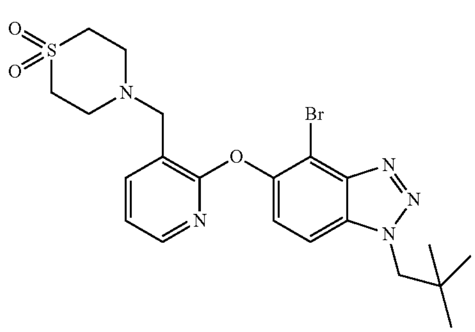 [SMILES: CC(C)(C)Cn1nnc2c(Br)c(Oc3ncccc3CN3CCS(=O)(=O)CC3)ccc21] | 4-bromo-1-(2,2-dimethylpropyl)-5-({3-[(1,1-dioxidothiomorpholin-4-yl)methyl]pyridin-2-yl}oxy)-1H-benzotriazole | [M + H] calc. 508.1 obs. 507.9 |

TABLE 2-continued

| Ex. | STRUCTURE | NAME | HRMS/LRMS |
|---|---|---|---|
| 334 | 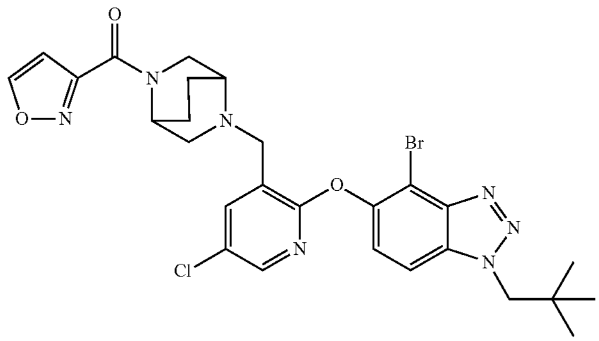 [SMILES: CC(C)(C)Cn1nnc2c(Br)c(Oc3ncc(Cl)cc3CN3CC4CCC3CN4C(=O)c3ccon3)ccc21] | 4-bromo-5-[(5-chloro-3-{[5-(isoxazol-3-ylcarbonyl)-2,5-diazabicyclo[2.2.2]oct-2-yl]methyl}pyridin-2-yl)oxy]-1-(2,2-dimethylpropyl)-1H-benzotriazole | [M + H]<br>calc. 616.1<br>obs. 616.3 |
| 335 | 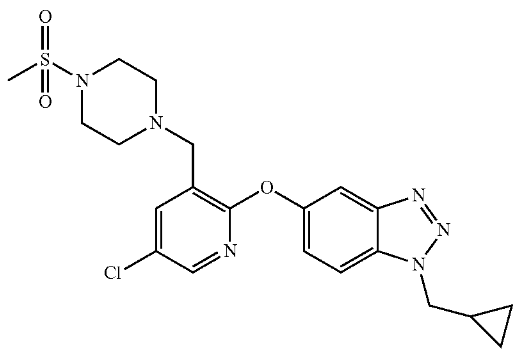 [SMILES: CS(=O)(=O)N1CCN(Cc2cc(Cl)cnc2Oc2ccc3c(c2)nnn3CC2CC2)CC1] | 5-[(5-chloro-3-{[4-(methylsulfonyl)piperazin-1-yl]methyl}pyridin-2-yl)oxy]-1-(cyclopropylmethyl)-1H-benzotriazole | [M + H]<br>calc. 477.1<br>obs. 476.9 |
| 336 | 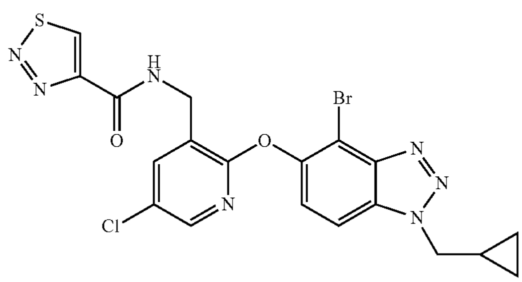 [SMILES: O=C(NCc1cc(Cl)cnc1Oc1ccc2c(nnn2CC2CC2)c1Br)c1csnn1] | N-[(2-{[4-bromo-1-(cyclopropylmethyl)-1H-benzotriazol-5-yl]oxy}-5-chloropyridin-3-yl)methyl]-1,2,3-thiadiazole-4-carboxamide | [M + H]<br>calc. 522.0<br>obs. 522.2 |
| 337 | 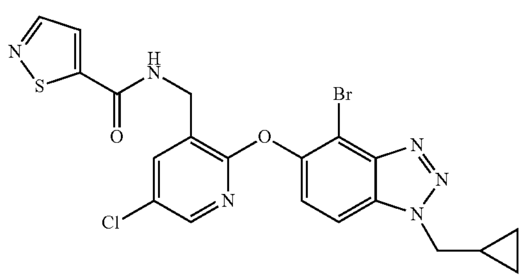 [SMILES: O=C(NCc1cc(Cl)cnc1Oc1ccc2c(nnn2CC2CC2)c1Br)c1ccns1] | N-[(2-{[4-bromo-1-(cyclopropylmethyl)-1H-benzotriazol-5-yl]oxy}-5-chloropyridin-3-yl)methyl]isothiazole-5-carboxamide | [M + H]<br>calc. 521.0<br>obs. 522.2 |
| 338 | 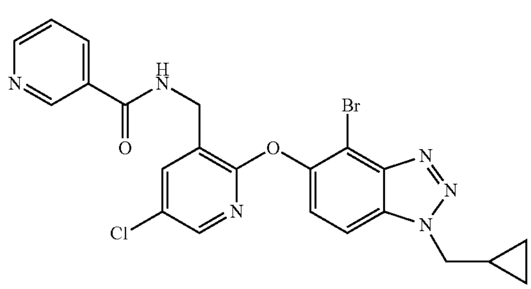 [SMILES: O=C(NCc1cc(Cl)cnc1Oc1ccc2c(nnn2CC2CC2)c1Br)c1cccnc1] | N-[(2-{[4-bromo-1-(cyclopropylmethyl)-1H-benzotriazol-5-yl]oxy}-5-chloropyridin-3-yl)methyl]pyridine-3-carboxamide | [M + H]<br>calc. 515.0<br>obs. 515.2 |

TABLE 2-continued

| Ex. | STRUCTURE | NAME | HRMS/LRMS |
|---|---|---|---|
| 339 | 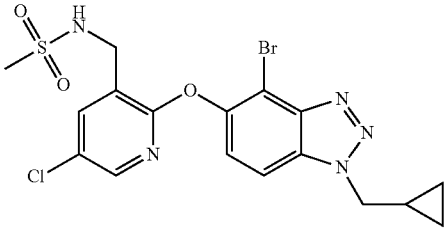 [SMILES: CS(=O)(=O)NCc1cc(Cl)cnc1Oc1ccc2c(nnn2CC2CC2)c1Br] | N-[(2-{[4-bromo-1-(cyclopropylmethyl)-1H-benzotriazol-5-yl]oxy}-5-chloropyridin-3-yl)methyl] methanesulfonamide | [M + H] calc. 488.0 obs. 488.1 |
| 340 | 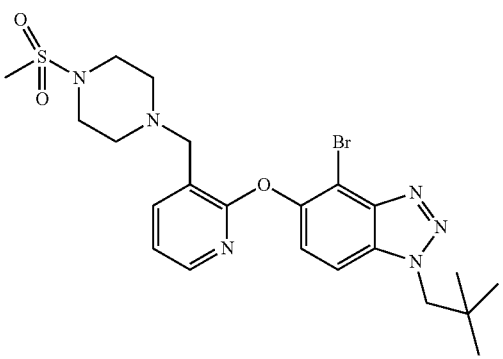 [SMILES: CC(C)(C)Cn1nnc2c(Br)c(Oc3ncccc3CN3CCN(S(C)(=O)=O)CC3)ccc21] | 4-bromo-1-(2,2-dimethylpropyl)-5-[(3-{[4-(methylsulfonyl) piperazin-1-yl]methyl}pyridin-2-yl)oxy]-1H-benzotriazole | [M + H] calc. 537.1 obs. 537.0 |
| 341 | 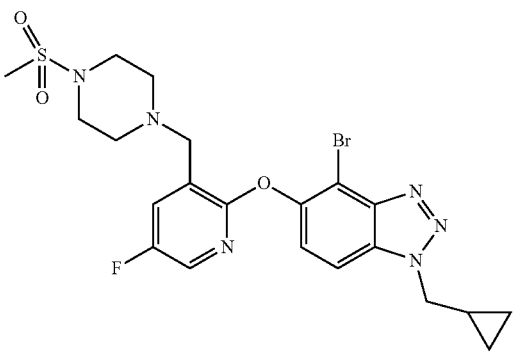 [SMILES: CS(=O)(=O)N1CCN(Cc2cc(F)cnc2Oc2ccc3c(nnn3CC3CC3)c2Br)CC1] | 4-bromo-1-(cyclopropylmethyl)-5-[(5-fluoro-3-{[4-(methylsulfonyl) piperazin-1-yl]methyl}pyridin-2-yl)oxy]-1H-benzotriazole | [M + H] calc. 539.1 obs. 538.9 |
| 342 | 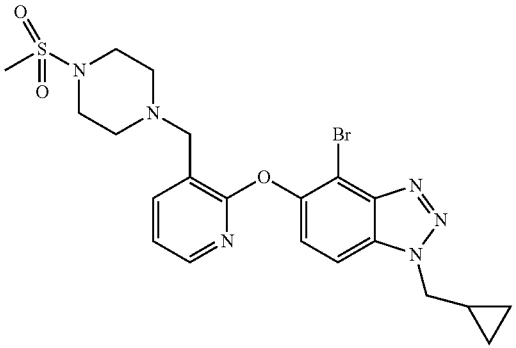 [SMILES: CS(=O)(=O)N1CCN(Cc2cccnc2Oc2ccc3c(nnn3CC3CC3)c2Br)CC1] | 4-bromo-1-(cyclopropylmethyl)-5-[(3-{[4-(methylsulfonyl) piperazin-1-yl]methyl}pyridin-2-yl)oxy]-1H-benzotriazole | [M + H] calc. 521.1 obs. 520.9 |

TABLE 2-continued

| Ex. | STRUCTURE | NAME | HRMS/LRMS |
|---|---|---|---|
| 343 | 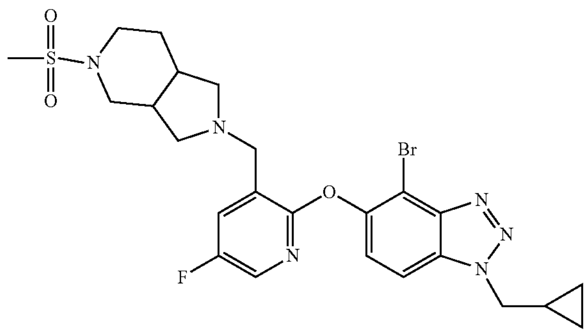 [SMILES: CS(=O)(=O)N1CCC2CN(Cc3cc(F)cnc3Oc3ccc4c(nnn4CC4CC4)c3Br)CC2C1] | 4-bromo-1-(cyclopropylmethyl)-5-[(5-fluoro-3-{[5-(methylsulfonyl)octahydro-2H-pyrrolo[3,4-c]pyridin-2-yl]methyl}pyridin-2-yl)oxy]-1H-benzotriazole | [M + H] calc. 580.1 obs. 580.3 |
| 344 | 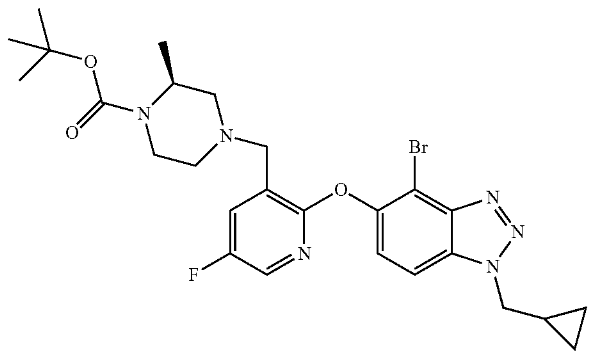 [SMILES: C[C@H]1CN(Cc2cc(F)cnc2Oc2ccc3c(nnn3CC3CC3)c2Br)CCN1C(=O)OC(C)(C)C] | tert-butyl (2S)-4-[(2-{[4-bromo-1-(cyclopropylmethyl)-1H-benzotriazol-5-yl]oxy}-5-fluoropyridin-3-yl)methyl]-2-methylpiperazine-1-carboxylate | [M + H] calc. 574.2 obs. 574.9 |
| 345 | 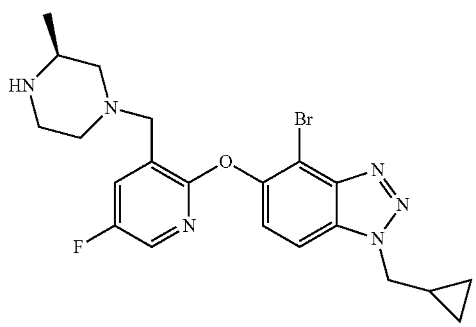 [SMILES: C[C@H]1CN(Cc2cc(F)cnc2Oc2ccc3c(nnn3CC3CC3)c2Br)CCN1] | 4-bromo-1-(cyclopropylmethyl)-5-[(5-fluoro-3-{[(3S)-3-methylpiperazin-1-yl]methyl}pyridin-2-yl)oxy]-1H-benzotriazole | [M + H] calc. 474.1 obs. 474.9 |
| 346 | 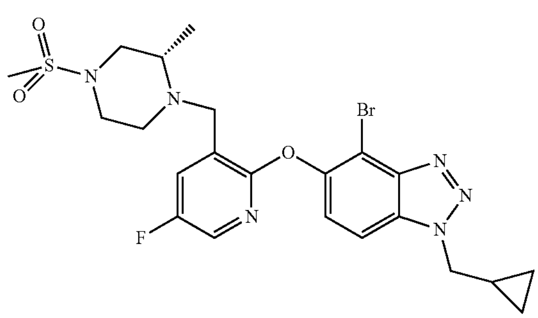 [SMILES: C[C@H]1CN(S(C)(=O)=O)CCN1Cc1cc(F)cnc1Oc1ccc2c(nnn2CC2CC2)c1Br] | 4-bromo-1-(cyclopropylmethyl)-5-[(5-fluoro-3-{[(2S)-2-methyl-4-(methylsulfonyl)piperazin-1-yl]methyl}pyridin-2-yl)oxy]-1H-benzotriazole | [M + H] calc. 552.1 obs. 552.8 |

TABLE 2-continued

| Ex. | STRUCTURE | NAME | HRMS/LRMS |
|---|---|---|---|
| 347 | 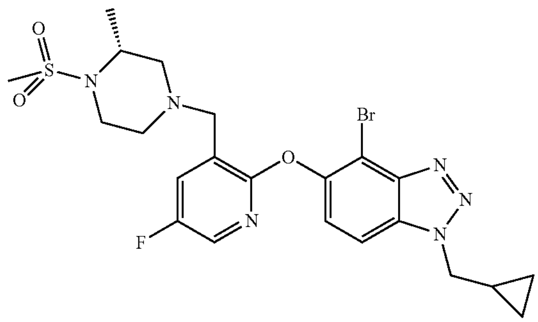 [SMILES: C[C@@H]1CN(Cc2cc(F)cnc2Oc2ccc3c(nnn3CC3CC3)c2Br)CCN1S(C)(=O)=O] | 4-bromo-1-(cyclopropylmethyl)-5-[(5-fluoro-3-{[(3R)-3-methyl-4-(methylsulfonyl)piperazin-1-yl]methyl}pyridin-2-yl)oxy]-1H-benzotriazole | [M + H] calc. 552.1 obs. 552.9 |
| 348 | 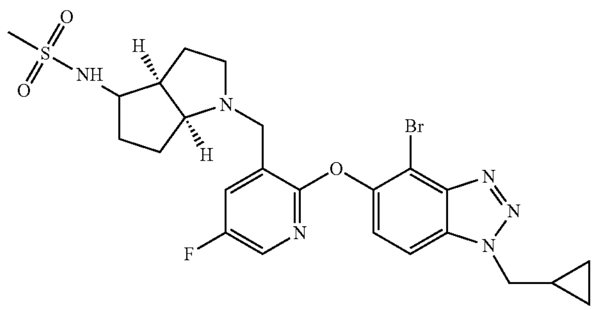 [SMILES: CS(=O)(=O)NC1CC[C@H]2[C@@H]1CCN2Cc1cc(F)cnc1Oc1ccc2c(nnn2CC2CC2)c1Br] | N-{(3aS,6aS)-1-[(2-{[4-bromo-1-(cyclopropylmethyl)-1H-benzotriazol-5-yl]oxy}-5-fluoropyridin-3-yl)methyl]octahydro-cyclopenta[b]pyrrol-4-yl}methanesulfonamide | [M + H] calc. 580.1 obs. 580.3 |
| 349 | 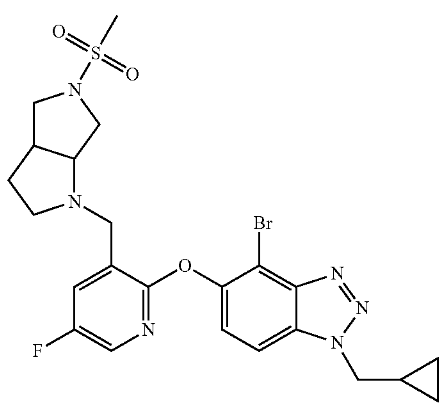 [SMILES: CS(=O)(=O)N1CC2CCN(Cc3cc(F)cnc3Oc3ccc4c(nnn4CC4CC4)c3Br)C2C1] | 4-bromo-1-(cyclopropylmethyl)-5-[(5-fluoro-3-{[5-(methylsulfonyl)hexahydropyrrolo[3,4-b]pyrrol-1(2H)-yl]methyl}pyridin-2-yl)oxy]-1H-benzotriazole | [M + H] calc. 567.1 obs. 567.2 |
| 350 | 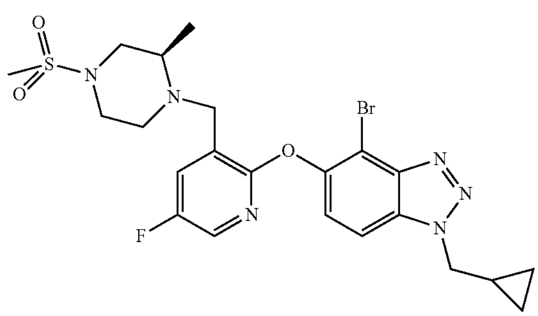 [SMILES: C[C@@H]1CN(S(C)(=O)=O)CCN1Cc1cc(F)cnc1Oc1ccc2c(nnn2CC2CC2)c1Br] | 4-bromo-1-(cyclopropylmethyl)-5-[(5-fluoro-3-{[(2R)-2-methyl-4-(methylsulfonyl)piperazin-1-yl]methyl}pyridin-2-yl)oxy]-1H-benzotriazole | [M + H] calc. 552.1 obs. 552.9 |

TABLE 2-continued

| Ex. | STRUCTURE | NAME | HRMS/LRMS |
|---|---|---|---|
| 351 | 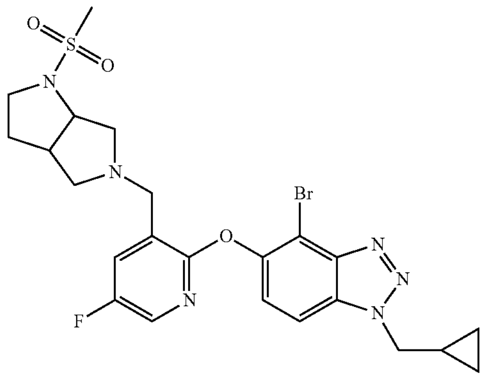 [SMILES: CS(=O)(=O)N1CCC2CN(Cc3cc(F)cnc3Oc3ccc4c(nnn4CC4CC4)c3Br)CC21] | 4-bromo-1-(cyclopropylmethyl)-5-[(5-fluoro-3-{[1-(methylsulfonyl)hexa-hydropyrrolo[3,4-b]pyrrol-5(1H)-yl]methyl}pyridin-2-yl)oxy]-1H-benzotriazole | [M + H]<br>calc. 567.1<br>obs. 567.2 |
| 352 | 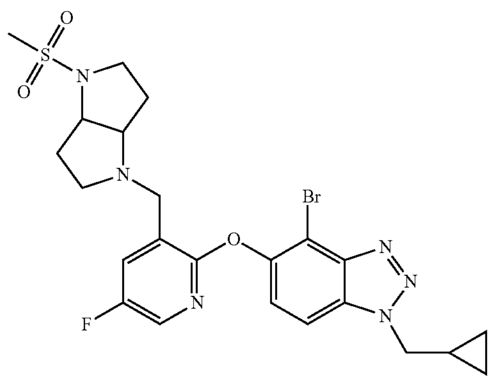 [SMILES: CS(=O)(=O)N1CCC2C1CCN2Cc1cc(F)cnc1Oc1ccc2c(nnn2CC2CC2)c1Br] | 4-bromo-1-(cyclopropylmethyl)-5-[(5-fluoro-3-{[4-(methylsulfonyl)hexa-hydropyrrolo[3,2-b]pyrrol-1(2H)-yl]methyl}pyridin-2-yl)oxy]-1H-benzotriazole | [M + H]<br>calc. 567.1<br>obs. 567.2 |
| 353 | 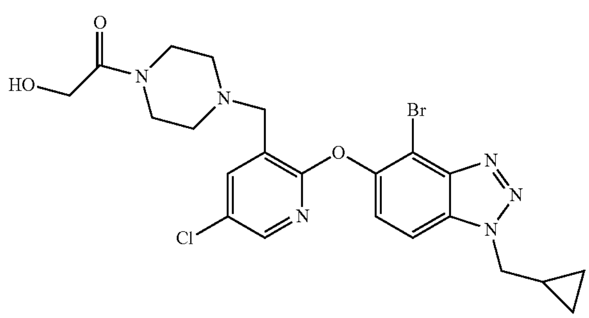 [SMILES: O=C(CO)N1CCN(Cc2cc(Cl)cnc2Oc2ccc3c(nnn3CC3CC3)c2Br)CC1] | 2-{4-[(2-{[4-bromo-1-(cyclopropylmethyl)-1H-benzotriazol-5-yl]oxy}-5-chloropyridin-3-yl)methyl]piperazin-1-yl}-2-oxoethanol | [M + H]<br>calc. 534.1<br>obs. 534.8 |
| 354 | 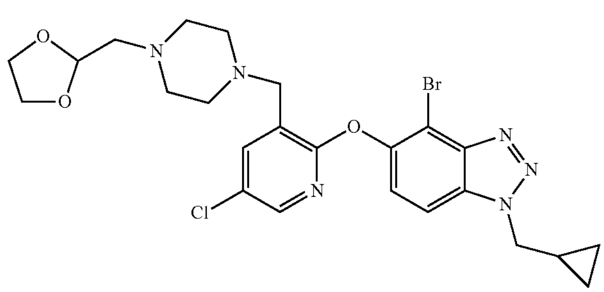 [SMILES: Clc1cnc(Oc2ccc3c(nnn3CC3CC3)c2Br)c(CN2CCN(CC3OCCO3)CC2)c1] | 4-bromo-5-[(5-chloro-3-{[4-(1,3-dioxolan-2-ylmethyl)piperazin-1-yl]methyl}pyridin-2-yl)oxy]-1-(cyclopropylmethyl)-1H-benzotriazole | [M + H]<br>calc. 562.1<br>obs. 563.1 |

TABLE 2-continued

| Ex. | STRUCTURE | NAME | HRMS/LRMS |
|---|---|---|---|
| 355 | 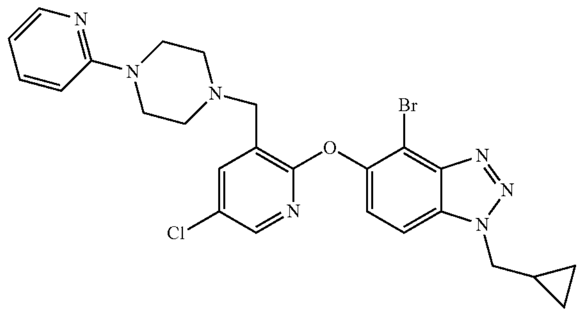 [SMILES: Clc1cnc(Oc2ccc3c(nnn3CC3CC3)c2Br)c(CN2CCN(c3ccccn3)CC2)c1] | 4-bromo-5-({5-chloro-3-[(4-pyridin-2-ylpiperazin-1-yl)methyl]pyridin-2-yl}oxy)-1-(cyclopropylmethyl)-1H-benzotriazole | [M + H] calc. 553.1 obs. 553.8 |
| 356 | 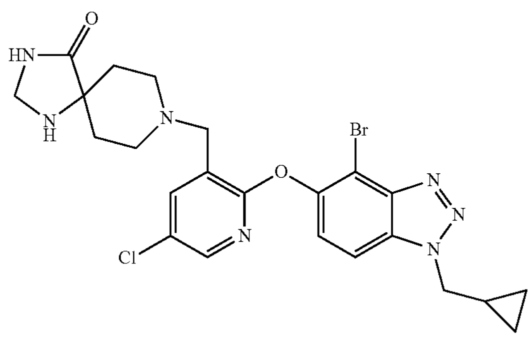 [SMILES: O=C1NCNC12CCN(Cc1cc(Cl)cnc1Oc1ccc3c(nnn3CC3CC3)c1Br)CC2] | 8-[(2-{[4-bromo-1-(cyclopropylmethyl)-1H-benzotriazol-5-yl]oxy}-5-chloropyridin-3-yl)methyl]-1,3,8-triazaspiro[4.5]decan-4-one | [M + H] calc. 545.1 obs. 546.0 |
| 357 | 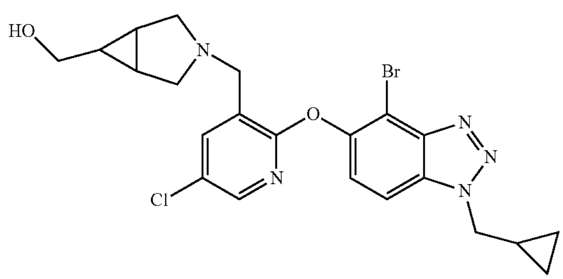 [SMILES: OCC1C2CN(Cc3cc(Cl)cnc3Oc3ccc4c(nnn4CC4CC4)c3Br)CC12] | {3-[(2-{[4-bromo-1-(cyclopropylmethyl)-1H-benzotriazol-5-yl]oxy}-5-chloropyridin-3-yl)methyl]-3-azabicyclo[3.1.0]hex-6-yl}methanol | [M + H] calc. 503.1 obs. 503.8 |
| 358 | 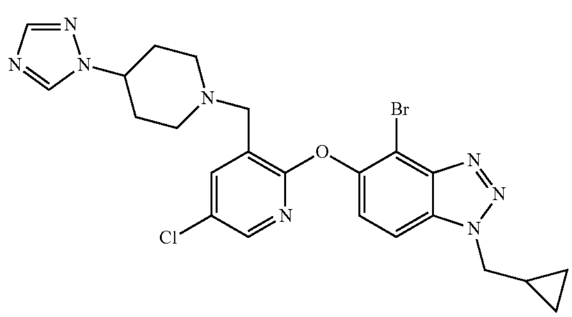 [SMILES: Clc1cnc(Oc2ccc3c(nnn3CC3CC3)c2Br)c(CN2CCC(n3cncn3)CC2)c1] | 4-bromo-5-[(5-chloro-3-{[4-(1H-1,2,4-triazol-1-yl)piperidin-1-yl]methyl}pyridin-2-yl)oxy]-1-(cyclopropylmethyl)-1H-benzotriazole | [M + H] calc. 542.1 obs. 543.0 |
| 359 | 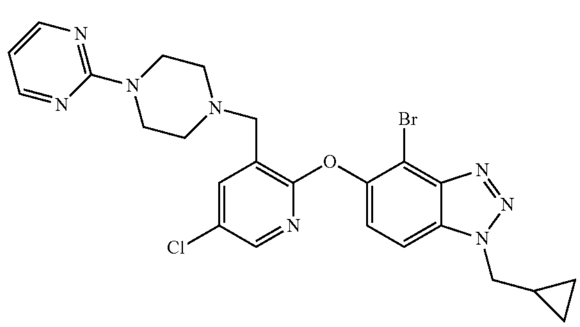 | 4-bromo-5-({5-chloro-3-[(4-pyrimidin-2-ylpiperazin-1-yl)methyl]pyridin-2-yl}oxy)-1-(cyclopropylmethyl)-1H-benzotriazole | [M + H] calc. 554.1 obs. 554.8 |

TABLE 2-continued

| Ex. | STRUCTURE | NAME | HRMS/LRMS |
|---|---|---|---|
| 360 | 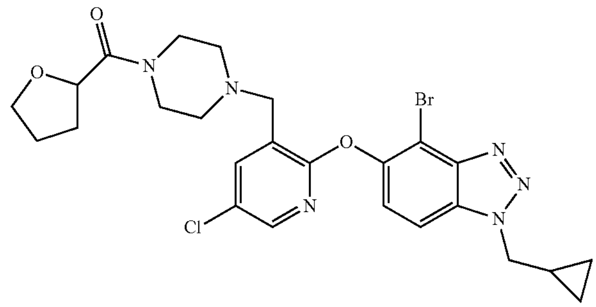 [SMILES: O=C(C1CCCO1)N1CCN(Cc2cc(Cl)cnc2Oc2ccc3c(nnn3CC3CC3)c2Br)CC1] | 4-bromo-5-[(5-chloro-3-{[4-(tetrahydrofuran-2-ylcarbonyl)piperazin-1-yl]methyl}pyridin-2-yl)oxy]-1-(cyclopropylmethyl)-1H-benzotriazole | [M + H] calc. 574.1 obs. 574.9 |
| 361 | 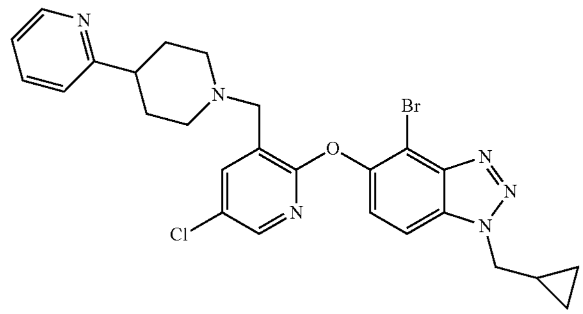 | 4-bromo-5-({5-chloro-3-[(4-pyridin-2-ylpiperidin-1-yl)methyl]pyridin-2-yl}oxy)-1-(cyclopropylmethyl)-1H-benzotriazole | [M + H] calc. 552.1 obs. 553.0 |
| 362 | 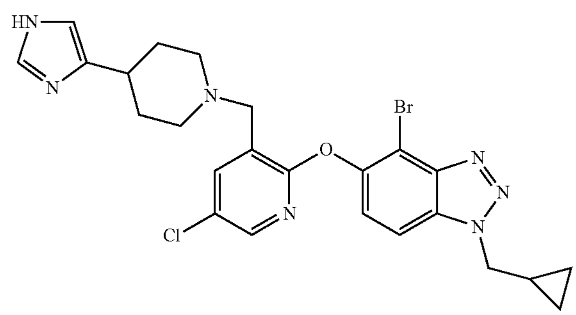 [SMILES: Clc1cnc(Oc2ccc3c(nnn3CC3CC3)c2Br)c(CN2CCC(c3c[nH]cn3)CC2)c1] | 4-bromo-5-[(5-chloro-3-{[4-(1H-imidazol-4-yl)piperidin-1-yl]methyl}pyridin-2-yl)oxy]-1-(cyclopropylmethyl)-1H-benzotriazole | [M + H] calc. 541.1 obs. 542.2 |
| 363 | 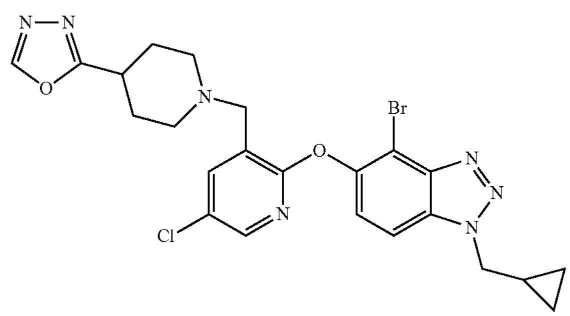 [SMILES: Clc1cnc(Oc2ccc3c(nnn3CC3CC3)c2Br)c(CN2CCC(c3nnco3)CC2)c1] | 4-bromo-5-[(5-chloro-3-{[4-(1,3,4-oxadiazol-2-yl)piperidin-1-yl]methyl}pyridin-2-yl)oxy]-1-(cyclopropylmethyl)-1H-benzotriazole | [M + H] calc. 543.1 obs. 543.8 |
| 364 | 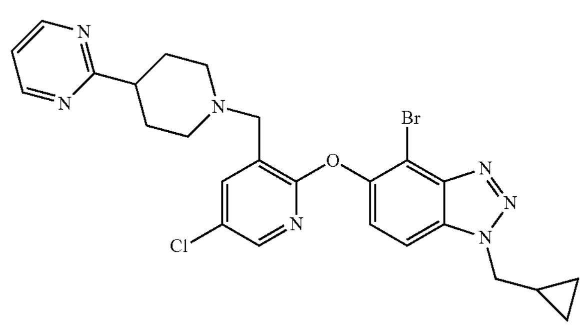 | 4-bromo-5-({5-chloro-3-[(4-pyrimidin-2-ylpiperidin-1-yl)methyl]pyridin-2-yl}oxy)-1-(cyclopropylmethyl)-1H-benzotriazole | [M + H] calc. 553.1 obs. 554.2 |

TABLE 2-continued

| Ex. | STRUCTURE | NAME | HRMS/LRMS |
|---|---|---|---|
| 365 | 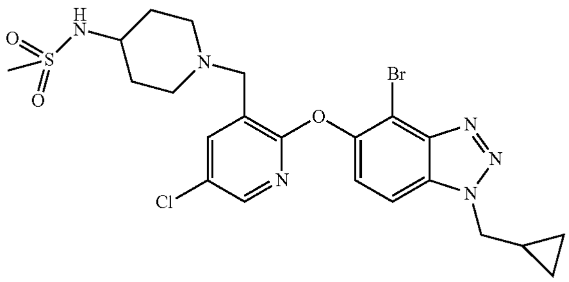 [SMILES: CS(=O)(=O)NC1CCN(Cc2cc(Cl)cnc2Oc2ccc3c(nnn3CC3CC3)c2Br)CC1] | N-{1-[(2-{[4-bromo-1-(cyclopropylmethyl)-1H-benzotriazol-5-yl]oxy}-5-chloropyridin-3-yl)methyl]piperidin-4-yl}methanesulfonamide | [M + H] calc. 568.1 obs. 568.8 |
| 366 | 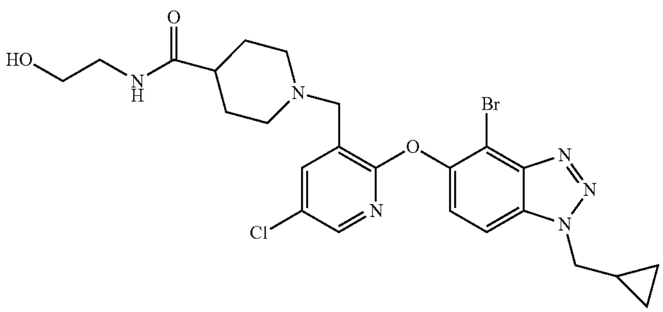 [SMILES: O=C(NCCO)C1CCN(Cc2cc(Cl)cnc2Oc2ccc3c(nnn3CC3CC3)c2Br)CC1] | 1-[(2-{[4-bromo-1-(cyclopropylmethyl)-1H-benzotriazol-5-yl]oxy}-5-chloropyridin-3-yl)methyl]-N-(2-hydroxyethyl)piperidine-4-carboxamide | [M + H] calc. 562.1 obs. 562.9 |
| 367 | 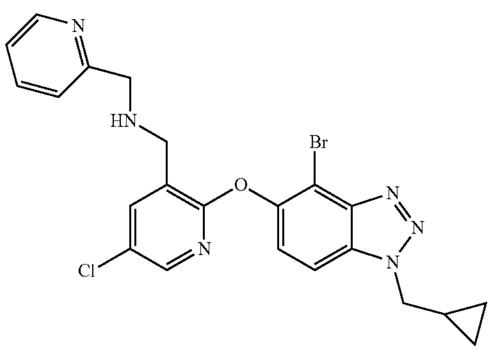 [SMILES: Clc1cnc(Oc2ccc3c(nnn3CC3CC3)c2Br)c(CNCc2ccccn2)c1] | 1-(2-{[4-bromo-1-(cyclopropylmethyl)-1H-benzotriazol-5-yl]oxy}-5-chloropyridin-3-yl)-N-(pyridin-2-ylmethyl)methanamine | [M + H] calc. 498.1 obs. 498.8 |
| 368 | 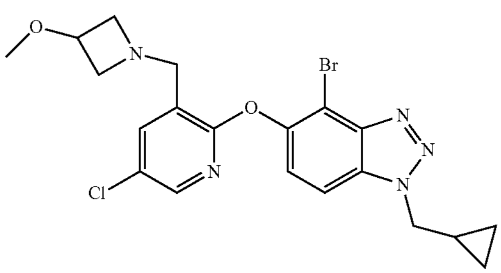 [SMILES: COC1CN(Cc2cc(Cl)cnc2Oc2ccc3c(nnn3CC3CC3)c2Br)C1] | 4-bromo-5-({5-chloro-3-[(3-methoxyazetidin-1-yl)methyl]pyridin-2-yl}oxy)-1-(cyclopropylmethyl)-1H-benzotriazole | [M + H] calc. 477.1 obs. 477.8 |
| 369 | 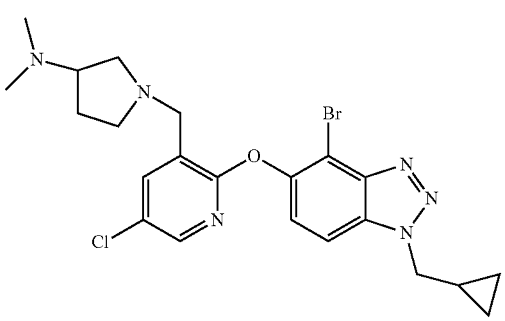 [SMILES: CN(C)C1CCN(Cc2cc(Cl)cnc2Oc2ccc3c(nnn3CC3CC3)c2Br)C1] | 1-[(2-{[4-bromo-1-(cyclopropylmethyl)-1H-benzotriazol-5-yl]oxy}-5-chloropyridin-3-yl)methyl]-N,N-dimethylpyrrolidin-3-amine | [M + H] calc. 504.1 obs. 504.9 |

TABLE 2-continued

| Ex. | STRUCTURE | NAME | HRMS/LRMS |
|---|---|---|---|
| 370 | 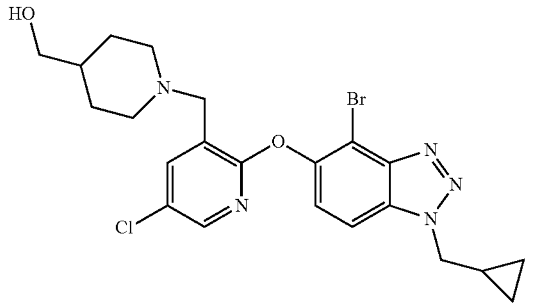 [SMILES: OCC1CCN(Cc2cc(Cl)cnc2Oc2ccc3c(nnn3CC3CC3)c2Br)CC1] | {1-[(2-{[4-bromo-1-(cyclopropylmethyl)-1H-benzotriazol-5-yl]oxy}-5-chloropyridin-3-yl)methyl]piperidin-4-yl}methanol | [M + H] calc. 505.1 obs. 505.9 |
| 371 | 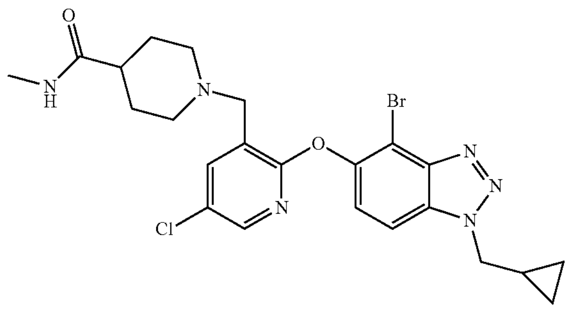 [SMILES: CNC(=O)C1CCN(Cc2cc(Cl)cnc2Oc2ccc3c(nnn3CC3CC3)c2Br)CC1] | 1-[(2-{[4-bromo-1-(cyclopropylmethyl)-1H-benzotriazol-5-yl]oxy}-5-chloropyridin-3-yl)methyl]-N-methylpiperidine-4-carboxamide | [M + H] calc. 532.1 obs. 532.9 |
| 372 | 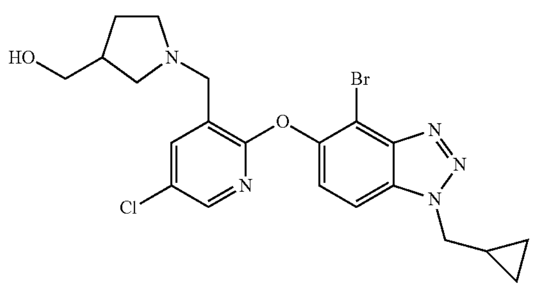 [SMILES: OCC1CCN(Cc2cc(Cl)cnc2Oc2ccc3c(nnn3CC3CC3)c2Br)C1] | {1-[(2-{[4-bromo-1-(cyclopropylmethyl)-1H-benzotriazol-5-yl]oxy}-5-chloropyridin-3-yl)methyl]pyrrolidin-3-yl}methanol | [M + H] calc. 491.1 obs. 491.9 |
| 373 | 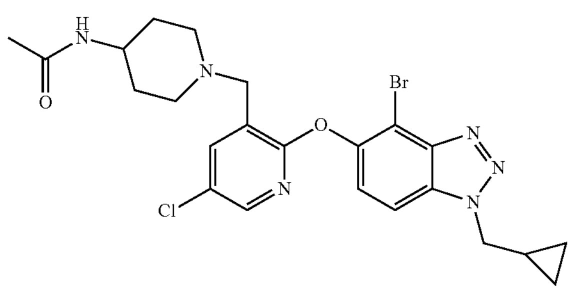 [SMILES: CC(=O)NC1CCN(Cc2cc(Cl)cnc2Oc2ccc3c(nnn3CC3CC3)c2Br)CC1] | N-{1-[(2-{[4-bromo-1-(cyclopropylmethyl)-1H-benzotriazol-5-yl]oxy}-5-chloropyridin-3-yl)methyl]piperidin-4-yl}acetamide | [M + H] calc. 532.1 obs. 532.9 |
| 374 | 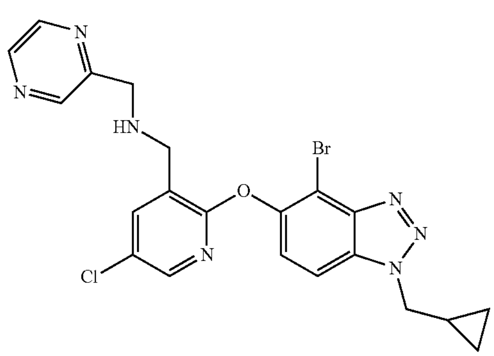 | 1-(2-{[4-bromo-1-(cyclopropylmethyl)-1H-benzotriazol-5-yl]oxy}-5-chloropyridin-3-yl)-N-(pyrazin-2-ylmethyl)methanamine | [M + H] calc. 499.1 obs. 499.8 |

TABLE 2-continued

| Ex. | STRUCTURE | NAME | HRMS/LRMS |
|---|---|---|---|
| 375 | 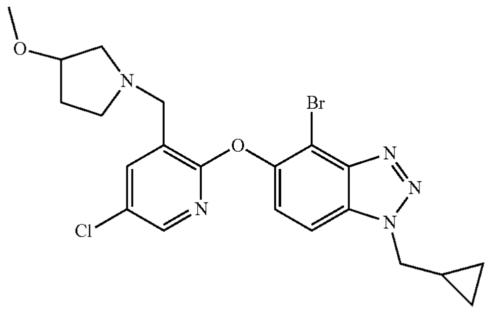 [SMILES: COC1CCN(Cc2cc(Cl)cnc2Oc2ccc3c(nnn3CC3CC3)c2Br)C1] | 4-bromo-5-({5-chloro-3-[(3-methoxypyrrolidin-1-yl)methyl]pyridin-2-yl}oxy)-1-(cyclopropylmethyl)-1H-benzotriazole | [M + H] calc. 491.1 obs. 491.8 |
| 376 | 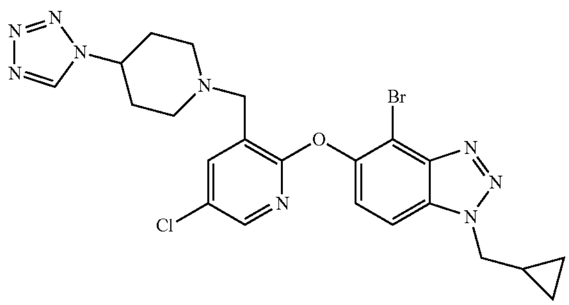 [SMILES: Clc1cnc(Oc2ccc3c(nnn3CC3CC3)c2Br)c(CN2CCC(n3cnnn3)CC2)c1] | 4-bromo-5-[(5-chloro-3-{[4-(1H-tetrazol-1-yl)piperidin-1-yl]methyl}pyridin-2-yl)oxy]-1-(cyclopropylmethyl)-1H-benzotriazole | [M + H] calc. 543.1 obs. 542.8 |
| 377 | 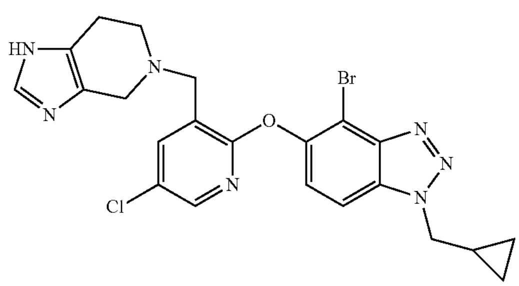 [SMILES: Clc1cnc(Oc2ccc3c(nnn3CC3CC3)c2Br)c(CN2CCc3[nH]cnc3C2)c1] | 4-bromo-5-{[5-chloro-3-(1,4,6,7-tetrahydro-5H-imidazo[4,5-c]pyridin-5-ylmethyl)pyridin-2-yl]oxy}-1-(cyclopropylmethyl)-1H-benzotriazole | [M + H] calc. 513.1 obs. 513.8 |
| 378 | 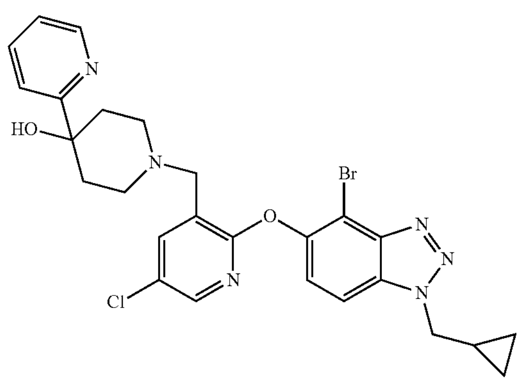 [SMILES: OC1(c2ccccn2)CCN(Cc2cc(Cl)cnc2Oc2ccc3c(nnn3CC3CC3)c2Br)CC1] | 1-[(2-{[4-bromo-1-(cyclopropylmethyl)-1H-benzotriazol-5-yl]oxy}-5-chloropyridin-3-yl)methyl]-4-pyridin-2-ylpiperidin-4-ol | [M + H] calc. 568.1 obs. 568.8 |
| 379 | 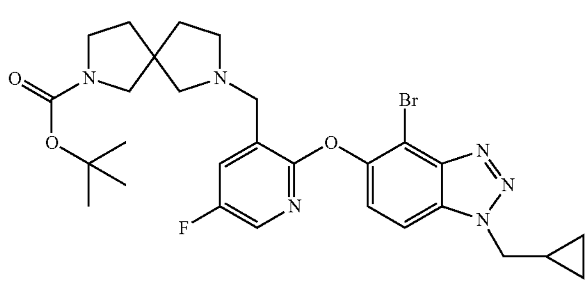 [SMILES: CC(C)(C)OC(=O)N1CCC2(CCN(Cc3cc(F)cnc3Oc3ccc4c(nnn4CC4CC4)c3Br)C2)C1] | tert-butyl 7-[(2-{[4-bromo-1-(cyclopropylmethyl)-1H-benzotriazol-5-yl]oxy}-5-fluoropyridin-3-yl)methyl]-2,7-diazaspiro[4.4]nonane-2-carboxylate | [M + H] calc. 603.2 obs. 603.2 |

TABLE 2-continued

| Ex. | STRUCTURE | NAME | HRMS/LRMS |
|---|---|---|---|
| 380 | 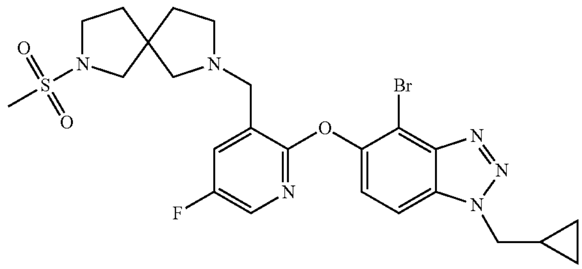 [SMILES: CS(=O)(=O)N1CCC2(CCN(Cc3cc(F)cnc3Oc3ccc4c(nnn4CC4CC4)c3Br)C2)C1] | 4-bromo-1-(cyclopropylmethyl)-5-[(5-fluoro-3-{[7-(methylsulfonyl)-2,7-diazaspiro[4.4]non-2-yl]methyl}pyridin-2-yl)oxy]-1H-benzotriazole | [M + H] calc. 581.1 obs. 581.1 |
| 381 | 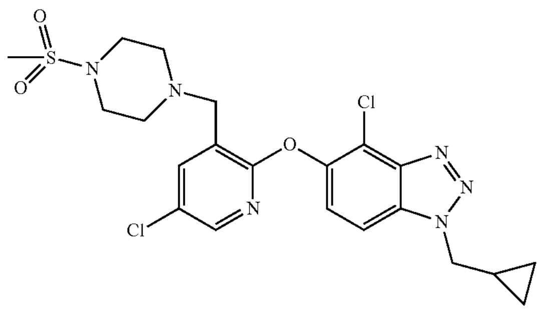 [SMILES: CS(=O)(=O)N1CCN(Cc2cc(Cl)cnc2Oc2ccc3c(nnn3CC3CC3)c2Cl)CC1] | 4-chloro-5-[(5-chloro-3-{[4-(methylsulfonyl)piperazin-1-yl]methyl}pyridin-2-yl)oxy]-1-(cyclopropylmethyl)-1H-benzotriazole | [M + H] calc. 510.1 obs. 510.9 |
| 382 | 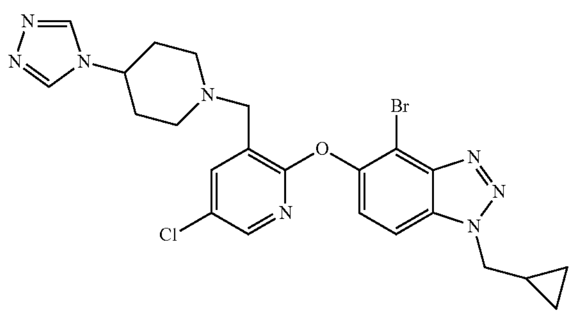 [SMILES: Clc1cnc(Oc2ccc3c(nnn3CC3CC3)c2Br)c(CN2CCC(n3cnnc3)CC2)c1] | 4-bromo-5-[(5-chloro-3-{[4-(4H-1,2,4-triazol-4-yl)piperidin-1-yl]methyl}pyridin-2-yl)oxy]-1-(cyclopropylmethyl)-1H-benzotriazole | [M + H] calc. 542.1 obs. 542.8 |
| 383 | 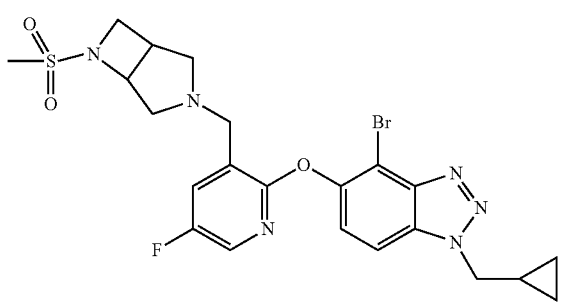 [SMILES: CS(=O)(=O)N1CC2CN(Cc3cc(F)cnc3Oc3ccc4c(nnn4CC4CC4)c3Br)CC21] | 4-bromo-1-(cyclopropylmethyl)-5-[(5-fluoro-3-{[6-(methylsulfonyl)-3,6-diazabicyclo[3.2.0]hept-3-yl]methyl}pyridin-2-yl)oxy]-1H-benzotriazole | [M + H] calc. 553.1 obs. 553.1 |
| 384 | 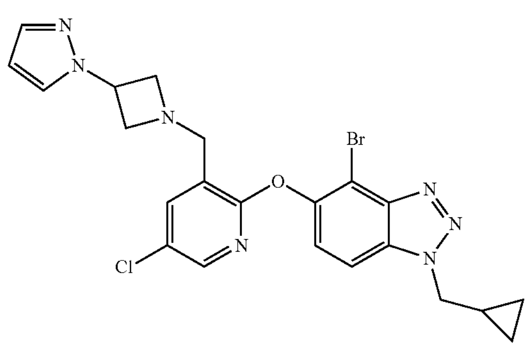 [SMILES: Clc1cnc(Oc2ccc3c(nnn3CC3CC3)c2Br)c(CN2CC(n3cccn3)C2)c1] | 4-bromo-5-[(5-chloro-3-{[3-(1H-pyrazol-1-yl)azetidin-1-yl]methyl}pyridin-2-yl)oxy]-1-(cyclopropylmethyl)-1H-benzotriazole | [M + H] calc. 513.1 obs. 513.9 |

TABLE 2-continued

| Ex. | STRUCTURE | NAME | HRMS/LRMS |
|---|---|---|---|
| 385 | 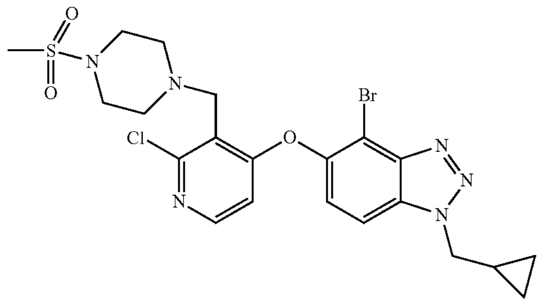 [SMILES: CS(=O)(=O)N1CCN(Cc2c(Oc3ccc4c(nnn4CC4CC4)c3Br)ccnc2Cl)CC1] | 4-bromo-5-[(2-chloro-3-{[4-(methylsulfonyl)piperazin-1-yl]methyl}pyridin-4-yl)oxy]-1-(cyclopropylmethyl)-1H-benzotriazole | [M + H] calc. 554.1 obs. 554.8 |
| 386 | 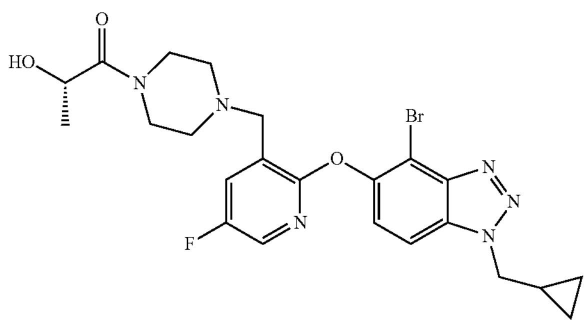 | (2S)-1-{4-[(2-{[4-bromo-1-(cyclopropylmethyl)-1H-benzotriazol-5-yl]oxy}-5-fluoropyridin-3-yl)methyl]piperazin-1-yl}-1-oxopropan-2-ol | [M + H] calc. 532.1 obs. 532.9 |
| 387 | 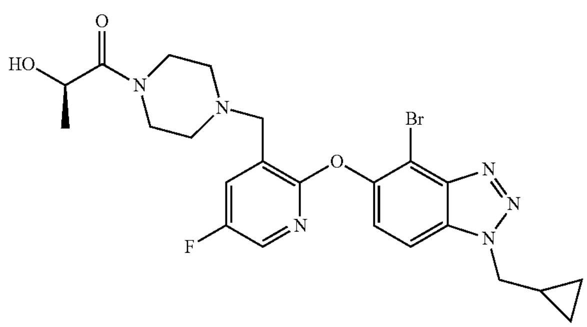 [SMILES: C[C@@H](O)C(=O)N1CCN(Cc2cc(F)cnc2Oc2ccc3c(nnn3CC3CC3)c2Br)CC1] | (2R)-1-{4-[(2-{[4-bromo-1-(cyclopropylmethyl)-1H-benzotriazol-5-yl]oxy}-5-fluoropyridin-3-yl)methyl]piperazin-1-yl}-1-oxopropan-2-ol | [M + H] calc. 532.1 obs. 532.9 |
| 388 | 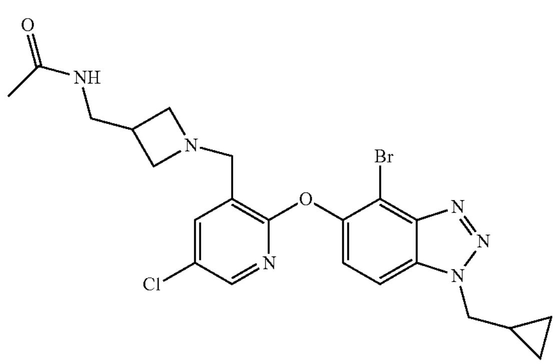 [SMILES: CC(=O)NCC1CN(Cc2cc(Cl)cnc2Oc2ccc3c(nnn3CC3CC3)c2Br)C1] | N-({1-[(2-{[4-bromo-1-(cyclopropylmethyl)-1H-benzotriazol-5-yl]oxy}-5-chloropyridin-3-yl)methyl]azetidin-3-yl}methyl)acetamide | [M + H] calc. 518.1 obs. 518.9 |

TABLE 2-continued

| Ex. | STRUCTURE | NAME | HRMS/LRMS |
|---|---|---|---|
| 389 | 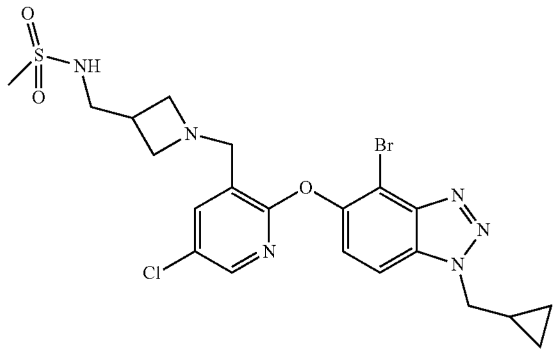 [SMILES: CS(=O)(=O)NCC1CN(Cc2cc(Cl)cnc2Oc2ccc3c(nnn3CC3CC3)c2Br)C1] | N-({1-[(2-{[4-bromo-1-(cyclopropylmethyl)-1H-benzotriazol-5-yl]oxy}-5-chloropyridin-3-yl)methyl]azetidin-3-yl}methyl)methanesulfonamide | [M + H] calc. 554.1 obs. 554.8 |
| 390 | 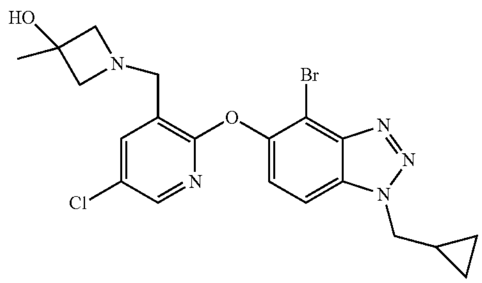 [SMILES: CC1(O)CN(Cc2cc(Cl)cnc2Oc2ccc3c(nnn3CC3CC3)c2Br)C1] | 1-[(2-{[4-bromo-1-(cyclopropylmethyl)-1H-benzotriazol-5-yl]oxy}-5-chloropyridin-3-yl)methyl]-3-methylazetidin-3-ol | [M + H] calc. 477.1 obs. 477.8 |
| 391 | 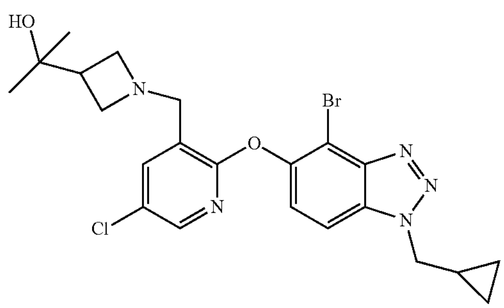 [SMILES: CC(C)(O)C1CN(Cc2cc(Cl)cnc2Oc2ccc3c(nnn3CC3CC3)c2Br)C1] | 2-{1-[(2-{[4-bromo-1-(cyclopropylmethyl)-1H-benzotriazol-5-yl]oxy}-5-chloropyridin-3-yl)methyl]azetidin-3-yl}propan-2-ol | [M + H] calc. 505.1 obs. 505.8 |
| 392 | 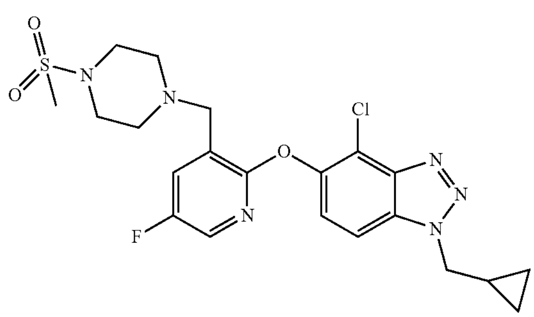 [SMILES: CS(=O)(=O)N1CCN(Cc2cc(F)cnc2Oc2ccc3c(nnn3CC3CC3)c2Cl)CC1] | 4-chloro-1-(cyclopropylmethyl)-5-[(5-fluoro-3-{[4-(methylsulfonyl)piperazin-1-yl]methyl}pyridin-2-yl)oxy]-1H-benzotriazole | [M + H] calc. 494.1 obs. 495.1 |
| 393 | 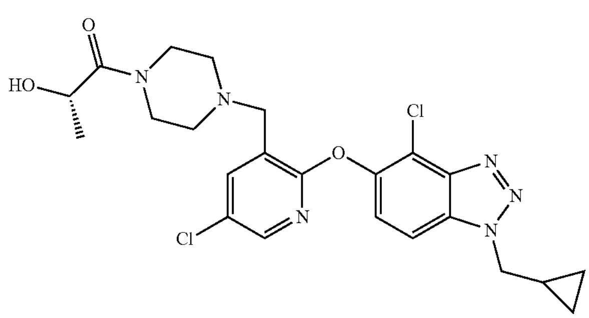 [SMILES: C[C@H](O)C(=O)N1CCN(Cc2cc(Cl)cnc2Oc2ccc3c(nnn3CC3CC3)c2Cl)CC1] | (2S)-1-{4-[(5-chloro-2-{[4-chloro-1-(cyclopropylmethyl)-1H-benzotriazol-5-yl]oxy}pyridin-3-yl)methyl]piperazin-1-yl}-1-oxopropan-2-ol | [M + H] calc. 504.1 obs. 505.2 |

TABLE 2-continued

| Ex. | STRUCTURE | NAME | HRMS/LRMS |
|---|---|---|---|
| 394 | 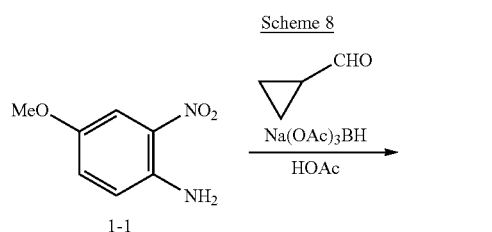 | (5-chloro-2-{[4-chloro-1-(cyclopropylmethyl)-1H-benzotriazol-5-yl]oxy}pyridin-3-yl)methanol | [M + H] calc. 364.0 obs. 365.2 |

Examples 395 and 396

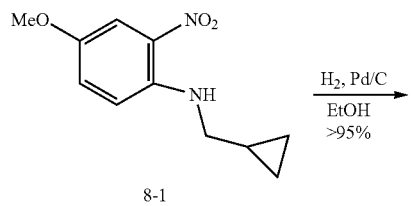

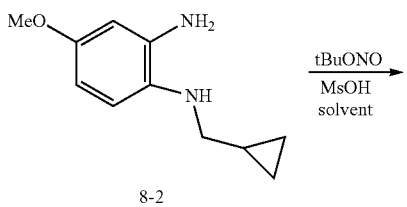

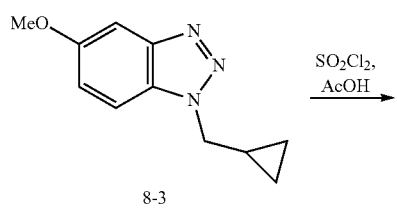

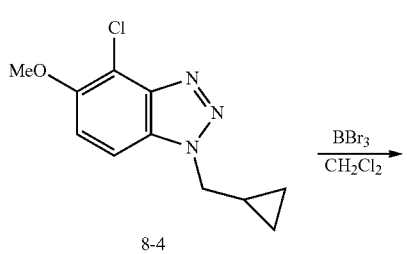

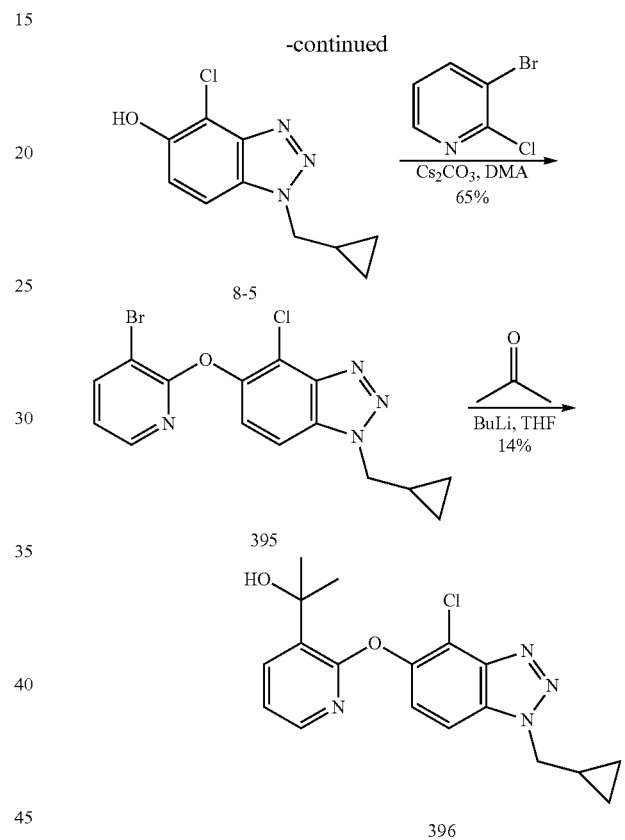

Step 1 Preparation of N-(cyclopropylmethyl)-4-methoxy-2-nitroaniline (8-1)

A 5 L vessel was charged 4-methoxy-2-nitroaniline (1-1, 160 g, 952 mmol) in dichloromethane (2.44 L), cooled to 10° C. and cyclopropanecarboxyaldehyde (100 g, 143 mmol) was added in four 25 gram portions. The vessel was charged with acetic acid (300 ml, 523 mmol) via an addition funnel fitted on the reactor and charged to the reaction mixture over 20 minutes. After 45 minutes, the vessel was charged with sodium triacetoxyborohydride (444 g, 209 mmol) portionwise. The mixture was warmed to ambient temperature over 4 hours and was stirred for an additional 14 hours. The mixture was treated with saturated aqueous sodium bicarbonate (100 mL) and poured into sodium bicarbonate (4 L) and dichloromethane. The organic extract was concentrated in vacuo, providing the titled compound 8-1.

Step 2 Preparation of N¹-(cyclopropylmethyl)-4-methoxybenzene-1,2-diamine (8-2)

N-(Cyclopropylmethyl)-4-methoxy-2-nitroaniline (8-1, 175 g) was dissolved in ethanol (1750 mL) and was added to a 4.0 L Hast 'C" Shaker can. The mixture was cooled to 10° C. and treated with 3% Pt/0.6% VG/C, deGussa (4.5 g). The vessel was sparged under nitrogen and then sparged three times with hydrogen at a setting of 40 psi and agitated for 2.5 hours. To a pre-washed solka-flok with ethanol, the reaction mixture was filtered through solka-flok through a sintered glass funnel to have about a ½ inch depth of solka-flok. The solka-flok was then washed with 1 L ethanol and concentrated in vacuo, providing the titled compound 8-2.

Step 3 Preparation of 1-(cyclopropylmethyl)-5-methoxy-1H-benzotriazole (8-3)

N¹-(Cyclopropylmethyl)-4-methoxybenzene-1,2-diamine (8-2, 10.8 g, 56.2 mmol) was dissolved in ethanol (80 mL) and treated with methanesulfonic acid (3.65 ml, 56.2 mmol) followed by isoamyl nitrite (7.56 ml, 56.2 mmol). The mixture was stirred for 15 minutes, diluted with ethyl acetate (1500 mL) and washed with saturated bicarbonate solution (500 mL×2). The organic extracts were concentrated in vacuo. The residue was purified by silica gel gradient chromatography (5-50% ethyl acetate in heptanes), providing the titled compound 8-3 as a tan solid.

Step 4 Preparation of 4-chloro-1-(cyclopropylmethyl)-5-methoxy-1H-benzotriazole (8-4)

1-(Cyclopropylmethyl)-5-methoxy-1H-benzotriazole (8-3, 10 g, 49 mmol) was dissolved in acetic acid (100 mL), cooled to 0° C. and treated with sulfuryl dichloride (4.8 mL, 59 mmol, 1.2 equiv) over three minutes. The mixture was warmed to ambient temperature over three hours and stirred for an additional 14 hours. The mixture was diluted with ethyl acetate and washed with aqueous saturated sodium bicarbonate. The organic layer was dried with magnesium sulfate, filtered and partially concentrated in vacuo to ~30 mL, which was then treated with water. The resulting precipitate was filtered, collected and dried in vacuo, providing the titled compound 8-4.

Step 5 Preparation of 4-chloro-1-(cyclopropylmethyl)-1H-benzotriazol-5-ol (8-5)

4-Chloro-1-(cyclopropylmethyl)-5-methoxy-1H-benzotriazole (8-4, 10.5 g, 44.2 mmol) was dissolved in dichloromethane (200 mL), cooled to 0° C. and treated with boron tribromide (88 mL, 1M dichloromethane solution, 88 mmol, 2 equiv). The ice bath was removed and the mixture was stirred for 4 hours at ambient temperature. The mixture was slowly treated with water (10 mL) and then treated with sodium hydroxide ON aqueous) until pH>10. After stirring for an additional 30 minutes, ammonium chloride (aqueous saturated) was added until the pH of the mixture was adjusted to pH 6-7. The aqueous mixture was exhaustively extracted with dichloromethane containing 5% methanol. The combined organic extracts were dried with sodium sulfate, filtered and concentrated in vacuo, providing the titled compound 8-5 as a light brown solid.

Step 6 Preparation of 5-[(3-bromopyridin-2-yl)oxy]-4-chloro-1-(cyclopropylmethyl)-1H-benzotriazole (395)

4-Chloro-1-(cyclopropylmethyl)-1H-benzotriazol-5-ol (8-5, 50 mg, 0.22 mmol, 1 equiv.) was dissolved in dimethylacetamide (1.5 mL) and treated with 3-bromo-2-chloropyridine (50 mg, 0.25 mmol, 1.15 equiv.) and cesium carbonate (146 mg, 0.45 mmol, 2 equiv). The mixture was stirred under microwave irradiation at 140° C. for 1 hour, treated with additional 3-bromo-2-chloropyridine (50 mg, 0.25 mmol, 1.15 equiv.) and cesium carbonate (80 mg, 0.24 mmol, 1 equiv.) and stirred for an additional hour at 140° C. under microwave irradiation. The mixture was extracted from water (50 mL) with ethyl acetate (3×50 mL) and the combined organic extracts were dried with sodium sulfate, filtered and concentrated in vacuo. The residue was purified via silica gel chromatography (100:0 to 50:50; hexanes:ethyl acetate) to provide the titled compound 395 as a white powder.

Step 7 Preparation of 2-(2-{[4-chloro-1-(cyclopropylmethyl)-1H-benzotriazol-5-yl]oxy}pyridin-3-yl)propan-2-ol (396)

5-[(3-Bromopyridin-2-yl)oxy]-4-chloro-1-(cyclopropylmethyl)-1H-benzotriazole (395, 33 mg, 0.09 mmol, 1 equiv) was dissolved in anhydrous tetrahydrofuran (2 mL), cooled to −70° C. and treated dropwise with n-butyllithium (2.5 M in tetrahydrofuran, 0.038 mL, 0.10 mmol, 1.1 equiv.). After 5 minutes, the mixture was treated with acetone (7.57 mg, 0.13 mmol, 1.5 equiv.). After an additional ten minutes at −70° C., the mixture was treated with water. The mixture was poured into water (40 mL) and extracted with ethyl acetate (3×50 mL). The combined organic extracts were dried with sodium sulfate, filtered and concentrated in vacuo. The residue was purified via preparative reverse phase HPLC (80:20 to 5:95; water containing 0.05% trifluoroacetic acid:acetonitrile containing 0.05% trifluoroacetic acid). The appropriate fractions were poured into sodium bicarbonate (saturated aqueous, 20 mL) and extracted with ethyl acetate (2×20 mL). The combined organic extracts were dried with sodium sulfate, filtered and concentrated in vacuo to afford the titled compound 396 as a white solid. $^1$H NMR (400 MHz, d$^6$-DMSO) δ 8.10 (dd, 1H, J=7.6, 1.9 Hz), 7.97 (d, 1H, J=8.9 Hz), 7.88 (dd, 1H, J=4.8, 1.8 Hz), 7.44 (d, 1H, J=9.2 Hz), 7.14 (dd, 1H, J=7.4, 4.6 Hz), 4.66 (d, 2H, J=7.5 Hz), 1.68 (s, 6H), 1.45-1.38 (m, 1H), 0.60-0.57 (m, 2H), 0.52-0.49 (m, 2H) ppm. High resolution mass spectrometry (ES+) m/z 359.1277 [(M+H)$^+$; calculated for $C_{18}H_{20}ClN_4O_2$: 359.1269].

The following compounds were prepared according to the general procedure described above, substituting the appropriate ketone or aldehyde for acetone (Step 7) or, substituting 2-chloroisonicotinaldehyde for 2-chloropyridine-3-carboxaldehyde (Step 6). The starting materials are either commercially available, known in the literature or may be prepared from commercially available reagents using conventional reactions well known in the art.

TABLE 3

| Ex. | STRUCTURE | NAME | HRMS/LRMS |
|---|---|---|---|
| 397 | 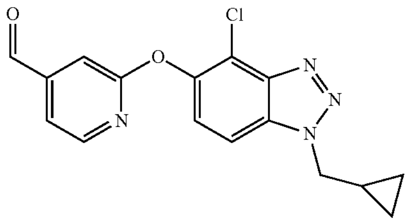 [SMILES: O=Cc1ccnc(Oc2ccc3c(nnn3CC3CC3)c2Cl)c1] | 2-{[4-chloro-1-(cyclopropylmethyl)-1H-benzotriazol-5-yl]oxy}pyridine-4-carbaldehyde | [M + H] calc'd 329.1 obs. 329.0 |
| 398 | 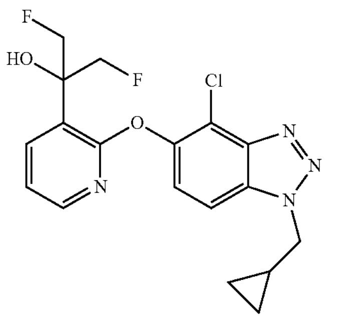 [SMILES: OC(CF)(CF)c1cccnc1Oc1ccc2c(nnn2CC2CC2)c1Cl] | 2-(2-{[4-chloro-1-(cyclopropylmethyl)-1H-benzotriazol-5-yl]oxy}pyridin-3-yl)-1,3-difluoropropan-2-ol | [M + H] calc. 395.1081 obs. 395.1091 |
| 399 | 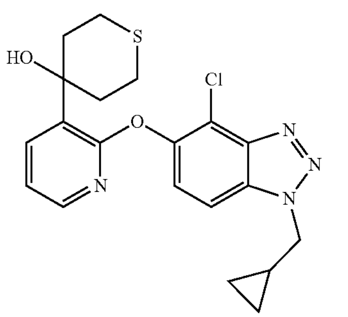 [SMILES: OC1(c2cccnc2Oc2ccc3c(nnn3CC3CC3)c2Cl)CCSCC1] | 4-(2-{[4-chloro-1-(cyclopropylmethyl)-1H-benzotriazol-5-yl]oxy}pyridin-3-yl)tetrahydro-2H-thiopyran-4-ol | [M + H] calc. 417.1147 obs. 417.1155 |
| 400 | 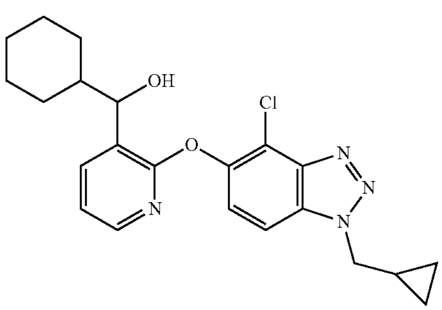 [SMILES: OC(c1cccnc1Oc1ccc2c(nnn2CC2CC2)c1Cl)C1CCCCC1] | (2-{[4-chloro-1-(cyclopropylmethyl)-1H-benzotriazol-5-yl]oxy}pyridin-3-yl)(cyclohexyl)methanol | [M + H] calc. 413.1739 obs. 413.1734 |
| 401 | 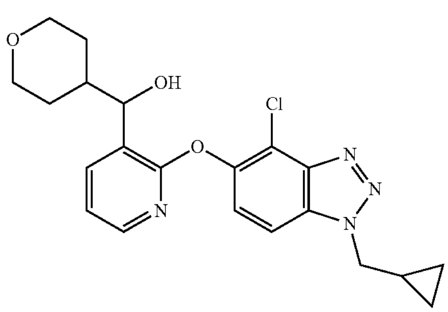 [SMILES: OC(c1cccnc1Oc1ccc2c(nnn2CC2CC2)c1Cl)C1CCOCC1] | (2-{[4-chloro-1-(cyclopropylmethyl)-1H-benzotriazol-5-yl]oxy}pyridin-3-yl)(tetrahydro-2H-pyran-4-yl)methanol | [M + H] calc. 415.1531 obs. 415.1528 |

TABLE 3-continued

| Ex. | STRUCTURE | NAME | HRMS/LRMS |
|---|---|---|---|
| 402 | 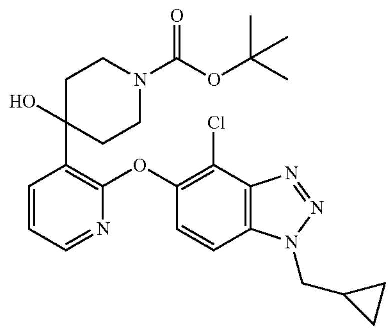 [SMILES: CC(C)(C)OC(=O)N1CCC(O)(c2cccnc2Oc2ccc3c(nnn3CC3CC3)c2Cl)CC1] | tert-butyl 4-(2-{[4-chloro-1-(cyclopropylmethyl)-1H-benzotriazol-5-yl]oxy}pyridin-3-yl)-4-hydroxypiperidine-1-carboxylate | [M + H] calc. 500.2059 obs. 500.2065 |
| 403 | 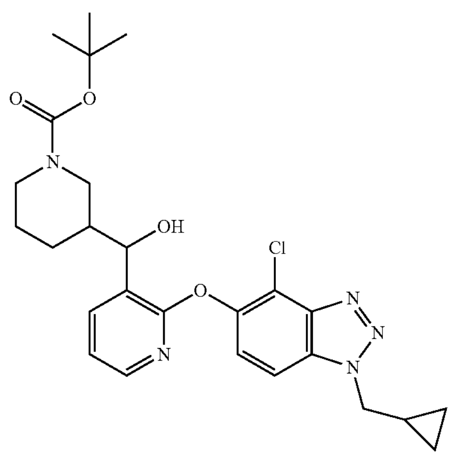 [SMILES: CC(C)(C)OC(=O)N1CCCC(C(O)c2cccnc2Oc2ccc3c(nnn3CC3CC3)c2Cl)C1] | tert-butyl 3-[(2-{[4-chloro-1-(cyclopropylmethyl)-1H-benzotriazol-5-yl]oxy}pyridin-3-yl)(hydroxy)methyl]piperidine-1-carboxylate | [M + H] calc. 514.2216 obs. 514.2218 |
| 404 | 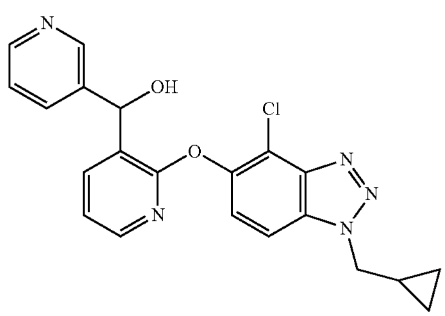 [SMILES: OC(c1cccnc1)c1cccnc1Oc1ccc2c(nnn2CC2CC2)c1Cl] | (2-{[4-chloro-1-(cyclopropylmethyl)-1H-benzotriazol-5-yl]oxy}pyridin-3-yl)(pyridin-3-yl)methanol | [M + H] calc. 408.1222 obs. 408.1214 |
| 405 | 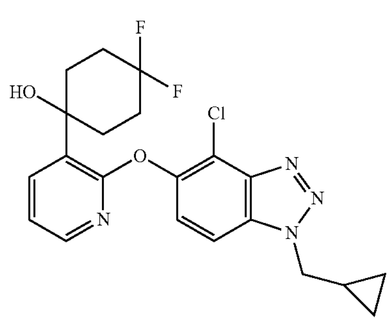 [SMILES: OC1(c2cccnc2Oc2ccc3c(nnn3CC3CC3)c2Cl)CCC(F)(F)CC1] | 1-(2-{[4-chloro-1-(cyclopropylmethyl)-1H-benzotriazol-5-yl]oxy}pyridin-3-yl)-4,4-difluorocyclohexanol | [M + H] calc. 435.1394 obs. 435.139 |

TABLE 3-continued

| Ex. | STRUCTURE | NAME | HRMS/LRMS |
|---|---|---|---|
| 406 | 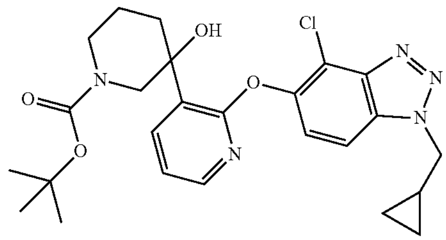 [SMILES: CC(C)(C)OC(=O)N1CCCC(O)(c2cccnc2Oc2ccc3c(nnn3CC3CC3)c2Cl)C1] | tert-butyl 3-(2-{[4-chloro-2-(cyclopropylmethyl)-1H-benzotriazol-5-yl]oxy}pyridin-3-yl)-3-hydroxypiperidine-1-carboxylate | [M + H] calc. 500.2059 obs. 500.2063 |
| 407 | 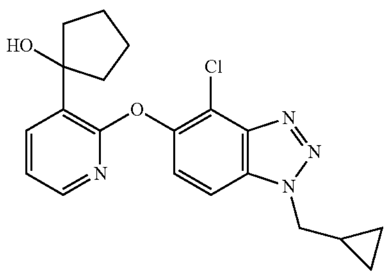 [SMILES: OC1(c2cccnc2Oc2ccc3c(nnn3CC3CC3)c2Cl)CCCC1] | 1-(2-{[4-chloro-1-(cyclopropylmethyl)-1H-benzotriazol-5-yl]oxy}pyridin-3-yl)cyclopentanol | [M + H] calc. 385.1426 obs. 385.1425 |
| 408 | 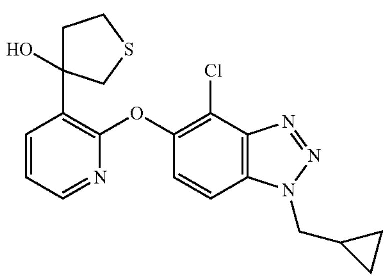 [SMILES: OC1(c2cccnc2Oc2ccc3c(nnn3CC3CC3)c2Cl)CCSC1] | 3-(2-{[4-chloro-1-(cyclopropylmethyl)-1H-benzotriazol-5-yl]oxy}pyridin-3-yl)tetrahydrothiophene-3-ol | [M + H] calc. 403.0990 obs. 403.0986 |
| 409 | 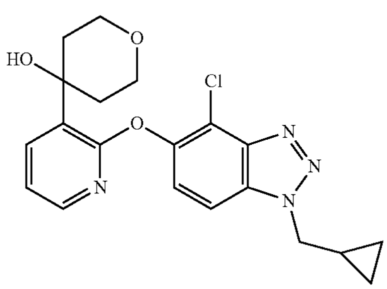 [SMILES: OC1(c2cccnc2Oc2ccc3c(nnn3CC3CC3)c2Cl)CCOCC1] | 4-(2-{[4-chloro-1-(cyclopropylmethyl)-1H-benzotriazol-5-yl]oxy}pyridin-3-yl)tetrahydro-2H-pyran-4-ol | [M + H] calc. 401.1375 obs. 401.1372 |
| 410 | 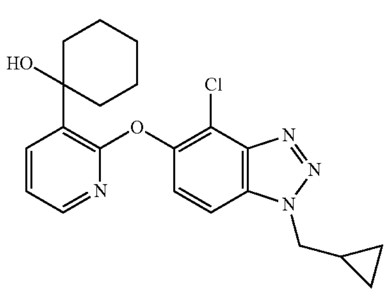 [SMILES: OC1(c2cccnc2Oc2ccc3c(nnn3CC3CC3)c2Cl)CCCCC1] | 1-(2-{[4-chloro-1-(cyclopropylmethyl)-1H-benzotriazol-5-yl]oxy}pyridin-3-yl)cyclohexanol | [M + H] calc. 399.1582 obs. 399.1577 |

TABLE 3-continued

| Ex. | STRUCTURE | NAME | HRMS/LRMS |
|---|---|---|---|
| 411 | 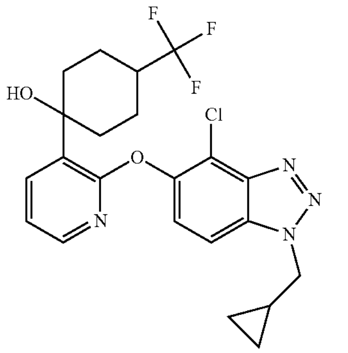 [SMILES: OC1(c2cccnc2Oc2ccc3c(nnn3CC3CC3)c2Cl)CCC(C(F)(F)F)CC1] | 1-(2-{[4-chloro-1-(cyclopropylmethyl)-1H-benzotriazol-5-yl]oxy}pyridin-3-yl)-4-(trifluoromethyl)cyclohexanol | [M + H] calc. 467.1456 obs. 467.1452 |
| 412 | 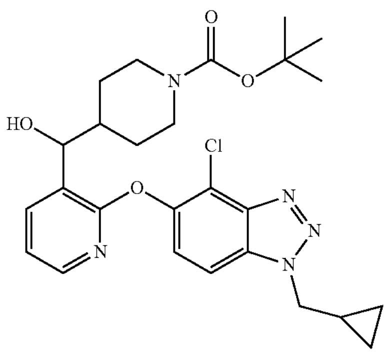 [SMILES: CC(C)(C)OC(=O)N1CCC(C(O)c2cccnc2Oc2ccc3c(nnn3CC3CC3)c2Cl)CC1] | tert-butyl 4-[(2-{[4-chloro-1-(cyclopropylmethyl)-1H-benzotriazol-5-yl]oxy}pyridin-3-yl)(hydroxy)methyl]piperidine-1-carboxylate | [M + H] calc. 514.2216 obs. 514.2211 |
| 413 | 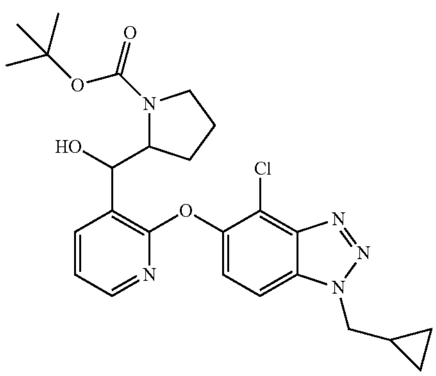 [SMILES: CC(C)(C)OC(=O)N1CCCC1C(O)c1cccnc1Oc1ccc2c(nnn2CC2CC2)c1Cl] | tert-butyl 2-[(2-{[4-chloro-1-(cyclopropylmethyl)-1H-benzotriazol-5-yl]oxy}pyridin-3-yl)(hydroxy)methyl]pyrrolidine-1-carboxylate | [M + H] calc. 500.2059 obs. 500.2047 |
| 414 | 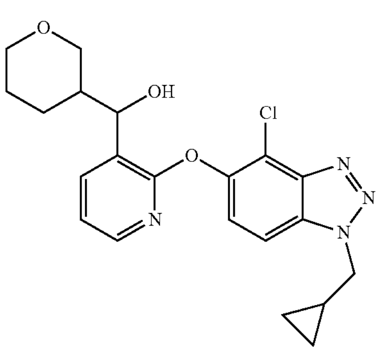 [SMILES: OC(c1cccnc1Oc1ccc2c(nnn2CC2CC2)c1Cl)C1CCCOC1] | (2-{[4-chloro-1-(cyclopropylmethyl)-1H-benzotriazol-5-yl]oxy}pyridin-3-yl)(tetrahydro-2H-pyran-3-yl)methanol | [M + H] calc. 415.1531 obs. 415.1529 |

TABLE 3-continued
| Ex. | STRUCTURE | NAME | HRMS/LRMS |
|---|---|---|---|
| 415 | 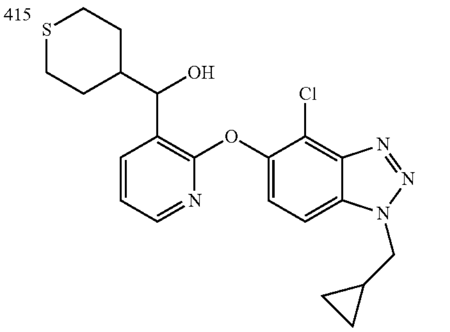 | (2-{[4-chloro-1-(cyclopropylmethyl)-1H-benzotriazol-5-yl]oxy}pyridin-3-yl)(tetrahydro-2H-thiopyran-4-yl)methanol | [M + H] calc. 431.1303 obs. 431.1301 |
| 416 | 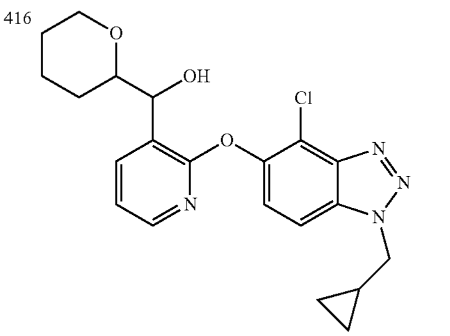 | (2-{[4-chloro-1-(cyclopropylmethyl)-1H-benzotriazol-5-yl]oxy}pyridin-3-yl)(tetrahydro-2H-pyran-2-yl)methanol | [M + H] calc. 415.1531 obs. 415.1529 |
Examples 417 and 418
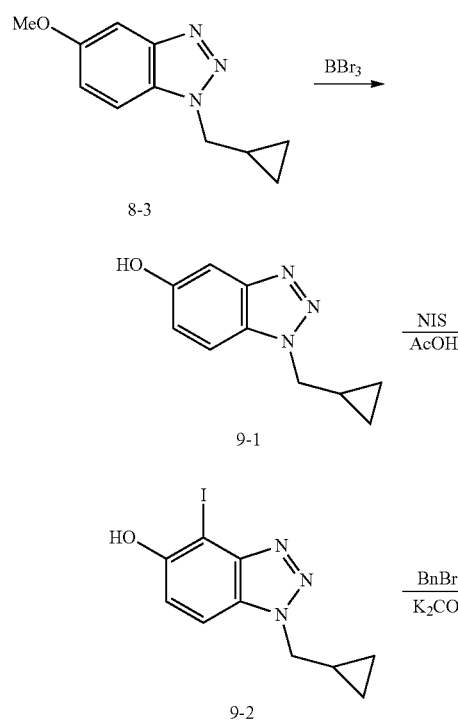
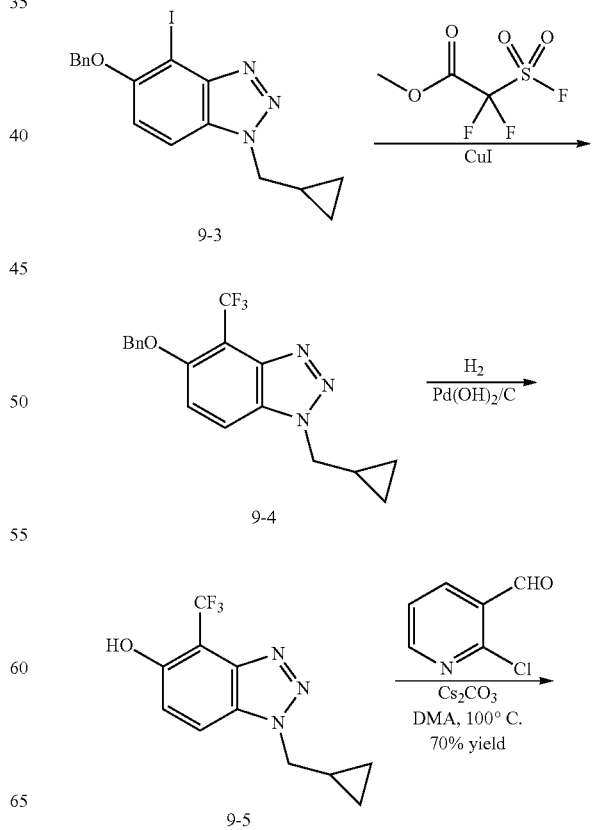

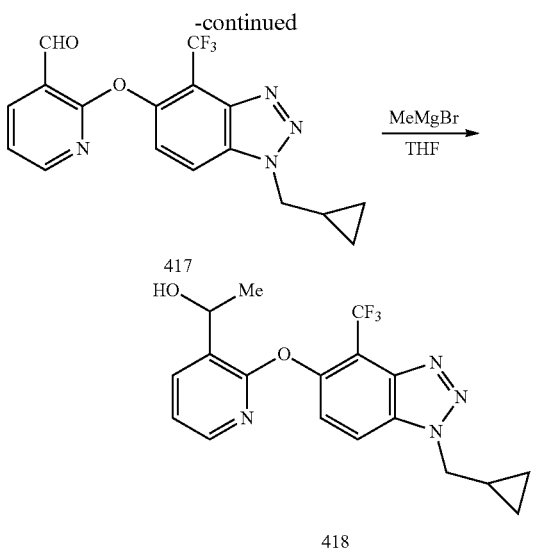

Step 1 Preparation of 1-(cyclopropylmethyl)-1H-benzotriazol-5-ol (9-1)

1-(Cyclopropylmethyl)-5-methoxy-1H-benzotriazole (8-3, 11.0 g, 54.1 mmol) was dissolved in dichloromethane (200 mL) and cooled to 0° C. The mixture was treated with boron tribromide (108 mL, 1 M dichloromethane solution, 108 mmol, 2 equiv) and warmed to ambient temperature. After stirring for 3 hours, the mixture was treated with sodium bicarbonate over 1 hour (~100 mL, aqueous saturated) and the mixture was stirred for an additional 14 hours. The mixture was neutralized to pH<5 with 12 N aqueous hydrochloric acid dropwise and the mixture was extracted with dichloromethane containing 10% methanol (4×750 mL). The combined organic extracts were dried with sodium sulfate, filtered and concentrated in vacuo, providing the titled compound 9-1.

Step 2 Preparation of 1-(cyclopropylmethyl)-4-iodo-1H-benzotriazol-5-ol (9-2)

1-(Cyclopropylmethyl)-1H-benzotriazol-5-ol (9-1, 5.41 g, 28.6 mmol) was dissolved in acetic acid (75 mL) and treated with N-iodosuccinimide (4.79 g, 21.3 mmol, 0.74 equiv) portionwise. After 15 minutes, the mixture was diluted with water (150 mL) and extracted with dichloromethane (2×100 mL). The combined organic extracts were dried with sodium sulfate, filtered and concentrated in vacuo, providing the titled compound 9-2.

Step 3 Preparation of 5-benzyloxy-1-(cyclopropylmethyl)-4-iodo-1H-benzotriazole (9-3)

1-(Cyclopropylmethyl)-4-iodo-1H-benzotriazol-5-ol (9-2, 9.01 g, 28.6 mmol) was suspended in degassed N,N-dimethylformamide (75 mL) and treated with benzylbromide (3.74 mL, 31.5 mmol, 1.1 equiv) and potassium carbonate (19.8 g, 143 mmol, 5 equiv). The mixture was placed into a preheated oil bath at 50° C. for 30 minutes, cooled to ambient temperature, and diluted with water (500 mL). The mixture was extracted with dichloromethane (2×500 mL) and the combined organic extracts were dried with sodium sulfate, filtered and concentrated in vacuo, providing the titled compound 9-3.

Step 4 Preparation of 5-benzyloxy-1-(cyclopropylmethyl)-4-(trifluoromethyl)-1H-benzotriazole (9-4)

5-Benzyloxy-1-(cyclopropylmethyl)-4-iodo-1H-benzotriazole (9-3, 1.29 g, 3.2 mmol), copper(I) iodide (1.21 g, 6.39 mmol, 2 equiv) and methyl 2,2-difluoro-2-(fluorosulfonyl) acetate (1.33 mL, 6.39 mmol, 2 equiv) were combined in degassed N,N-dimethylformamide (25 mL) at ambient temperature and placed into a preheated oil bath at 100° C. for 1.5 hours. The mixture was cooled to ambient temperature, poured into water (200 mL), treated with ethyl acetate (100 mL) and Celite. The mixture was aged for 30 minutes, filtered, and partitioned. The aqueous layer was further extracted with ethyl acetate (2×100 mL) and the combined organic extracts were washed with sodium bicarbonate (100 mL, aqueous saturated) and brine (50 mL) and then dried with sodium sulfate, filtered and concentrated in vacuo. The residue was purified by silica gel gradient chromatography (100:0 to 25:75; hexanes:ethyl acetate), providing the titled compound 9-4 as a colorless oil.

Step 5 Preparation of 1-(cyclopropylmethyl)-4-(trifluoromethyl)-1H-benzotriazol-5-ol (9-5)

5-Benzyloxy-1-(cyclopropylmethyl)-4-(trifluoromethyl)-1H-benzotriazole (9-4, 5.04 g, 14.5 mmol) was dissolved in 1:1 mixture of methanol/ethyl acetate (40 mL). The mixture was sparged under nitrogen, treated with Pearlman's catalyst (2 g, 0.2 wt equiv) and then sparged under hydrogen (1 atm) and stirred vigorously for 90 minutes. The reaction mixture was filtered through a pad of Celite, which was washed with methanol (500 mL) and concentrated in vacuo, providing the titled compound 9-5.

Step 6 Preparation of 2-{[1-(cyclopropylmethyl)-4-(trifluoromethyl)-1H-benzotriazol-5-yl]oxy}pyridine-3-carbaldehyde (417)

1-(Cyclopropylmethyl)-4-(trifluoromethyl)-1H-benzotriazol-5-ol (9-5, 35 mg, 0.14 mmol, 1 equiv.) and 2-chloropyridine-3-carbaldehyde (29 mg, 0.20 mmol, 1.5 equiv.) were dissolved in N,N-dimethylacetamide (1.5 mL) and treated with cesium carbonate (89 mg, 0.27 mmol, 2 equiv.). The mixture was irradiated at 100° C. in a microwave reactor for 30 minutes, cooled to ambient temperature and poured into water (30 mL). The mixture was extracted with ethyl acetate (3×20 mL) and the combined organic extracts were dried with sodium sulfate, filtered and concentrated in vacuo to afford the titled compound 417.

Step 7 Preparation of (±)-1-(2-{[1-(cyclopropylmethyl)-4-(trifluoromethyl)-1H-benzotriazol-5-yl]oxy}pyridin-3-yl)ethanol (418)

2-{[1-(Cyclopropylmethyl)-4-(trifluoromethyl)-1H-benzotriazol-5-yl]oxy}pyridine-3-carbaldehyde (417, 20 mg, 0.055 mmol, 1 equiv.) was dissolved in tetrahydrofuran (2 mL), cooled to 0° C. and treated with methylmagnesium bromide (28 μL, 0.083 mmol, 1.5 equiv). After stirring for 30 minutes, the mixture was poured into water (10 mL) and was extracted with ethyl acetate (3×20 mL). The combined organic extracts were dried with sodium sulfate, filtered and concentrated in vacuo. The residue was purified via preparative reverse phase HPLC (gradient 80:20 to 5:95; water containing 0.05% trifluoroacetic acid:acetonitrile containing 0.05% trifluoroacetic acid) to provide the titled compound 418. High resolution mass spectrometry (ES+) m/z=379.1374, [(M+H)$^+$ calculated for $C_{18}H_{18}F_3N_4O_2$: 379.1376].

The compound shown in Table 4 was synthesized according to the Reaction Schemes and Scheme 9.

TABLE 4

| Ex. | Structure | Name | LRMS or HRMS |
|---|---|---|---|
| 419 | 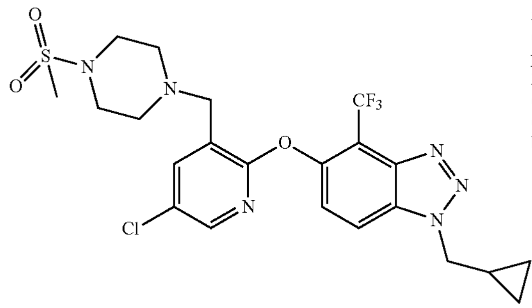 | 5-[(5-chloro-3-{[4-(methylsulfonyl)piperazin-1-yl]methyl}pyridin-2-yl)oxy]-1-(cyclopropylmethyl)-4-(trifluoromethyl)-1H-benzotriazole | [M + H] calc. 545.1 obs. 545.8 |
| 420 | 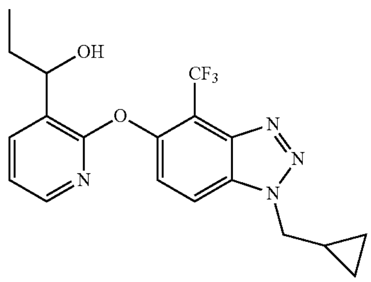 [SMILES: CCC(O)c1cccnc1Oc1ccc2c(nnn2CC2CC2)c1C(F)(F)F] | 1-(2-{[1-(cyclopropylmethyl)-4-(trifluoromethyl)-1H-benzotriazol-5-yl]oxy}pyridin-3-yl)propan-1-ol | [M + H] calc. 393.1 obs. 393.8 |
| 421 | 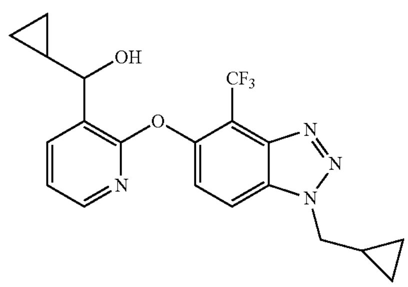 [SMILES: OC(c1cccnc1Oc1ccc2c(nnn2CC2CC2)c1C(F)(F)F)C1CC1] | cyclopropyl(2-{[1-(cyclopropylmethyl)-4-(trifluoromethyl)-1H-benzotriazol-5-yl]oxy}pyridin-3-yl)methanol | [M + H] calc. 405.1 obs. 405.8 |

Example 422

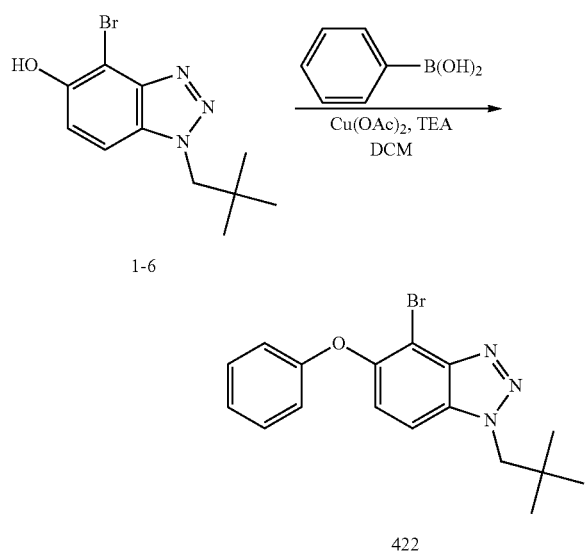

Scheme 10

4-bromo-1-(2,2-dimethylpropyl)-5-phenoxy-1H-benzotriazole (422)

4-Bromo-1-(2,2-dimethylpropyl)-1H-1,2,3-benzotriazol-5-ol (1-6) (100 mg, 0.352 mmol, 1.0 equiv.), copper(II) acetate (63.9 mg, 0.352 mmol, 1.0 equiv.), phenylboronic acid (86 mg, 0.704 mmol, 2.0 equiv.) and freshly milled 4 Å molecular sieves were dried in vacuo and then suspended in anhydrous $CH_2Cl_2$ (3.5 mL) and TEA (245 μl, 1.760 mmol, 5.0 equiv.). The mixture was stirred ambient temperature for 18 hours, after which the mixture was filtered. The filtrate was concentrated in vacuo and the residue was purified via reverse phase HPLC (water/acetonitrile gradient containing 0.1% TFA) to provide 422. $^1$H NMR ($CDCl_3$) δ 7.42 (1H, d, J=8.87 Hz), 7.36-7.30 (2H, m), 7.21 (1H, d, J=8.87 Hz), 7.12-7.07 (1H, m), 6.95 (2H, dd, J=7.97, 1.44 Hz), 4.40 (2H, s), 1.06 (9H, s) ppm. LRMS m/z (M+H) 360.0 and 362.0 (intensity ratio ~1:1) found, 360.1 and 362.1 required.

The compound shown in Table 5 was synthesized according to the Reaction Schemes and Scheme 10.

TABLE 5

| Ex. | Structure | Name | LRMS or HRMS |
|---|---|---|---|
| 423 | 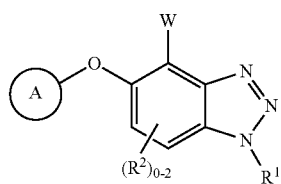 | 4-bromo-1-(2,2-dimethylpropyl)-5-pyridin-4-yloxy-1H-benzotriazole | [M + H] calc. 361.1 obs. 361.0 |

What is claimed is:

1. A compound according to Formula A

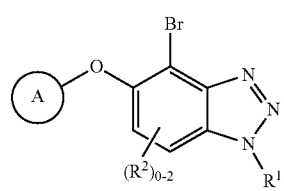

or a pharmaceutically acceptable salt thereof, wherein:

W is Cl, Br, CN or $CF_3$;

$R^1$ is selected from the group consisting of: $C_{1-8}$alkyl, $C_{2-8}$alkenyl, $C_{2-8}$alkynyl, $C_{3-6}$cycloalkyl and $C_{3-6}$cycloalkyl$C_{1-4}$alkyl, any of which may bear up to 5 halogen substituents;

each $R^2$ is independently selected from the group consisting of: halogen, methyl, $CF_3$, methoxy and CN;

A is selected from phenyl, naphthyl or heteroaryl, any of which is optionally substituted with up to 4 substituents selected from $R^3$;

each $R^3$ is independently selected from the group consisting of: halo, —CN, —$NO_2$, —C($R^a$)$_2$—N(X)$_2$, —C($R^a$)$_2$—N(X)C(O)—X, —C($R^a$)$_2$—N(X)S(O)$_k$—X, —C($R^a$)$_2$—N(X)C(O)—O—X, —C(O)—X, —C(O)—O—X, —C(O)—N(X)$_2$, —S(O)$_k$—X, —S(O)$_k$N(X)$_2$, —N(X)$_2$, —O—X, —N(X)C(O)—X, —N(X)S(O)$_k$—X, —N(X)C(O)—O—X, —N(X)C(O)N(X)$_2$, —N(R)SO$_2$N(X)$_2$ and X, excluding H;

each X is independently selected from the group consisting of: H, $C_{1-8}$alkyl, $C_{2-6}$alkenyl, $C_{2-6}$alkynyl, $C_{3-10}$cycloalkyl, $C_{3-10}$cycloalkenyl, aryl, heteroaryl, heterocycle, $C_{3-10}$cycloalkyl-C($R^a$)$_2$—, $C_{3-10}$cycloalkenyl-C($R^a$)$_2$—, aryl-C($R^a$)$_2$—, heteroaryl-C(Ra)$_2$— and heterocycle-C(Ra)$_2$-, wherein each member of the group excluding hydrogen is optionally substituted from one up to the maximum number of substitutable positions with one or more substituents independently selected from the group consisting of: CN, halo, $R^b$, —O—$R^b$, —N(R)—$R^b$, —N(R)C(O)—$R^b$, —N(R)S(O)$_2$—$R^b$, —N(R)—C(O)—O—$R^b$, —C(O)—N(R)—$R^b$, —C(O)—O—$R^b$, —C(O)—$R^b$, —C(O)—C(Ra)$_2$-$R^b$, —C(O)—C($R^a$)$_2$—S(O)$_2$—$R^b$, —C($R^a$)$_2$—N(R)—$R^b$, —SO$_2$—N(R)—$R^b$, —Si(CH$_3$)$_2$($R^b$), —C($R^a$)$_2$—$R^b$ and —SO$_2$—$R^b$;

each k is independently 0, 1 or 2;

each R is independently selected from the group consisting of: H and $C_{1-4}$alkyl;

each $R^a$ is independently selected from the group consisting of: H, OH and $C_{1-4}$alkyl;

each $R^b$ is independently selected from the group consisting of: H, $C_{1-4}$alkyl, $C_{2-4}$alkenyl, $C_{2-4}$alkynyl, $C_{3-6}$cycloalkyl, phenyl, benzyl, heterocycle and heteroaryl, wherein each member of the group excluding hydrogen is optionally substituted with 1 to 3 substituents independently selected from: halogen, cyano, hydroxy and methyl;

heteroaryl at each occurrence independently means a 5- or 6-membered monocyclic aromatic or 9- or 10-membered bicyclic aromatic, wherein at least one atom in the aromatic is selected from N,N-oxide, O and S, the sulfur optionally oxidized to sulfone or sulfoxide, and the remaining atoms are selected from C, N,N-oxide, O and S, the sulfur optionally oxidized to sulfone or sulfoxide; and heterocycle at each occurrence independently means a 4- to 7-membered monocyclic non-aromatic ring, an 8- to 11-membered bi-cyclic, including spiro-cyclic, non- or partially-aromatic ring or a 12- to 20-membered tricyclic, including spiro-cyclic portions, non- or partially-aromatic ring, each optionally substituted with 1 to 2 oxo groups, wherein at least one atom is selected from N(R), O and S, the sulfur optionally oxidized to sulfone or sulfoxide, and the remaining atoms are selected from C, N(R), O and S, the sulfur optionally oxidized to sulfone or sulfoxide.

2. A compound according to Formula I

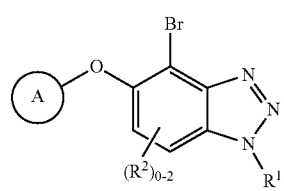

or a pharmaceutically acceptable salt thereof, wherein:

$R^1$ is selected from the group consisting of: $C_{1-8}$alkyl, $C_{2-8}$alkenyl, $C_{2-8}$alkynyl, $C_{3-6}$cycloalkyl and $C_{3-6}$cycloalkyl$C_{1-4}$alkyl, any of which may bear up to 5 halogen substituents;

each $R^2$ is independently selected from the group consisting of: halogen, methyl, $CF_3$, methoxy and CN;

A is selected from phenyl, naphthyl or heteroaryl, any of which is optionally substituted with up to 4 substituents selected from $R^3$;

each $R^3$ is independently selected from the group consisting of: halogen, OH, CN, $CF_3$, $R^5$, $OR^4$, $SR^5$, $SO_2R^5$, SO$_2$N(R$^4$)$_2$, COR$^4$, CO$_2$R$^5$, CON(R$^4$)$_2$, N(R$^4$)$_2$, NR$^4$COR$^5$, NR$^4$CO$_2$R$^5$, —C$_{1-4}$alkyl-N(R$^4$)$_2$, —C$_{1-4}$alkyl-NR$^4$COR$^5$ and —C$_{1-4}$alkyl-NR$^4$CO$_2$R$^5$;

wherein each R$^4$ (when present) is independently selected from the group consisting of:

(1) H, C$_{1-6}$alkyl, C$_{2-6}$alkenyl, C$_{2-6}$alkynyl, C$_{3-10}$cycloalkyl, C$_{3-10}$cycloalkylC$_{1-4}$alkyl, C$_{3-10}$cycloalkenyl and C$_{3-10}$cycloalkenylC$_{1-4}$alkyl, wherein each said C$_{1-6}$alkyl, C$_{2-6}$alkenyl, C$_{2-6}$alkynyl, C$_{3-10}$cycloalkyl, C$_{3-10}$cycloalkylC$_{1-4}$alkyl, C$_{3-10}$cycloalkenyl and C$_{3-10}$cycloalkenylC$_{1-4}$alkyl, is unsubstituted or substituted with 1, 2, or 3 halogen atoms, or with OH, CN, CF$_3$, or C$_{1-4}$alkoxy;

(2) phenyl, benzyl or heteroaryl, optionally bridged with a methylene, any of which optionally bear up to 3 substituents independently selected from halogen, OH, CN, CF$_3$, C$_{1-4}$alkyl, C$_{3-6}$cycloalkyl, phenyl, C$_{1-4}$alkoxy, amino, C$_{1-4}$alkylamino and di(C$_{1-4}$alkyl)amino; and (3) Het, optionally bridged with a methylene and said Het optionally bearing up to 3 substituents independently selected from halogen, OH, oxo, CN, CF$_3$, C$_{1-4}$alkyl, C$_{3-6}$cycloalkyl, phenyl, heteroaryl, C$_{1-4}$alkoxy, acetyl, amino, C$_{1-4}$alkylamino and di(C$_{1-4}$alkyl)amino;

or when two R$^4$ group are attached to the same nitrogen atom, they may be joined together with said nitrogen atom to form a non-aromatic monocyclic, a non-aromatic or partially aromatic bicyclic or a non-aromatic spiro-linked heterocyclic system of up to 12 ring atoms which optionally bears up to 4 substitutents independently selected from halogen, OH, oxo, CN, CF$_3$, C$_{1-4}$alkyl, C$_{3-6}$cycloalkyl, phenyl, heteroaryl, C$_{1-4}$alkoxy, acetyl, amino, C$_{1-4}$alkylamino and di(C$_{1-4}$alkyl)amino;

R$^5$ has the same definition as R$^4$ except that R$^5$ is not H;

each "heteroaryl" independently refers to 5- or 6-membered aromatic monocyclic or 9- or 10-membered aromatic bicyclic ring systems, in which at least one ring atom is selected from N, O and S, excluding tetrazole; and "Het" refers to nonaromatic or partially aromatic mono- or bicyclic heterocyclic systems of up to 10 ring atoms, in which at least one ring atom is selected from N, O and S, where the sulfur atom may be in the form of the S-oxide or S,S-dioxide.

3. The compound according to claim 2 wherein R$^2$ is not present.

4. The compound according to claim 2 wherein R$^1$ is selected from 2,2-dimethylpropyl, 1,2,2-trimethylpropyl, 4,4,4-trifluorobutyl, cyclopropylmethyl and cyclobutylmethyl.

5. The compound according to claim 2 wherein A is selected from pyridine, pyrazine and pyrimidine.

6. The compound according to claim 5 wherein A is pyridine.

7. A compound Formula Ia

Ia or a pharmaceutically acceptable salt thereof, wherein: one of Y or Z is nitrogen and the other is carbon, or both Y and Z are carbon; and wherein each R$^3$ is independently selected from the group consisting of: cyano, trifluoromethyl, methoxy, methoxycarbonyl, acetyl, formyl, halogen, phenyl and C$_{1-4}$alkyl, wherein said phenyl is optionally substituted with 1 to 5 halogen atoms and said C$_{1-4}$alkyl is optionally substituted with hydroxyl.

8. The compound according to claim 7 wherein Y and Z are carbon.

9. The compound according to claim 7 wherein Y is nitrogen and Z is carbon.

10. The compound according to claim 7 wherein Y is carbon and Z is nitrogen.

11. The compound according to claim 2 of Formula Ib:

Ib or a pharmaceutically acceptable salt thereof, wherein R$^6$ is H or C$_{1-3}$alkyl.

12. The compound according to claim 11 wherein:
R$^1$ is selected from 2,2-dimethylpropyl, 1,2,2-trimethylpropyl, 4,4,4-trifluorobutyl, cyclopropylmethyl and cyclobutylmethyl; and
R$^3$ is halogen.

13. A compound according to Formula B

B or a pharmaceutically acceptable salt thereof, wherein:
W is Cl, Br, CN or CF$_3$;
R$^1$ is selected from the group consisting of: C$_{1-8}$alkyl, C$_{2-8}$alkenyl, C$_{2-8}$alkynyl, C$_{3-6}$cycloalkyl and C$_{3-6}$cycloalkylC$_{1-4}$alkyl, any of which may bear up to 5 halogen substituents;
R$^i$ is selected from H, F and Cl;
R$^{ii}$ is selected from the group consisting of: CN, halo, R$^b$, —O—R$^b$, —N(R)—R$^b$, —N(R)C(O)—R$^b$, —N(R)S(O)$_2$—R$^b$, —N(R)—C(O)—O—R$^b$, —C(O)—N(R)—R$^b$, —C(O)—O—R$^b$, —C(O)—R$^b$, —C(O)—C(Ra)$_2$-R$^b$, —C(O)—C(R$^a$)$_2$—S(O)$_2$—R$^b$, —C(R$^a$)$_2$—N(R)—R$^b$, —SO$_2$—N(R)—R$^b$, —Si(CH$_3$)$_2$(R$^b$), —C(R$^a$)$_2$—R$^b$ and —SO$_2$—R$^b$;
each R is independently selected from the group consisting of: H and C$_{1-4}$alkyl;
each R$^a$ is independently selected from the group consisting of: H, OH and C$_{1-4}$alkyl;

each $R^b$ is independently selected from the group consisting of: H, $C_{1-4}$alkyl, $C_{2-4}$alkenyl, $C_{2-4}$alkynyl, $C_{3-6}$cycloalkyl, phenyl, benzyl, heterocycle and heteroaryl, wherein each member of the group excluding hydrogen is optionally substituted with 1 to 3 substituents independently selected from: halogen, cyano, hydroxy and methyl;

N-Het is a 6-membered monocyclic non-aromatic ring having a nitrogen atom bonded to the methylene bridge, optionally containing one additional heteroatom selected from N(R), O and S, the sulfur optionally oxidized to sulfone or sulfoxide, and the remaining atoms being carbon;

heteroaryl at each occurrence independently means a 5- or 6-membered monocyclic aromatic or 9- or 10-membered bicyclic aromatic, wherein at least one atom in the aromatic is selected from N,N-oxide, O and S, the sulfur optionally oxidized to sulfone or sulfoxide, and the remaining atoms are selected from C, N,N-oxide, O and S, the sulfur optionally oxidized to sulfone or sulfoxide; and heterocycle at each occurrence independently means a 4- to 7-membered monocyclic non-aromatic ring, an 8- to 11-membered bi-cyclic, including spiro-cyclic, non- or partially-aromatic ring or a 12- to 20-membered tri-cyclic, including spiro-cyclic portions, non- or partially-aromatic ring, each optionally substituted with 1 to 2 oxo groups, wherein at least one atom is selected from N(R), O and S, the sulfur optionally oxidized to sulfone or sulfoxide, and the remaining atoms are selected from C, N(R), O and S, the sulfur optionally oxidized to sulfone or sulfoxide.

14. The compound according to claim 13 wherein N-Het is piperazine.

15. A compound according to Formula C

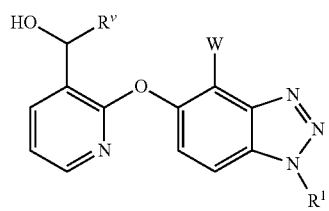

C or a pharmaceutically acceptable salt thereof, wherein:
W is Cl, Br, CN or $CF_3$;
$R^1$ is selected from the group consisting of: $C_{1-8}$alkyl, $C_{2-8}$alkenyl, $C_{2-8}$alkynyl, $C_{3-6}$cycloalkyl and $C_{3-6}$cycloalkyl$C_{1-4}$alkyl, any of which may bear up to 5 halogen substituents;
$R^v$ is independently selected from the group consisting of: $C_{1-6}$alkyl, $C_{3-10}$cycloalkyl, aryl, heteroaryl and heterocycle, wherein each member of the group is optionally substituted from one up to the maximum number of substitutable positions with one or more substituents independently selected from the group consisting of: CN, halo, $R^b$, —O—$R^b$, —N(R)—$R^b$, —N(R)C(O)—$R^b$, —N(R)S(O)$_2$—$R^b$, —N(R)—C(O)—O—$R^b$, —C(O)—N(R)—$R^b$, —C(O)—O—$R^b$, —C(O)—$R^b$, —C(O)—C(Ra)$_2$-$R^b$, —C(O)—C($R^a$)$_2$—S(O)$_2$—$R^b$, —C($R^a$)$_2$—N(R)—$R^b$, —SO$_2$—N(R)—$R^b$, —Si(CH$_3$)$_2$($R^b$), —C($R^a$)$_2$$R^b$ and —SO$_2$—$R^b$;
each R is independently selected from the group consisting of: H and $C_{1-4}$alkyl;

each $R^a$ is independently selected from the group consisting of: H, OH and $C_{1-4}$alkyl;

each $R^b$ is independently selected from the group consisting of: H, $C_{1-4}$alkyl, $C_{2-4}$alkenyl, $C_{2-4}$alkynyl, $C_{3-6}$cycloalkyl, phenyl, benzyl, heterocycle and heteroaryl, wherein each member of the group excluding hydrogen is optionally substituted with 1 to 3 substituents independently selected from: halogen, cyano, hydroxy and methyl;

heteroaryl at each occurrence independently means a 5- or 6-membered monocyclic aromatic or 9- or 10-membered bicyclic aromatic, wherein at least one atom in the aromatic is selected from N,N-oxide, O and S, the sulfur optionally oxidized to sulfone or sulfoxide, and the remaining atoms are selected from C, N,N-oxide, O and S, the sulfur optionally oxidized to sulfone or sulfoxide; and heterocycle at each occurrence independently means a 4- to 7-membered monocyclic non-aromatic ring, an 8- to 11-membered bi-cyclic, including spiro-cyclic, non- or partially-aromatic ring or a 12- to 20-membered tri-cyclic, including spiro-cyclic portions, non- or partially-aromatic ring, each optionally substituted with 1 to 2 oxo groups, wherein at least one atom is selected from N(R), O and S, the sulfur optionally oxidized to sulfone or sulfoxide, and the remaining atoms are selected from C, N(R), O and S, the sulfur optionally oxidized to sulfone or sulfoxide.

16. A compound according to claim 1 of Formula D

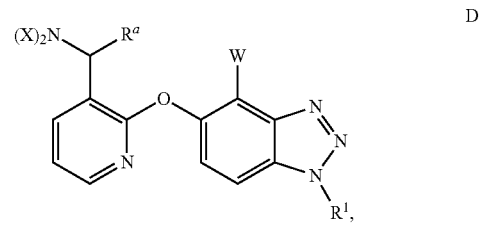

D or a pharmaceutically acceptable salt thereof.

17. A compound selected from the group consisting of:
2-{[4-bromo-1-(cyclobutylmethyl)-1H-benzotriazol-5-yl]oxy}pyridine-3-carbonitrile;
1-(2-{[4-bromo-1-(2,2-dimethylpropyl)-1H-1,2,3-benzotriazol-5-yl]oxy}pyridin-3-yl)ethanone;
1-(2-{[4-bromo-1-(2,2-dimethylpropyl)-1H-1,2,3-benzotriazol-5-yl]oxy}pyridin-3-yl)ethanol;
2-(2-{[4-bromo-1-(cyclobutylmethyl)-1H-benzotriazol-5-yl]oxy}pyridin-3-yl)propan-2-ol;
4-bromo-1-(cyclobutylmethyl)-5-[(3-methylpyrazin-2-yl)oxy]-1H-benzotriazole;
4-bromo-1-(cyclobutylmethyl)-5-[(3-methoxypyrazin-2-yl)oxy]-1H-benzotriazole;
4-bromo-1-(cyclobutylmethyl)-5-[(3-methylpyrazin-2-yl)oxy]-1H-benzotriazole;
1-(2-{[4-bromo-1-(cyclobutylmethyl)-1H-benzotriazol-5-yl]oxy}pyridin-3-yl)ethanol;
1-(2-{[4-bromo-1-(cyclopropylmethyl)-1H-benzotriazol-5-yl]oxy}pyridin-3-yl)ethanone;
1-(2-{[4-bromo-1-(cyclopropylmethyl)-1H-benzotriazol-5-yl]oxy}pyridin-3-yl)ethanol;
(1S)-(2-{[4-bromo-1-(cyclopropylmethyl)-1H-benzotriazol-5-yl]oxy}pyridin-3-yl)ethanol;
(1R)-(2-{[4-bromo-1-(cyclopropylmethyl)-1H-benzotriazol-5-yl]oxy}pyridin-3-yl)ethanol;

2-{[4-bromo-1-(cyclopropylmethyl)-1H-benzotriazol-5-yl]oxy}pyridine-3-carbaldehyde;
2-{[4-bromo-1-(cyclopropylmethyl)-1H-benzotriazol-5-yl]oxy}quinoline-3-carbaldehyde;
2-{[4-bromo-1-(cyclopropylmethyl)-1H-benzotriazol-5-yl]oxy}-6-methylquinoline-3-carbaldehyde;
(2-{[4-bromo-1-(cyclopropylmethyl)-1H-benzotriazol-5-yl]oxy}pyridin-3-yl)methanol;
1-(2-{[4-bromo-1-(cyclopropylmethyl)-1H-benzotriazol-5-yl]oxy}quinolin-3-yl)ethanol;
1-(2-{[4-bromo-1-(cyclopropylmethyl)-1H-benzotriazol-5-yl]oxy}-6-methylquinolin-3-yl)ethanol;
5-bromo-2-{[4-bromo-1-(cyclopropylmethyl)-1H-benzotriazol-5-yl]oxy}pyridine-3-carbaldehyde;
6-{[4-bromo-1-(cyclopropylmethyl)-1H-benzotriazol-5-yl]oxy}pyridine-3-carbaldehyde;
4-bromo-1-(cyclopropylmethyl)-5-[(4-methoxypyrimidin-2-yl)oxy]-1H-benzotriazole;
6-{[4-bromo-1-(cyclopropylmethyl)-1H-benzotriazol-5-yl]oxy}pyridine-3-carbonitrile;
4-bromo-1-(cyclopropylmethyl)-5-[(4-phenylpyrimidin-2-yl)oxy]-1H-benzotriazole;
4-{[4-bromo-1-(cyclopropylmethyl)-1H-benzotriazol-5-yl]oxy}-7-methylthieno[3,2-d]pyrimidine;
4-bromo-1-(cyclopropylmethyl)-5-{[6-(1H-imidazol-1-yl)pyrimidin-4-yl]oxy}-1H-benzotriazole;
1-(5-bromo-2-{[4-bromo-1-(cyclopropylmethyl)-1H-benzotriazol-5-yl]oxy}pyridin-3-yl)ethanol;
2-(2-{[4-bromo-1-(cyclopropylmethyl)-1H-benzotriazol-5-yl]oxy}pyridin-3-yl)propan-2-ol;
1-(6-{[4-bromo-1-(cyclopropylmethyl)-1H-benzotriazol-5-yl]oxy}pyridin-3-yl)ethanol;
1-(2-{[4-bromo-1-(cyclopropylmethyl)-1H-benzotriazol-5-yl]oxy}-5-phenylpyridin-3-yl)ethanol;
(6-{[4-bromo-1-(cyclopropylmethyl)-1H-benzotriazol-5-yl]oxy}pyridin-3-yl)(phenyl)methanol;
2-{[4-bromo-1-(cyclopropylmethyl)-1H-benzotriazol-5-yl]oxy}-5-phenylpyridine-3-carbaldehyde;
2-{[4-bromo-1-(cyclopropylmethyl)-1H-benzotriazol-5-yl]oxy}-5-chloropyridine-3-carbaldehyde;
1-(2-{[4-bromo-1-(cyclopropylmethyl)-1H-benzotriazol-5-yl]oxy}-5-chloropyridin-3-yl)ethanol;
3-{[4-bromo-1-(cyclopropylmethyl)-1H-benzotriazol-5-yl]oxy}pyridine-2-carbonitrile;
5-{[4-bromo-1-(cyclopropylmethyl)-1H-benzotriazol-5-yl]oxy}pyridine-2-carbonitrile;
3-{[4-bromo-1-(cyclopropylmethyl)-1H-benzotriazol-5-yl]oxy}pyridine-2-carbaldehyde;
(3-{[4-bromo-1-(cyclopropylmethyl)-1H-benzotriazol-5-yl]oxy}pyridin-2-yl)methanol;
4-bromo-1-(cyclopropylmethyl)-5-{[2-(methoxymethyl)pyridin-3-yl]oxy}-1H-benzotriazole;
1-(3-{[4-bromo-1-(cyclopropylmethyl)-1H-benzotriazol-5-yl]oxy}pyridin-2-yl)ethanol;
1-(3-{[4-bromo-1-(cyclopropylmethyl)-1H-benzotriazol-5-yl]oxy}pyridin-2-yl)prop-2-yn-1-ol;
4-bromo-1-(cyclopropylmethyl)-5-{[2-(methoxymethyl)-1-oxidopyridin-3-yl]oxy}-1H-benzotriazole;
1-(3-{[4-bromo-1-(cyclopropylmethyl)-1H-benzotriazol-5-yl]oxy}pyridin-2-yl)ethanone;
1-(5-{[4-bromo-1-(cyclopropylmethyl)-1H-benzotriazol-5-yl]oxy}pyridin-2-yl)ethanone;
1-(5-{[4-bromo-1-(cyclopropylmethyl)-1H-benzotriazol-5-yl]oxy}pyridin-2-yl)ethanol;
1-(3-{[4-bromo-1-(cyclopropylmethyl)-1H-benzotriazol-5-yl]oxy}pyridin-2-yl)-2-(dimethylamino)ethanol;
methyl 5-{[4-bromo-1-(cyclopropylmethyl)-1H-benzotriazol-5-yl]oxy}pyridine-2-carboxylate;
(5-{[4-bromo-1-(cyclopropylmethyl)-1H-benzotriazol-5-yl]oxy}pyridin-2-yl)methanol;
1-(3-{[4-bromo-1-(cyclopropylmethyl)-1H-benzotriazol-5-yl]oxy}pyridin-2-yl)-2-methylpropan-1-ol;
1-(3-{[4-bromo-1-(cyclopropylmethyl)-1H-benzotriazol-5-yl]oxy}pyridin-2-yl)-2-methylprop-2-en-1-ol;
1-(3-{[4-bromo-1-(cyclopropylmethyl)-1H-benzotriazol-5-yl]oxy}pyridin-2-yl)-2,2,2-trifluoro ethanol;
(3-{[4-bromo-1-(cyclopropylmethyl)-1H-benzotriazol-5-yl]oxy}pyridin-2-yl)(cyclopropyl)methanol;
1-(2-{[4-bromo-1-(cyclopropylmethyl)-1H-benzotriazol-5-yl]oxy}pyridin-3-yl)ethane-1,2-diol;
1-(2-{[4-bromo-1-(cyclopropylmethyl)-1H-benzotriazol-5-yl]oxy}pyridin-3-yl)-2-methoxyethanol;
2-(2-{[4-bromo-1-(cyclopropylmethyl)-1H-benzotriazol-5-yl]oxy}pyridin-3-yl)-2-methoxyethanol;
4-bromo-1-(cyclopropylmethyl)-5-{[3-(1,2-dimethoxyethyl)pyridin-2-yl]oxy}-1H-benzotriazole;
4-bromo-1-(cyclopropylmethyl)-5-{[3-(1-fluoroethyl)pyridin-2-yl]oxy}-1H-benzotriazole;
2-(2-{[4-bromo-1-(cyclobutylmethyl)-1H-benzotriazol-5-yl]oxy}pyridin-3-yl)propan-2-ol;
(2-{[4-bromo-1-(cyclopropylmethyl)-1H-benzotriazol-5-yl]oxy}-5-fluoropyridin-3-yl)(cyclopropyl)methanol;
(2-{[4-bromo-1-(2,2-dimethylpropyl)-1H-benzotriazol-5-yl]oxy}pyridin-3-yl)(cyclopropyl)methanol;
1-(2-{[4-bromo-1-(2,2-dimethylpropyl)-1H-benzotriazol-5-yl]oxy}pyridin-3-yl)-2,2-dimethylpropan-1-ol;
(2-{[4-bromo-1-(2,2-dimethylpropyl)-1H-benzotriazol-5-yl]oxy}pyridin-3-yl)(cyclopropyl)methanol;
1-(2-{[4-bromo-1-(cyclopropylmethyl)-1H-benzotriazol-5-yl]oxy}pyridin-3-yl)prop-2-en-1-ol;
(2-{[4-bromo-1-(cyclopropylmethyl)-1H-benzotriazol-5-yl]oxy}pyridin-3-yl)(cyclopropyl)methanol;
(2-{[4-bromo-1-(cyclopropylmethyl)-1H-benzotriazol-5-yl]oxy}pyridin-3-yl)(phenyl)methanol;
1-(2-{[4-bromo-1-(cyclopropylmethyl)-1H-benzotriazol-5-yl]oxy}-5-methylpyridin-3-yl)ethanol;
1-(2-{[4-bromo-1-(cyclopropylmethyl)-1H-benzotriazol-5-yl]oxy}pyridin-3-yl)-3-methylbutan-1-ol;
1-[2-{[4-bromo-1-(cyclopropylmethyl)-1H-benzotriazol-5-yl]oxy}-5-(trifluoromethyl)pyridin-3-yl]ethanol;
1-(2-{[4-bromo-1-(cyclopropylmethyl)-1H-benzotriazol-5-yl]oxy}-5-fluoropyridin-3-yl)ethanol;
1-(2-{[4-bromo-1-(cyclopropylmethyl)-1H-benzotriazol-5-yl]oxy}-6-methylpyridin-3-yl)ethanol;
ethyl 2-{[4-bromo-1-(cyclopropylmethyl)-1H-benzotriazol-5-yl]oxy}pyridine-3-carboxylate;
(2-{[4-bromo-1-(2,2-dimethylpropyl)-1H-benzotriazol-5-yl]oxy}-5-fluoropyridin-3-yl)methanol;
1-(2-{[4-bromo-1-(cyclopropylmethyl)-1H-benzotriazol-5-yl]oxy}pyridin-3-yl)-2,2-dimethylpropan-1-ol;
(2-{[4-bromo-1-(cyclopropylmethyl)-1H-benzotriazol-5-yl]oxy}-5-fluoropyridin-3-yl)(cyclopropyl)methanol;
(2-{[4-bromo-1-(cyclopropylmethyl)-1H-benzotriazol-5-yl]oxy}pyridin-3-yl)methanol;
1-(2-{[4-bromo-1-(2,2-dimethylpropyl)-1H-benzotriazol-5-yl]oxy}-5-chloropyridin-3-yl)ethanol;
(2-{[4-bromo-1-(2,2-dimethylpropyl)-1H-benzotriazol-5-yl]oxy}-5-chloropyridin-3-yl)(cyclopropyl)methanol;
1-(2-{[4-bromo-1-(cyclopropylmethyl)-1H-benzotriazol-5-yl]oxy}pyridin-3-yl)-2-methylpropane-1,2-diol;
(2-{[4-bromo-1-(cyclopropylmethyl)-1H-benzotriazol-5-yl]oxy}-5-fluoropyridin-3-yl)methanol;

1-(2-{[4-bromo-1-(cyclopropylmethyl)-1H-benzotriazol-5-yl]oxy}pyridin-3-yl)propan-1-ol;
1-(2-{[4-bromo-1-(2,2-dimethylpropyl)-1H-benzotriazol-5-yl]oxy}pyridin-3-yl)-2,2-dimethylpropan-1-ol;
(2-{[4-bromo-1-(cyclopropylmethyl)-1H-benzotriazol-5-yl]oxy}-5-chloropyridin-3-yl)methanol;
(2-{[4-bromo-1-(2,2-dimethylpropyl)-1H-benzotriazol-5-yl]oxy}-5-chloropyridin-3-yl)methanol;
1-(2-{[4-bromo-1-(2,2-dimethylpropyl)-1H-benzotriazol-5-yl]oxy}-5-fluoropyridin-3-yl)ethanol;
(2-{[4-bromo-1-(2,2-dimethylpropyl)-1H-benzotriazol-5-yl]oxy}-5-fluoropyridin-3-yl)(cyclopropyl)methanol;
1-(2-{[4-bromo-1-(2,2-dimethylpropyl)-1H-benzotriazol-5-yl]oxy}-5-fluoropyridin-3-yl)ethanol;
1-(2-{[4-bromo-1-(2,2-dimethylpropyl)-1H-benzotriazol-5-yl]oxy}-5-chloropyridin-3-yl)ethanol;
(2-{[4-bromo-1-(2,2-dimethylpropyl)-1H-benzotriazol-5-yl]oxy}-5-chloropyridin-3-yl)(cyclopropyl)methanol;
(2-{[4-bromo-1-(cyclopropylmethyl)-1H-benzotriazol-5-yl]oxy}pyridin-3-yl)(pyridin-2-yl)methanol;
1-(2-{[4-bromo-1-(cyclopropylmethyl)-1H-benzotriazol-5-yl]oxy}pyridin-3-yl)propan-1-ol;
1-(2-{[4-bromo-1-(cyclopropylmethyl)-1H-benzotriazol-5-yl]oxy}pyridin-3-yl)propan-1-ol;
1-(2-{[4-bromo-1-(cyclopropylmethyl)-1H-benzotriazol-5-yl]oxy}pyridin-3-yl)-2,2-dimethylpropan-1-ol;
1-(2-{[4-bromo-1-(cyclopropylmethyl)-1H-benzotriazol-5-yl]oxy}pyridin-3-yl)prop-2-en-1-ol;
(2-{[4-bromo-1-(cyclopropylmethyl)-1H-benzotriazol-5-yl]oxy}pyridin-3-yl)(cyclopropyl)methanol;
1-(2-{[4-bromo-1-(cyclopropylmethyl)-1H-benzotriazol-5-yl]oxy}-5-methylpyridin-3-yl)ethanol;
1-[2-{[4-bromo-1-(cyclopropylmethyl)-1H-benzotriazol-5-yl]oxy}-5-(trifluoromethyl)pyridin-3-yl]ethanol;
1-(2-{[4-bromo-1-(cyclopropylmethyl)-1H-benzotriazol-5-yl]oxy}pyridin-3-yl)-2-methylpropan-1-ol;
1-(2-{[4-bromo-1-(cyclopropylmethyl)-1H-benzotriazol-5-yl]oxy}-5-fluoropyridin-3-yl)ethanol;
(2-{[4-bromo-1-(2,2-dimethylpropyl)-1H-benzotriazol-5-yl]oxy}pyridin-3-yl)methanol;
1-(2-{[4-bromo-1-(cyclopropylmethyl)-1H-benzotriazol-5-yl]oxy}pyridin-3-yl)-1-cyclopropylethanol;
1-(2-{[4-bromo-1-(2,2-dimethylpropyl)-1H-benzotriazol-5-yl]oxy}pyridin-3-yl)ethanol;
1-[2-({4-bromo-1-[(2,2-difluorocyclopropyl)methyl]-1H-benzotriazol-5-yl}oxy)pyridin-3-yl]ethanol;
[2-({4-bromo-1-[(2,2-difluorocyclopropyl)methyl]-1H-benzotriazol-5-yl}oxy)pyridin-3-yl]methanol;
1-(2-{[4-bromo-1-(cyclopropylmethyl)-1H-benzotriazol-5-yl]oxy}pyridin-3-yl)-2,2,2-trifluoroethanol;
3-(2-{[4-bromo-1-(2,2-dimethylpropyl)-1H-benzotriazol-5-yl]oxy}pyridin-3-yl)-3-hydroxypropanenitrile;
1-(2-{[4-bromo-1-(2,2-dimethylpropyl)-1H-benzotriazol-5-yl]oxy}pyridin-3-yl)-2,2,2-trifluoroethanol;
[2-({4-bromo-1-[(2,2-difluorocyclopropyl)methyl]-1H-benzotriazol-5-yl}oxy)-5-chloropyridin-3-yl]methanol;
(1S)-(2-{[4-bromo-1-(2,2-dimethylpropyl)-1H-benzotriazol-5-yl]oxy}pyridin-3-yl)ethanol;
(1R)-(2-{[4-bromo-1-(2,2-dimethylpropyl)-1H-benzotriazol-5-yl]oxy}pyridin-3-yl)ethanol;
2-{[4-bromo-1-(4,4,4-trifluorobutyl)-1H-benzotriazol-5-yl]oxy}benzonitrile;
2-{[4-bromo-1-(4,4,4-trifluorobutyl)-1H-benzotriazol-5-yl]oxy}pyridine-3-carbonitrile;
4-bromo-1-(2,2-dimethylpropyl)-5-{[3-(trifluoromethyl)pyridin-2-yl]oxy}-1H-benzotriazole;
2-{[4-bromo-1-(2,2-dimethylpropyl)-1H-benzotriazol-5-yl]oxy}pyridine-3-carbonitrile;
2-{[4-bromo-1-(2,2-dimethylpropyl)-1H-benzotriazol-5-yl]oxy}benzonitrile;
4-bromo-1-(2,2-dimethylpropyl)-5-(pyridin-2-yloxy)-1H-benzotriazole;
4-bromo-1-(2,2-dimethylpropyl)-5-(pyrazin-2-yloxy)-1H-benzotriazole;
4-bromo-1-(2,2-dimethylpropyl)-5-{[6-(trifluoromethyl)pyridin-2-yl]oxy}-1H-benzotriazole;
4-bromo-1-(2,2-dimethylpropyl)-5-{[4-(trifluoromethyl)pyridin-2-yl]oxy}-1H-benzotriazole;
2-{[4-bromo-1-(2,2-dimethylpropyl)-1H-benzotriazol-5-yl]oxy}pyridine-4-carbonitrile;
4-bromo-1-(2,2-dimethylpropyl)-5-[(6-methylpyridin-2-yl)oxy]-1H-benzotriazole;
4-bromo-5-{[3-chloro-5-(trifluoromethyl)pyridin-2-yl]oxy}-1-(2,2-dimethylpropyl)-1H-benzotriazole;
4-bromo-1-(2,2-dimethylpropyl)-5-[(5-methylpyridin-2-yl)oxy]-1H-benzotriazole;
4-bromo-1-(2,2-dimethylpropyl)-5-[(3-methylpyridin-2-yl)oxy]-1H-benzotriazole;
4-bromo-1-(2,2-dimethylpropyl)-5-[(6-methoxypyrazin-2-yl)oxy]-1H-benzotriazole;
4-bromo-1-(2,2-dimethylpropyl)-5-[(3-methylpyrazin-2-yl)oxy]-1H-benzotriazole;
4-bromo-1-(2,2-dimethylpropyl)-5-[(3-methoxypyrazin-2-yl)oxy]-1H-benzotriazole;
4-bromo-5-[(4-chloropyrimidin-2-yl)oxy]-1-(2,2-dimethylpropyl)-1H-benzotriazole;
4-bromo-1-(2,2-dimethylpropyl)-5-[(4-methoxypyrimidin-2-yl)oxy]-1H-benzotriazole;
4-bromo-1-(2,2-dimethylpropyl)-5-[(6-methylpyridazin-3-yl)oxy]-1H-benzotriazole;
4-bromo-1-(2,2-dimethylpropyl)-5-(pyrimidin-2-yloxy)-1H-benzotriazole;
4-bromo-1-(2,2-dimethylpropyl)-5-(pyrimidin-2-yloxy)-1H-benzotriazole;
methyl 3-{[4-bromo-1-(2,2-dimethylpropyl)-1H-benzotriazol-5-yl]oxy}pyrazine-2-carboxylate;
4-bromo-1-(2,2-dimethylpropyl)-5-[(4-methylpyrimidin-2-yl)oxy]-1H-benzotriazole;
4-bromo-1-(2,2-dimethylpropyl)-5-[(6-methoxypyrimidin-4-yl)oxy]-1H-benzotriazole;
4-bromo-5-[(3,5-difluoropyridin-2-yl)oxy]-1-(2,2-dimethylpropyl)-1H-benzotriazole;
4-bromo-5-[(2-chloropyridin-4-yl)oxy]-1-(2,2-dimethylpropyl)-1H-benzotriazole;
4-bromo-1-(2,2-dimethylpropyl)-5-[(5-pyrimidin-5-yl-1,3-thiazol-2-yl)oxy]-1H-benzotriazole;
2-{[4-bromo-1-(2,2-dimethylpropyl)-1H-benzotriazol-5-yl]oxy}-3-(trifluoromethyl)benzonitrile;
4-bromo-1-(2,2-dimethylpropyl)-5-[(5-iodopyridin-2-yl)oxy]-1H-benzotriazole;
4-bromo-1-(2,2-dimethylpropyl)-5-{[5-(trifluoromethyl)pyridin-2-yl]oxy}-1H-benzotriazole;
3-{[4-bromo-1-(2,2-dimethylpropyl)-1H-benzotriazol-5-yl]oxy}pyrazine-2-carbonitrile;
2-{[4-bromo-1-(2,2-dimethylpropyl)-1H-benzotriazol-5-yl]oxy}-6-(4-fluorophenyl)pyridine-3-carbonitrile;
4-bromo-1-(2,2-dimethylpropyl)-5-[(4-methylpyridin-2-yl)oxy]-1H-benzotriazole;
1-{[4-bromo-1-(2,2-dimethylpropyl)-1H-benzotriazol-5-yl]oxy}isoquinoline;
methyl 6-{[4-bromo-1-(2,2-dimethylpropyl)-1H-benzotriazol-5-yl]oxy}pyridine-3-carboxylate;

2-{[4-bromo-1-(2,2-dimethylpropyl)-1H-benzotriazol-5-yl]oxy}-4,6-dimethylpyridine-3-carbonitrile;
4-bromo-5-[(5-bromopyridin-2-yl)oxy]-1-(2,2-dimethylpropyl)-1H-benzotriazole;
4-bromo-1-(2,2-dimethylpropyl)-5-[(5-methylpyrimidin-2-yl)oxy]-1H-benzotriazole;
4-bromo-5-[(6-bromopyridin-2-yl)oxy]-1-(2,2-dimethylpropyl)-1H-benzotriazole;
1-(3-{[4-bromo-1-(2,2-dimethylpropyl)-1H-benzotriazol-5-yl]oxy}pyridin-2-yl)ethanone;
2-(2-{[4-bromo-1-(2,2-dimethylpropyl)-1H-benzotriazol-5-yl]oxy}pyridin-3-yl)propan-2-ol;
1-(3-{[4-bromo-1-(2,2-dimethylpropyl)-1H-benzotriazol-5-yl]oxy}pyridin-2-yl)ethanol;
2-(3-{[4-bromo-1-(2,2-dimethylpropyl)-1H-benzotriazol-5-yl]oxy}pyridin-2-yl)propan-2-ol;
1-(2-{[4-bromo-1-(2,2-dimethylpropyl)-1H-benzotriazol-5-yl]oxy}pyridin-4-yl)ethanone;
6-{[4-bromo-1-(2,2-dimethylpropyl)-1H-benzotriazol-5-yl]oxy}pyridine-3-carbonitrile;
4-bromo-5-(pyridin-2-yloxy)-1-(4,4,4-trifluorobutyl)-1H-benzotriazole;
4-bromo-5-(pyrazin-2-yloxy)-1-(4,4,4-trifluorobutyl)-1H-benzotriazole;
4-bromo-5-[(3-methylpyrazin-2-yl)oxy]-1-(4,4,4-trifluorobutyl)-1H-benzotriazole;
1-(6-{[4-bromo-1-(2,2-dimethylpropyl)-1H-benzotriazol-5-yl]oxy}pyridin-3-yl)ethanone;
1-(6-{[4-bromo-1-(2,2-dimethylpropyl)-1H-benzotriazol-5-yl]oxy}pyridin-3-yl)ethanol;
2-(6-{[4-bromo-1-(2,2-dimethylpropyl)-1H-benzotriazol-5-yl]oxy}pyridin-3-yl)propan-2-ol;
2-{[4,6-dibromo-1-(4,4,4-trifluorobutyl)-1H-benzotriazol-5-yl]oxy}pyridine-3-carbonitrile;
4-bromo-5-[(3-methoxypyrazin-2-yl)oxy]-1-(4,4,4-trifluorobutyl)-1H-benzotriazole;
4-bromo-5-[(4-chloropyridin-2-yl)oxy]-1-(2,2-dimethylpropyl)-1H-benzotriazole;
4-bromo-1-(2,2-dimethylpropyl)-5-[(6-fluoropyridin-2-yl)oxy]-1H-benzotriazole;
4-bromo-1-(2,2-dimethylpropyl)-5-({3-[1-(1,1-dioxidothio-morpholin-4-yl)ethyl]pyridin-2-yl}oxy)-1H-benzotriazole;
5-acetyl-2-{[4-bromo-1-(2,2-dimethylpropyl)-1H-benzotriazol-5-yl]oxy}-6-methylpyridine-3-carbonitrile;
5-acetyl-2-{[4-bromo-1-(2,2-dimethylpropyl)-1H-benzotriazol-5-yl]oxy}-6-methylpyridine-3-carbonitrile;
2-{[4-bromo-1-(2,2-dimethylpropyl)-1H-benzotriazol-5-yl]oxy}-5-(1-hydroxyethyl)-6-methylpyridine-3-carbonitrile;
2-{[4-bromo-1-(2,2-dimethylpropyl)-1H-benzotriazol-5-yl]oxy}-5-(1-methyl-1H-pyrazol-4-yl)pyridine-3-carbonitrile;
2-{[4-bromo-1-(2,2-dimethylpropyl)-1H-benzotriazol-5-yl]oxy}-1,3-thiazole-5-carbonitrile;
2-{[4-bromo-1-(2,2-dimethylpropyl)-1H-benzotriazol-5-yl]oxy}quinazoline-7-carbonitrile;
2-{[4-bromo-1-(2,2-dimethylpropyl)-1H-benzotriazol-5-yl]oxy}quinoline-3-carbonitrile;
3-bromo-5-{[4-bromo-1-(2,2-dimethylpropyl)-1H-benzotriazol-5-yl]oxy}pyridine-2-carbonitrile;
4-{[4-bromo-1-(2,2-dimethylpropyl)-1H-benzotriazol-5-yl]oxy}pyridine-3-carbonitrile;
4-{[4-bromo-1-(2,2-dimethylpropyl)-1H-benzotriazol-5-yl]oxy}pyrimidine-5-carbonitrile;
5-{[4-bromo-1-(2,2-dimethylpropyl)-1H-benzotriazol-5-yl]oxy}pyrazine-2-carbonitrile;
6-{[4-bromo-1-(2,2-dimethylpropyl)-1H-benzotriazol-5-yl]oxy}pyrazine-2-carbonitrile;
5-{[4-bromo-1-(2,2-dimethylpropyl)-1H-benzotriazol-5-yl]oxy}-1,3-dimethyl-1H-pyrazole-4-carbonitrile;
1-(2-{[4-bromo-1-(2,2-dimethylpropyl)-1H-benzotriazol-5-yl]oxy}quinolin-3-yl)ethanone;
2-{[4-bromo-1-(2,2-dimethylpropyl)-1H-benzotriazol-5-yl]oxy}pyridine-3-carbaldehyde;
2-{[4-bromo-1-(2,2-dimethylpropyl)-1H-benzotriazol-5-yl]oxy}quinoline-3-carbaldehyde;
1-(2-{[4-bromo-1-(2,2-dimethylpropyl)-1H-benzotriazol-5-yl]oxy}quinolin-3-yl)ethanol;
1-(2-{[4-bromo-1-(2,2-dimethylpropyl)-1H-benzotriazol-5-yl]oxy}quinolin-3-yl)propan-1-ol;
1-(2-{[4-bromo-1-(2,2-dimethylpropyl)-1H-benzotriazol-5-yl]oxy}pyridin-3-yl)propan-1-ol;
1-(2-{[4-bromo-1-(4,4,4-trifluorobutyl)-1H-benzotriazol-5-yl]oxy}pyridin-3-yl)ethanone;
1-(2-{[4-bromo-1-(4,4,4-trifluorobutyl)-1H-benzotriazol-5-yl]oxy}pyridin-3-yl)ethanol;
(2-{[4-bromo-1-(2,2-dimethylpropyl)-1H-benzotriazol-5-yl]oxy}quinolin-3-yl)(phenyl)methanol;
1-(3-{[4-bromo-1-(2,2-dimethylpropyl)-1H-benzotriazol-5-yl]oxy}pyrazin-2-yl)ethanone;
2-(3-{[4-bromo-1-(2,2-dimethylpropyl)-1H-benzotriazol-5-yl]oxy}pyrazin-2-yl)propan-2-ol;
1-(3-{[4-bromo-1-(2,2-dimethylpropyl)-1H-benzotriazol-5-yl]oxy}pyrazin-2-yl)ethanol;
1-[2-({4-bromo-1-[(1R)-1,2,2-trimethylpropyl]-1H-benzotriazol-5-yl}oxy)pyridin-3-yl]ethanone;
1-[2-({4-bromo-1-[(1R)-1,2-dimethylpropyl]-1H-benzotriazol-5-yl}oxy)pyridin-3-yl]ethanone;
1-[2-({4-bromo-1-[(1R)-1,2,2-trimethylpropyl]-1H-benzotriazol-5-yl}oxy)pyridin-3-yl]ethanol;
4-Bromo-1-(cyclopropylmethyl)-5-({3-[(4,4-difluoropiperidin-1-yl)methyl]pyridin-2-yl}oxy)-1H-benzotriazole;
(2-{[4-bromo-1-(cyclopropylmethyl)-1H-1,2,3-benzotriazol-5-yl]oxy}-5-chloropyridin-3-yl)methanol;
(2-{[4-bromo-1-(cyclopropylmethyl)-1H-1,2,3-benzotriazol-5-yl]oxy}pyridin-3-yl)methyl methanesulfonate;
4-bromo-5-({5-chloro-3-[(3-methoxyazetidin-1-yl)methyl]pyridin-2-yl}oxy)-1-(cyclopropylmethyl)-1H-1,2,3-benzotriazole;
4-bromo-5-[(5-chloro-3-{[4-(methylsulfonyl)piperazin-1-yl]methyl}pyridin-2-yl)oxy]-1-(cyclopropylmethyl)-1H-benzotriazole;
4-bromo-1-(cyclopropylmethyl)-5-{[3-(piperidin-1-ylmethyl)pyridin-2-yl]oxy}-1H-benzotriazole;
1-(2-{[4-bromo-1-(cyclopropylmethyl)-1H-benzotriazol-5-yl]oxy}pyridin-3-yl)-N,N-dimethylmethanamine;
4-bromo-1-(cyclopropylmethyl)-5-{[3-(pyrrolidin-1-ylmethyl)pyridin-2-yl]oxy}-1H-benzotriazole;
(2-{[4-chloro-1-(cyclopropylmethyl)-1H-benzotriazol-5-yl]oxy}pyridin-3-yl)(cyclopropyl)methanol;
4-bromo-1-(cyclopropylmethyl)-5-[(3-{[2-(trifluoromethyl)piperidin-1-yl]methyl}pyridin-2-yl)oxy]-1H-benzotriazole;
4-bromo-1-(cyclopropylmethyl)-5-({3-[(3,3-difluoropiperidin-1-yl)methyl]pyridin-2-yl}oxy)-1H-benzotriazole;
4-bromo-1-(cyclopropylmethyl)-5-({3-[(3-methylpiperidin-1-yl)methyl]pyridin-2-yl}oxy)-1H-benzotriazole;
4-bromo-1-(cyclopropylmethyl)-5-({3-[(3-fluoropiperidin-1-yl)methyl]pyridin-2-yl}oxy)-1H-benzotriazole;
5-({3-[(4-acetylpiperazin-1-yl)methyl]pyridin-2-yl}oxy)-4-bromo-1-(cyclopropylmethyl)-1H-benzotriazole;

4-bromo-1-(cyclopropylmethyl)-5-[(3-{[4-(2,2,2-trifluoroethyl)piperazin-1-yl]methyl}pyridin-2-yl)oxy]-1H-benzotriazole;
4-bromo-1-(cyclopropylmethyl)-5-({3-[(4-methylpiperazin-1-yl)methyl]pyridin-2-yl}oxy)-1H-benzotriazole;
4-bromo-1-(cyclopropylmethyl)-5-[(3-{[4-(1-methyl-1H-pyrazol-4-yl)piperazin-1-yl]methyl}pyridin-2-yl)oxy]-1H-benzotriazole;
4-[(2-{[4-bromo-1-(cyclopropylmethyl)-1H-benzotriazol-5-yl]oxy}pyridin-3-yl)methyl]-1-methylpiperazin-2-one;
5-({3-[(4-benzyl-4-fluoropiperidin-1-yl)methyl]pyridin-2-yl}oxy)-4-bromo-1-(cyclopropylmethyl)-1H-benzotriazole;
1-[(2-{[4-bromo-1-(cyclopropylmethyl)-1H-benzotriazol-5-yl]oxy}pyridin-3-yl)methyl]-4-phenylpiperidine-4-carbonitrile;
N-[(2-{[4-bromo-1-(cyclopropylmethyl)-1H-benzotriazol-5-yl]oxy}pyridin-3-yl)methyl]-2,2,2-trifluoroethanamine;
4-bromo-1-(cyclopropylmethyl)-5-({3-[(3,4-difluoropyrrolidin-1-yl)methyl]pyridin-2-yl}oxy)-1H-benzotriazole;
4-bromo-1-(cyclopropylmethyl)-5-[(3-{[3-(fluoromethyl)pyrrolidin-1-yl]methyl}pyridin-2-yl)oxy]-1H-benzotriazole;
1-[(2-{[4-bromo-1-(cyclopropylmethyl)-1H-benzotriazol-5-yl]oxy}pyridin-3-yl)methyl]-4-fluoropyrrolidin-3-ol;
1-[(2-{[4-bromo-1-(cyclopropylmethyl)-1H-benzotriazol-5-yl]oxy}pyridin-3-yl)methyl]pyrrolidin-3-one;
4-bromo-1-(cyclopropylmethyl)-5-({3-[(3,3-difluoropyrrolidin-1-yl)methyl]pyridin-2-yl}oxy)-1H-benzotriazole;
1-[(2-{[4-bromo-1-(cyclopropylmethyl)-1H-benzotriazol-5-yl]oxy}pyridin-3-yl)methyl]piperidin-4-ol;
ethyl 1-[(2-{[4-bromo-1-(cyclopropylmethyl)-1H-benzotriazol-5-yl]oxy}pyridin-3-yl)methyl]-4-fluoropiperidine-4-carboxylate;
4-bromo-1-(cyclopropylmethyl)-5-({3-[(4,4-dimethylpiperidin-1-yl)methyl]pyridin-2-yl}oxy)-1H-benzotriazole;
1-[(2-{[4-bromo-1-(cyclopropylmethyl)-1H-benzotriazol-5-yl]oxy}pyridin-3-yl)methyl]-4-fluoropiperidine-4-carbonitrile;
4-bromo-1-(cyclopropylmethyl)-5-({3-[(4-cyclopropylpiperidin-1-yl)methyl]pyridin-2-yl}oxy)-1H-benzotriazole;
1-[(2-{[4-bromo-1-(cyclopropylmethyl)-1H-benzotriazol-5-yl]oxy}pyridin-3-yl)methyl]piperidine-4-carbonitrile;
4-bromo-1-(cyclopropylmethyl)-5-[(3-{[4-(trifluoromethyl)piperidin-1-yl]methyl}pyridin-2-yl)oxy]-1H-benzotriazole;
4-bromo-1-(cyclopropylmethyl)-5-({3-[(4-methylpiperidin-1-yl)methyl]pyridin-2-yl}oxy)-1H-benzotriazole;
1-[(2-{[4-bromo-1-(cyclopropylmethyl)-1H-benzotriazol-5-yl]oxy}pyridin-3-yl)methyl]-4-methylpiperidin-4-ol;
4-bromo-1-(cyclopropylmethyl)-5-{[3-(morpholin-4-ylmethyl)pyridin-2-yl]oxy}-1H-benzotriazole;
N-[(2-{[4-bromo-1-(cyclopropylmethyl)-1H-benzotriazol-5-yl]oxy}pyridin-3-yl)methyl]-N-ethylethanamine;
4-bromo-5-[(5-chloro-3-{[4-(2,2,2-trifluoroethyl)piperazin-1-yl]methyl}pyridin-2-yl)oxy]-1-(cyclopropylmethyl)-1H-benzotriazole;
4-bromo-5-({5-chloro-3-[(3,3-difluoropyrrolidin-1-yl)methyl]pyridin-2-yl}oxy)-1-(cyclopropylmethyl)-1H-benzotriazole;
N-[(2-{[4-bromo-1-(cyclopropylmethyl)-1H-benzotriazol-5-yl]oxy}-5-chloropyridin-3-yl)methyl]-2,2,2-trifluoroethanamine;
N-[(2-{[4-bromo-1-(cyclopropylmethyl)-1H-benzotriazol-5-yl]oxy}-5-fluoropyridin-3-yl)methyl]-2,2,2-trifluoroethanamine;
N-[(2-{[4-bromo-1-(cyclopropylmethyl)-1H-benzotriazol-5-yl]oxy}pyridin-3-yl)methyl]-2-fluoroethanamine;
N-[(2-{[4-bromo-1-(cyclopropylmethyl)-1H-benzotriazol-5-yl]oxy}pyridin-3-yl)methyl]-2,2-difluoroethanamine;
4-bromo-1-(2,2-dimethylpropyl)-5-({3-[1-(1,1-dioxidothiomorpholin-4-yl)ethyl]pyridin-2-yl}oxy)-1H-benzotriazole;
4-bromo-5-[(5-chloro-3-{[4-(methylsulfonyl)piperazin-1-yl]methyl}pyridin-2-yl)oxy]-1-(cyclopropylmethyl)-1H-benzotriazole;
4-bromo-5-[(5-chloro-3-{[4-(2,2,2-trifluoroethyl)piperazin-1-yl]methyl}pyridin-2-yl)oxy]-1-(2,2-dimethylpropyl)-1H-benzotriazole;
7-[(2-{[4-bromo-1-(2,2-dimethylpropyl)-1H-benzotriazol-5-yl]oxy}-5-chloropyridin-3-yl)methyl]-3-(trifluoromethyl)-5,6,7,8-tetrahydro[1,2,4]triazolo[4,3-a]pyrazine;
4-bromo-5-{[5-chloro-3-(2,5-diazabicyclo[2,2,2]oct-2-ylmethyl)pyridin-2-yl]oxy}-1-(2,2-dimethylpropyl)-1H-benzotriazole;
2-{[4-bromo-1-(cyclopropylmethyl)-1H-benzotriazol-5-yl]oxy}pyridine-3-carboxamide;
4-bromo-1-(cyclopropylmethyl)-5-({3-[1-(1,1-dioxidothiomorpholin-4-yl)ethyl]-5-fluoropyridin-2-yl}oxy)-1H-benzotriazole;
4-bromo-5-({5-chloro-3-[(1,1-dioxidothiomorpholin-4-yl)methyl]pyridin-2-yl}oxy)-1-(cyclopropylmethyl)-1H-benzotriazole;
1-(2-{[4-bromo-1-(cyclopropylmethyl)-1H-benzotriazol-5-yl]oxy}pyridin-3-yl)-N,N-dimethylmethanamine;
4-bromo-5-{[5-chloro-3-(pyrrolidin-1-ylmethyl)pyridin-2-yl]oxy}-1-(cyclopropylmethyl)-1H-benzotriazole;
N-[1-(2-{[4-bromo-1-(cyclopropylmethyl)-1H-benzotriazol-5-yl]oxy}pyridin-3-yl)ethyl]isoxazole-3-carboxamide;
4-bromo-5-{[5-chloro-3-(piperidin-1-ylmethyl)pyridin-2-yl]oxy}-1-(cyclopropylmethyl)-1H-benzotriazole;
5-({3-[(4-acetylpiperazin-1-yl)methyl]-5-chloropyridin-2-yl}oxy)-4-bromo-1-(cyclopropylmethyl)-1H-benzotriazole;
4-bromo-5-({5-chloro-3-[(4-methylpiperazin-1-yl)methyl]pyridin-2-yl}oxy)-1-(cyclopropylmethyl)-1H-benzotriazole;
4-bromo-5-{[5-chloro-3-(morpholin-4-ylmethyl)pyridin-2-yl]oxy}-1-(cyclopropylmethyl)-1H-benzotriazole;
5-[(2-{[4-bromo-1-(2,2-dimethylpropyl)-1H-benzotriazol-5-yl]oxy}-5-chloropyridin-3-yl)methyl]-4,5,6,7-tetrahydroisoxazolo[4,5-c]pyridin-3-ol;
1-(2-{[4-bromo-1-(cyclopropylmethyl)-1H-benzotriazol-5-yl]oxy}pyridin-3-yl)ethanamine;
5-({3-[(4-acetyl-1,4-diazepan-1-yl)methyl]-5-fluoropyridin-2-yl}oxy)-4-bromo-1-(cyclopropylmethyl)-1H-benzotriazole;
N-[(2-{[4-bromo-1-(cyclopropylmethyl)-1H-benzotriazol-5-yl]oxy}pyridin-3-yl)methyl]-1,3-oxazole-2-carboxamide;

N-[(2-{[4-bromo-1-(cyclopropylmethyl)-1H-benzotriazol-5-yl]oxy}pyridin-3-yl)methyl]isothiazole-5-carboxamide;

N-[(2-{[4-bromo-1-(cyclopropylmethyl)-1H-benzotriazol-5-yl]oxy}pyridin-3-yl)methyl]acetamide;

N-[(2-{[4-bromo-1-(cyclopropylmethyl)-1H-benzotriazol-5-yl]oxy}pyridin-3-yl)methyl]methanesulfonamide;

4-[(2-{[4-bromo-1-(cyclopropylmethyl)-1H-benzotriazol-5-yl]oxy}-5-chloropyridin-3-yl)methyl]-N,N-dimethylpiperazine-1-carboxamide;

4-[(2-{[4-bromo-1-(cyclopropylmethyl)-1H-benzotriazol-5-yl]oxy}-5-chloropyridin-3-yl)methyl]-N,N-dimethylpiperazine-1-sulfonamide;

methyl 4-[(2-{[4-bromo-1-(cyclopropylmethyl)-1H-benzotriazol-5-yl]oxy}-5-chloropyridin-3-yl)methyl]piperazine-1-carboxylate;

1-[(2-{[4-bromo-1-(cyclopropylmethyl)-1H-benzotriazol-5-yl]oxy}-5-chloropyridin-3-yl)methyl]piperidin-4-ol;

N-[(2-{[4-bromo-1-(cyclopropylmethyl)-1H-benzotriazol-5-yl]oxy}pyridin-3-yl)methyl]isoxazole-3-carboxamide;

N-[(2-{[4-bromo-1-(cyclopropylmethyl)-1H-benzotriazol-5-yl]oxy}pyridin-3-yl)methyl]-1,2,3-thiadiazole-4-carboxamide;

N-[(2-{[4-bromo-1-(cyclopropylmethyl)-1H-benzotriazol-5-yl]oxy}pyridin-3-yl)methyl]pyridine-3-carboxamide;

tert-butyl 2-[(2-{[4-bromo-1-(cyclopropylmethyl)-1H-benzotriazol-5-yl]oxy}-5-fluoropyridin-3-yl)methyl]-2,6-diazaspiro[3.5]nonane-6-carboxylate;

4-bromo-1-(cyclopropylmethyl)-5-[(5-fluoro-3-{[6-(methylsulfonyl)-2,6-diazaspiro[3.5]non-2-yl]methyl}pyridin-2-yl)oxy]-1H-benzotriazole;

4-bromo-5-[(5-chloro-3-{[3-(methylsulfonyl)-3,8-diazabicyclo[3.2.1]oct-8-yl]methyl}pyridin-2-yl)oxy]-1-(cyclopropylmethyl)-1H-benzotriazole;

1-{4-[(2-{[4-bromo-1-(cyclopropylmethyl)-1H-benzotriazol-5-yl]oxy}-5-chloropyridin-3-yl)methyl]piperazin-1-yl}-2-methyl-1-oxopropan-2-ol;

1-{4-[(2-{[4-bromo-1-(cyclopropylmethyl)-1H-benzotriazol-5-yl]oxy}-5-fluoropyridin-3-yl)methyl]piperazin-1-yl}-2-methyl-1-oxopropan-2-ol;

4-bromo-1-(2,2-dimethylpropyl)-5-({3-[(1,1-dioxidothiomorpholin-4-yl)methyl]-5-fluoropyridin-2-yl}oxy)-1H-benzotriazole;

4-bromo-1-(cyclopropylmethyl)-5-({3-[(1,1-dioxidothiomorpholin-4-yl)methyl]pyridin-2-yl}oxy)-1H-benzotriazole;

4-bromo-5-({5-chloro-3-[(1S,4S)-2,5-diazabicyclo[2.2.1]hept-2-ylmethyl]pyridin-2-yl}oxy)-1-(cyclopropylmethyl)-1H-benzotriazole;

4-bromo-1-(cyclopropylmethyl)-5-({3-[(1,1-dioxidothiomorpholin-4-yl)methyl]-5-fluoropyridin-2-yl}oxy)-1H-benzotriazole;

1-[(2-{[4-bromo-1-(cyclopropylmethyl)-1H-benzotriazol-5-yl]oxy}-5-chloropyridin-3-yl)methyl]-1,4-diazepan-5-one;

1-[(2-{[4-bromo-1-(cyclopropylmethyl)-1H-benzotriazol-5-yl]oxy}-5-chloropyridin-3-yl)methyl]-4-methyl-1,4-diazepan-5-one;

1-[(2-{[4-bromo-1-(cyclopropylmethyl)-1H-benzotriazol-5-yl]oxy}-5-chloropyridin-3-yl)methyl]-4-methylpiperidin-4-ol;

4-[(2-{[4-bromo-1-(cyclopropylmethyl)-1H-benzotriazol-5-yl]oxy}-5-chloropyridin-3-yl)methyl]piperazin-2-one;

4-[(2-{[4-bromo-1-(cyclopropylmethyl)-1H-benzotriazol-5-yl]oxy}-5-chloropyridin-3-yl)methyl]-N-methylpiperazine-1-carboxamide;

5-({3-[(4-acetyl-1,4-diazepan-1-yl)methyl]-5-chloropyridin-2-yl}oxy)-4-bromo-1-(cyclopropylmethyl)-1H-benzotriazole;

4-bromo-5-[(5-chloro-3-{[4-(methylsulfonyl)-1,4-diazepan-1-yl]methyl}pyridin-2-yl)oxy]-1-(cyclopropylmethyl)-1H-benzotriazole;

tert-butyl [(2-{[4-bromo-1-(cyclopropylmethyl)-1H-benzotriazol-5-yl]oxy}-5-chloropyridin-3-yl)methyl]carbamate;

N-[(2-{[4-bromo-1-(cyclopropylmethyl)-1H-benzotriazol-5-yl]oxy}-5-chloropyridin-3-yl)methyl]isoxazole-3-carboxamide;

5-({3-[(4-acetylpiperazin-1-yl)methyl]-5-fluoropyridin-2-yl}oxy)-4-bromo-1-(cyclopropylmethyl)-1H-benzotriazole;

N-[(2-{[4-bromo-1-(cyclopropylmethyl)-1H-benzotriazol-5-yl]oxy}-5-fluoropyridin-3-yl)methyl]isoxazole-3-carboxamide;

4-bromo-1-(cyclopropylmethyl)-5-[(5-fluoro-3-{[8-(methylsulfonyl)-3,8-diazabicyclo[3,2,1]oct-3-yl]methyl}pyridin-2-yl)oxy]-1H-benzotriazole;

N-[(2-{[4-bromo-1-(cyclopropylmethyl)-1H-benzotriazol-5-yl]oxy}-5-chloropyridin-3-yl)methyl]acetamide;

ethyl [(2-{[4-bromo-1-(cyclopropylmethyl)-1H-benzotriazol-5-yl]oxy}-5-chloropyridin-3-yl)methyl]carbamate;

1-[(2-{[4-bromo-1-(cyclopropylmethyl)-1H-benzotriazol-5-yl]oxy}-5-chloropyridin-3-yl)methyl]piperidine-4-carboxylic acid;

1-[(2-{[4-bromo-1-(cyclopropylmethyl)-1H-benzotriazol-5-yl]oxy}-5-chloropyridin-3-yl)methyl]piperidine-3-carboxylic acid;

4-bromo-1-(cyclopropylmethyl)-5-[(5-fluoro-3-{[(3R)-3-methyl-4-(methylsulfonyl)piperazin-1-yl]methyl}pyridin-2-yl)oxy]-1H-benzotriazole;

4-bromo-1-(cyclopropylmethyl)-5-[(5-fluoro-3-{[4-(isoxazol-3-ylcarbonyl)piperazin-1-yl]methyl}pyridin-2-yl)oxy]-1H-benzotriazole;

N-[(2-{[4-bromo-1-(cyclopropylmethyl)-1H-benzotriazol-5-yl]oxy}-5-chloropyridin-3-yl)methyl]-1H-imidazole-2-carboxamide;

4-bromo-5-[(6-chloro-3-{[4-(methylsulfonyl)piperazin-1-yl]methyl}pyridin-2-yl)oxy]-1-(2,2-dimethylpropyl)-1H-benzotriazole;

4-[(2-{[4-bromo-1-(cyclopropylmethyl)-1H-benzotriazol-5-yl]oxy}-5-chloropyridin-3-yl)methyl]-1-methylpiperazin-2-one;

N-(2-{[(2-{[4-bromo-1-(cyclopropylmethyl)-1H-benzotriazol-5-yl]oxy}-5-chloropyridin-3-yl)methyl]amino}ethyl)methanesulfonamide;

4-bromo-5-[(5-chloro-3-{[4-(methylsulfonyl)piperidin-1-yl]methyl}pyridin-2-yl)oxy]-1-(cyclopropylmethyl)-1H-benzotriazole;

tert-butyl (1S,4S)-5-[(2-{[4-bromo-1-(cyclopropylmethyl)-1H-benzotriazol-5-yl]oxy}-5-chloropyridin-3-yl)methyl]-2,5-diazabicyclo[2.2.1]heptane-2-carboxylate;

4-bromo-5-{[5-chloro-3-(5,6-dihydroimidazo[1,2-a]pyrazin-7(8H)-ylmethyl)pyridin-2-yl]oxy}-1-(cyclopropylmethyl)-1H-benzotriazole;

4-[(2-{[4-bromo-1-(cyclopropylmethyl)-1H-benzotriazol-5-yl]oxy}-5-chloropyridin-3-yl)methyl]-N-methylpiperazine-1-sulfonamide;

5-[(5-chloro-3-{[4-(methylsulfonyl)piperazin-1-yl]methyl}pyridin-2-yl)oxy]-1-(cyclopropylmethyl)-1H-benzotriazole-4-carbonitrile;

tert-butyl 7-[(2-{[4-bromo-1-(cyclopropylmethyl)-1H-benzotriazol-5-yl]oxy}-5-fluoropyridin-3-yl)methyl]-2,7-diazaspiro[3.5]nonane-2-carboxylate;

4-bromo-1-(cyclopropylmethyl)-5-[(5-fluoro-3-{[2-(methylsulfonyl)-2,7-diazaspiro[3.5]non-7-yl]methyl}pyridin-2-yl)oxy]-1H-benzotriazole;

4-bromo-5-[(5-chloro-3-{[4-(methylsulfonyl)piperazin-1-yl]methyl}pyridin-2-yl)oxy]-1-[(2,2-difluorocyclopropyl)methyl]-1H-benzotriazole;

4-bromo-1-(cyclopropylmethyl)-5-[(5-fluoro-3-{[3-(methylsulfonyl)-3,8-diazabicyclo[3.2.1]oct-8-yl]methyl}pyridin-2-yl)oxy]-1H-benzotriazole;

tert-butyl (1R,4R)-5-[(2-{[4-bromo-1-(cyclopropylmethyl)-1H-benzotriazol-5-yl]oxy}-5-chloropyridin-3-yl)methyl]-2,5-diazabicyclo[2.2.1]heptane-2-carboxylate;

4-bromo-5-({5-chloro-3-[(1R,4R)-2,5-diazabicyclo[2.2.1]hept-2-ylmethyl]pyridin-2-yl}oxy)-1-(cyclopropylmethyl)-1H-benzotriazole;

4-bromo-5-[(5-chloro-3-{[(1R,4R)-5-(methylsulfonyl)-2,5-diazabicyclo[2.2.1]hept-2-yl]methyl}pyridin-2-yl)oxy]-1-(cyclopropylmethyl)-1H-benzotriazole;

tert-butyl 5-[(2-{[4-bromo-1-(cyclopropylmethyl)-1H-benzotriazol-5-yl]oxy}-5-fluoropyridin-3-yl)methyl]-2,5-diazabicyclo[2.2.2]octane-2-carboxylate;

4-bromo-5-[(5-chloro-3-{[(1S,4S)-5-(methylsulfonyl)-2,5-diazabicyclo[2.2.1]hept-2-yl]methyl}pyridin-2-yl)oxy]-1-(cyclopropylmethyl)-1H-benzotriazole;

4-bromo-1-(cyclopropylmethyl)-5-{[3-(2,5-diazabicyclo[2.2.2]oct-2-ylmethyl)-5-fluoropyridin-2-yl]oxy}-1H-benzotriazole;

4-bromo-5-[(5-chloro-3-{[3-(methylsulfonyl)pyrrolidin-1-yl]methyl}pyridin-2-yl)oxy]-1-(cyclopropylmethyl)-1H-benzotriazole;

4-bromo-5-[(5-chloro-3-{[4-(methoxyacetyl)piperazin-1-yl]methyl}pyridin-2-yl)oxy]-1-(cyclopropylmethyl)-1H-benzotriazole;

4-bromo-1-(cyclopropylmethyl)-5-[(5-fluoro-3-{[2-(methylsulfonyl)-2,6-diazaspiro[3.5]non-6-yl]methyl}pyridin-2-yl)oxy]-1H-benzotriazole;

2-{4-[(2-{[4-bromo-1-(cyclopropylmethyl)-1H-benzotriazol-5-yl]oxy}-5-chloropyridin-3-yl)methyl]piperazin-1-yl}-2-oxoethyl acetate;

2-{4-[(2-{[4-bromo-1-(cyclopropylmethyl)-1H-benzotriazol-5-yl]oxy}-5-chloropyridin-3-yl)methyl]piperazin-1-yl}-2-oxoethanol;

4-bromo-1-(cyclopropylmethyl)-5-[(5-fluoro-3-{[5-(methylsulfonyl)-2,5-diazabicyclo[2.2.2]oct-2-yl]methyl}pyridin-2-yl)oxy]-1H-benzotriazole;

4-bromo-5-[(5-chloro-3-{[4-(methylsulfonyl)piperazin-1-yl]methyl}pyridin-2-yl)oxy]-1-[(2,2-difluorocyclopropyl)methyl]-1H-benzotriazole;

1-{4-[(2-{[4-bromo-1-(cyclopropylmethyl)-1H-benzotriazol-5-yl]oxy}-5-chloropyridin-3-yl)methyl]piperazin-1-yl}-1-oxopropan-2-ol;

1-{4-[(2-{[4-bromo-1-(cyclopropylmethyl)-1H-benzotriazol-5-yl]oxy}-5-chloropyridin-3-yl)methyl]piperazin-1-yl}-1-oxopropan-2-ol;

4-bromo-5-[(5-chloro-3-{[4-(1,3-thiazol-2-yl)piperazin-1-yl]methyl}pyridin-2-yl)oxy]-1-(cyclopropylmethyl)-1H-benzotriazole;

tert-butyl (2R)-4-[(2-{[4-bromo-1-(cyclopropylmethyl)-1H-benzotriazol-5-yl]oxy}-5-fluoropyridin-3-yl)methyl]-2-methylpiperazine-1-carboxylate;

1-({4-[(2-{[4-bromo-1-(cyclopropylmethyl)-1H-benzotriazol-5-yl]oxy}-5-chloropyridin-3-yl)methyl]piperazin-1-yl}carbonyl)cyclopropanol;

4-bromo-1-(cyclopropylmethyl)-5-[(5-fluoro-3-{[(3R)-3-methylpiperazin-1-yl]methyl}pyridin-2-yl)oxy]-1H-benzotriazole;

4-bromo-5-{[5-chloro-3-(piperazin-1-ylmethyl)pyridin-2-yl]oxy}-1-(cyclopropylmethyl)-1H-benzotriazole;

4-bromo-1-(cyclopropylmethyl)-5-[(5-fluoro-3-{[4-(methylsulfonyl)piperazin-1-yl]methyl}pyridin-2-yl)oxy]-1H-benzotriazole;

tert-butyl 4-[(2-{[4-bromo-1-(cyclopropylmethyl)-1H-benzotriazol-5-yl]oxy}-5-chloropyridin-3-yl)methyl]piperazine-1-carboxylate;

4-bromo-1-(cyclopropylmethyl)-5-[(6-fluoro-3-{[4-(methylsulfonyl)piperazin-1-yl]methyl}pyridin-2-yl)oxy]-1H-benzotriazole;

4-bromo-5-({5-chloro-3-[(1,1-dioxidothiomorpholin-4-yl)methyl]pyridin-2-yl}oxy)-1-(2,2-dimethylpropyl)-1H-benzotriazole;

4-bromo-1-(cyclopropylmethyl)-5-[(5-fluoro-3-{[6-(isoxazol-3-ylcarbonyl)-2,6-diazaspiro[3.5]non-2-yl]methyl}pyridin-2-yl)oxy]-1H-benzotriazole;

4-bromo-1-(cyclopropylmethyl)-5-[(5-fluoro-3-{[(3aR,6aS)-5-(methylsulfonyl)hexahydropyrrolo[3,4-c]pyrrol-2(1H)-yl]methyl}pyridin-2-yl)oxy]-1H-benzotriazole;

4-bromo-5-[(6-chloro-3-{[4-(methylsulfonyl)piperazin-1-yl]methyl}pyridin-2-yl)oxy]-1-(cyclopropylmethyl)-1H-benzotriazole;

4-bromo-5-[(5-chloro-3-{[4-(methylsulfonyl)piperazin-1-yl]methyl}pyridin-2-yl)oxy]-1-(2,2-dimethylpropyl)-1H-benzotriazole;

4-bromo-1-(2,2-dimethylpropyl)-5-({3-[(1,1-dioxidothiomorpholin-4-yl)methyl]pyridin-2-yl}oxy)-1H-benzotriazole;

4-bromo-5-[(5-chloro-3-{[5-(isoxazol-3-ylcarbonyl)-2,5-diazabicyclo[2.2.2]oct-2-yl]methyl}pyridin-2-yl)oxy]-1-(2,2-dimethylpropyl)-1H-benzotriazole;

5-[(5-chloro-3-{[4-(methylsulfonyl)piperazin-1-yl]methyl}pyridin-2-yl)oxy]-1-(cyclopropylmethyl)-1H-benzotriazole;

N-[(2-{[4-bromo-1-(cyclopropylmethyl)-1H-benzotriazol-5-yl]oxy}-5-chloropyridin-3-yl)methyl]-1,2,3-thiadiazole-4-carboxamide;

N-[(2-{[4-bromo-1-(cyclopropylmethyl)-1H-benzotriazol-5-yl]oxy}-5-chloropyridin-3-yl)methyl]isothiazole-5-carboxamide;

N-[(2-{[4-bromo-1-(cyclopropylmethyl)-1H-benzotriazol-5-yl]oxy}-5-chloropyridin-3-yl)methyl]pyridine-3-carboxamide;

N-[(2-{[4-bromo-1-(cyclopropylmethyl)-1H-benzotriazol-5-yl]oxy}-5-chloropyridin-3-yl)methyl]methanesulfonamide;

4-bromo-1-(2,2-dimethylpropyl)-5-[(3-{[4-(methylsulfonyl)piperazin-1-yl]methyl}pyridin-2-yl)oxy]-1H-benzotriazole;

4-bromo-1-(cyclopropylmethyl)-5-[(5-fluoro-3-{[4-(methylsulfonyl)piperazin-1-yl]methyl}pyridin-2-yl)oxy]-1H-benzotriazole;

4-bromo-1-(cyclopropylmethyl)-5-[(3-{[4-(methylsulfonyl)piperazin-1-yl]methyl}pyridin-2-yl)oxy]-1H-benzotriazole;

4-bromo-1-(cyclopropylmethyl)-5-[(5-fluoro-3-{[5-(methylsulfonyl)octahydro-2H-pyrrolo[3,4-c]pyridin-2-yl]methyl}pyridin-2-yl)oxy]-1H-benzotriazole;

tert-butyl (2S)-4-[(2-{[4-bromo-1-(cyclopropylmethyl)-1H-benzotriazol-5-yl]oxy}-5-fluoropyridin-3-yl)methyl]-2-methylpiperazine-1-carboxylate;

4-bromo-1-(cyclopropylmethyl)-5-[(5-fluoro-3-{[(3S)-3-methylpiperazin-1-yl]methyl}pyridin-2-yl)oxy]-1H-benzotriazole;

4-bromo-1-(cyclopropylmethyl)-5-[(5-fluoro-3-{[(2S)-2-methyl-4-(methylsulfonyl)piperazin-1-yl]methyl}pyridin-2-yl)oxy]-1H-benzotriazole;

4-bromo-1-(cyclopropylmethyl)-5-[(5-fluoro-3-{[(3R)-3-methyl-4-(methylsulfonyl)piperazin-1-yl]methyl}pyridin-2-yl)oxy]-1H-benzotriazole;

N-{(3aS,6aS)-1-[(2-{[4-bromo-1-(cyclopropylmethyl)-1H-benzotriazol-5-yl]oxy}-5-fluoropyridin-3-yl)methyl]octahydrocyclopenta[b]pyrrol-4-yl}methanesulfonamide;

4-bromo-1-(cyclopropylmethyl)-5-[(5-fluoro-3-{[5-(methylsulfonyl)hexahydropyrrolo[3,4-b]pyrrol-1(2H)-yl]methyl}pyridin-2-yl)oxy]-1H-benzotriazole;

4-bromo-1-(cyclopropylmethyl)-5-[(5-fluoro-3-{[(2R)-2-methyl-4-(methylsulfonyl)piperazin-1-yl]methyl}pyridin-2-yl)oxy]-1H-benzotriazole;

4-bromo-1-(cyclopropylmethyl)-5-[(5-fluoro-3-{[1-(methylsulfonyl)hexahydropyrrolo[3,4-b]pyrrol-5(1H)-yl]methyl}pyridin-2-yl)oxy]-1H-benzotriazole;

4-bromo-1-(cyclopropylmethyl)-5-[(5-fluoro-3-{[4-(methylsulfonyl)hexahydropyrrolo[3,2-b]pyrrol-1(2H)-yl]methyl}pyridin-2-yl)oxy]-1H-benzotriazole;

2-{4-[(2-{[4-bromo-1-(cyclopropylmethyl)-1H-benzotriazol-5-yl]oxy}-5-chloropyridin-3-yl)methyl]piperazin-1-yl}-2-oxoethanol;

4-bromo-5-[(5-chloro-3-{[4-(1,3-dioxolan-2-ylmethyl)piperazin-1-yl]methyl}pyridin-2-yl)oxy]-1-(cyclopropylmethyl)-1H-benzotriazole;

4-bromo-5-({5-chloro-3-[(4-pyridin-2-ylpiperazin-1-yl)methyl]pyridin-2-yl}oxy)-1-(cyclopropylmethyl)-1H-benzotriazole;

8-[(2-{[4-bromo-1-(cyclopropylmethyl)-1H-benzotriazol-5-yl]oxy}-5-chloropyridin-3-yl)methyl]-1,3,8-triazaspiro[4.5]decan-4-one;

{3-[(2-{[4-bromo-1-(cyclopropylmethyl)-1H-benzotriazol-5-yl]oxy}-5-chloropyridin-3-yl)methyl]-3-azabicyclo[3.1.0]hex-6-yl}methanol;

4-bromo-5-[(5-chloro-3-{[4-(1H-1,2,4-triazol-1-yl)piperidin-1-yl]methyl}pyridin-2-yl)oxy]-1-(cyclopropylmethyl)-1H-benzotriazole;

4-bromo-5-({5-chloro-3-[(4-pyrimidin-2-ylpiperazin-1-yl)methyl]pyridin-2-yl}oxy)-1-(cyclopropylmethyl)-1H-benzotriazole;

4-bromo-5-[(5-chloro-3-{[4-(tetrahydrofuran-2-ylcarbonyl)piperazin-1-yl]methyl}pyridin-2-yl)oxy]-1-(cyclopropylmethyl)-1H-benzotriazole;

4-bromo-5-({5-chloro-3-[(4-pyridin-2-ylpiperidin-1-yl)methyl]pyridin-2-yl}oxy)-1-(cyclopropylmethyl)-1H-benzotriazole;

4-bromo-5-[(5-chloro-3-{[4-(1H-imidazol-4-yl)piperidin-1-yl]methyl}pyridin-2-yl)oxy]-1-(cyclopropylmethyl)-1H-benzotriazole;

4-bromo-5-[(5-chloro-3-{[4-(1,3,4-oxadiazol-2-yl)piperidin-1-yl]methyl}pyridin-2-yl)oxy]-1-(cyclopropylmethyl)-1H-benzotriazole;

4-bromo-5-({5-chloro-3-[(4-pyrimidin-2-ylpiperidin-1-yl)methyl]pyridin-2-yl}oxy)-1-(cyclopropylmethyl)-1H-benzotriazole;

N-{1-[(2-{[4-bromo-1-(cyclopropylmethyl)-1H-benzotriazol-5-yl]oxy}-5-chloropyridin-3-yl)methyl]piperidin-4-yl}methanesulfonamide;

1-[(2-{[4-bromo-1-(cyclopropylmethyl)-1H-benzotriazol-5-yl]oxy}-5-chloropyridin-3-yl)methyl]-N-(2-hydroxyethyl)piperidine-4-carboxamide;

1-(2-{[4-bromo-1-(cyclopropylmethyl)-1H-benzotriazol-5-yl]oxy}-5-chloropyridin-3-yl)-N-(pyridin-2-ylmethyl)methanamine;

4-bromo-5-({5-chloro-3-[(3-methoxyazetidin-1-yl)methyl]pyridin-2-yl}oxy)-1-(cyclopropylmethyl)-1H-benzotriazole;

1-[(2-{[4-bromo-1-(cyclopropylmethyl)-1H-benzotriazol-5-yl]oxy}-5-chloropyridin-3-yl)methyl]-N,N-dimethylpyrrolidin-3-amine;

{1-[(2-{[4-bromo-1-(cyclopropylmethyl)-1H-benzotriazol-5-yl]oxy}-5-chloropyridin-3-yl)methyl]piperidin-4-yl}methanol;

1-[(2-{[4-bromo-1-(cyclopropylmethyl)-1H-benzotriazol-5-yl]oxy}-5-chloropyridin-3-yl)methyl]-N-methylpiperidine-4-carboxamide;

{1-[(2-{[4-bromo-1-(cyclopropylmethyl)-1H-benzotriazol-5-yl]oxy}-5-chloropyridin-3-yl)methyl]pyrrolidin-3-yl}methanol;

N-{1-[(2-{[4-bromo-1-(cyclopropylmethyl)-1H-benzotriazol-5-yl]oxy}-5-chloropyridin-3-yl)methyl]piperidin-4-yl}acetamide;

1-(2-{[4-bromo-1-(cyclopropylmethyl)-1H-benzotriazol-5-yl]oxy}-5-chloropyridin-3-yl)-N-(pyrazin-2-ylmethyl)methanamine;

4-bromo-5-({5-chloro-3-[(3-methoxypyrrolidin-1-yl)methyl]pyridin-2-yl}oxy)-1-(cyclopropylmethyl)-1H-benzotriazole;

4-bromo-5-[(5-chloro-3-{[4-(1H-tetrazol-1-yl)piperidin-1-yl]methyl}pyridin-2-yl)oxy]-1-(cyclopropylmethyl)-1H-benzotriazole;

4-bromo-5-{[5-chloro-3-(1,4,6,7-tetrahydro-5H-imidazo[4,5-c]pyridin-5-ylmethyl)pyridin-2-yl]oxy}-1-(cyclopropylmethyl)-1H-benzotriazole;

1-[(2-{[4-bromo-1-(cyclopropylmethyl)-1H-benzotriazol-5-yl]oxy}-5-chloropyridin-3-yl)methyl]-4-pyridin-2-ylpiperidin-4-ol;

tert-butyl 7-[(2-{[4-bromo-1-(cyclopropylmethyl)-1H-benzotriazol-5-yl]oxy}-5-fluoropyridin-3-yl)methyl]-2,7-diazaspiro[4.4]nonane-2-carboxylate;

4-bromo-1-(cyclopropylmethyl)-5-[(5-fluoro-3-{[7-(methylsulfonyl)-2,7-diazaspiro[4.4]non-2-yl]methyl}pyridin-2-yl)oxy]-1H-benzotriazole;

4-chloro-5-[(5-chloro-3-{[4-(methylsulfonyl)piperazin-1-yl]methyl}pyridin-2-yl)oxy]-1-(cyclopropylmethyl)-1H-benzotriazole;

4-bromo-5-[(5-chloro-3-{[4-(4H-1,2,4-triazol-4-yl)piperidin-1-yl]methyl}pyridin-2-yl)oxy]-1-(cyclopropylmethyl)-1H-benzotriazole;

4-bromo-1-(cyclopropylmethyl)-5-[(5-fluoro-3-{[6-(methylsulfonyl)-3,6-diazabicyclo[3.2.0]hept-3-yl]methyl}pyridin-2-yl)oxy]-1H-benzotriazole;

4-bromo-5-[(5-chloro-3-{[3-(1H-pyrazol-1-yl)azetidin-1-yl]methyl}pyridin-2-yl)oxy]-1-(cyclopropylmethyl)-1H-benzotriazole;

4-bromo-5-[(2-chloro-3-{[4-(methylsulfonyl)piperazin-1-yl]methyl}pyridin-4-yl)oxy]-1-(cyclopropylmethyl)-1H-benzotriazole;

(2S)-1-{4-[(2-{[4-bromo-1-(cyclopropylmethyl)-1H-benzotriazol-5-yl]oxy}-5-fluoropyridin-3-yl)methyl]piperazin-1-yl}-1-oxopropan-2-ol;

(2R)-1-{4-[(2-{[4-bromo-1-(cyclopropylmethyl)-1H-benzotriazol-5-yl]oxy}-5-fluoropyridin-3-yl)methyl]piperazin-1-yl}-1-oxopropan-2-ol;

N-({1-[(2-{[4-bromo-1-(cyclopropylmethyl)-1H-benzotriazol-5-yl]oxy}-5-chloropyridin-3-yl)methyl]azetidin-3-yl}methyl)acetamide;

N-({1-[(2-{[4-bromo-1-(cyclopropylmethyl)-1H-benzotriazol-5-yl]oxy}-5-chloropyridin-3-yl)methyl]azetidin-3-yl}methyl)methanesulfonamide;

1-[(2-{[4-bromo-1-(cyclopropylmethyl)-1H-benzotriazol-5-yl]oxy}-5-chloropyridin-3-yl)methyl]-3-methylazetidin-3-ol;

2-{1-[(2-{[4-bromo-1-(cyclopropylmethyl)-1H-benzotriazol-5-yl]oxy}-5-chloropyridin-3-yl)methyl]azetidin-3-yl}propan-2-ol;

4-chloro-1-(cyclopropylmethyl)-5-[(5-fluoro-3-{[4-(methylsulfonyl)piperazin-1-yl]methyl}pyridin-2-yl)oxy]-1H-benzotriazole;

(2S)-1-{4-[(5-chloro-2-{[4-chloro-1-(cyclopropylmethyl)-1H-benzotriazol-5-yl]oxy}pyridin-3-yl)methyl]piperazin-1-yl}-1-oxopropan-2-ol;

(5-chloro-2-{[4-chloro-1-(cyclopropylmethyl)-1H-benzotriazol-5-yl]oxy}pyridin-3-yl)methanol;

5-[(3-bromopyridin-2-yl)oxy]-4-chloro-1-(cyclopropylmethyl)-1H-benzotriazole;

2-(2-{[4-chloro-1-(cyclopropylmethyl)-1H-benzotriazol-5-yl]oxy}pyridin-3-yl)propan-2-ol;

2-{[4-chloro-1-(cyclopropylmethyl)-1H-benzotriazol-5-yl]oxy}pyridine-4-carbaldehyde;

2-(2-{[4-chloro-1-(cyclopropylmethyl)-1H-benzotriazol-5-yl]oxy}pyridin-3-yl)-1,3-difluoropropan-2-ol;

4-(2-{[4-chloro-1-(cyclopropylmethyl)-1H-benzotriazol-5-yl]oxy}pyridin-3-yl)tetrahydro-2H-thiopyran-4-ol;

(2-{[4-chloro-1-(cyclopropylmethyl)-1H-benzotriazol-5-yl]oxy}pyridin-3-yl)(cyclohexyl)methanol;

(2-{[4-chloro-1-(cyclopropylmethyl)-1H-benzotriazol-5-yl]oxy}pyridin-3-yl)(tetrahydro-2H-pyran-4-yl)methanol;

tert-butyl 4-(2-{[4-chloro-1-(cyclopropylmethyl)-1H-benzotriazol-5-yl]oxy}pyridin-3-yl)-4-hydroxypiperidine-1-carboxylate;

tert-butyl 3-[(2-{[4-chloro-1-(cyclopropylmethyl)-1H-benzotriazol-5-yl]oxy}pyridin-3-yl)(hydroxy)methyl]piperidine-1-carboxylate;

(2-{[4-chloro-1-(cyclopropylmethyl)-1H-benzotriazol-5-yl]oxy}pyridin-3-yl)(pyridin-3-yl)methanol;

1-(2-{[4-chloro-1-(cyclopropylmethyl)-1H-benzotriazol-5-yl]oxy}pyridin-3-yl)-4,4-difluorocyclohexanol;

tert-butyl 3-(2-{[4-chloro-1-(cyclopropylmethyl)-1H-benzotriazol-5-yl]oxy}pyridin-3-yl)-3-hydroxypiperidine-1-carboxylate;

1-(2-{[4-chloro-1-(cyclopropylmethyl)-1H-benzotriazol-5-yl]oxy}pyridin-3-yl)cyclopentanol;

3-(2-{[4-chloro-1-(cyclopropylmethyl)-1H-benzotriazol-5-yl]oxy}pyridin-3-yl)tetrahydrothiophene-3-ol;

4-(2-{[4-chloro-1-(cyclopropylmethyl)-1H-benzotriazol-5-yl]oxy}pyridin-3-yl)tetrahydro-2H-pyran-4-ol;

1-(2-{[4-chloro-1-(cyclopropylmethyl)-1H-benzotriazol-5-yl]oxy}pyridin-3-yl)cyclohexanol;

1-(2-{[4-chloro-1-(cyclopropylmethyl)-1H-benzotriazol-5-yl]oxy}pyridin-3-yl)-4-(trifluoromethyl)cyclohexanol;

tert-butyl 4-[(2-{[4-chloro-1-(cyclopropylmethyl)-1H-benzotriazol-5-yl]oxy}pyridin-3-yl)(hydroxy)methyl]piperidine-1-carboxylate;

tert-butyl 2-[(2-{[4-chloro-1-(cyclopropylmethyl)-1H-benzotriazol-5-yl]oxy}pyridin-3-yl)(hydroxy)methyl]pyrrolidine-1-carboxylate;

(2-{[4-chloro-1-(cyclopropylmethyl)-1H-benzotriazol-5-yl]oxy}pyridin-3-yl)(tetrahydro-2H-pyran-3-yl)methanol;

(2-{[4-chloro-1-(cyclopropylmethyl)-1H-benzotriazol-5-yl]oxy}pyridin-3-yl)(tetrahydro-2H-thiopyran-4-yl)methanol;

(2-{[4-chloro-1-(cyclopropylmethyl)-1H-benzotriazol-5-yl]oxy}pyridin-3-yl)(tetrahydro-2H-pyran-2-yl)methanol;

2-{[1-(cyclopropylmethyl)-4-(trifluoromethyl)-1H-benzotriazol-5-yl]oxy}pyridine-3-carbaldehyde;

1-(2-{[1-(cyclopropylmethyl)-4-(trifluoromethyl)-1H-benzotriazol-5-yl]oxy}pyridin-3-yl)ethanol;

5-[(5-chloro-3-{[4-(methylsulfonyl)piperazin-1-yl]methyl}pyridin-2-yl)oxy]-1-(cyclopropylmethyl)-4-(trifluoromethyl)-1H-benzotriazole;

1-(2-{[1-(cyclopropylmethyl)-4-(trifluoromethyl)-1H-benzotriazol-5-yl]oxy}pyridin-3-yl)propan-1-ol;

cyclopropyl(2-{[1-(cyclopropylmethyl)-4-(trifluoromethyl)-1H-benzotriazol-5-yl]oxy}pyridin-3-yl)methanol;

4-bromo-1-(2,2-dimethylpropyl)-5-phenoxy-1H-benzotriazole; and 4-bromo-1-(2,2-dimethylpropyl)-5-pyridin-4-yloxy-1H-benzotriazole;

or a pharmaceutically acceptable salt of any of the foregoing compounds.

18. A pharmaceutical composition comprising a compound according to claim 1 in combination with a pharmaceutically acceptable carrier.

* * * * *